US009150483B2

(12) United States Patent
Huetten et al.

(10) Patent No.: US 9,150,483 B2
(45) Date of Patent: Oct. 6, 2015

(54) AQUEOUS SOLUTION COMPRISING ACRYLIC ACID AND THE CONJUGATE BASE THEREOF

(75) Inventors: Frank Huetten, Mannheim (DE); Otto Machhammer, Mannheim (DE); Thomas Daniel, Waldsee (DE); Markus Ottenbacher, Wilhelmsfeld (DE); Daniel Pfeiffer, Hassloch (DE); Stefanie Herzog, Mannheim (DE); Manfred Heilig, Speyer (DE); Klaus Joachim Mueller-Engel, Stutensee (DE)

(73) Assignee: BASF SE, Ludwigshafen (DE)

( * ) Notice: Subject to any disclaimer, the term of this patent is extended or adjusted under 35 U.S.C. 154(b) by 391 days.

(21) Appl. No.: 13/483,705

(22) Filed: May 30, 2012

(65) Prior Publication Data

US 2013/0005925 A1    Jan. 3, 2013

Related U.S. Application Data

(60) Provisional application No. 61/492,822, filed on Jun. 3, 2011.

(30) Foreign Application Priority Data

Jun. 3, 2011 (DE) .......................... 10 2011 076 931

(51) Int. Cl.
  *C07C 51/25* (2006.01)
  *C07C 51/42* (2006.01)
  *C07C 57/04* (2006.01)
  *C07C 51/47* (2006.01)

(52) U.S. Cl.
  CPC ............... *C07C 51/252* (2013.01); *C07C 51/42* (2013.01); *C07C 57/04* (2013.01); *C07C 51/47* (2013.01)

(58) Field of Classification Search
  CPC ...... C07C 51/42; C07C 51/47; C07C 51/252; C07C 57/04
  See application file for complete search history.

(56) References Cited

U.S. PATENT DOCUMENTS

| | | | |
|---|---|---|---|
| 3,147,084 A | 9/1964 | Franzen et al. | |
| 4,256,783 A | 3/1981 | Takada et al. | |
| 4,293,347 A | 10/1981 | Haschke et al. | |
| 4,438,217 A | 3/1984 | Takata et al. | |
| 5,115,011 A | 5/1992 | Harada et al. | |
| 5,733,075 A | 3/1998 | Basteck | |
| 6,382,313 B2 | 5/2002 | Mitsumoto et al. | |
| 6,441,228 B2 | 8/2002 | Nakahara et al. | |
| 6,966,973 B2 | 11/2005 | Nakahara et al. | |
| 2005/0096445 A1 | 5/2005 | Fuchs et al. | |
| 2008/0119626 A1 | 5/2008 | Fujimaru et al. | |
| 2008/0161512 A1 | 7/2008 | Kawano et al. | |
| 2008/0183014 A1* | 7/2008 | Diefenbacher et al. | 562/600 |
| 2010/0041549 A1 | 2/2010 | Weismantel et al. | |

FOREIGN PATENT DOCUMENTS

| | | |
|---|---|---|
| CN | 1656054 A | 8/2005 |
| CN | 101589015 A | 11/2009 |
| DE | 1 995-516 U | 10/1968 |
| DE | 2 201 528 | 11/1972 |
| DE | 28 30 765 A1 | 1/1980 |
| DE | 29 03 218 A1 | 8/1980 |
| DE | 29 09 671 A1 | 10/1980 |
| DE | 25 13 405 C2 | 10/1982 |
| DE | 24 07 236 C2 | 2/1983 |
| DE | 33 00 044 A1 | 7/1983 |
| DE | 33 38 380 C2 | 10/1988 |
| DE | 40 23 239 A1 | 1/1992 |
| DE | 41 01 879 A1 | 7/1992 |
| DE | 44 31 949 A1 | 3/1995 |
| DE | 44 31 957 A1 | 3/1995 |
| DE | 43 35 172 A1 | 4/1995 |
| DE | 43 35 973 A1 | 4/1995 |
| DE | 44 42 346 A1 | 5/1996 |
| DE | 195 28 646 A1 | 2/1997 |
| DE | 195 39 295 A1 | 4/1997 |
| DE | 196 24 674 A1 | 1/1998 |
| DE | 197 36 105 A1 | 2/1999 |
| DE | 198 35 247 A1 | 2/1999 |
| DE | 197 40 252 A1 | 3/1999 |
| DE | 197 40 253 A1 | 3/1999 |
| DE | 197 40 493 A1 | 3/1999 |
| DE | 197 46 210 A1 | 4/1999 |
| DE | 198 15 281 A1 | 10/1999 |
| DE | 198 38 845 A1 | 3/2000 |
| DE | 198 39 782 A1 | 3/2000 |
| DE | 198 55 913 A1 | 6/2000 |
| DE | 199 02 562 A1 | 7/2000 |
| DE | 199 10 506 A1 | 9/2000 |
| DE | 199 10 508 A1 | 9/2000 |
| DE | 199 27 624 A1 | 12/2000 |
| DE | 199 55 176 A1 | 1/2001 |
| DE | 199 48 241 A1 | 4/2001 |
| DE | 199 48 248 A1 | 4/2001 |
| DE | 199 48 523 A1 | 4/2001 |
| DE | 199 55 168 A1 | 5/2001 |

(Continued)

OTHER PUBLICATIONS

English Translation of DE 10336386 A1; Diehl et al; Mar. 2004.*
U.S. Appl. No. 14/069,759, filed Nov. 1, 2013, Mueller et al.

*Primary Examiner* — Karuna P Reddy
(74) *Attorney, Agent, or Firm* — Oblon, McClelland, Maier & Neustadt, L.L.P.

(57) ABSTRACT

An aqueous solution comprising acrylic acid and the conjugate base thereof in a total amount of at least 10% by weight, based on the weight of the aqueous solution, and propionic acid and the conjugate base thereof, formic acid and the conjugate base thereof, acetic acid and the conjugate base thereof, benzoic acid and the conjugate base thereof, maleic anhydride, maleic acid and the conjugate bases thereof, phthalic anhydride, phthalic acid and the conjugate bases thereof, acrolein, benzaldehyde, 2-furaldehyde, and at least 20 mol % of at least one alkali metal cation;
  process for preparing this solution; and
  the use of this solution for preparation of polymer by free-radical polymerization.

14 Claims, 2 Drawing Sheets

(56) References Cited

FOREIGN PATENT DOCUMENTS

| | | |
|---|---|---|
| DE | 100 36 881 A1 | 2/2002 |
| DE | 100 46 928 A1 | 4/2002 |
| DE | 100 46 957 A1 | 4/2002 |
| DE | 100 63 161 A1 | 6/2002 |
| DE | 100 63 162 A1 | 6/2002 |
| DE | 101 22 787 A1 | 6/2002 |
| DE | 101 22 788 A1 | 6/2002 |
| DE | 101 01 695 A1 | 7/2002 |
| DE | 101 43 565 A1 | 10/2002 |
| DE | 101 38 101 A1 | 11/2002 |
| DE | 101 59 825 A1 | 6/2003 |
| DE | 102 21 202 A1 | 7/2003 |
| DE | 102 21 203 A1 | 7/2003 |
| DE | 102 20 494 A1 | 11/2003 |
| DE | 102 23 058 A1 | 12/2003 |
| DE | 102 28 859 A1 | 1/2004 |
| DE | 102 32 482 A1 | 1/2004 |
| DE | 103 13 209 A1 | 3/2004 |
| DE | 103 36 386 A1 | 3/2004 |
| DE | 10336386 A1 * | 3/2004 |
| DE | 102 43 625 A1 | 4/2004 |
| DE | 102 45 585 A1 | 4/2004 |
| DE | 102 46 119 A1 | 4/2004 |
| DE | 103 32 758 A1 | 5/2004 |
| DE | 103 53 014 A1 | 6/2004 |
| DE | 103 60 057 A1 | 7/2004 |
| DE | 103 13 208 A1 | 10/2004 |
| DE | 103 25 488 A1 | 12/2004 |
| DE | 103 47 664 A1 | 12/2004 |
| DE | 10 2004 025 445 A1 | 2/2005 |
| DE | 10 2004 032 129 A1 | 3/2005 |
| DE | 10 2004 021 763 A1 | 5/2005 |
| DE | 10 2004 021 764 A1 | 6/2005 |
| DE | 103 51 269 A1 | 6/2005 |
| DE | 103 60 396 A1 | 7/2005 |
| DE | 103 61 456 A1 | 7/2005 |
| DE | 103 61 515 A1 | 7/2005 |
| DE | 10 2004 004 496 A1 | 8/2005 |
| DE | 10 2005 009 469 A1 | 8/2005 |
| DE | 600 12 108 T2 | 8/2005 |
| DE | 10 2004 017 150 A1 | 10/2005 |
| DE | 10 2004 017 151 A1 | 10/2005 |
| DE | 10 2004 061 770 A1 | 7/2006 |
| DE | 10 2005 009 891 A1 | 9/2006 |
| DE | 10 2005 013 039 A1 | 9/2006 |
| DE | 10 2005 015 37 A1 | 10/2006 |
| DE | 10 2005 018 702 A1 | 10/2006 |
| DE | 10 2005 022 798 A1 | 11/2006 |
| DE | 10 2005 037 678 A1 | 2/2007 |
| DE | 10 2005 056 377 A1 | 5/2007 |
| DE | 10 2005 057 197 A1 | 6/2007 |
| DE | 601 24 481 T2 | 9/2007 |
| DE | 10 2006 024 901 A1 | 11/2007 |
| DE | 10 2007 029 053 A1 | 1/2008 |
| DE | 10 2006 045 088 A1 | 3/2008 |
| DE | 10 2006 045 089 A1 | 3/2008 |
| DE | 10 2007 019 597 A1 | 5/2008 |
| DE | 10 2007 025 869 A1 | 7/2008 |
| DE | 10 2008 040 340 A1 | 2/2009 |
| DE | 10 2008 042 009 A1 | 4/2009 |
| DE | 10 2008 042 010 A1 | 4/2009 |
| DE | 10 2007 055 086 A1 | 5/2009 |
| DE | 10 2009 027 401 A1 | 2/2010 |
| DE | 10 2009 000 987 A1 | 4/2010 |
| DE | 102 42 746 B4 | 7/2010 |
| DE | 10 2010 030 279 A1 | 10/2010 |
| DE | 10 2010 001 228 A1 | 2/2011 |
| DE | 10 2010 042 216 A1 | 6/2011 |
| DE | 10 2010 028 328 A1 | 11/2011 |
| DE | 10 2010 023 312 A1 | 12/2011 |
| EP | 0 015 565 A1 | 9/1980 |
| EP | 0 253 409 A2 | 1/1988 |
| EP | 0 257 565 A1 | 3/1988 |
| EP | 0 279 374 A1 | 8/1988 |
| EP | 0 293 224 A1 | 11/1988 |
| EP | 0 293 859 A1 | 12/1988 |
| EP | 0 316 682 A1 | 5/1989 |
| EP | 0 372 706 A2 | 6/1990 |
| EP | 0 383 224 A2 | 8/1990 |
| EP | 0 575 897 A1 | 12/1993 |
| EP | 0 608 838 A2 | 8/1994 |
| EP | 0 609 750 A1 | 8/1994 |
| EP | 0 616 998 A1 | 9/1994 |
| EP | 0 668 104 A1 | 8/1995 |
| EP | 0 700 714 A1 | 3/1996 |
| EP | 0 700 893 A1 | 3/1996 |
| EP | 714 700 A2 | 6/1996 |
| EP | 0 807 465 A1 | 11/1997 |
| EP | 0 854 129 A1 | 7/1998 |
| EP | 0 990 636 A1 | 4/2000 |
| EP | 1 095 685 A1 | 5/2001 |
| EP | 1 106 598 A2 | 6/2001 |
| EP | 1 237 937 A0 | 9/2002 |
| EP | 1 345 881 A1 | 9/2003 |
| EP | 1 710 227 A1 | 10/2006 |
| JP | 3-178949 | 8/1991 |
| JP | 3-294239 | 12/1991 |
| JP | 11-35519 | 2/1999 |
| WO | WO 98/24746 A1 | 6/1998 |
| WO | WO 99/42494 A1 | 8/1999 |
| WO | WO 00/53557 A1 | 9/2000 |
| WO | WO 00/53558 A1 | 9/2000 |
| WO | WO 00/53559 A1 | 9/2000 |
| WO | WO 00/53560 A1 | 9/2000 |
| WO | WO 01/38402 A1 | 5/2001 |
| WO | WO 01/77056 A1 | 10/2001 |
| WO | WO 01/96270 A2 | 12/2001 |
| WO | WO 01/96271 A2 | 12/2001 |
| WO | WO 02/09839 A1 | 2/2002 |
| WO | WO 02/24620 A2 | 3/2002 |
| WO | WO 02/50011 A1 | 6/2002 |
| WO | WO 02/055469 A1 | 7/2002 |
| WO | WO 03/002623 A1 | 1/2003 |
| WO | WO 03/078378 A1 | 9/2003 |
| WO | WO 03/095410 A1 | 11/2003 |
| WO | WO 03/095411 A1 | 11/2003 |
| WO | WO 2004/007450 A1 | 1/2004 |
| WO | WO 2004/035514 A1 | 4/2004 |
| WO | WO 2004/085362 A1 | 10/2004 |
| WO | WO 2004/085369 A1 | 10/2004 |
| WO | WO 2004/108267 A1 | 12/2004 |
| WO | WO 2005/007609 A1 | 1/2005 |
| WO | WO 2005/049453 A1 | 6/2005 |
| WO | WO 2005/049543 A1 | 6/2005 |
| WO | WO 2005/073160 A1 | 8/2005 |
| WO | WO 2006/002703 A1 | 1/2006 |
| WO | WO 2006/008083 A1 | 1/2006 |
| WO | WO 2006/008224 A2 | 1/2006 |
| WO | WO 2006/053731 A1 | 5/2006 |
| WO | WO 2006/073160 A1 | 7/2006 |
| WO | WO 2006/092272 A2 | 9/2006 |
| WO | WO 2006/092405 A1 | 9/2006 |
| WO | WO 2006/092415 A1 | 9/2006 |
| WO | WO 2006/114506 A1 | 11/2006 |
| WO | WO 2007/074044 A1 | 7/2007 |
| WO | WO 2007/074045 A1 | 7/2007 |
| WO | WO 2007/082827 A1 | 7/2007 |
| WO | WO 2007/090991 | 8/2007 |
| WO | WO 2008/009599 A1 | 1/2008 |
| WO | WO 2008/034778 A1 | 3/2008 |
| WO | WO 2008/034783 A1 | 3/2008 |
| WO | WO 2008/077767 A1 | 7/2008 |
| WO | WO 2008/104577 A1 | 9/2008 |
| WO | WO 2008/116840 A1 | 10/2008 |
| WO | WO 2009/133042 A2 | 11/2009 |
| WO | WO 2010/003884 A1 | 1/2010 |
| WO | WO 2010/012586 A1 | 2/2010 |
| WO | WO 2010/066601 A2 | 6/2010 |

* cited by examiner

AQUEOUS SOLUTION COMPRISING ACRYLIC ACID AND THE CONJUGATE BASE THEREOF

The present invention relates to an aqueous solution comprising acrylic acid and the conjugate base thereof in a total amount, calculated as acrylic acid, of at least 10% by weight, based on the weight of the aqueous solution, and, based on the total amount of acrylic acid and the conjugate base thereof present in the aqueous solution, calculated as acrylic acid, ≥50 ppm by weight in total of propionic acid and the conjugate base thereof, calculated as propionic acid,
≥200 ppm by weight in total of formic acid and the conjugate base thereof, calculated as formic acid,
≥3000 ppm by weight in total of acetic acid and the conjugate base thereof, calculated as acetic acid,
≤10 ppm by weight in total of benzoic acid and the conjugate base thereof, calculated as benzoic acid,
≤10 ppm by weight in total of maleic anhydride (MAn), maleic acid (MAc) and the conjugate bases thereof, calculated as maleic acid,
≤10 ppm by weight in total of phthalic anhydride (PAn), phthalic acid (PAc) and the conjugate bases thereof, calculated as phthalic acid,
≤50 ppm by weight of acrolein,
≤50 ppm by weight of benzaldehyde,
≥50 ppm by weight of 2-furaldehyde, and
at least 20 mol % of at least one alkali metal cation.

The present invention also relates to a process for preparing the aforementioned aqueous solutions and to the use of such aqueous solutions for preparation of polymers (for example water-superabsorbent polymers).

Figure 1:
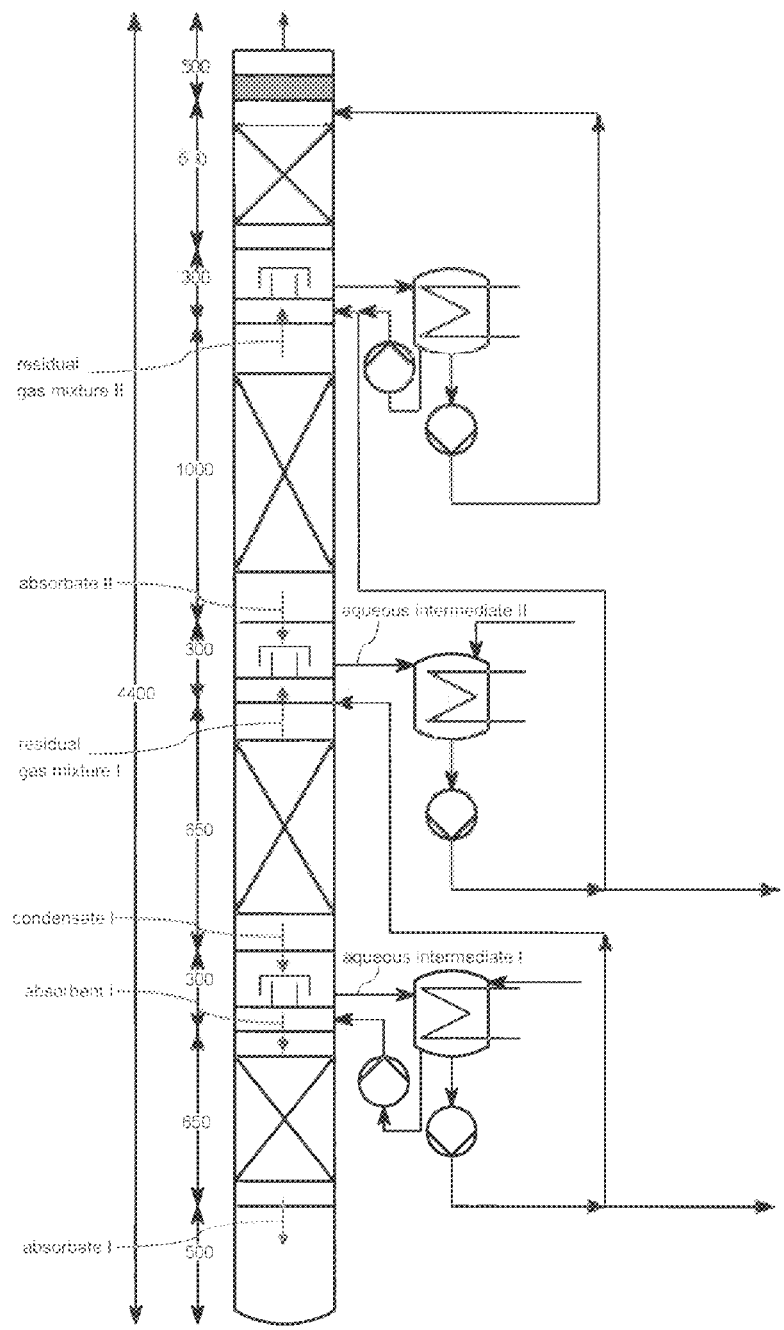
FIG. 1 shows a schematic diagram of separating column K.

A carboxylic acid in this document is a compound which has at least one carboxyl group (—COOH).

If the compound has only one carboxyl group, it is called a monocarboxylic acid. If the compound has two or more carboxyl groups, it is called a di- or polycarboxylic acid.

Examples of monocarboxylic acids are acrylic acid, formic acid, acetic acid, propionic acid and benzoic acid. Examples of dicarboxylic acids are maleic acid and phthalic acid.

Carboxylic acids are counted among the Brønsted acids. When a monocarboxylic acid reacts with a Brønsted base, the carboxyl group releases a proton ($H^+$) to the Brønsted base. The carboxyl group gives rise to a carboxylate group (—$COO^-$) and the carboxylic acid gives rise to the conjugate Brønsted base thereof (the corresponding anion), which is referred to in this document as conjugate base for short.

In the case of a di- or polycarboxylic acid, only one or more than one carboxyl group can release its proton to a Brønsted base. The resulting different anions shall all be referred to in this document as conjugate bases (in the Brønsted sense) of the di- or polycarboxylic acid.

Acrylic acid is an important ethylenically unsaturated compound, which has a marked tendency to free-radical polymerization as such, in the form of the conjugate base thereof or esterified with alcohols, and in this way is suitable for formation of polymers of a wide variety of different types by free-radical polymerization.

One way of obtaining acrylic acid is by a heterogeneously catalyzed gas phase partial oxidation of at least one $C_3$ precursor compound of acrylic acid with molecular oxygen over catalysts in the solid state at elevated temperature (cf., for example, WO 2009/133042). The term "$C_3$ precursor compound of acrylic acid" encompasses especially those chemical compounds which are obtainable in a formal sense by reduction of acrylic acid. Known $C_3$ precursors of acrylic acid are, for example, propane, propene, acrolein, propionaldehyde, propanol and propionic acid. However, the term shall also comprise precursor compounds of the aforementioned compounds, for example glycerol (proceeding from glycerol, acrylic acid can be obtained, for example, by heterogeneously catalyzed oxidative dehydration in the gas phase; cf., for example, EP-A 1710227, WO 06/114506 and WO 06/092272).

Due to numerous parallel and further reactions which proceed in the course of the catalytic gas phase partial oxidation of a $C_3$ precursor compound (for example, there is always also a minor degree of full combustion of starting materials, intermediates and/or end products to $CO_2$ and $H_2O$ in parallel to the target reaction), and due to the inert diluent gases to be used in the course of the partial oxidation, the catalytic gas phase partial oxidation does not give pure acrylic acid, but rather a reaction gas mixture (a product gas mixture) which comprises essentially acrylic acid, the inert diluent gases, by-products and conversion products.

The particularly characteristic constituents other than acrylic acid in the product gas mixture include low molecular weight aldehydes such as acrolein, 2-furaldehyde and benzaldehyde, low molecular weight aliphatic carboxylic acids (=low molecular weight alkanecarboxylic acids) such as formic acid, acetic acid and propionic acid, aromatic carboxylic acids or carboxylic anhydrides such as benzoic acid, phthalic acid and phthalic anhydride, and olefinically unsaturated carboxylic acids or carboxylic anhydrides such as maleic acid and maleic anhydride. The further typical product gas mixture constituents include not only $CO_2$ but especially water, which is firstly a typical partial oxidation by-product and secondly an inert diluent gas which is frequently used alongside inert diluent gases such as CO, noble gases and/or $N_2$ for example, and which, for example, reduces the ignitibility of the reaction mixture and is capable of absorbing some of the heat of reaction. In a corresponding manner, $CO_2$ is frequently not only a partial oxidation by-product, but also an inert diluent gas used in addition.

According to the contemplated use of the acrylic acid prepared by partial oxidation as described above, the non-acrylic acid constituents of the product gas mixture which have been detailed in a representative manner above are disadvantageous in different ways and to a different degree (cf. WO 03/095411).

In the preparation of esters of acrylic acid, presence of carboxylic acids other than acrylic acid (for example the low molecular weight aliphatic carboxylic acids) and/or the anhydrides thereof has a particularly adverse effect, since these likewise react with the esterification alcohol and in this way reduce the desired yield of the target ester. Furthermore, the low molecular weight aliphatic carboxylic acids are substances with an intense odor which can lead to considerable nuisance even in low concentrations (for example in the production of polymers into which they are not polymerized). The low molecular weight aldehydes generally impair the free-radical polymerization characteristics of acrylic acid, of the conjugate base thereof and of the esters thereof, either because they slow or even inhibit the polymerization or because they reduce the molecular weights or polymer chain lengths which are established in the polymerization. However, they are generally incorporated into the polymer.

The aromatic carboxylic acids or anhydrides thereof are not entirely safe in toxicological terms. Another disadvantage is that they are not polymerized into polymers obtained by free-radical polymerization. Secondly, they are also able to enter into hydrogen bonds with acrylic acid and the conjugate base thereof (in monomeric and in free-radically polymerized form), and they can therefore firstly be removed only with difficulty from the polymers thereof, but secondly can be released continuously from these polymers to the environment thereof over prolonged periods. For as long as they remain in the polymer, they can be the cause of discoloration thereof.

In a similar manner, the above remarks apply to the olefinically unsaturated carboxylic acids other than acrylic acid. The tendency thereof to free-radical polymerization is generally less marked than that of acrylic acid, which is why they have an increased probability of forming residual monomers which remain in unpolymerized form in corresponding free-radical polymerizations. These residual monomers are likewise not entirely safe in toxicological terms due to their ethylenically unsaturated double bond.

In hydrogen-bonded form, they are likewise difficult to remove from the polymers obtained, but can nevertheless be released gradually to the environment over prolonged periods.

Water as a companion of acrylic acid is disadvantageous in that water in acrylic acid accelerates the unwanted diacrylic acid formation by Michael addition of acrylic acid onto itself, such that significant amounts of diacrylic acid can form in the course of storage of water-comprising acrylic acid even during a comparatively short storage period. The tendency of diacrylic acid to free-radical polymerization is likewise less marked than that of acrylic acid. Moreover, both polymerized and unpolymerized diacrylic acid tend to eliminate monomeric acrylic acid again under thermal stress.

Against the background outlined, the traditional procedure has therefore generally been to isolate, from the product gas mixture of the partial oxidation, an acrylic acid which has an acrylic acid content normally of at least 96% by weight and which comprises essentially all companions of acrylic acid present in the product gas mixture of the partial oxidation only to a comparatively homogeneously reduced degree.

The acrylic acid is generally first absorbed comparatively selectively from the product gas mixture into an absorbent, and then removed from the resulting absorbate, for example by means of rectificative separation processes or by means of extractive and rectificative separation processes (cf., for example, DE-A 10 2009 027 401).

In this way, an acrylic acid is obtained without having been tailored for a particular end use, but rather can be sent to different uses without having to accept any particularly marked disadvantages. In addition, it can be purified further by additional crystallizative (cf., for example, EP-A 616998) and/or rectificative (cf., for example, DE-A 4335172) measures and subsequently sent to those uses in which particularly high demands are made on the purity of the acrylic acid.

However, the cost for the versatility of the acrylic acid obtainable as described above is the requirement for comparatively high separation complexity which is also accompanied, for example, by a substantial removal of the water present in the product gas mixture of the partial oxidation, even though numerous further uses of the acrylic acid proceed in aqueous medium.

One of these further uses is the preparation of polymers in which at least a portion of the polymerized acrylic acid is present in a form neutralized with alkali metal bases, for example NaOH (cf., for example, DE-A 102004004496).

Such polymers generally have a marked absorption capacity for aqueous liquids and are also known by the "superabsorbents" name (cf., for example, US 2010/0041549 and "Modern Superabsorbent Polymer Technology", Buchholz/Graham, Wiley-VCH, New York, 1998).

The production of superabsorbents typically comprises a free-radical polymerization from an aqueous solution comprising acrylic acid and the conjugate base thereof in a total amount, calculated as acrylic acid, of at least 10% by weight, based on the weight of the aqueous solution. In addition, the aqueous solution comprises, based on the molar total amount of acrylic acid and of the conjugate base thereof (the acrylate anion) present therein, normally at least 20 mol % of at least one alkali metal cation. The latter typically originates from at least one alkali metal base, for example NaOH, which neutralizes at least a portion of the acrylic acid present in the aqueous solution and provides positively charged counterions (alkali metal cations) to the acrylate anions formed as the conjugate (Brønsted) base.

Superabsorbents were originally used essentially exclusively in hygiene articles, such as diapers and incontinence products. Against this background, particularly high purity demands were made on the acrylic acid used for production thereof. Finally, the hygiene articles comprising the polymer which absorbs aqueous solutions in a superabsorbent manner should not only be toxicologically safe, but also not exhibit any unwanted discoloration, be odor-neutral, and have a particularly marked absorption capacity for aqueous solutions and a marked retention capacity for the absorbed aqueous solution (the latter properties are promoted by long polymer chains). Acrylic acids with corresponding purity can be obtained from the product gas mixture of the heterogeneously catalyzed partial gas phase oxidation, for example by the procedure disclosed in DE-A 102007055086, which is a combination of fractional condensation and crystallization (cf. also DE-A 10221202 and WO 2010/003884 or WO 2004/035514, and US 2008/0119626, US 2008/0161512 and WO 2006/008083). A comparable procedure is recommended in WO 2008/116840.

Numerous new fields of use outside the hygiene sector have now been developed for superabsorbents.

One sector in which superabsorbents find a multitude of applications is in construction chemistry. For example, they are used in mortars as a thickener and/or water store. In addition, superabsorbents are nowadays used in firefighting. For instance, fire extinguishers comprising superabsorbents and water in the form of what are called gel extinguishers have the advantage that they act only at the seat of the fire and thus do not damage power cables and the like. In horticulture, superabsorbents are used as water stores for plants. In this case, the superabsorbent releases water absorbed therein to the plant homogeneously over prolonged periods, and so it can survive without being watered for a long period. In cable sheathing, it is advantageous to use a layer of superabsorbent which serves to protect the cable from moisture. As soon as water penetrates through the outer shell, the superabsorbent swells with absorption of water and closes the entry site. Superabsorbent is also used in flooding protection. In this case, sacks filled with a mixture of sand and superabsorbent are used instead of plain sandbags.

While the high quality demand described is essentially the crucial criterion in the case of use of superabsorbents in the hygiene sector, a particularly crucial feature aside from satisfactory quality in the case of use of superabsorbents outside the hygiene sector is the feature of economic viability.

However, a quality of the superabsorbent which is still satisfactory for end uses outside the hygiene sector can also be achieved proceeding from an acrylic acid having the following representative fingerprint of impurities present therein (the figures are based on the amount of acrylic acid present in the acrylic acid):

≥50 ppm by weight of propionic acid,
≥200 ppm by weight of formic acid,
≥3000 ppm by weight of acetic acid,
≤10 ppm by weight of benzoic acid,
≤10 ppm by weight of total amount of maleic anhydride and maleic acid, calculated as maleic acid,
≤10 ppm by weight of total amount of phthalic anhydride and phthalic acid, calculated as phthalic acid,
≤50 ppm by weight of acrolein,
≤50 ppm by weight of benzaldehyde,
≤50 ppm by weight of 2-furaldehyde, and
≥50 ppm by weight of water.

One reason for this is that the low molecular weight aliphatic carboxylic acids are toxicologically safe, and merely substantial freedom from odor is sufficient in the applications detailed.

Furthermore, satisfactory chain lengths of the relevant polymer are sufficient for satisfactory absorption/retention characteristics in the superabsorbent, and therefore slightly elevated aldehyde contents are still acceptable in the target use sector outside hygiene applications.

However, the depletion of benzoic acid, phthalic acid and maleic acid (or the anhydrides thereof) should still be rigorous when obtaining the acrylic acid, since these can possibly be released from the polymer to the environment over the course of time in the contemplated applications outside the hygiene sector.

The importance of elevated water contents has already been discussed.

A production of the corresponding superabsorbent which arises from the above thus comprises a free-radical polymerization from an aqueous solution which comprises acrylic acid and the conjugate base thereof in a total amount, calculated as acrylic acid, of at least 10% by weight, based on the weight of the aqueous solution, and, based on the total amount of acrylic acid and the conjugate base thereof present in the aqueous solution, calculated as acrylic acid, ≥50 ppm by weight in total of propionic acid and the conjugate base thereof, calculated as propionic acid,
≥200 ppm by weight in total of formic acid and the conjugate base thereof, calculated as formic acid,
≥3000 ppm by weight in total of acetic acid and the conjugate base thereof, calculated as acetic acid,
≤10 ppm by weight in total of benzoic acid and the conjugate base thereof, calculated as benzoic acid,
≤10 ppm by weight in total of maleic anhydride, maleic acid and the conjugate bases thereof, calculated as maleic acid,
≤10 ppm by weight in total of phthalic anhydride, phthalic acid and the conjugate base thereof, calculated as phthalic acid,
≤50 ppm by weight of acrolein,
≤50 ppm by weight of benzaldehyde,
≤50 ppm by weight of 2-furaldehyde, and
at least 20 mol % of an alkali metal cation (it will be appreciated that such aqueous solutions are also suitable, inter alia, for preparation of low molecular weight polyacrylates which can be used, for example, as flocculants (cf. EP-A 372 706) or as dispersants).

The present invention provides such aqueous solutions and a tailored and hence particularly economically viable process for obtaining them. An essential feature of this preparation process is that it has a much lower separation complexity as compared with the known prior art processes, since, for example, there is no need for a substantial removal of the water present in the product gas mixture of the partial oxidation. Furthermore, the inventive procedure produces such aqueous solutions with the option of the direct further use thereof (i.e. as what is called a "ready mix").

In contrast, the procedures recommended in DE-A 10221203 are unsatisfactory. This is primarily because the procedures recommended therein for preparation of an aqueous solution comprising acrylic acid in partly neutralized form, from which the relevant free-radical polymerization is to be effected, do not achieve satisfactory separation of acrylic acid and the unwanted secondary components benzoic acid, phthalic acid and maleic acid, and the anhydrides thereof.

This applies both to the procedure of direct absorption of acrylic acid from the product gas mixture of the partial oxidation into an aqueous alkali metal base, and to the procedure of an initially condensative transfer of the acrylic acid from the product gas mixture into the liquid phase with subsequent addition of at least one alkali metal base to the liquid phase comprising the acrylic acid.

Inventive aqueous solutions are generally obtainable by processes for preparing aqueous target product solutions comprising acrylic acid and the conjugate base thereof, which comprise the following process measures:

at least one $C_3$ precursor compound of acrylic acid is passed as a constituent of a reaction gas input mixture comprising the at least one $C_3$ precursor compound of acrylic acid, molecular oxygen and at least one inert diluent gas other than $CO_2$ and water through a partial oxidation zone (charged with catalysts in the solid state) and partially oxidized therein to acrylic acid by a heterogeneously catalyzed gas phase partial oxidation over (the) catalysts present in the solid state with the molecular oxygen to obtain a product gas mixture comprising $CO_2$, water, the target product acrylic acid, the secondary constituents formic acid, acetic acid, propionic acid, benzoic acid, acrolein, benzaldehyde, 2-furaldehyde, phthalic anhydride and/or phthalic acid, maleic anhydride and/or maleic acid, and at least one inert diluent gas other than $CO_2$ and water, the product gas mixture conducted out of the partial oxidation zone, optionally after its temperature has been reduced in a cooling zone by direct and/or indirect cooling, is conducted through an absorption zone I in which an absorbent I conducted in cocurrent or in countercurrent to the product gas mixture, on the route of the product gas mixture through absorption zone I, scrubs the secondary constituents benzoic acid, phthalic acid and/or the anhydride thereof and maleic acid and/or the anhydride thereof out of the product gas mixture by absorption to form an absorbate I, the absorbate I is discharged from absorption zone I and the scrubbed product gas mixture conducted out of absorption zone I is conducted through a condensation zone I and, on the route of the scrubbed product gas mixture through condensation zone I, an aqueous acrylic acid solution also comprising the secondary constituents formic acid, acetic acid, propionic acid, acrolein, benzaldehyde and 2-furaldehyde in dissolved form is condensed as condensate I out of the scrubbed product gas mixture by direct and/or indirect cooling thereof, with the proviso that there remains a $CO_2$— and water-comprising residual gas mixture I which, aside from the at least one inert diluent gas other than $CO_2$ and water, and acetic acid, propionic acid, acrolein, benzaldehyde and 2-furaldehyde as secondary constituents, still comprises at least 10% of the amount of acrylic acid present in the product gas mixture, at least a portion of condensate I is conducted as absorbent I into the absorption zone I, and any remaining residual amount of condensate I is conducted out of condensation zone I as aqueous intermediate I, the residual gas mixture I conducted out of condensation zone I is passed through an absorption zone II in which an aqueous alkali metal base is conducted in cocurrent or in countercurrent to the residual gas mixture I as absorbent II and, on the route of the residual gas mixture I through the absorption zone II, scrubs out not only acrylic acid but also $CO_2$, and also the secondary constituents formic acid, acetic acid, propionic acid, acrolein, benzaldehyde and 2-furaldehyde, out of residual gas mixture I by absorption to form an aqueous alkali metal acrylate solution as absorbate II, leaving a residual gas mixture II which comprises, aside from the at least one inert diluent gas other than $CO_2$ and water and a residual amount of acrylic acid, also water, residual gas mixture II is conducted out of absorption zone II, and absorbate II is withdrawn from absorption zone II as aqueous intermediate II, if no aqueous intermediate I is conducted out of condensation zone I, the acrolein, benzaldehyde and 2-furaldehyde secondary constituents present in the aqueous intermediate II are absorbed therefrom by extraction with an organic extractant, and the remaining aqueous raffinate II is removed from the organic extract II formed as the aqueous target product solution comprising acrylic acid and the conjugate base thereof, if aqueous intermediate I is conducted out of condensation zone I, the acrolein, benzaldehyde and 2-furaldehyde secondary constituents present in aqueous intermediate II are absorbed therefrom by extraction with an organic extractant, and the remaining aqueous raffinate II is removed from the organic extract II formed, and the acrolein, benzaldehyde and 2-furaldehyde secondary constituents present in the aqueous intermediate I are absorbed therefrom by extraction with an organic extractant, and the remaining aqueous raffinate I is removed from the organic extract I formed, and the aqueous raffinate II and the aqueous raffinate I are combined (merged) to give the aqueous target product solution comprising the acrylic acid and the conjugate base thereof, from which $CO_2$ is optionally outgassed, or the aqueous intermediate II and the aqueous intermediate I are combined (merged) to give an aqueous intermediate III, and the acrolein, benzaldehyde and 2-furaldehyde secondary constituents present in the aqueous intermediate III, from which $CO_2$ is optionally outgassed beforehand, are absorbed therefrom by extraction with an organic extractant, and the remaining aqueous raffinate III is removed from the organic extract III formed as the aqueous target product solution comprising acrylic acid and the conjugate base thereof.

Such preparation processes constitute processes according to the invention in this application.

Advantageously in accordance with the invention, the temperature of the product gas mixture comprising the acrylic acid as the target product, coming from the partial oxidation, before it is supplied to the absorption zone I, is reduced by direct and/or indirect cooling in a cooling zone, while it flows through the cooling zone.

This is because the temperature of the product gas mixture leaving the gas phase partial oxidation, according to the embodiment of the gas phase partial oxidation employed, can vary within a wide range. The temperature of the product gas mixture leaving the gas phase partial oxidation is frequently 150 to 350° C., in many cases 200 to 320° C. or to 300° C., or 220 to 300° C., sometimes up to 500° C.

Temperatures favorable in accordance with the invention for the product gas mixture comprising the acrylic acid as the target product are, on entry thereof into the absorption zone I, 90 to 180° C., preferably 95 to 170° C. or 100 to 160° C., and more preferably 100 to 150° C. or 100 to 130° C.

When the temperature of the product gas mixture is reduced in the cooling zone by indirect cooling, an indirect heat exchanger normally used for this purpose has at least one primary space and at least one secondary space separated from the at least one primary space by a material dividing wall. A fluid refrigerant flows through the at least one primary space, while the product gas mixture to be cooled simultaneously flows through the at least one secondary space. The material dividing wall serves as a surface for transfer of heat from the at least one secondary space into the at least one primary space. Useful indirect heat exchangers for the inventive purposes are, for example, shell and tube heat exchangers or plate heat exchangers, as known, for example, from documents DE-A 10313208, U.S. Pat. No. 6,382,313 B2, DE-A 102007025869, DE-A 102007019597 and DE-A 102004061770 as aftercoolers or intermediate coolers. Useful fluid refrigerants include, for example, water, salt melts, ionic liquids and oils, and all other fluids mentioned in aforementioned documents.

Preferably in accordance with the invention, the temperature of the product gas mixture of the partial oxidation is reduced, however, by direct cooling with a cooling liquid which is suitable in accordance with the invention and is preferably sprayed finely, and partially evaporates in the course thereof. Useful cooling liquids of this kind include, for example, precooled, comparatively pure, acrylic acids or solutions thereof in water. However, it is particularly advantageous in the process according to the invention to directly cool the product gas mixture using absorbate I discharged from absorption zone I.

For the purpose of indirectly cooling an absorbate I used as such a cooling liquid, it can be conducted through an indirect heat exchanger. All common indirect heat exchangers are suitable in this respect. Preferred examples include shell and tube heat exchangers, plate heat exchangers and air coolers. Suitable cooling media are, for example, air in the case of the corresponding air cooler, and cooling liquids, especially water, in the case of the other heat exchangers. Such indirect cooling of absorbate I used as cooling liquid is, however, not indispensable in the process according to the invention.

In the case of direct cooling of the product gas mixture, the cooling zone is a direct cooler (also referred to in the specialist literature as a quench apparatus). In principle, useful direct coolers are all apparatuses known in the prior art for this purpose (for example spray scrubbers, Venturi scrubbers, bubble columns or other apparatuses with sprayed surfaces). Preferably in accordance with the invention, the direct coolers of this kind used are Venturi scrubbers or spray coolers. Preferably, the sprayed cooling liquid (e.g. the absorbate I) and the product gas mixture to be cooled flow in cocurrent through a spray cooler. Especially in the latter case, and in particular when the (preferably sprayed) cooling liquid used is absorbate I, the cooled product gas mixture, in a mixture with the cooling liquid, is conducted out of the cooling zone into absorption zone I. In the case of direct cooling of the product gas mixture, especially when the cooling liquid used is absorbate I, the cooling effect results in particular from partial evaporation of the cooling liquid during the cooling operation. The temperature of the cooling liquid, especially when it is absorbate I, on entry into the cooling zone (into the direct cooler), appropriately in accordance with the invention, is 90 to 120° C.

Especially in the case of a spray cooler operated in cocurrent (cf. also DE-A 10063161 and EP-A 1345881), the direct cooler does not require any internals to increase the contact surface area between the finely sprayed droplets of the cooling liquid and the product gas mixture to be cooled. However, a direct cooler may of course comprise such internals (for example structured packings, random packings and/or mass transfer trays of any kind). If the direct cooler has the aforementioned internals, the cooling liquid (e.g. the absorbate I) and the product gas mixture will, appropriately in application terms, be conducted through the direct cooler (through the cooling zone) in countercurrent. Advantageously in application terms, a direct cooler thermally insulated from the environment (for example with mineral wool) will be used.

It will be appreciated that, in the process according to the invention, in the case of direct cooling of the product gas mixture with absorbate I as cooling liquid, not the entire amount of absorbate I conducted out of (discharged from) the absorption zone I will be supplied to the direct cooler (to the cooling zone), but rather only a portion of the absorbate I conducted out of absorption zone I. Advantageously in application terms, the absorbate I is conveyed with a radial centrifugal pump according to DE-A 10228859. The other, significantly smaller portion of absorbate I not used for direct cooling in the cooling zone then constitutes the outlet for the unwanted absorptives present in the absorbate I, for example benzoic acid, phthalic acid and phthalic anhydride, and maleic acid and maleic anhydride.

It is also possible in the process according to the invention to employ a combination of indirect and direct cooling in the cooling zone in order to reduce the temperature of the acrylic acid-comprising product gas mixture from the heterogeneously catalyzed gas phase partial oxidation of the at least one $C_3$ precursor compound.

The absorbent I can, in the process according to the invention, in principle be conducted either in cocurrent or in countercurrent to the product gas mixture flowing through absorption zone I (conducted through absorption zone I) in absorption zone I. This is because, in absorption zone I of the inventive procedure, one theoretical plate is normally sufficient to absorb the substances to be absorbed from the product gas mixture by absorbent I (the absorptives) into the absorbent I to the desired degree in absorption zone I.

As in DE 10347664 and in DE 1020070550086, the term "theoretical plate" means (as always in this document) that spatial unit in the corresponding zone which brings about an enrichment according to the thermodynamic equilibrium.

In the cocurrent case, the absorption zone I is typically a space free of separating internals, in which the absorbent is conducted having been sprayed to fine droplets. The configuration thereof may be like a direct cooler recommended for the cooling zone.

Advantageously in accordance with the invention, in the process according to the invention, in absorption zone I, the absorbent I is conducted in countercurrent to the product gas stream conducted through absorption zone I, and the number of theoretical plates, appropriately in application terms, is adjusted to values of ≥1 by separating internals mounted in absorption zone I.

Advantageously in economic terms, the number of theoretical plates in absorption zone I does not normally exceed five theoretical plates. It is generally in the range of ≥1 to ≤3. In addition, the absorption zone I will appropriately be operated "adiabatically", i.e. with thermal insulation from the environment.

As always in the case of thermal separation processes in which at least two material phases are conducted in countercurrent to one another, separating internals in absorption zone I pursue the purpose of increasing the available exchange area between the material phases conducted in countercurrent to one another, over which the mass and energy transfer between the material phases which causes the separating action desired is effected. Useful internals of this kind for absorption zone I are in principle all separating internals known in the prior art. These include, more particularly, mass transfer trays, structured packings and/or random packings. Among the mass transfer trays are bubble-cap trays, sieve trays (e.g. forced sieve trays or trickle sieve trays (dual-flow trays)), valve trays (for example with fixed valves or in the form of valve plate trays) and/or Thormann® trays. Possible random packings are those composed of rings, spirals, saddles, Raschig, Intos or Pall rings, Berl or Intalox saddles, Top-Pak etc., or braids. Structured packings suitable for absorption zone I are, for example, structured packings from Julius Montz GmbH in D-40705 Hilden, for example the Montz-Pak B1-350 packing, or packings from Sulzer Chemtech in CH-4123 Allschwill (formerly Kühni), for example the Rombopak 9M packing.

The absorbent I (=absorption liquid I) used in the process according to the invention is the aqueous acrylic acid solution which is obtained in the process according to the invention as condensate I in condensation zone I from the product gas mixture scrubbed in absorption zone I. This can be cooled additionally (for example by indirect heat exchange) on its route out of condensation zone I and into absorption zone I.

Appropriately in application terms, the absorbent I in the process according to the invention is supplied to absorption zone I with a temperature in the range from 40 to 70° C., preferably in the range from 45 to 65° C.

In general, the aqueous condensate I comprises acrylic acid to an extent of at least 20% by weight (of its weight). The aqueous condensate I preferably comprises acrylic acid to an extent of at least 30% or to an extent of at least 40% by weight. More preferably in accordance with the invention, the aqueous condensate I comprises acrylic acid to an extent of at least 50% by weight. Normally, the aqueous condensate I in the process according to the invention will, however, not comprise acrylic acid to an extent of more than 95% by weight, usually not to an extent of more than 90% by weight (of its weight). Very particularly advantageously, the acrylic acid content in the aqueous condensate I is 50 to 80% by weight or 50 to 70% by weight, based in each case on the weight of condensate I.

If only a small portion, if any, of condensate I is withdrawn from condensation zone I as aqueous intermediate I in the process according to the invention, this measure in the process according to the invention is typically accompanied by increased acrylic acid contents in the aqueous condensate I.

The cooling of the product gas mixture scrubbed in absorption zone I for the purpose of obtaining an aqueous acrylic acid solution as condensate I can in principle be effected either by indirect or by direct cooling. It is of course also possible to employ a combination of indirect and direct cooling for the above purpose. Indirect cooling can be performed as in the cooling zone by means of appropriate indirect heat exchangers (condensers, e.g. surface condensers), in which the gas mixture to be cooled does not come into contact with the refrigerant used as a coolant (for example, the indirect heat exchangers recommended for the cooling zone are employable).

Preferably in accordance with the invention, the product gas mixture scrubbed in absorption zone I is, however, cooled in condensation zone I by direct cooling (for example using pure acrylic acid or the aqueous solution thereof as cooling liquid).

For this purpose, advantageously in accordance with the invention, a portion of the condensate I formed in condensation zone I is withdrawn from condensation zone I. For the purpose of cooling it, it is conducted through an indirect heat exchanger and, on completion of cooling, recycled as liquid coolant into condensation zone I and directly contacted therein with the product gas mixture which has been scrubbed in absorption zone I and is to be cooled.

The difference between that temperature with which the proportion of condensate I used as cooling liquid is withdrawn from condensation zone I, and that temperature with which it is recycled into condensation zone I in cooled form after flowing through the indirect heat exchanger, will, appropriately in application terms, be 10 to 30° C., frequently 15 to 25° C.

For the purpose of direct cooling, the cooling liquid can be sprayed in condensation zone I, for example to give fine droplets, and conducted either in cocurrent or in countercurrent to the gas mixture to be cooled. In general, condensation zone I in this case will not have any internals to increase the exchange surface area between cooling liquid and gas mixture to be cooled (in a simple manner, condensation zone I in this case can be configured, for example, as an empty circular cylindrical column (or as such a column section) whose length is much greater than its cross section).

Preferably in accordance with the invention, condensation zone I will, however, be equipped with internals which are typically used as separating internals to increase separation efficacy in thermal separation processes. Useful separating internals of this kind are especially all of those which are also recommended as suitable for absorption zone I in this document. Cooling liquid (generally unsprayed) and gas mixture to be cooled are, appropriately in application terms, conducted in countercurrent to one another through the internals (preferably (as always in the process according to the invention), the cooling liquid is conveyed by means of a radial centrifugal pump according to DE-A 10228859). Since the proportion of condensate I which is used as cooling liquid in condensation zone I is conducted in a circuit via condensation zone I and through the cooling heat exchanger, the separating action which results in condensation zone I in this operating mode is naturally limited to values of ≤1 theoretical plate. Normally, therefore, in the process according to the invention, for example, not more than six mass transfer trays, usually 1 to 3 mass transfer trays (or corresponding amounts of structured packings and/or random packings) will be used as "separating" internals in condensation zone I. Useful mass transfer trays of this kind for this purpose are especially bubble-cap trays, sieve trays (e.g. forced sieve trays or trickle sieve trays (dual-flow trays)), valve trays (for example with a fixed valve or in the form of valve plate trays) and/or Thormann® trays.

The residual gas mixture I which remains in gaseous form in condensation zone I when the aqueous acrylic acid solution (condensate I, absorbent I) is obtained should, in the process according to the invention, still comprise at least 10% of the amount of acrylic acid present in the product gas mixture formed as a result of the partial oxidation (the comparison is based on the flow rate (kg/h) of the acrylic acid stream present in the product gas mixture stream and the flow rate (kg/h) of the acrylic acid stream present in the stream of residual gas mixture I). Residual gas mixture I in the process according to the invention will preferably still comprise at least 15%, or at least 20%, and more preferably at least 25%, or at least 30%, of the amount of acrylic acid present in the product gas mixture of the partial oxidation. In limiting cases of the inventive procedure, the amount of acrylic acid present in residual gas mixture I may be up to 99.8% or up to 99.5% of the amount of acrylic acid present in the product gas mixture of the partial oxidation. High acrylic acid contents in residual gas mixture I generally result in the process according to the invention when only a small amount of aqueous intermediate I, if any, is conducted out of condensation zone I.

When the aim in the process according to the invention is comparatively small amounts of acrylic acid in residual gas mixture I based on the amount of acrylic acid present in the product gas mixture of the partial oxidation, it is appropriate in accordance with the invention to additionally superimpose an absorption of acrylic acid present in the product gas mixture stream scrubbed in absorption zone I in water as an absorbent on the condensation of an aqueous acrylic acid solution brought about in accordance with the invention in condensation zone I by appropriate cooling of the product gas mixture stream scrubbed in absorption zone I. In this case, the aqueous acrylic acid solution obtained as "condensate I" in condensation zone I is a mixture of a "condensate" and an "absorbate in water". It is of course possible to superimpose the above additional absorption of acrylic acid in water on an indirect and/or direct cooling employed for the purpose of the intended condensation in condensation zone I. Preferably in accordance with the invention, a water absorbent supplied to condensation zone I will be conducted in countercurrent to the product gas mixture scrubbed in absorption zone I in condensation zone I. However, cocurrent operation is likewise possible (appropriately with water sprayed to give fine droplets). Advantageously in application terms, in the process according to the invention, an additional absorption of acrylic acid in water will be superimposed in condensation zone I when the cooling of the product gas mixture scrubbed in absorption zone I is configured as a direct cooling in condensation zone I. This is the case especially when the cooling liquid used is a portion of condensate I which has been conducted through an indirect heat exchanger and circulated via condensation zone I. Appropriately, the cooling liquid and the water absorbent in the aforementioned cases are conducted through condensation zone I in cocurrent. Advantageously in accordance with the invention, it moves in countercurrent to the stream of product gas mixture scrubbed in absorption zone I and conducted through condensation zone I.

In addition to acrylic acid and water, the aqueous condensate I normally also comprises the secondary constituents formic acid, acetic acid, propionic acid, acrolein, benzaldehyde and 2-furaldehyde in dissolved form. The residual gas mixture I which remains (in gaseous form) in condensation zone I and comprises $CO_2$ and water comprises, in addition to the at least 10% of the amount of acrylic acid still present in the product gas mixture and the at least one inert diluent gas other than $CO_2$ and water, normally also acetic acid, propionic acid, acrolein, benzaldehyde and 2-furaldehyde.

The proportion of the condensate I which is obtained in condensation zone I and is neither supplied as absorbent I to absorption zone I nor is used as cooling liquid for direct cooling in condensation zone I is conducted out of condensation zone I as aqueous intermediate I. The temperature thereof is frequently 50 to 70° C.

Since the absorption conducted in the absorption zone I in the context of the inventive procedure is essentially a physical absorption (which means that absorptives having an elevated boiling point, for example phthalic anhydride, maleic anhydride and benzoic acid, are normally absorbed preferentially), the acrylic acid content of absorbent I has an advantageous effect on the scrubbing which is the aim of the invention in absorption zone I. Increasing acrylic acid content of absorbent I is generally accompanied in the process according to the invention by increased separating action in absorption zone I in relation to the intended removal of phthalic anhydride, phthalic acid, maleic anhydride, maleic acid and benzoic acid from the acrylic acid target product.

The option of optionally conducting aqueous intermediate I out of condensation zone I in addition to the obligatory production of aqueous intermediate II in the process according to the invention constitutes a particularly advantageous feature of the inventive procedure. This is more particularly because the division of the acrylic acid stream present in the product gas mixture stream of the partial oxidation (the division of the amount of acrylic acid present in the product gas mixture of the partial oxidation) between the two streams of aqueous intermediate II and aqueous intermediate I (between aqueous intermediate II and aqueous intermediate I) can be configured in a comparatively variable manner in the process according to the invention.

This is advantageous in that later combination of aqueous intermediate I and aqueous intermediate II (before or after an inventive extraction with an organic extractant) opens up the possibility, without any significant change in the inventive procedure and with one and the same apparatus arrangement, of producing an at least partly neutralized aqueous target product solution comprising acrylic acid and the conjugate base thereof as a "ready mix" (as an aqueous mixture which can be supplied directly to the contemplated (further) use), the degree of neutralization of which can be varied within a wide range, in each case appropriately for any directly subsequent use thereof. The water content of the aqueous target product solution can thus also be adjusted appropriately for the application in a simple manner.

It will be appreciated that water and/or aqueous alkali solution (aqueous alkali metal base) can be added to aqueous intermediates I, II and III prior to the inventive extraction thereof with an organic extractant, in order to additionally adjust the water content and/or the degree of neutralization of the raffinate removed after the particular extraction.

Frequently, the molar ratio M (=TI/TII) of molar total amount TI of acrylic acid and conjugate base thereof present in aqueous intermediate I to molar total amount TII of acrylic acid and conjugate base thereof present in aqueous intermediate II (the comparison is based on the flow rates (mol/h) of the total molar flow of acrylic acid and the conjugate base thereof present in the particular aqueous intermediate stream) in the process according to the invention will be ≥0 to 6:1 or 1:6 to 6:1, or ≥0 to 5:1 or 1:5 to 5:1, advantageously ≥0 to 4:1 or 1:4 to 4:1, or ≥0 to 3:1 or 1:3 to 3:1. Ratios M particularly favorable in accordance with the invention are also the ratios 2:1 to 5:1 or 2:1 to 4:1. The ratio M may, however, optionally also be ≥0 to 2:1 or 1:2 to 2:1, or else 1:1.

If an absorption with water is superimposed on the condensation in condensation zone I in the process according to the invention, it is advantageous in accordance with the invention when, in the case of condensation by direct cooling with a cooling liquid (e.g. cooled condensate I), the temperature of the water absorbent supplied to condensation zone I and the temperature of the cooling liquid supplied to condensation zone I do not differ significantly from one another. Frequently, the water absorbent is supplied to condensation zone I with a temperature in the range from 1 to 40° C., or from 5 to 35° C., or 10 to 30° C., preferably from 15 to 25° C.

It is possible in principle, as always in this document, in the case of an application of a direct cooling and an absorption superimposed on one another in one process zone, also to supply the appropriate cooling liquid and the absorbent to the corresponding process zone as a liquid mixture combined beforehand.

The combination can be effected prior to the indirect heat exchanger in which the cooling liquid is cooled. In this case, the cooling liquid flows through the heat exchanger in a mixture with the absorbent.

Incidentally, the flow rate of a water stream (kg/h) supplied as absorbent to condensation zone I in the process according to the invention is normally less than the flow rate of the stream (kg/h) of cooling liquid (e.g. cooled condensate I) supplied simultaneously to condensation zone I for the purpose of direct cooling. In general, the flow rate of the water stream is less than 50%, frequently less than 40%, usually less than 30% or less than 20% of the flow rate of the cooling liquid stream supplied (for example of the stream of cooled condensate I). In general, the aforementioned percentage is, however, at values of ≥1%, frequently at values of ≥5%.

It will be appreciated that it is also possible to dispense with the superimposition of an absorption in water in condensation zone I in the process according to the invention.

The water content of inventive aqueous solutions comprising acrylic acid and the conjugate base thereof (aqueous target product solutions) may, based on the weight of the particular aqueous solution, for example, be 15 to 85% by weight, or 30 to 80% by weight, or 40 to 70% by weight, or preferably 50 to 65% by weight or 55 to 60% by weight. Preferably in accordance with the invention, the aforementioned water content is ≤65% by weight, more preferably ≤60% by weight.

The absorbent II used in the process according to the invention is an aqueous alkali metal base. The term "aqueous alkali metal base" in this document covers aqueous solutions which comprise at least one alkali metal salt from the group consisting of the alkali metal oxides, the alkali metal hydroxides, the alkali metal carbonates, the alkali metal hydrogencarbonates and the hydrates of the aforementioned salts in dissolved form. The term "aqueous alkali metal base" shall, in this document, additionally also include aqueous suspensions of the aforementioned alkali metal salts in which at least one of the aforementioned salts is present as a finely divided solid. Aqueous alkali metal base can be prepared, for example, in a simple manner by dissolving the at least one alkali metal salt in water, or in a mixture of water and aqueous condensate II, or only in aqueous condensate II. In other words, advantageously in accordance with the invention, the aqueous alkali metal base also comprises aqueous condensate II.

Preferably in accordance with the invention, the at least one alkali metal salt is a salt of lithium (e.g. $Li_2O$, $LiOH$, $LiHCO_3$, $Li_2CO_3$), a salt of sodium (e.g. $Na^2O$, $NaOH$, $NaHCO_3$, $Na^2CO_3$) and/or a salt of potassium (e.g. $K_2O$, $KOH$, $KHCO_3$, $K_2O_3$) and/or a hydrate of these salts. More preferably in accordance with the invention, the at least one alkali metal salt is a salt of potassium and/or a salt of sodium. Most preferably, the at least one alkali metal salt is a salt of sodium. KOH is preferred among the potassium salts, and NaOH among the sodium salts. In other words, particularly advantageously in the process according to the invention, an aqueous solution of KOH and/or an aqueous solution of NaOH is used as absorbent II ($K^+$ constitutes a plant nutrient in an advantageous manner in accordance with the invention; NaOH is particularly inexpensive).

The content of the at least one alkali metal salt in the aqueous absorbent II will be guided in the inventive procedure by factors including the target water content of the aqueous target product solution.

It may, based on the weight of the aqueous absorbent II (especially in the case of an aqueous solution of NaOH and/or KOH), for example, be ≥10% by weight, or ≥20% by weight, or ≥30% by weight, or a ≥40% by weight. In general, the aforementioned alkali metal salt content will not exceed 60% by weight (frequently 50% by weight). In the case of an aqueous solution of NaOH and/or KOH as absorbent II, the NaOH and/or KOH content thereof in the process according to the invention will frequently be 20 to 40% by weight or 20 to 30% by weight.

The at least one alkali metal salt dissolved in the aqueous alkali metal base may, in the process according to the invention, have purities of ≥99.9% by weight, or ≥99.99% by weight. However, lower purities are also usable for the process according to the invention. For example, an aqueous NaOH solution used as absorbent II can be prepared by dissolving sodium hydroxide in water comprising up to 5% by weight of NaCl, based on the weight thereof. It is also possible for the aqueous alkali metal base (optionally in addition to any NaCl present) to have small contents of iron salts, as recommended in US 2008/0119626. In addition, the aqueous alkali metal base (optionally in addition to any NaCl and/or iron salt present) may comprise small amounts of salts of polyvalent cations (for example divalent, trivalent and/or tetravalent cations), which, according to the teaching of WO 2008/009599 and of U.S. Pat. No. 5,115,011, can act as internal crosslinkers in the production of aqueous solutions of superabsorbent polymer. Useful such polyvalent cations include especially $Mn^{2+}$, $Zn^{2+}$, $Mg^{2+}$, $Ca^{2+}$, $Sr^{2+}$, $Al^{3+}$, $Fe^{3+}$, $Cr^{3+}$, $Ti^{4+}$ and $Zr^{4+}$. With regard to possible counterions and amounts for use, reference is made to WO 2008/009599.

The temperature with which an aqueous alkali metal base is supplied as absorbent II to absorption zone II in the process according to the invention may, for example, be 0 to 60° C., or 5 to 60° C., or 10 to 50° C., or 15 to 40° C., or 15 to 30° C. The range of lower temperatures is preferred in accordance with the invention. In other words, aqueous alkali metal bases are frequently supplied to absorption zone II at a temperature in the range from 0 to 45° C., or from 5 to 40° C., or from 10 to 35° C. or 15 to 30° C.

The absorbent II and the residual gas mixture I conducted out of condensation zone I and through absorption zone II can be conducted either in cocurrent or in countercurrent to one another within absorption zone II. The configuration of absorption zone II may, in the simplest case, be that of a direct cooler recommended for the cooling zone (cf. also DE-A 10220494, especially column 4).

In the case of cocurrent operation, absorption zone II will not normally have any separating internals. In addition, absorbent II (the aqueous alkali metal base), in the case of cocurrent operation of absorption zone II, will advantageously be supplied in the form of fine droplets (for example sprayed to fine droplets).

Preferably in accordance with the invention, in the process according to the invention in absorption zone II, absorbent II is conducted in countercurrent to the residual gas mixture I conducted through absorption zone II. Appropriately in application terms, absorption zone II in the case of such countercurrent operation has separating internals. Useful separating internals of this kind for absorption zone II include all of those which are listed as suitable for absorption zone I in this document. In addition, in countercurrent operation, absorbent II is typically supplied to absorption zone II as a coherent phase (not sprayed).

The pH of the aqueous alkali metal base (of absorbent II) in the process according to the invention (based on a measurement at 25° C. and 1 atm (1.01 bar) with a glass electrode configured as a combination electrode) will generally be at least 8, preferably at least 10, more preferably at least 12 and most preferably at least 14 (a solution of 50 g of sodium carbonate in one liter of water has a pH of about 11.5; the pH of a one molar aqueous sodium hydroxide solution is about 14).

Normally, the molar ratio MR (=TAI/TAII) of the molar total amount TAI of alkali metal cations present in absorbent II (in the aqueous alkali metal base) to the molar total amount TAII of acrylic acid present in the scrubbed product gas mixture (which is conducted out of absorption zone I into condensation zone I) (the comparison is based on the flow rates (mol/h) of the overall stream of alkali metal cations present in the stream of absorbent II and of the acrylic acid stream present in the stream of the scrubbed product gas mixture) in the process according to the invention will be at least 20:100, or at least 30:100, preferably at least 40:100 or at least 50:100, more preferably at least 60:100 or at least 70:100. It may also be at least 80:100, or at least 90:100, or at least 100:100. In general, MR in the process according to the invention will not be above 200:100 or not above 150:100, frequently not above 140:100 or not above 130:100, or not above 110:100. In other words, ratios MR in the range from 100 to 110:100, or in the range from 105 to 110:100, are not unusual in the process according to the invention. Preferably in accordance with the invention, the ratio MR will be 50 to 95:100, particularly advantageously 60 to 90:100, very particularly advantageously 60 to 80:100, or 60 to 85:100, or 60 to 75:100, or 65 to 75:100.

In order to essentially completely scrub the acrylic acid present in residual gas mixture I, as a function of the ratio M selected in the process according to the invention, out of residual gas mixture I in absorption zone II, it is appropriate in application terms when the molar ratio MR*(=TAI/TAII*) of the molar total amount TAI of alkali metal cations present in absorbent II (in the aqueous alkali metal base) to the molar total amount TAII* of acrylic acid present in residual gas mixture I (the comparison is based on the flow rates (mol/h) of the overall stream of alkali metal cations present in the stream of absorbent II and of the acrylic acid stream present in the stream of residual gas mixture I) in the process according to the invention is at least 50:100 or at least 60:100, preferably at least 70:100 or at least 80:100, and more preferably at least 90:100 or at least 100:100.

This is attributable, inter alia, to the fact that the formation of absorbate II in absorption zone II in the case of ratios MR* of at least 100:100 in the process according to the invention, with increasing ratio MR*, proceeds increasingly (essentially) as a chemisorption of the acrylic acid out of residual gas mixture I. Chemisorptions are generally characterized by particularly high absorption coefficients. The result of this is that, at ratios MR*≥100:100 in absorption zone II, one theoretical plate is normally sufficient to essentially quantitatively absorb the acrylic acid to be absorbed from residual gas mixture I by absorbent II in absorption zone II.

In the case of ratios MR*<100:100, the acrylic acid is absorbed from residual gas mixture I into absorbent II as a superimposition of a chemisorption (chemical absorption) and a physisorption (physical absorption), in which the weight of the latter grows with decreasing MR*.

With decreasing MR*, absorption zone II therefore, appropriately in application terms, has more than one theoretical plate. In general, the number of theoretical plates in absorption zone II is not more than five and is frequently at values of ≤3. In other words, in absorption zone II, the use of 1 to 6 and frequently 1 to 3 mass transfer trays (or a corresponding charge with structured packings or random packings) is sufficient to bring about the separating action which is the aim of the invention.

Frequently employed ratios MR* in the process according to the invention are 90:100 to 110:100. For reasons of very substantial removal of the acrylic acid from residual gas mixture I, ratios MR above 110:100 are actually not required. Especially when ratios M employed in the process according to the invention are ≥1:1, or ≥2:1, or ≥3:1, a ratio MR* of up to 110:100 for the degree of neutralization desired in the aqueous target product solution (in the aqueous intermediate III or in the mixture of aqueous raffinate I and aqueous raffinate II) may, however, no longer be sufficient. It will be appreciated that, in these cases, in the process according to the invention, it is also possible to employ ratios MR* which are ≥120:100, or ≥130:100, or ≥140:100, or ≥150:100, or ≥200:100, or ≥250:100, or ≥300:100, or ≥400:100. In general, in the process according to the invention, the ratio MR* will not exceed the ratio of 1000:100, or 800:100, or 600:100. When residual gas mixture I comprises, in addition to acrylic acid, significant molar amounts of $CO_2$, the latter ($H_2CO_3$ is a much weaker acid than acrylic acid, and so the latter is at first absorbed with distinct preference) is also absorbed into aqueous absorbate II to an increasing degree with increasing MR* and is bound in aqueous absorbate II at least partly in the form of alkali metal carbonate and/or alkali metal hydrogencarbonate. In these cases, on combination of aqueous intermediate I and aqueous intermediate II, or of aqueous raffinate I and aqueous raffinate II, there is generally marked outgassing of $CO_2$, which, advantageously in accordance with the invention, is additionally promoted. Alternatively, in absorption zone II, a smaller ratio MR* can also be employed in absorption zone II in such cases, and the amount of (aqueous) alkali metal base additionally required for the desired degree of neutralization in the aqueous target product solution can be supplied subsequently (for example directly to the aqueous intermediate II, to the aqueous intermediate I, to the aqueous intermediate III and/or to the aqueous raffinate III; or directly to the aqueous raffinate I, to the aqueous raffinate II and/or to the mixture of aqueous raffinate I and aqueous raffinate II; preference is given in accordance with the invention to an addition prior to the aldehyde extraction to be conducted in accordance with the invention, since it counteracts the transfer of acrylic acid into the extractant) later on the route of the inventive preparation of the aqueous target product solution. The latter procedure is advantageous in that it is not normally associated with any obligatory $CO_2$ outgassing. The former procedure (use of increased ratios MR*) can be configured in a simpler manner in terms of measurement and control technology.

Frequently, in the process according to the invention, increased ratios M are accompanied by increased ratios MR*.

In the above context, the ratio $R_{AC}$ of molar amount of acrylic acid present in the product gas mixture of the partial oxidation to molar amount of $CO_2$ present in the same product gas mixture is advantageously not less than 2 and preferably not less than 3.

Generally, it is favorable in the given context for the process according to the invention when the product gas mixture of the partial oxidation, based on the total volume thereof, comprises not more than 20% by volume, or not more than 15% by volume, or not more than 10% by volume, preferably not more than 7% by volume and more preferably not more than 5% by volume or not more than 4% by volume of $CO_2$. In general, the product gas mixture of the partial oxidation, based on the total volume thereof, will, however, comprise at least 0.05% by volume, frequently at least 0.1% by volume and in many cases at least 0.2% by volume or at least 0.3% by volume of $CO_2$.

Advantageously in application terms, the product gas mixture of the partial oxidation, based on the total volume thereof, will comprise not more than 50% by volume, preferably not more than 40% by volume and more preferably not more than 25% by volume of $H_2O$. In general, the water vapor content of the aforementioned product gas mixture will, however, be at least 1% by volume or at least 3% by volume or at least 5% by volume.

The acrylic acid content of the product gas mixture from the partial oxidation zone is, based on the total volume thereof, appropriately in accordance with the invention at least 0.5% by volume, frequently at least 2% by volume or at least 3% by volume. It is typically not more than 20% or not more than 15% by volume, and in many cases not more than 10% by volume.

Since the chemisorption in absorption zone II of the process according to the invention proceeds exothermically, it is appropriate in accordance with the invention to superimpose a direct and/or indirect cooling of the residual gas mixture I conducted through absorption zone II on the absorption in absorption zone II. Advantageously in accordance with the invention, such a cooling is performed as a direct cooling, and the cooling liquid used is particularly advantageously a portion of absorbate II.

For this purpose, appropriately in application terms, an appropriate substream of absorbate II is conducted out of absorption zone II and, for the purpose of cooling it, through an indirect heat exchanger (cf. WO 2010/003884) and, on completion of cooling, recycled into absorption zone II as liquid coolant and contacted directly therein with the stream of residual gas mixture I. In this way, the substream of absorbate II used as cooling liquid is circulated through the indirect heat exchanger and absorption zone II (appropriately in application terms, the substream of absorbate II is conveyed with a radial centrifugal pump according to DE-A 10228859). The difference between that temperature with which the substream of absorbate II is withdrawn from absorption zone II, and that temperature with which it is recycled into absorption zone II in cooled form after passing through the indirect heat exchanger, will, appropriately in application terms, be 5 to 30° C., frequently 5 to 15° C. The absorbent II and a portion of absorbate II circulated as cooling liquid through an indirect heat exchanger and absorption zone II are sensibly conducted through absorption zone II in cocurrent (preferably in countercurrent to residual gas mixture I). In principle, the two can also be combined to a mixture prior to the entry thereof into absorption zone II. In principle, this mixture formation can be undertaken before the substream of absorbate II withdrawn from absorption zone II, which constitutes the cooling liquid, enters the indirect heat exchanger for the purpose of cooling thereof, such that the entire mixture is conducted through the heat exchanger. In this case, "absorbent II" and "cooling liquid" are supplied to absorption zone II with the same temperature. It will be appreciated that absorbent II and the cooling liquid can also be conducted into absorption zone II with different temperatures. Appropriately in application terms, such a temperature difference is relatively small (generally not greater than 25° C.; the temperature of the cooling liquid is normally the lower). The flow rate of the stream of absorbate II (kg/h) conducted through an indirect heat exchanger as cooling liquid may, in the process according to the invention, be several times the flow rate of the stream of absorbent II (kg/h) supplied to absorption zone II. Typically, the value will, however, not be more than five times more. In principle, in the process according to the invention, absorption zone II will advantageously be operated in such a way that the residual gas mixture II conducted out of absorption zone II comprises not more than 5%, preferably not more than 3% and more preferably not more than 1% of the amount of acrylic acid present in the product gas mixture formed as a result of the partial oxidation (the comparison is based on the flow rate (kg/h) of the acrylic acid stream present in the product gas mixture and the flow rate (kg/h) of the acrylic acid stream present in the stream of residual gas mixture II). Residual gas mixture II will, however, in addition to the at least one inert diluent gas other than $CO_2$ and water and a residual amount of acrylic acid, especially also comprise water.

In addition to acrylic acid, in absorption zone II, especially the carboxylic acids of chemical similarity to acrylic acid, viz. formic acid, acetic acid and propionic acid, are absorbed from residual gas mixture I into absorbate II. It will be appreciated that the absorbate II will normally also comprise the secondary constituents acrolein, benzaldehyde and 2-furaldehyde. The $CO_2$ which is normally at least partly scrubbed out of residual gas mixture I in absorption zone II is present in aqueous absorbate II at least partly dissolved in the form of alkali metal carbonate and/or hydrogencarbonate.

The proportion of absorbate II which is obtained in absorption zone II and is not used as cooling liquid for the purpose of superimposition of direct cooling in absorption zone II is conducted out of absorption zone II as aqueous intermediate II. The temperature thereof is frequently 40 to 60° C.

Cooling liquids used for the purpose of direct cooling in this document are cooled in indirect heat exchangers in the process according to the invention generally using air or water (in the case of cooling temperatures down to 50° C.), river water (in the case of cooling temperatures down to 30° C.) and cooling brines (in the case of cooling temperatures <30° C.).

The residual gas mixture II conducted out of absorption zone II comprises, as already stated, in addition to a remaining residual amount of acrylic acid and the at least one inert diluent gas other than $CO_2$ and water, especially water. Residual gas mixture II also normally comprises the predominant amount of the acrolein present in the product gas mixture formed in the partial oxidation zone and constitutes, in the process according to the invention, a main outlet for acrolein (based on the acrolein flow rates in kg/h present in each case, (the stream of) residual gas mixture II comprises typically ≥60%, preferably ≥70% or ≥80%, and more preferably ≥90%, of the acrolein (stream) present in the product gas mixture (stream)).

When the aqueous alkali metal base used as absorbent comprises at least one alkali metal hydrogencarbonate and/or alkali metal carbonate in dissolved form, for example, appropriate chemical reaction with the acrylic acid absorptive within absorption zone II can result in the evolution of $CO_2$ which is conducted out of absorption zone II as constituent of residual gas mixture II. The associated withdrawal of heat from the liquid phase brings about advantageous cooling thereof. Otherwise, residual gas mixture II will still comprise $CO_2$, especially when a ratio MR*≤100:100 is employed in absorption zone II.

Especially when the acrylic acid content of residual gas mixture II is comparatively low, a portion of residual gas mixture II can be circulated as cycle gas (i.e. recycled into the partial oxidation zone), and used as a particularly economically viable source of inert diluent gas for production of the reaction gas input mixture comprising the at least one $C_3$ precursor compound of acrylic acid and molecular oxygen, which is then supplied to the heterogeneously catalyzed gas phase partial oxidation of the $C_3$ precursor compound to acrylic acid (which is then used for the heterogeneously catalyzed partial gas phase oxidation of the $C_3$ precursor compound present in the reaction gas input mixture to acrylic acid over catalysts in the solid state in the partial oxidation zone).

The basic principle of such a cycle gas method is known from the prior art processes (cf., for example, DE-A 102007055086, WO 2004/085362, WO 2004/007450, DE-A 10360396, DE-A 10336386, DE-A 10353014, DE-A 102010001228 and the prior art cited in these documents).

The noncirculated portion of residual gas mixture II is normally sent to incineration (cf. WO 2006/08224 and DE-A 19624674).

Appropriately in application terms, the residual gas mixture II conducted out of absorption zone II will, however, be conducted through a condensation zone II and, on the route of residual gas mixture II through condensation zone II, an aqueous condensate II will be condensed out by direct and/or indirect cooling thereof, leaving a residual gas mixture III which consists, inter alia, of the at least one inert diluent gas other than $CO_2$ and water and is substantially free of acrylic acid. The formation of the aqueous condensate II is, advantageously in application terms, conducted in such a way that the residual gas mixture III which then remains comprises the predominant amount of the acrolein present in the partial oxidation zone and functions as a main outlet thereof (based on the acrolein flow rates present in each case in kg/h, residual gas mixture III then comprises typically ≥60%, preferably ≥70% or ≥80%, and more preferably ≥90%, of the acrolein present in the product gas mixture).

With the residual gas mixture III conducted out of condensation zone II, the subsequent procedure may be as recommended above for residual gas mixture II which has not already been conducted through a condensation zone II. In other words, a portion of residual gas mixture III can be circulated as cycle gas and be reused as a source of inert diluent gas for production of the reaction gas input mixture comprising the at least one $C_3$ precursor compound of acrylic acid and molecular oxygen, which is then supplied to the heterogeneously catalyzed gas phase partial oxidation of the $C_3$ precursor compound to acrylic acid. The uncirculated proportion of residual gas mixture III can again be sent to incineration. It will be appreciated that the entire residual gas mixture III can also be sent to incineration.

The at least one inert diluent gas other than $CO_2$ and water, of which residual gas mixture III normally essentially consists, is generally at least one gas from the group consisting of $N_2$, CO, noble gases, for example He, Ne and Ar, and methane, ethane and propane. The at least one inert diluent gas other than $CO_2$ and water is firstly helpful in absorbing the heat of reaction released in the partial oxidation of the $C_3$ precursor compound of acrylic acid and secondly generally ensures, at the same time, safe operation of the heterogeneously catalyzed gas phase partial oxidation of the $C_3$ precursor, by either keeping the reaction gas mixture in the partial oxidation zone outside the explosion range or within a region of the explosive range which can still be controlled safely (cf., for example, DE-A 19740253, DE-A 19740252, DE-A 10232482, DE-A 10243625, DE-A 10332758 and WO 2004/035514).

Typically, the at least one inert diluent gas other than $CO_2$ and water is converted to acrylic acid to an extent of less than 95 mol %, preferably to an extent of less than 97 mol % and more preferably to an extent of less than 99 mol % in the heterogeneously catalyzed partial gas phase oxidation of the $C_3$ precursor compound (in the case of an inert diluent gas mixture, based on each mixture constituent alone and on a single pass of the reaction gas mixture through the partial oxidation zone).

Typically, the at least one inert diluent gas other than $CO_2$ and water has a boiling point at standard pressure (1.01 bar) of $\leq 0°$ C., preferably a boiling point of $\leq -10°$ C. and more preferably a boiling point of $\leq -20°$ C.

In general, the proportion of the at least one inert diluent gas other than $CO_2$ and water in the product gas mixture of the heterogeneously catalyzed gas phase partial oxidation of the at least one $C_3$ precursor compound is 30 to 90% by volume, or 40 to 90% by volume, preferably 50 to 85% by volume, or 60 to 85% by volume, and more preferably 70 to 85% by volume or 75 to 85% by volume.

Correspondingly, the proportion of the at least one inert diluent gas other than $CO_2$ and water in the reaction gas input mixture comprising the at least one $C_3$ precursor compound for the heterogeneously catalyzed gas phase partial oxidation of the at least one $C_3$ precursor compound to acrylic acid may be 30 to 90% by volume, or 40 to 90% by volume, preferably 50 to 85% by volume, or 60 to 85% by volume, and more preferably 70 to 85% by volume or 75 to 85% by volume.

A preferred inert diluent gas other than $CO_2$ and water in the process according to the invention is molecular nitrogen.

In general, the at least one inert diluent gas other than $CO_2$ and water (both in the product gas mixture of the heterogeneously catalyzed gas phase partial oxidation of the at least one $C_3$ precursor compound and in the reaction gas input mixture which comprises the at least one $C_3$ precursor compound and is used for the gas phase partial oxidation) therefore consists to an extent of at least 40% by volume, preferably to an extent of at least 50% by volume, or to an extent of at least 60% by volume, more preferably to an extent of at least 70% by volume, or to an extent of at least 80% by volume, and most preferably to an extent of at least 90% by volume or to an extent of at least 95% by volume of molecular nitrogen (based in each case on the total volume thereof).

The at least one inert diluent gas other than $CO_2$ and water (both in the product gas mixture and in the reaction gas input mixture) may also consist, for example, of propane to an extent of up to 50% by volume or more. This is the case, for example, when the at least one $C_3$ precursor compound is propene which has been obtained by a partial heterogeneously catalyzed dehydrogenation of propane (cf., for example, DE-A 102005009891).

The above-described boiling characteristics of the at least one inert diluent gas other than $CO_2$ and water are advantageous in accordance with the invention in that the at least one inert diluent gas other than $CO_2$ and water remains essentially in gaseous form on its route through the different absorption and condensation zones of the process according to the invention, and in this way brings about a reduction in the partial acrylic acid pressure in the particular gas phase in the particular absorption or condensation zone of the process according to the invention (when the reaction gas input mixture for the partial oxidation already comprises $CO_2$ as a constituent, it acts in a corresponding manner (apart from the fact, for example, that $CO_2$ can be absorbed in absorption zone II into the aqueous alkali metal base used as absorbent II)). The same applies to $CO_2$ formed as a by-product in the course of partial oxidation, and to $O_2$ which has not been converted in the partial oxidation and remains in the product gas mixture.

This is advantageous in that it opens up the possibility, in the process according to the invention, of configuring the particular process conditions in the different absorption and condensation zones to be variable within a comparatively wide range in each case without bringing about unwanted ("premature") condensation of the acrylic acid. For example, the working pressure (the absolute pressure) in the different absorption and condensation zones of the process according to the invention may be 0.5 to 5 bar. It will frequently be 1.05 to 4 bar, or 1.1 to 3 bar or 1.5 to 3 bar.

The aforementioned pressure ranges are, in accordance with the statements made so far, also possible pressure ranges for the partial oxidation zone.

It will be appreciated that $CO_2$ and/or water already present in the reaction gas input mixture for the partial oxidation zone, with regard to the partial oxidation, acts essentially in the same way as the different possible inert diluent gases other than these. Preferably in accordance with the invention, the reaction gas input mixture (based on the total volume thereof) for the partial oxidation comprises not more than 20% by volume, or not more than 15% by volume, or not more than 10% by volume, preferably not more than 7% by volume and more preferably not more than 5% by volume or not more than 4% by volume of $CO_2$.

Otherwise, a condensation zone II in the process according to the invention can in principle be configured like condensation zone I.

In other words, the residual gas mixture II conducted out of absorption zone II into a condensation zone II, for the purpose of condensation of water present in residual gas mixture II in condensation zone II, can in principle be cooled either by indirect or by direct cooling. It will be appreciated that indirect and direct cooling can also be employed in combination in condensation zone II for the aforementioned purpose.

Indirect cooling can be performed by means of appropriate indirect heat exchangers (condensers, e.g. surface condensers) in which the residual gas mixture II to be cooled does not come into contact with the fluid refrigerant conducted through the heat exchanger as a coolant. Preferably in accordance with the invention, residual gas mixture II is cooled in condensation zone II, however, by direct cooling (in other words, the configuration of condensation zone II may in the simplest case be designed like the direct cooler recommended for the cooling zone). For this purpose, advantageously in accordance with the invention, a portion of condensate II is withdrawn from aqueous condensate II formed in condensation zone II. For the purpose of cooling it, this is conducted through at least one indirect heat exchanger (it is appropriately conveyed with a pump; as always in this document, advantageously in accordance with the invention, a radial centrifugal pump according to DE-A 10228859 is used for this purpose) and, after cooling therein, recycled as liquid coolant into condensation zone II and contacted directly therein with the residual gas mixture II to be cooled. As a coolant for the portion of condensate II withdrawn from the condensation zone II, in addition to cooling water, the $C_3$ precursor compound (e.g. propene or propane), for example, can be conducted through at least one of the indirect heat exchangers. This evaporates in the process and can subsequently be used for configuration of the reaction gas mixture for the gas phase partial oxidation.

The difference between that temperature with which the proportion of condensate II used as cooling liquid is withdrawn from condensation zone II, and that temperature with which it is recycled into condensation zone II in cooled form after flowing through the indirect heat exchanger, will, appropriately in application terms, be 5 to 30° C., frequently 5 to 15° C.

For the purpose of direct cooling, the cooling liquid in condensation zone II, for example having been sprayed to fine droplets, can be conducted either in cocurrent or in countercurrent to the residual gas mixture II to be cooled. In general, condensation zone II in this case will not have any internals to additionally increase the exchange area between cooling liquid and residual gas mixture II to be cooled (in a simple manner, condensation zone II in this case can be configured, for example, as an empty circular cylindrical column (or as such a column section) whose length is much greater than its cross section). Corresponding configurations are possible for condensation zone I.

Preferably in accordance with the invention, condensation zone II will, however, be equipped with internals which are typically used as separating internals to increase the separation efficacy in thermal separation processes. Useful separating internals of this kind are especially all of those which are recommended as suitable in this document for absorption zone I. Cooling liquid (preferably in unsprayed form) and residual gas mixture II to be cooled are, appropriately in application terms, conducted in countercurrent to one another through condensation zone II and the internals present therein. Since the proportion of condensate II used as cooling liquid in condensation zone II is circulated through condensation zone II and through the cooling heat exchanger, the separating action which results in condensation zone II in this mode of operation is naturally restricted to values of ≤1 theoretical plate. Frequently, the temperature of the cooling liquid (of the corresponding proportion of condensate II) of condensation zone II will be supplied from the indirect heat exchanger with a temperature of 20 to 40° C.

Normally, for the aforementioned reasons, in the process according to the invention, for example, not more than one to three mass transfer trays (or the corresponding amounts of structured packings and/or random packings) will be used as "separating" internals in condensation zone II. Useful mass transfer trays of this kind for this purpose are especially bubble-cap trays, sieve trays (e.g. forced sieve trays or trickle sieve trays (dual-flow trays)), valve trays (for example with a fixed valve or in the form of valve plate trays) and/or Thormann® trays.

The proportion of the aqueous solution obtained as condensate II in condensation zone II which is not used as cooling liquid for reasons of direct cooling in condensation zone II is conducted out of condensation zone II. Appropriately in accordance with the invention, it will be used to obtain the aqueous alkali metal base used as absorbent II and/or supplied to absorption zone II in addition to absorbent II. In principle, the condensate II conducted out of condensation zone II (it frequently has a temperature in the range from 30 to 50° C.) could also, for example, be disposed of or used in some other way.

The residual gas mixture III remaining in gaseous form in the condensation in condensation zone II will, in the process according to the invention, frequently be conducted out of condensation zone II with a temperature in the range from 30 to 50° C.

In the process according to the invention, the product gas mixture can be conveyed out of the partial oxidation zone and through absorption zone I, condensation zone I, absorption zone II, optionally a condensation zone II and optionally a cooling zone with the aid of a compressor system which brings at least a portion of the constituents of the reaction gas input mixture comprising the at least one $C_3$ precursor compound (for example the air used as the source for molecular oxygen) from a low starting pressure to an elevated final pressure (cf., for example, DE-A 10353014).

In general, the compressor system will comprise at least one radial compressor as recommended in DE-A 10353014. The elevated pressure level of the reaction gas input mixture comprising the at least one $C_3$ precursor compound subsequently bears (brings about) both the conveying of the reaction gas input mixture through the partial oxidation zone and the subsequent conveying of the resulting product gas mixture through the different cooling, absorption and condensation zones of the process according to the invention.

Due to the pressure drop associated with the conveying, both a residual gas mixture II and a residual gas mixture III in the inventive procedure are normally at a lower pressure level than the reaction gas input mixture comprising the at least one $C_3$ precursor compound for the heterogeneously catalyzed partial gas phase oxidation.

Cycle gas conduction of residual gas mixture II or residual gas mixture III is therefore, appropriately in application terms, performed with the aid of at least one compressor (cf. DE-A 10353014) from the aforementioned compressor system (for example a radial compressor or a radial fan), which sucks in the appropriate residual gas mixture and recompresses it to the pressure level required for the partial oxidation zone. This compressor may be an independent cycle gas compressor. It will be appreciated that the aforementioned compression task can also be assumed additionally by another air compressor used.

On the route to the cycle gas compression, the corresponding residual gas mixture, preferably in application terms, may pass through another indirect heat exchanger in which the temperature of the residual gas mixture is increased by, for example, 5 or 10 to 20° C., in order to counteract any possible condensation of residual gas mixture constituents in the course of transport to the compressor or in the course of compression.

The above-described conveying with the aid of a compressor system will be employed especially when the partial oxidation zone has been charged with a fixed catalyst bed consisting of a bed of shaped bodies, through which the reaction gas input mixture must flow, and the different absorption and condensation zones have separating internals through which the product gas mixture and the constituents thereof must flow, since the pressure drops which are established along the flow path in this case are comparatively high.

Under circumstances including those when the partial oxidation zone is configured, for example, in the form of shell and tube reactors, the reaction tubes of which are not filled with a fixed catalyst bed which consists of a bed of shaped bodies and which has a comparatively high flow resistance, but which instead have reaction tubes whose reaction tube inner wall is coated with the catalytic active composition and whose reaction tube interior is otherwise empty (as recommended, for example, by DE-A 19839782), the relevant conveying can also be configured in some other way, since the flow resistance of such reaction tubes is comparatively low.

For example, the cooling, absorption and condensation zones of the process according to the invention, in the case of such a comparatively low flow resistance of the partial oxidation zone, advantageously in application terms, can be configured as jet pumps (ejectors) (cf., for example, FIG. 7 of DE-A 102006045088).

The basic principle of a jet pump is that a liquid motive jet leaving a nozzle with high velocity sucks in, entrains and compressively conveys gas from its environment. The cooling liquid and/or absorption liquid to be used in the particular zone is thus appropriately in each case used as such a motive jet of a jet pump, which then sucks in and compressively conveys the reaction gas input mixture to be conveyed or the product gas mixture to be conveyed. In this case, residual gas mixture II or residual gas mixture III normally has a higher working pressure than the reaction gas input mixture comprising the at least one $C_3$ precursor compound, in which case it therefore does not require any additional compressor for the circulation thereof. The pumps which convey the respective cooling liquid and/or absorption liquid in this case assume the task of the compressor system which is typically used and introduce the energy required for conveying of the gas mixtures. Any further compressor system is dispensable in this case.

A cooling zone may be configured in the process according to the invention appropriately like the direct coolers (quench systems) disclosed in documents DE-A 102007055086, DE-A 102010001228, DE-A 10243625, WO 2004/035514, WO 2005/007609 and DE-A 10336386 for direct cooling of a partial oxidation product gas mixture, as a separate apparatus.

Absorption zone I, condensation zone I, absorption zone II and a condensation zone II optionally employed in addition can be configured in the process according to the invention in a particularly simple manner as separation sections (spatial regions, column sections) present in one and the same separating column and arranged one on top of another in the aforementioned sequence, the product gas mixture, optionally cooled beforehand, being supplied to the separating column into the bottom space thereof which concludes it at the bottom, and flowing through the separating column from the bottom upward. Advantageously in application terms, the bottom space has a narrowed cross section as compared with the column sections which adjoin it in the upward direction, as recommended in EP-A 1095685. The cooling required in the column section corresponding to a condensation zone is advantageously configured as direct cooling.

The cooling liquid circulated through a cooling heat exchanger and through the appropriate column section is preferably condensate formed in the particular section (this applies correspondingly when (preferably) direct cooling is superimposed in absorption zone II; the liquid circulated through an indirect heat exchanger is then absorbate II).

In the particular column section which forms (constitutes) an absorption or condensation zone, the absorption and/or cooling liquid used is appropriately conducted in countercurrent to the ascending gas mixture.

The particular column sections have, as separating/internal surface area-increasing internals, preferably mass transfer trays (normally not more than six in each case). Bubble-cap trays, sieve trays (e.g. dual-flow trays), valve trays (for example with a fixed valve or in the form of valve plate trays) and/or Thormann® trays are particularly suitable as such. Structured packings or random packings can also be employed.

The bottom space is the space below the lowermost separating/internal surface area-increasing internal of the column section which forms absorption zone I. Absorbate I accumulates therein and is conducted out therefrom.

Direct cooling of the product gas mixture from the partial oxidation in a direct cooler connected upstream of the separating column is advantageously effected with absorbate I withdrawn from the bottom space as cooling liquid. The resulting mixture of product gas mixture and cooling liquid is advantageously fed into the bottom space of the separating column above the liquid level of absorbate I.

The column section which constitutes an absorption or condensation zone is, appropriately in application terms, delimited from the column section which adjoins it in the upward direction by means of (at least) one chimney tray. The principle of the chimney tray is known in the prior art. Chimney trays suitable in accordance with the invention are described, for example, in documents DE-A 10159825, DE-A 102010001228, DE-A 10200705508 and DE-A 102005009469.

The particular chimney tray functions simultaneously as a collecting tray for liquid which accumulates thereon, for example accumulating absorbate or condensate.

A chimney tray present between absorption zone I and condensation zone I, and one present between absorption zone II and any condensation zone II employed, may, in addition to its indispensable perviosity for gas flowing from the bottom upward in the separating column, also have limited perviosity to liquid accumulating thereon (for example condensate I or condensate II) into the absorption zone I or absorption zone II adjoining in the downward direction in each case.

It will be appreciated, however, that it is also possible for condensate accumulating on such a chimney tray (e.g. condensate I) first to be conducted out of the separating column from this chimney tray and subsequently to be fed back to the appropriate absorption zone (conducted back into the appropriate column section) (for example as absorbent I into absorption zone I (into absorption section I)). In other words, it is also possible in principle for the aforementioned chimney trays to be completely impervious to liquid which accumulates thereon (e.g. condensate).

A chimney tray present between condensation zone I (condensation section I) and absorption zone II (the absorption section) will, in the process according to the invention, appropriately in application terms, be configured so as to be impervious to absorbate II which accumulates thereon.

At the top of the separating column, advantageously in accordance with the invention, is mounted a droplet separator (demister), as, for example, employed in a similar manner and known from documents DE-A 102010001228 and EP-A 316682. The demister counteracts droplet entrainment by residual gas mixture II or residual gas mixture III.

Each individual section which represents an absorption or condensation zone in a separating column as just described can of course quite generally, and in an entirely equivalent manner to the purpose of performance of an inventive procedure, also be configured as an independent, smaller separating column. One (each) arrangement of absorption/condensation zones "one on top of another" in the separation column just described can accordingly also be configured as an arrangement "in succession" in a series connection of correspondingly smaller separating columns.

If an aqueous intermediate I is not conducted out of condensation zone I in the course of execution of a process according to the invention, the process produces exclusively aqueous intermediate II which, in addition to acrylic acid partly neutralized with aqueous alkali metal base, normally comprises, as unwanted secondary constituents, also acrolein (normally only in comparatively small residual amounts), benzaldehyde and 2-furaldehyde. The content of these secondary constituents (especially of the latter two) in the aqueous intermediate II is generally too high for a free-radical polymerization from the aqueous intermediate II which is the aim in the given context of the invention.

By extraction with an organic extractant (this is an organic solvent which has a miscibility gap with water (or with the aqueous intermediate to be extracted) under the extraction conditions, such that a phase separation can develop between organic extract and aqueous raffinate in the course of extraction), it is possible to absorb acrolein, benzaldehyde and 2-furaldehyde present in excessively high amounts in aqueous intermediate II (as extraction material II) comparatively selectively into the organic extractant.

The remaining aqueous phase comprises acrolein, benzaldehyde and 2-furaldehyde only to a comparatively selectively depleted extent and is referred to as (aqueous) raffinate II. It is not miscible homogeneously under the extraction conditions with the solution of acrolein, benzaldehyde and 2-furaldehyde in the organic extractant formed as organic extract II. Separation of the aqueous raffinate II from the organic extract II affords an aqueous target product solution comprising acrylic acid and the conjugate base thereof, from which it is possible to perform the free-radical polymerization which is the aim in the context of the invention.

It will be appreciated that water and/or aqueous alkali metal base can also be added to the aqueous intermediate II prior to extraction thereof with the organic extractant, in order to additionally influence the water content and/or pH of the aqueous raffinate II which forms in the extraction. Appropriately in accordance with the invention, the additional amounts will be such that they are appropriate to the contemplated further use of the aqueous raffinate II formed in the extraction.

One basis for the success of an extraction to be performed as described is that both the affinity of acrylic acid and that of alkali metal acrylate for water are much more marked than their affinity for an organic solvent, while the relevant organic aldehydes, conversely, prefer the organic solvent as an environment.

If it is foreseeable in the individual case on the basis of the boundary conditions under which the process according to the invention is performed in each case that the aqueous raffinate II obtained cannot be fed directly to the further use thereof, the aqueous raffinate II can be stored intermediately in a storage tank. High degrees of neutralization of raffinate II are found to be advantageous, since they counteract both unwanted Michael addition and unwanted free-radical polymerization. Examples of useful storage tanks and storage conditions include those as disclosed in WO 2005/049453, WO 2008/034778 and WO 2008/034783.

Instead of storing the aqueous raffinate II, it is alternatively also possible to store the aqueous intermediate II in a corresponding manner. In this case, it will only be sent to extraction thereof with an organic extractant when there is a need for aqueous raffinate II for an appropriate subsequent use.

If the execution of a process according to the invention involves not only withdrawal of aqueous intermediate II from absorption zone II but additionally also conduction of aqueous intermediate I out of condensation zone I (as is advantageous in many cases), two fundamentally different process variants are available for a removal of the organic aldehydes acrolein (only in comparatively low residual amounts), benzaldehyde and 2-furaldehyde normally present in excessively high amounts for the inventive purposes in the two aqueous intermediates.

In one procedure, aqueous intermediate II and aqueous intermediate I are first combined (merged, mixed) to give an aqueous intermediate III.

It is of course possible, before, during and/or after combination to give aqueous intermediate III, to add water and/or aqueous alkali metal base to the aqueous intermediates I, II, III involved in the combination (i.e. prior to the extraction of aqueous intermediate III), in order to additionally influence the water content and/or pH (degree of neutralization) of the aqueous raffinate III which forms in the extraction. These additional amounts will, appropriately in accordance with the invention, be such that they are appropriate to the contemplated further use of the aqueous raffinate III formed in the extraction (the addition thereof may also be exclusively or additionally to raffinate III).

The further procedure with the aqueous intermediate III finally obtained may subsequently be as described for a sole aqueous intermediate II. In other words (either immediately after production thereof or after appropriate intermediate storage of aqueous intermediate III), it is possible by extraction with an organic extractant to comparatively selectively absorb acrolein (only in comparatively small residual amounts), benzaldehyde and 2-furaldehyde present in excessively high amounts in aqueous intermediate III (as extraction material III) into the organic extractant.

The remaining aqueous phase comprises acrolein, benzaldehyde and 2-furaldehyde only to a comparatively selectively depleted degree and is referred to as (aqueous) raffinate III. It is not miscible homogeneously under the extraction conditions with the solution of acrolein, benzaldehyde and 2-furaldehyde in the organic extractant formed as organic extract III. Separation of aqueous raffinate III from the organic extract III affords an aqueous target product solution comprising acrylic acid and the conjugate base thereof, from which the free-radical polymerization which is the aim in the context of the invention can be performed. The above-described procedure will generally be employed when there is an immediate need for aqueous raffinate III for an appropriate further use (it will be appreciated that it is also possible to intermediately store aqueous raffinate III after preparation thereof until the time of such a further use).

Alternatively to the procedure described, it is also possible to proceed as follows. If aqueous intermediate I is conducted out of condensation zone I, the secondary constituents acrolein, benzaldehyde and 2-furaldehyde present in aqueous intermediate II (either immediately after production thereof or after appropriate intermediate storage of aqueous intermediate II) are absorbed therefrom by extraction with an organic extractant and the remaining aqueous raffinate II is removed from the organic extract II formed, and the secondary constituents acrolein, benzaldehyde and 2-furaldehyde present in the aqueous intermediate I (either immediately after production thereof or after appropriate intermediate storage (spatially separately from a corresponding intermediate storage of aqueous intermediate II) of aqueous intermediate I) are absorbed therefrom by extraction with an organic extractant, and the remaining aqueous raffinate I is removed from the organic extract I formed, and aqueous raffinate II and aqueous raffinate I (optionally after preceding spatially separate intermediate storage of the two aqueous raffinates I, II) are combined (merged, mixed) to give the aqueous target product solution comprising the acrylic acid and the conjugate base thereof. It is of course also possible to add water and/or aqueous alkali metal base before, during and/or after the combination of the two aqueous raffinates I, II (such an addition can also be made exclusively and/or additionally to one or both aqueous intermediates prior to the extraction). The described procedure of a separate extraction of aqueous intermediate I and aqueous intermediate II is advisable especially when there is no immediate need for aqueous target product solution for an appropriate further use. In this case, it is appropriate in application terms to intermediately store aqueous intermediate I and aqueous intermediate II in spatial separation, and subsequently to subject the two aqueous intermediates I and II, also in spatial separation, to an inventive extraction with an organic extractant.

In an alternative configuration of the inventive procedure, it is also possible to proceed in such a way that only the aqueous intermediate II is subjected to an inventive extraction to remove organic aldehydes present therein. The aqueous intermediate I conducted out of condensation zone I is, in contrast, subjected to a crystallizative removal of acrylic acid present therein (this procedure is advisable especially when the aqueous intermediate I has had to be stored intermediately). For the purpose of such a crystallizative removal, it is possible in principle to employ all known crystallization processes (for example those mentioned in DE-A 19838845 and in DE-A 102005015637) (cf., for example, EP-A 616998, WO 2006/092415 and WO 2006/092405). These include, in addition to the layer crystallization processes (dynamic (e.g. falling-film crystallization or in cooled flow tube) and/or static), especially the process of suspension crystallization. The latter is preferred in accordance with the invention.

Acrylic acid suspension crystals formed and mother liquor remaining can be separated from one another, for example, by centrifugation. By subsequently washing the crystal cake remaining in the centrifugation with acrylic acid melt removed beforehand, the separation between mother liquor and crystals can be improved. Preferably in accordance with the invention, the separation between remaining mother liquor and acrylic acid suspension crystals formed is performed with the aid of a wash column (preferably with a dynamic wash column and more preferably with a hydraulic wash column), as recommended, for example, in documents WO 01/77056, WO 03/078378 and WO 02/055469. Otherwise, it is also possible in this context to make use of the teachings of WO 0209839, DE-A 10036881, WO 2004/035514, DE-A 10122787, DE-A 10122788, DE-A 10223058, DE-A 102007055086, DE-A 102005018702, DE-A 10242746, DE-A 102008040340, DE-A 102008042009, DE-A 102008042010, DE-A 102009000987 and DE-A 102010030279. The mother liquor removed can subsequently be recycled into one or more of the different separation zones of the inventive procedure (for example into absorption zone I, into condensation zone I, into any condensation zone II used, into any cooling zone used and/or into absorption zone II). Preferably in accordance with the invention, the mother liquor remaining is recycled into absorption zone I and supplied, for example, to the aqueous absorbent I as a constituent thereof. The glacial acrylic acid crystals removed can subsequently be combined with the aqueous raffinate II obtained from the aqueous intermediate II to give an inventive aqueous target product solution.

Instead of a crystallizative removal of acrylic acid from aqueous intermediate solution I, it is also possible to employ a rectificative removal in which the aldehydes present are bound to what are called aldehyde scavengers prior to the rectification, as recommended, for example, in DE-A 10138101 and in DE-A 10220494 (in column 15).

Any intermediate storage of aqueous intermediate I, aqueous intermediate II, aqueous raffinate I, aqueous raffinate II, aqueous raffinate III and/or aqueous target product solution will be undertaken in the process according to the invention, in principle, at minimum temperatures, but preferably above the particular melting point (the intermediate storage will preferably be undertaken under lean air).

Normally, the product gas mixture obtained in the process according to the invention in the partial oxidation zone as a result of the heterogeneously catalyzed partial gas phase oxidation of the at least one $C_3$ precursor compound performed therein comprises $CO_2$ (carbon dioxide) formed as a by-product. This is because there is generally also a small degree of full combustion of intermediates, by-products and/or the at least one $C_3$ precursor compound in the partial oxidation zone.

In addition, $CO_2$ may also already have been supplied as a diluting inert gas to the reaction gas input mixture comprising the at least one $C_3$ precursor compound for the partial oxidation zone in the process according to the invention (for example also as a constituent of circulated residual gas mixture II or residual gas mixture III).

This carbon dioxide can, as already described, be taken up in absorption zone II in the process according to the invention predominantly to completely from the residual gas mixture I which flows through it into the aqueous alkali metal base used therein as absorbent II, and be bound in the aqueous absorbate II which forms in absorption zone II to a significant degree as alkali metal carbonate and/or alkali metal hydrogencarbonate present predominantly in dissolved form therein (especially in the case of employment of an elevated ratio MR* in absorption zone II). In addition, the aqueous alkali metal base used as absorbent II may already comprise alkali metal carbonate and/or alkali metal hydrogencarbonate.

The combination of aqueous intermediate I and aqueous intermediate II, or of aqueous raffinate I and aqueous raffinate II, can therefore result, in the process according to the invention, through chemical reaction of acid (e.g. acrylic acid) present in aqueous intermediate I or in aqueous raffinate I with alkali metal carbonate and/or alkali metal hydrogencarbonate present in aqueous intermediate II or in aqueous raffinate II, in marked reformation of gaseous $CO_2$, which can be substantially outgassed from the mixture which arises on combination. Advantageously in accordance with the invention, such $CO_2$ outgassing of such aqueous intermediate III or of such aqueous mixture of aqueous raffinate I and aqueous raffinate II will then be performed (an advantageous phenomenon which accompanies such $CO_2$ outgassing (especially in the case of $CO_2$ outgassing of aqueous intermediate III) is additionally stripping of the liquid phase to free it of acrolein still present therein).

In a particularly simple manner in application terms, $CO_2$ outgassing can be undertaken in a vessel in which the liquid to be outgassed is stirred. By reducing the working pressure and/or by raising the temperature, $CO_2$ outgassing can be promoted. Preferably in accordance with the invention, the $CO_2$ outgassing will be promoted essentially exclusively by an appropriate temperature increase, and preference is therefore given to using heatable stirred vessels at this point. Typically, the temperature of the liquid to be outgassed as described is kept within the range from 95 to 115° C., preferably in the range from 100 to 110° C.

In principle, the $CO_2$ outgassing can also be promoted by passing an inert stripping gas through the liquid to be outgassed. This inert stripping gas may, for example, be molecular nitrogen, air or lean air (molecular nitrogen-enriched air). Molecular oxygen-comprising stripping gas would be preferred in accordance with the invention at this point, since molecular oxygen has polymerization-inhibiting action both on acrylic acid and on alkali metal acrylate dissolved in aqueous medium. Overall, $CO_2$ outgassing promoted by means of stripping gas is less preferred in accordance with the invention.

It is possible in principle to proceed with the $CO_2$-containing offgas obtained in the $CO_2$ outgassing as with residual gas mixture II or residual gas mixture III. In other words, it can be disposed of, for example by incineration. Secondly, $CO_2$-containing offgas can also be reused as cycle gas for the purpose of inert dilution of the reaction gas input mixture. In general, the $CO_2$-containing offgas also comprises water and acrylic acid. It can therefore, in the same way as residual gas mixture II, prior to the incineration and/or cycle gas recycling thereof, also be subjected to a condensation in order to condense out water and acrylic acid present therein as aqueous acrylic acid solution. The aqueous condensate comprising acrylic acid obtained in this case can subsequently be recycled back into the liquid which is to be outgassed and/or has already been outgassed. In order to avoid losses of acrylic acid, the "$CO_2$ offgas" still comprising water and acrylic acid can also be conducted into absorption zone I in addition to the product gas mixture from the partial oxidation zone.

Very substantial $CO_2$ outgassing of such aqueous intermediate III is advantageous in the process according to the invention in that this avoids later outgassing in the course of the subsequent extraction of aqueous intermediate III, which promotes undisrupted running of the phase separation into raffinate III and extract III. After $CO_2$ outgassing has ended, it is generally appropriate to dissolve molecular oxygen (preferably up to saturation) in aqueous intermediate III for reasons of inhibition of polymerization by, for example, passing through air or lean air. Such a content of dissolved molecular oxygen is advantageous in the process according to the invention for reasons of stability for all aqueous phases comprising acrylic acid and/or alkali metal acrylate.

Especially when an elevated ratio MR* is not employed in absorption zone II, $CO_2$ outgassing of the aqueous intermediate II or III obtained can frequently be dispensed with. This is because there is then generally only comparatively limited $CO_2$ absorption in parallel to the absorption of the acrylic acid. Otherwise, it is also still possible to outgas $CO_2$ in the course of production of water-superabsorbent polymer (for example in the course of gel drying and/or postcrosslinking).

In principle, the inventive extraction of aqueous intermediate I, aqueous intermediate II or aqueous intermediate III can be executed in the same way.

Useful extraction apparatus for performance of the extraction includes all of that known for liquid-liquid extractions (cf. also columns 12/13 in DE-A 10220494). In this apparatus, a maximum contact area (phase interface) is created between the particular aqueous intermediate as extraction material and the organic extractant which is not homogeneously miscible under the extraction conditions. For this purpose, one of the two liquid phases (which becomes the disperse phase) is distributed in the other liquid phase (which forms the continuous phase) (for example with the aid of a stirrer or of a static mixer). The form of division is frequently that of small droplets. On completion of mass transfer of the extraction material into the extractant, the divided liquid phase (for example in the form of droplets whose longest dimension is advantageously in the range from 1 to 10 mm, preferably in the range from 2 to 5 mm) is combined again to give a homogeneous phase. Given a sufficient difference in the mass densities ($g/cm^3$ or $kg/m^3$) of aqueous raffinate remaining and organic extract formed, this combination can be driven by gravity (the total volume of the disperse phase present in the column is normally lower than that of the continuous phase present in the column). This procedure is preferred in accordance with the invention.

In the case of a smaller difference in the mass density, the combination can also be driven by means of centrifugation by the active centrifugal force. For the purpose of the combination described, the superimposition of an electrical field may also be appropriate.

In the simplest case, the extraction apparatus used in the process according to the invention is a combination of a mixer and a settler. Useful mixers include both static mixers and stirred vessels. They can be stirred using all common stirrers. Examples include disk stirrers, impeller stirrers, crossbeam stirrers, grid stirrers, blade stirrers, anchor stirrers, paddle stirrers, propeller stirrers, helical stirrers and multilevel pulsed countercurrent stirrers. In multilevel stirrers, two or more stirrers are mounted one on top of another or in succession on a common axis. Preference is given to using a two-level impeller stirrer.

Useful settlers include settling vessels of any kind. The settling vessels used are preferably horizontal vessels. In the case of batchwise operation, mixers and settlers can be combined with one another. In other words, mixing and settling are effected in the same vessel.

However, preference is given to performing the extraction continuously. In this case, the substance to be extracted (the aldehydes) are transferred from the donor phase (from the aqueous intermediate) to the acceptor phase (to the organic extractant (to the organic solvent)) in the mixer, to which the two liquid phases are supplied continuously. The two phases which normally have a different mass density are separated (for example due to gravity) in a settler which is spatially separate from the mixer and to which the mixture of the two phases obtained continuously in the mixer is supplied continuously. In the case of a sufficient difference in the mass densities, this is appropriately a settling vessel. Internals mounted transverse to the flow direction in the settling vessel can promote the separation of the feed from the mixer into the phases of higher and lower specific gravity in the settling vessel. Useful internals in principle include all common internals. These may, for example, be perforated sheets, trays, structured packings and/or random packings. Among the random packings, preference is given to those comprising rings, spirals, saddles, Raschig, Intos or Pall rings, Berl or Intalox saddles, Top-Pak etc., or braids. Particular preference is given to perforated sheets in combination with random packings. The residence time in the settling vessel is typically 0.05 to 2 h. The aqueous raffinate and the organic extract are conducted continuously out of the settler.

Normally, an apparatus consisting of a mixer and a settler realizes one theoretical plate. If one such theoretical plate is insufficient to achieve the objective of the invention, the remaining aqueous raffinate, in batchwise operation, is extracted once again with fresh extractant, etc.

In continuous operation, the separating action can be improved by connecting several mixer-settler apparatuses in series to form a cascade. Appropriately in application terms, extraction material and extractant are then conducted through the cascade in countercurrent with the aid of pumps. In principle, the mixer-settler units of such a cascade (in many cases also called a battery) can also be connected in cocurrent or crosscurrent.

In general, for the inventive purposes, a cascade which is operated in countercurrent and comprises not more than five mixer-settler units is adequate. In many cases, appropriately operated cascades of four or three mixer-settler units are even adequate.

In a mixer-settler unit, a centrifuge can also be used as a settler in an inventive extraction. Such units are referred to as centrifugal extractors. Centrifugal extractors suitable in accordance with the invention are, for example, the Podbielniak extractor and the Lurgi-Westfalia extractor.

The extraction of an aqueous intermediate which is to be performed in accordance with the invention will preferably, however, be performed in a continuous extraction column which typically has separating internals and to which the two phases are supplied by means of pumps. In principle, the separating action can also be improved by operating more than one extraction column in series connection.

The phase of higher specific gravity (in the process according to the invention, frequently the aqueous intermediate to be extracted) is supplied continuously to the extraction column at the upper end thereof, and the phase of lower specific gravity (in the process according to the invention, frequently the organic extractant) to the extraction column at the lower end thereof (generally each distributed homogeneously over the column cross section with the aid of appropriate distributor systems). In the column, the two phases move in countercurrent to one another under the influence of gravity. The phase of lower specific gravity ascends in the extraction column and the phase of higher specific gravity descends in the extraction column.

In principle, either the liquid phase of higher specific gravity or that of lower specific gravity may be the disperse phase, and the other phase in each case the continuous phase. Preferably in accordance with the invention, the aqueous intermediate is the disperse phase and the organic extractant the continuous phase. This is advantageous in accordance with the invention (especially in industrial scale operation) in that, in the case of any occurrence of unwanted free-radical polymerization of acrylic acid and/or alkali metal acrylate dissolved in the aqueous intermediate, it normally proceeds in a locally limited manner in the aqueous droplet in question.

When the phase of lower specific gravity among the two is dispersed (i.e. is present in droplet form), the phase separation proceeds in a separation region at the top of the extraction column. This may then have an increased cross section compared to the rest of the column cross section and comprise coalescence-promoting internals. The phase of lower specific gravity which settles out therein is conducted out of the column continuously (as top product).

In the converse case, in which the phase of higher specific gravity is dispersed, the phase separation takes place in the bottom of the extraction column. This region may then have an increased cross section as compared with the rest of the column cross section, and comprise coalescence-promoting internals. The phase of higher specific gravity which settles out therein is conducted continuously out of the column (as bottom product). Regulators or siphon tubes regulate the output in each case such that, upstream of the output site, a separation layer is maintained between phases of lower and higher specific gravity, and the liquid level in the extraction column remains essentially constant. If the disperse phase is the one of higher specific gravity, it is advantageously supplied to the column below the separation layer. If the disperse phase is the one of lower specific gravity, it is advantageously supplied to the column above the separation layer. In principle, the phase separation can also in each case be undertaken in downstream settlers provided outside the separation column.

The continuous phase is conducted out of the extraction column at the opposite end thereof in each case.

Useful separating internals of an extraction column for the inventive extraction include structured packings, random packings and/or sieve trays, as also used in rectification columns. They have the task of counteracting premature coalescence of the disperse, distributed phase and/or enabling multiple repetition of distribution and combination of the disperse phase along the longitudinal axis of the extraction column. Particularly preferred for the inventive extraction are extraction columns with energy input, by which the multiplication of mixing and settling along the longitudinal axis of the extraction column is promoted.

Extraction columns suitable in accordance with the invention which are charged with structured packings (more particularly structured or ordered) and/or random packings can be operated either with or without energy input. Among the random packings, preference is given to those comprising rings, spirals, saddles, Raschig, Intos or Pall rings, barrel or Intalox saddles, Top-Pak etc. Structured packings particularly suitable for extraction columns for use in accordance with the invention are, for example, structured packings from Julius Montz GmbH in D-40705 Hilden, for example the Montz-Pak B1-350 structured packing. Preference is given to using perforated structured packings. Packed columns with structured packings are known per se to those skilled in the art and are described, for example, in Chem.-Ing. Tech. 58 (1986) No. 1, p. 19-31, and in Technische Rundschau Sulzer 2/1979, p. 49 ff, from Gebrüder Sulzer Aktiengesellschaft in Winterthur, Switzerland.

In the case of an extraction column filled with structured packings and/or random packings without energy input, the extraction column on startup is, appropriately in application terms, filled with the continuous phase, and the disperse phase is supplied via distributors. Such distributors may be, for example, ring distributors, comb distributors or star distributors. These are essentially pipes which diverge, for example, in a star-shaped manner, and from which the disperse phase flows and drips. They are especially suitable for distributed supply of the liquid phase of higher specific gravity. In general, the distributor tubes extend over the particular cross-sectional length of the normally circular cylindrical extraction column and have a homogeneous pipe cross section. They have, over their length, (generally circular) exit orifices (bores) normally having an identical cross section. If the disperse phase is supplied at the top of the column, the exit orifices appropriately point downward. If the disperse phase is supplied at the bottom of the column, the exit orifices appropriately point upward. The diameter (longest dimension) of the aforementioned passage orifices will typically be 1 to 10 mm, preferably 3 to 6 mm and in many cases 2 to 5 mm. Accordingly, the result is droplet sizes with longest dimensions which are within the same range and are favorable for inventive extractions (longest dimension=longest straight line connecting two points on the surface).

Alternatively, the disperse phase can also be divided using a sieve tray by which it is conducted into the column and dropletized. The flow rates of continuous liquid phase and disperse liquid phase supplied/removed at a later stage are then selected so as to establish a steady operating state in which the ratio of total volume $V_C$ of continuous phase present in the extraction column to total volume $V_D$ present in the extraction column of disperse phase present in the extraction column is appropriately in the range of $V_C:V_D=10:1$ to $1.1:1$, preferably $5:1$ to $1.5:1$ (these ratios are generally advantageous in the inventive operation of inventive extraction columns).

The material of the structured packings and/or random packings should (as is quite generally the case for separating internals in extraction columns) be selected such that they have good wetting by the continuous liquid phase and poor or zero wetting by the disperse liquid phase, since the droplets of the disperse phase can otherwise coalesce prematurely on the structured packings and/or random packings and the two liquid phases as a result move past one another in countercurrent with reduced extractive action. If the aqueous intermediate to be extracted, in the course of inventive extraction thereof, constitutes the disperse phase (which is preferred in the case of industrial scale performance), separating internals made of Teflon® or Teflon-coated separating internals are preferred in accordance with the invention. The same applies to the distributors which are then used for distribution of this disperse phase.

Instead of Teflon, it is also possible to use other plastics.

If the organic extractant constitutes the disperse phase and the aqueous intermediate the continuous phase in the inventive extraction, ceramic has been found to be useful for the separating internals and distributors.

Internals and distributors made of metal can disadvantageously be wetted both by the aqueous intermediate and by the organic extractant. In general, however, aqueous intermediate is better at wetting stainless steel. Apart from the separating internals, the extraction unit for the inventive extraction of aqueous intermediate (like the other apparatus units too for the process according to the invention) is manufactured from DIN material 1.4571 (to DIN EN 10020). It is alternatively also possible to use the materials recommended in U.S. Pat. No. 6,966,973 B2 and U.S. Pat. No. 6,441,228 B2. This is especially true when the liquid phases relevant in accordance with the invention comprise not only acrylic acid but also glyoxal. In this case, preference is given to simultaneous inhibition of polymerization according to the teaching of DE-A 102010042216.

Useful extraction columns charged with structured packings and/or random packings with energy input for the extraction to be performed in accordance with the invention are especially stirred columns, as shown schematically in FIG. 369a in "Grundoperationen chemischer Verfahrenstechnik [Basic Operations in Chemical Process Technology], W. R. A. Vauck and H. A. Müller, Verlag Theodor Steinkopf, $4^{th}$ edition, Dresden 1974" (referred to in this document as "source I"). In these columns, stirred column sections essentially free of separating internals (mixing zones) alternate with unstirred column sections equipped with structured packings and/or random packings (calm zones) in flow direction. The energy input is effected by the stirring. The stirring constantly creates new interfaces for mass transfer. Appropriately in application terms, all stirrers are on a common shaft conducted through the extraction column from the top downward.

As an alternative to stirred columns, it is also possible to use rotary disk columns, as shown schematically in FIG. 369b in source I, as extraction columns operated with energy input for the inventive extraction of an aqueous intermediate I, II or III. These extraction columns do not have any (pronounced) mixing and calm zones clearly delimited from one another. In other words, the component operations of "mixing" and "separating" do not proceed in a spatially resolved manner. Typically, the circular cylindrical shell of these extraction columns is equipped with stator rings on the inner wall thereof. A shaft conducted from the top downward centrally in the middle of the column cross section then bears rotor disks in such a way that one rotor disk rotates between every two stator rings. The rotating rotor disks, which may also be perforated, bring about the mixing effect.

Stirred or rotary disk columns suitable for the inventive purposes are, for example, the RDC (rotating disk contractor) column, the ARD (asymmetrical rotating disk) column, the Kühni column (stirred column according to Kühni design) and the QVF stirred cell extractor.

In addition, sieve tray columns are particularly suitable for the inventive extraction of aqueous intermediate. These can be divided into cross flow sieve tray columns and pulsed sieve tray columns. The latter are particularly preferred for the inventive intermediate extraction.

A schematic diagram of a cross flow sieve tray column is shown in FIG. 369c in source I. The continuous phase is conducted therein from one sieve tray to the next sieve tray via shafts, and only the disperse phase, due to the difference in mass density between the two liquid phases, is forced through the passage orifices (generally holes, i.e. circular passage orifices) of the sieve trays, and constantly redispersed.

The pulsed sieve tray columns are extraction columns with energy input. The two phases are conducted therein through the passage orifices (generally holes, i.e. circular passage orifices) in the sieve tray. In other words, the sieve trays here do not have any shafts. As a result, on the upward stroke of the pulsation, the phase of lower specific gravity is forced upward through the holes of the sieve tray, and on the downward stroke the phase of higher specific gravity is correspondingly forced downward. Among the two phases, that phase which has the lower total combined volume in the column normally constitutes the disperse phase. The pulsator used is usually a piston pump. This is normally at the lower end of the pulsed sieve tray column and is in fluid connection with the column interior. Periodic movement of the displacer (piston) of the piston pump back and forth moves the entire liquid column up and down in an oscillating (pulsed) manner in the pulsed sieve tray column, and the stroke (the amplitude) must not be less than the thickness of the sieve trays and generally not greater than 75% of the distance between two successive sieve trays. In this way, the two liquid phases are forced periodically to flow through the sieve tray holes: the liquid phase of lower specific gravity on the upward stroke, and the liquid phase of higher specific gravity on the downward stroke. The disperse distribution is thus renewed periodically.

As an alternative to the oscillating upward and downward motion of the entire liquid column, the sieve trays in the column itself can also be moved up and down, as is the case, for example, in the Karr column.

Finally, it should also be emphasized that it is also possible to use, for the inventive extraction of the aqueous intermediate, extraction columns equipped with holdup packings as separating internals (for example with Alpha PACK® DSP). These are structured packings in which a "disperser plate" (a sieve tray) is mounted at the upper or lower end. If the phase of higher specific gravity constitutes the disperse phase, this plate is mounted at the upper end of the structured packing; if the phase of lower specific gravity is the disperse phase, this plate is mounted at the lower end of the structured packing. Between every two structured packings mounted one on top of another, a separating space free of internals is left. Such extraction columns are, appropriately in application terms, likewise used in pulsed operation.

It is also possible to operate columns with purely random packing and columns with purely structured packing in a pulsed manner. In the case of sieve tray columns having no downcomers, pulsed operation is obligatory.

The inventive extraction of an aqueous intermediate I, II or III for the purpose of absorption of acrolein, benzaldehyde and 2-furaldehyde present in dissolved form therein into the organic extractant is not normally associated with any marked exothermicity. Against this background, there is no need to control the temperature of the extraction column. Appropriately in application terms, it is generally thermally insulated on the outside. On the industrial scale, it is advantageously manufactured from stainless steel with wall thicknesses of 5 to 20 mm.

The temperature with which the aqueous extraction material and the organic extractant are supplied to the extraction may be in the range from 1 to 80° C. Preferably in accordance with the invention, it will be 20 to 50° C. and more preferably 25 to 35° C. Preferably in accordance with the invention, extraction material and extractant are supplied to the inventive extraction of the aqueous intermediate at the same temperature. Appropriately in application terms, the difference between the two temperatures will not be more than 20° C.

Frequently, the aforementioned temperature difference will be $\geq 0°$ C. and $\leq 15°$ C. or $\geq 0°$ C. and $\leq 10°$ C.

When the aqueous intermediate to be extracted is aqueous intermediate III which has been subjected beforehand to a thermally promoted $CO_2$ outgassing, it is appropriate in accordance with the invention to cool it in an indirect heat exchanger prior to extraction thereof. The same applies when the organic extractant is extractant removed subsequently, for example by rectification, from the organic extract removed and recycled into the extraction of aqueous intermediate.

The ratio $M_O:M_I$ of mass flow rate $M_O$ [kg/h] of organic extractant supplied to the extraction column to mass flow rate $M_I$ [kg/h] of aqueous intermediate (of aqueous extraction material) supplied to the extraction column may, in the process according to the invention, be 0.1 to 10, advantageously 0.1 to 5, preferably 0.1 to 2 and more preferably 0.1 to 1.

The number of theoretical plates in an extraction column suitable for the inventive extraction of aqueous intermediate may be 1 to 15. Preferably in accordance with the invention, it will be 3 to 10 and more preferably 4 to 8.

Normally, the vapor pressure in the extraction column will be essentially atmospheric pressure (approx. 1.01 bar).

Only in the case of use of a comparatively volatile organic extractant will the vapor pressure in the extraction column be significantly above atmospheric pressure. This procedure, however, is less preferred in accordance with the invention. In the liquid phases, the pressure is typically essentially conveying pressure, which may be up to 6 bar.

Otherwise, the remarks on pages 718 to 738 of source I apply correspondingly to the inventive extraction of aqueous intermediate.

Useful organic extractants for the purpose of aldehyde extraction from aqueous intermediate I, II or III are essentially all organic solvents which have a miscibility gap with the aqueous intermediate under the extraction conditions (typically in the temperature range of 1 to 80° C.). Suitable organic extractants thus include those organic solvents whose solubility in water at 20° C. and standard pressure is less than 10% by weight, preferably less than 7% by weight, more preferably less than 5% by weight and most preferably less than 1% by weight (the stated amount is based in each case on the resulting solution).

Among these, preference is given to those whose mass density in $kg/m^3$ differs from the mass density (likewise in $kg/m^3$) of the extraction material to be extracted (of the aqueous intermediate) by $\geq 10$ $kg/m^3$, preferably by $\geq 15$ or $\geq 25$ $kg/m^3$, more preferably by $\geq 30$ or $\geq 40$ $kg/m^3$ and most preferably by $\geq 50$ $kg/m^3$ (based on the pressure employed in the extraction and the temperature employed in the extraction (the extraction conditions)). In general, the aforementioned mass density difference will, however, not exceed 300 $kg/m^3$. It will usually be $\leq 250$ $kg/m^3$, in some cases even $\leq 200$ $kg/m^3$ or $\leq 150$ $kg/m^3$.

In addition, it is favorable for the process according to the invention when the dynamic viscosity of the organic extractant under the extraction conditions is less than the dynamic viscosity of the aqueous intermediate to be extracted.

When the aqueous intermediate is the disperse phase and the organic extractant is the continuous phase, this leads to accelerated mass transfer between the two phases and ultimately enables shorter columns for the same separation outcome.

Dynamic viscosities of the organic extractant under the extraction conditions of $\leq 1$ mPa·s, better $\leq 0.9$ mPa·s, are therefore preferred in accordance with the invention. In general, the dynamic viscosity of the organic extractant under the extraction conditions will not be less than 0.3 mPa·s. In principle, the dynamic viscosity of the organic extractant for aqueous intermediate I, II or III under extraction conditions may be up to 100 mPa·s. In other words, useful extractants also include those whose dynamic viscosity under the extraction conditions is >1 mP·s to 50 mPa·s, or 2 to 10 mPa·s.

It is additionally favorable for the aldehyde extraction from aqueous intermediate when the interfacial tension between the two liquid phases under the extraction conditions is comparatively high.

It is additionally advantageous when the organic extractant does not have any amine group —$NH_2$, any sulfo group —$SO_3$, any carboxyl group —COOH or any anhydride group —COOCO—. In addition, the organic extractant should as far as possible not react chemically with water (i.e. be hydrolysis-stable) under the extraction conditions, and have minimum solubility in water or in the aqueous intermediate I, II or III.

Against the background of the statements made so far, useful extractants suitable in accordance with the invention for the aldehyde extraction from aqueous intermediate include:

aromatic hydrocarbons, for example benzene and diphenyl, alkyl-substituted aromatic hydrocarbons, for example toluene, ethylbenzene, o-xylene, m-xylene, p-xylene and cumene, halogenated aromatic hydrocarbons, for example monochlorobenzene, monobromobenzene and monofluorobenzene, paraffinic hydrocarbons (linear, branched or cyclic), for example $C_6$- to $C_{16}$-alkanes such as hexane, heptane, octane and cyclohexane, or $C_{10}$- to $C_{14}$-alkanes such as tetradecane, technical hydrocarbons such as petroleum ether and gasoline fractions, halogenated paraffinic hydrocarbons, for example chloroform, dichloromethane, chloroethane, 1,1-dichloroethane, 1,2-dichloroethane, dichloropropane, for example 1,3-dichloropropane and 1,2-dichloropropane, and trichloroethane, alkyl ethers and aryl ethers of aromatic hydrocarbons, for example 2,4-di-tert-butylphenol, 2,6-di-tert-butylphenol, anisole and diphenyl ether, aliphatic and cycloaliphatic ethers having at least 4 carbon atoms, such as diethyl ether, methyl tert-butyl ether, diisopropyl ether, di-n-butyl ether and ethyl tert-butyl ether, aromatic carbonyl compounds such as benzophenone, aliphatic and cycloaliphatic ketones having at least 5 carbon atoms, such as methyl propyl ketone, methyl isopropyl ketone, methyl butyl ketone, methyl isobutyl ketone, methyl amyl ketone, methyl isoamyl ketone, diethyl ketone, ethyl propyl ketone, ethyl butyl ketone, diisopropyl ketone, diisobutyl ketone, cyclohexanone and trimethylcyclohexanone, esters of aliphatic $C_1$-$C_4$-monocarboxylic acids and $C_1$-$C_6$-alkanols or cycloalkanols, and having a total of preferably 4 to 10 and more preferably 5 to 8 carbon atoms, such as isobutyl formate, ethyl acetate, isobutyl acetate, amyl acetate, isoamyl acetate, cyclohexyl acetate, n-hexyl acetate, isobutyl propionate, isobutyl butyrate and isobutyl isobutyrate, halogenated and/or aryl-substituted alkanols, for example hexafluoro-2-phenyl-2-propanol, and
the dialkyl esters of aliphatic, olefinic and aromatic dicarboxylic acids, for example diethyl maleate, dimethyl phthalate and diethyl phthalate.

It will be appreciated that the organic extractant used for the purpose relevant in accordance with the invention may also be mixtures of the aforementioned extractants. The examples include the eutectic mixture of 2,4-di-tert-butylphenol (40% by weight) and 2,6-di-tert-butylphenol (60% by weight), mixtures of 70 to 75% by weight of diphenyl ether and 25 to 30% by weight of diphenyl, and mixtures consisting of a mixture of 70 to 75% by weight of diphenyl ether and 25 to 30% by weight of diphenyl (such a mixture is commercially available, for example, as Diphyl®), and, based on the mixture, 0.1 to 25% by weight of o-dimethyl phthalate. It is also possible to use long-chain monoalkanecarboxylic acids, for example 2-ethylhexanoic acid, octanoic acid, nonanoic acid and/or decanoic acid as extractants suitable for the inventive purpose.

Among the aforementioned extractants, preferred extractants for the purpose relevant in accordance with the invention are 1,3-dichloropropane, 1,2-dichloropropane, 1,1-dichloroethane and the eutectic mixture of 2,4-di-tert-butylphenol and 2,6-di-tert-butylphenol. Extractants particularly preferred in accordance with the invention have been found to be, in extraction tests, Diphyl, toluene, chlorobenzene, fluorobenzene and benzene.

Since the extractants are selected such that, in the extraction, they have very good absorption of the aldehydes present in the aqueous intermediate, viz. acrolein, benzaldehyde and 2-furfural (in particular the latter two), but at the same time very poor or zero absorption of acrylic acid and the conjugate base thereof, the constituents which are normally also present in the aqueous intermediate and are chemically similar to acrylic acid, viz. propionic acid and the conjugate base thereof, formic acid and the conjugate base thereof and acetic acid and the conjugate base thereof, remain for that reason in the aqueous raffinate together with the acrylic acid and the conjugate base thereof in the course of the inventive aldehyde extraction.

A process performed as described for production of aqueous raffinate I, or of aqueous raffinate III, or of a mixture of aqueous raffinate I and aqueous raffinate II (this mixture can optionally be subjected to a $CO_2$ outgassing prior to the free-radical polymerization) may be followed directly by a process for free-radical polymerization which incorporates the acrylic acid and conjugate base thereof present in the particular aqueous raffinate into a polymer (alternatively, the particular aqueous raffinate can be stored in a corresponding manner as described in documents WO 2005/049543, DE-A 2006045089 and DE-A 102006045088 in a reservoir vessel (storage tank) at temperatures of, for example, 25° C. and under lean air blanketing). In other words, the aqueous raffinates produced in accordance with the invention can be used directly for preparation of free-radical polymers (polymers obtained by free-radical initiation). Before, during and/or after the polymerization, it is possible to add further alkali metal base, aqueous solution thereof (aqueous alkali metal base) and/or water.

The reaction mixture subjected to the free-radical polymerization in each case comprises an amount of aqueous raffinate and the additives required for the performance of the particular polymerization.

These additives may optionally comprise comonomers (another possible additive is glacial acrylic acid (GAA)). These are generally likewise monoethylenically unsaturated compounds other than acrylic acid and the conjugate base thereof, with preferably good water solubility, for example methacrylic acid, maleic acid, itaconic acid, 2-acrylamido-2-methylpropanesulfonic acid, amides of the acids mentioned, alkali metal salts of the acids mentioned, ammonium salts of the acids mentioned, monohydroxyalkyl esters of acrylic acid, monohydroxyalkyl esters of methacrylic acid, N-vinylformamide etc.

The comonomers may also be monoethylenically unsaturated compounds with sparing water solubility, such as styrene, (meth)acrylic esters of monohydric alcohols, acrylonitrile, methacrylonitrile, and vinyl esters such as vinyl acetate and vinyl propionate. If the proportion of the monomers of sparing water solubility based on the monomers present overall in the reaction mixture (free-radically polymerizable, at least monoethylenically unsaturated compounds) is high, an aqueous polymer dispersion, for example, is obtained in the course of free-radical polymerization; if the proportion is low, an aqueous polymer solution is generally obtained.

Frequently, the total amount of monomers other than acrylic acid and the conjugate base thereof in the polymerization reaction mixture, based on the total amount of monomers present, is ≤40 mol %, or ≤30 mol %, or ≤20 mol %, or ≤10 mol %, or ≤5 mol %.

The above also applies in the case of a free-radical polymerization with the aim of preparation of aqueous solutions of superabsorbent polymer, in which low or vanishingly small comonomer contents are preferred. This is a crosslinked and therefore essentially water-insoluble polymer.

Such polymers are obtainable by virtue of the aqueous reaction mixture for the free-radical polymerization comprising, in addition to acrylic acid and the conjugate base thereof, and optionally the comonomers mentioned (the proportion of which is preferably low and more preferably vanishingly small), a small added amount of at least one so-called core crosslinker. The latter is a compound having at least two ethylenically unsaturated bonds. Examples of suitable core crosslinkers (also called internal crosslinkers) are N,N'-methylenebisacrylamide, diacrylates or dimethacrylates of polyalkylene glycols with relative molar masses (based on $^1H$) of 100 to 1500, trimethylolpropane trimethacrylate, at least diacrylated or dimethacrylated reaction products of trimethylolpropane with 1 to 8 mol of ethylene oxide per OH group, especially the fully acrylated or methacrylated reaction products of trimethylolpropane with 2 to 6 mol of ethylene oxide per OH group, triallylamine and tetraallylammonium chloride. Further examples of suitable internal crosslinkers can be found in the prior art (for example in WO 2006/05373 on pages 9 and 10, and in WO 03/002623 and in DE-A 10220494).

In general, the aqueous reaction mixture for the free-radical polymerization, based on the weight thereof, comprises 0.001 to 5% by weight, preferably 0.01 to 2% by weight, of at least one core crosslinker. Based on the molar total amount of acrylic acid, conjugate base thereof and the comonomers present in the polymerization reaction mixture, the reaction mixture comprises frequently 0.001 to 5 mol %, or 0.005 to 2 mol %, preferably 0.05 to 0.2 mol %, of at least one internal crosslinker (core crosslinker).

In addition, the aqueous reaction mixture normally comprises at least one added polymerization initiator by which the free-radical polymerization is triggered (in principle, the free-radical polymerization can also be triggered, for example, by the action of electron beams on the aqueous reaction mixture). The polymerization initiators used may be all compounds which decompose to free radicals under the polymerization conditions, for example peroxides, hydroperoxides, hydrogen peroxide, persulfates, azo compounds and redox initiators. In many cases, it is advantageous to use mixtures of different polymerization initiators, for example mixtures of hydrogen peroxide and sodium peroxodisulfate and/or potassium peroxodisulfate. Suitable organic peroxides are, for example, acetyl acetone peroxide, tert-butyl hydroperoxide, dibenzoyl peroxide and cumene hydroperoxide. Further suitable free-radical polymerization initiators can be found in the prior art (for example on pages 17 and 18 of WO 03/002623, and in column 10 of DE-A 10220494). Useful polymerization initiators are also photoinitiators which are induced to form free radicals by the action of electromagnetic radiation. These may be α-splitters, H-abstracting systems, or else azides. Examples include benzophenone derivatives.

Typically, the reaction mixture for the free-radical polymerization, based on the total amount of acrylic acid, conjugate base thereof, comonomers other than these two and conjugate bases thereof, and also core crosslinkers, present therein (i.e. based on the total amount of monomers present), comprises 0.001 to 5% by weight, preferably 0.01 to 5% by weight and more preferably 0.05 to 2% by weight of at least one added polymerization initiator. Specifically, the free-radical polymerization of an aqueous reaction mixture of the composition as described can be performed, for example, as detailed in documents WO 2008/009599, EP-A 1237937, DE 60012108 T2, EP-A 0372706, WO 99/42494, WO 01/38402, WO 03/002623, US 2010/0041549 A1 and WO 2006/053731, and the other prior art cited in these documents and in the present application. As a result of the free-radical polymerization, a gel is generally obtained, which still comprises the aqueous medium surrounding the polymerization in bound form.

By drying the gel at temperatures of typically 80 to 250° C., or 120° C. to 200° C., and subsequent grinding, a fine polymer powder is obtained, which is already capable of superabsorbing aqueous solutions.

The absorption and retention characteristics of the superabsorbent are typically additionally improved by surface postcrosslinking of the aforementioned polymer powder particles (cf. DE-A 10220494). Useful surface postcrosslinkers include compounds which can react with functional groups of the polymer present in the powder (for example having carboxyl and/or carboxylate groups). Typically, the polymer particles are sprayed with at least one solution of at least one postcrosslinker in an inert solvent such as water, monohydric alcohol, polyhydric alcohol or a mixture of at least two of the aforementioned substances. To trigger or accelerate the surface postcrosslinking (for example a condensation reaction which brings about the latter), the polymer particles surface sprayed as described are kept at a temperature in the range from 50 to 250° C., preferably from 115 to 190° C. Examples of postcrosslinkers include polyols such as ethylene glycol, 1,2-propanediol, 1,4-butanediol and glycerol, and di- and poly-N-methylol compounds such as methylenebis(N-methylol-methacrylamide). Further suitable postcrosslinkers can be found in the prior art (cf., for example, WO 03/002623, WO 2006/053731, US 2010/0041549, US 2008/0119626 and WO 2008/009599, and the other prior art cited in these documents and in the present application).

It is also possible to free-radically polymerize the aqueous reaction mixture by droplet polymerization, as described by way of example in WO 2008/009599. Polymerization and drying are superimposed here on one another.

Due to the comparatively high temperatures employed in the course of gel drying and in the course of postcrosslinking (there is typically additional gas flow through the gel drying), organic extractant present in small amounts in aqueous raffinate II prepared in accordance with the invention, or raffinate III, or a mixture of aqueous raffinate I and aqueous raffinate II, each of which forms the basis of the reaction mixture for the free-radical polymerization, is normally removed from the polymer formed in the course of drying and/or postcrosslinking, and therefore a removal of such an extractant content from aqueous raffinate prior to the free-radical polymerization is not indispensable.

It will be appreciated that such a prior removal can also be undertaken in a comparatively simple manner. One option is to remove the comparatively small amounts of organic extractant present in aqueous raffinate obtained in accordance with the invention by adsorption (for example by means of activated carbon as an adsorbent). An alternative option is to remove the (first) organic extractant remaining in dissolved form in the aqueous raffinate obtained in accordance with the invention therefrom, for its part by extraction. The (second) organic extractant used for that purpose will, appropriately in application terms, be an organic solvent whose solubility in the aqueous raffinate is very much lower than that of the (first) organic extractant present dissolved in the aqueous raffinate. The first organic extractant remaining in dissolved form in the aqueous raffinate will then be absorbed therefrom into the second organic extractant. In this way, the organic extractant content of aqueous raffinate II, or of aqueous raffinate III, or of a mixture of aqueous raffinate I and aqueous raffinate II, can be adjusted effortlessly to the range from 1 to 1000 ppm by weight, based on the weight of the raffinate, recommended in US-A 2008/0119626 and US-A 2008/0161512. Of course, the value may also be slightly lower than the lower limit of 1 ppm by weight. In general, 1 to 3 theoretical plates are sufficient for this separation task (one theoretical plate is usually sufficient). Examples of possible second organic extractants include hexane, heptane, octane, nonane, decane, undecane, dodecane, tridecane, tetradecane, cyclohexane, pentadecane, hexadecane, heptadecane, octadecane, nonadecane, eicosane, docosane, tricosane and tetracosane.

Alternatively, however, it is also possible to exploit the fact that many (first) organic extractants suitable in accordance with the invention have a comparatively low boiling point at standard pressure and/or form comparatively low-boiling azeotropes in small amounts with water (can be stripped with steam).

In both cases, the first organic extractant can be removed by rectification from the aqueous raffinate comprising it in dissolved form (for example, toluene can be removed comparatively simply (i.e. with comparatively low energy expenditure) in this manner, which makes toluene a first organic extractant which is particularly preferred in accordance with the invention).

Appropriately in application terms, the rectificative removal can be performed in a rectification column which has separating internals and has solely a stripping section. The separating internals used for this purpose may in principle be all separating internals which are known in the prior art for rectification columns and have already been named several times in this document. Preference is given in accordance with the invention to using dual-flow trays as separating internals.

The number of theoretical plates may vary within the range from 1 to 50. Appropriately in application terms, it will be 5 to 20. The hole diameter (the diameter of the passage orifices in the dual-flow trays) will generally be 8 to 50 mm, preferably 10 to 35 mm. The trays are typically arranged equidistantly. The tray separation is frequently 300 to 800 mm, in many cases 400 to 600 mm and frequently 500 mm. For example, with the aid of a liquid ring pump, the top pressure in the stripping column is, appropriately in application terms, adjusted to a value in the range from 0.1 to 1 bar (in principle, instead of (as an alternative to) a liquid ring pump to generate the reduced pressure, it is always possible in this document also to use a steam ejector (a steam-operated jet pump) or a water ejector (a jet pump operated with a liquid water jet)). The bottom pressure of the column may correspondingly be 0.1 to 5 bar. The feed of aqueous raffinate to the column is preferably at the uppermost (theoretical) plate. Internal and/or external indirect heat exchangers of conventional design (for example Robert evaporators, forced circulation shell and tube heat transferors, forced circulation shell and tube flash heat transferors, plate heat transferors etc.; cf., for example, EP-A 854129) and/or jacket heating (the heat carrier used is advantageously steam obtained with the waste heat of the partial oxidation) can be used to supply the thermal energy required for the separation to the bottom of the separation column. It is preferably supplied via external circulation evaporators with natural or forced circulation. Particular preference is given to using external circulation evaporators with forced circulation (optionally flash circulation).

Quite generally, it is advantageously possible in the process according to the invention, in all cases where evaporators are required (acrylic acid and/or the conjugate base thereof are potentially deposit-forming substances due to their tendency to unwanted polymerization) to use thin-film evaporators (for example those of the Luwa®, or Sambay®, or Sako® KV or Sako KH type). Appropriately in application terms, Sambay evaporators are especially suitable for the inventive purposes.

Heat transferors suitable in accordance with the invention include those described in WO 2009/133042 and in DE-A 19539295.

Possible bottom temperatures may be 50 to 100° C. The aqueous raffinate can be fed in essentially with the same temperature with which it is withdrawn from the aldehyde extraction of the aqueous intermediate.

The aqueous raffinate freed of first organic extractant remaining is conducted continuously out of the bottom of the stripping column and, as already described for aqueous raffinate still comprising first organic extractant, sent to storage thereof and/or a downstream process for free-radical polymerization.

The vapor phase is condensed above the uppermost (theoretical) plate. The condensation is preferably effected by indirect cooling. The indirect heat exchanger required for this purpose may also be outside the stripping column. The condensate formed, the temperature of which may, for example, be 20 to 40° C., is, appropriately in application terms, fed to a phase separator, out of which the separating phases can be conducted separately. The aqueous phase is recycled into the stripping column as reflux (preferably to the uppermost (theoretical) plate). The stripped organic phase can be recycled as "fresh" first organic extractant into the aldehyde extraction (column) and/or incinerated. What remains in gaseous form in the top condensation is normally sent to offgas disposal via the liquid ring pump. The operating liquid present in the liquid ring pump is, appropriately in application terms, condensation product formed from aqueous and/or organic phase (the lower the vapor pressure of the operating liquid, the lower the pressures which can be obtained with a liquid ring pump). Advantageously in accordance with the invention, liquid ring pumps used in the process according to the invention are operated as recommended in DE-A 10143565.

Instead of supplying the separation energy required to the column bottom by indirect heat exchange, the separation energy can also be supplied by a direct route, by introducing steam into the bottoms liquid. In this case, an indirect evaporator may not be required. For this purpose, steam can be used with a starting pressure of 1.5 to 100 bar (on entry through, for example, an entry valve into the stripping column, the steam expands to the internal column pressure). The temperature thereof may be 120° C. to 311° C.

Further promotion of the stripping of first organic extractant out of aqueous raffinate comprising it in dissolved form by additional flow of a low-condensability gas (for example air, lean air, molecular nitrogen) through the rectification column from the bottom to the top of the column is generally not required. Otherwise, the stripping column is operated with thermal insulation on the outside.

In the case of the organic extracts II, or III, or I and II, obtained in the course of inventive removal of the aldehydes acrolein, benzaldehyde and 2-furaldehyde from aqueous intermediate II, or III, or I and II, it is economically appropriate to remove the extractant present therein from these again, and recycle it into the inventive extraction. Advantageously in accordance with the invention, this removal can be performed by rectification in a rectification unit comprising at least one rectifying section and at least one stripping section. The rectification unit may be of a design known per se. It is typically configured as a rectification column having separating internals, as known from the prior art (cf., for example, DE-A 10336386 and DE-A 102010001228). Useful separating internals of this kind in principle include all separating internals commonly used for rectifications. These include especially trays, structured packings and/or random packings. Among the mass transfer trays, preference is given to bubble-cap trays, sieve trays (e.g. forced sieve trays or trickle sieve trays (dual-flow trays)), valve trays (for example with a fixed valve or in the form of valve plate trays) and/or Thormann trays. Particularly suitable among the random packings are those comprising rings, spirals, saddles, Raschig, Intos or Pall rings, Bed or Intalox saddles, Top-Pak etc., or braids. Most preferably, structured packings will be used as separating internals for the rectification column for the rectificative separation of the extract. These may be structured and/or unstructured packings. Unstructured packings are beds of bodies of defined shape present in a gas-pervious container. These may be rings, cylinders, saddles or the like. To reduce the pressure drop with simultaneous intensification of the vapor phase-liquid phase contact by means of increased surface areas, the side faces of the bodies are in many cases fractured. This gives rise to very complex structures, for example the Hiflow ring or Hiflow saddle.

Structured packings generally have a relatively low pressure drop with simultaneously relatively high separation performance. In the case of such packings, metal fabrics or sheets are folded and/or wound so as to result in intensive deflection of the vapor and of the liquid and associated intensive contact between the two. Further structuring of the surface and introduction of holes additionally increase both the wettability of the packing surface and the mass transfer. Suitable packings in accordance with the invention for the relevant rectificative separation are especially those from Montz, for example Montz B1 type, A3 type, BSH type, M type and MN type structured packings.

The thermal energy required for the rectificative separation can be supplied to the bottom of the rectification column via internal and/or external indirect heat exchangers of conventional design (for example thin-film evaporators, Robert evaporators, forced circulation shell and tube heat transferors, forced circulation shell and tube flash heat transferors, plate heat transferors etc.; cf., for example, EP-A 854129) and/or via jacket heating (the heat carrier used is advantageously steam obtained with the waste heat of the partial oxidation).

In the case of use of a rectification column with a comparatively large column cross section, it is advisable to use several evaporators (indirect heat transferors) connected in series or parallel. Preferably, in this case, 2 to 4 indirect heat exchangers (evaporators) are operated in parallel. The use of forced circulation flash evaporators is preferred here in accordance with the invention.

In terms of process technology, two limiting cases preferred in accordance with the invention can be compared with one another. In the first case, the organic extractant used for the aldehyde extraction of the aqueous intermediate (e.g. Diphyl®) at standard pressure (1.01 bar) has a boiling point higher than that of benzaldehyde at the same pressure.

In this case, the organic extract conducted continuously out of the aldehyde extraction is supplied continuously to the rectification column in the middle part thereof or lower (but at least 2 (generally up to 5) theoretical plates above the column bottom (this is the space below the lowermost internal in the rectification column)). Since the aldehyde extraction, as already stated, is performed at comparatively moderate temperatures, the organic extract comprising the aldehydes in dissolved form, on its route from the extraction to the rectification column, appropriately in application terms, is conducted through an indirect heat transferor to increase its temperature. Advantageously, the temperature is increased to a value corresponding essentially to that present at the feed point into the rectification column. For example, this temperature may be in the range of 160 to 190° C., or in the range of 170 to 180° C. The fluid heat carrier conducted simultaneously through the indirect heat transferor will, preferably in accordance with the invention, be bottoms liquid conducted out of the rectification column. This is organic extractant essentially freed of the unwanted aldehydes in the rectification column. In the inventive rectification, it can be conducted out of the bottom of the rectification column with a temperature of 170 to 200° C. It can subsequently leave the aforementioned indirect heat transferor with a temperature of 120 to 130° C. In order to compensate for extractant losses suffered, the extractant stream leaving the indirect heat transferor can be supplemented with fresh organic extractant and then recycled into the aldehyde extraction of aqueous intermediate. Further indirect heat exchange against refrigerants, for example water, can lower the temperature of the extractant further on the way back. It will be appreciated that the heating of organic extract supplied to the rectification column and the cooling of purified organic extractant conducted out of the bottom of the extraction column can also be performed in spatially separate indirect heat exchangers with alternative heat carriers or refrigerants (for example steam or water).

Appropriately in application terms, the rectificative aldehyde removal in the case described is performed at a column top pressure reduced with a liquid ring pump. This pressure may, for example, be 50 to 150 mbar or 70 to 140 mbar. Useful operating liquid for the liquid ring pump may, for example, be condensation product or water-diluted condensation product. The bottom pressure arises from the top pressure, the number and type of separating column internals, and the fluid-dynamic requirements of the rectification, and is frequently 150 to 250 mbar, or 160 to 200 mbar. In general, 5 to 10 theoretical plates in the rectification unit (in the rectification column) are sufficient.

The low boiler stream which reaches the top of the column can be condensed, for example, indirectly in indirect heat exchangers (the coolant used may, for example, be surface water), which are known per se to those skilled in the art and are not subject to any particular restriction, and/or directly, for example in a quench configured as a spray cooler. It is preferably effected by direct cooling. For this purpose, already condensed low boiler fraction is cooled by means of an indirect heat exchanger (typically to a temperature of 20° C. to 50° C.) and the cooled condensate is sprayed above the withdrawal point thereof in the vapor.

This spraying can be effected in a separate apparatus or in the rectification unit (in the rectification column) itself. In the case of spraying in the rectification unit, the withdrawal point is advantageously configured as a collecting tray. The direct condensation of the low boiler stream can also be performed in several stages, preferably with decreasing temperature in the upward direction. Internals which improve the mixing of the cooled condensate with the vapor can enhance the effect of the direct cooling. Useful internals for this purpose include all separating internals already mentioned in this document.

A portion of low boiler condensate formed (which comprises the unwanted aldehydes) is fed from the rectificative separation to the disposal thereof. Another portion is used as reflux in the rectification unit (in the rectification column). The temperature of the reflux liquid is typically 20° C. to 50° C. The constituents which remain in gaseous form in the top condensation are normally sent to offgas disposal via the liquid ring pump.

In an improved embodiment of the first limiting case preferred in accordance with the invention in terms of process technology, the rectifying section of the rectification unit will be configured as a side draw column. In other words, a portion of the (reflux) liquid which accumulates on a collecting tray between the top of the column and the feed point of the organic extract laden with the aldehydes into the rectification column is conducted out of the rectification column therefrom as the aldehyde outlet.

In one embodiment, only a comparatively small portion, required as reflux liquid, of the constituents which are present in the low boiler stream and have a boiling point of 0° C. at standard pressure (1.01 bar) from the low boiler stream which then still reaches the top of the column can be condensed out by direct and/or indirect cooling as just described. The remaining residual gas stream comprising acrylic acid can, in this case, be recycled, for example conveyed with compression by the liquid ring pump, into at least one zone from the group consisting of absorption zone I, condensation zone I, absorption zone II, an optional cooling zone and an optional condensation zone II. Appropriately in application terms, the recycling is effected predominantly or exclusively into absorption zone II. In order to avoid unwanted condensation, the gas stream can be heated by indirect heat exchange upstream of the liquid ring pump.

In another embodiment, the constituents which are present in the low boiler stream which still reaches the top of the column and have a boiling point of 0° C. at standard pressure will be condensed out in a comparatively quantitative manner by direct and/or indirect cooling. Only a portion of the condensate obtained is used as reflux liquid for the rectification column (the residual stream remaining in uncondensed form is supplied to offgas disposal via the liquid ring pump). The other portion of the condensate formed, which comprises acrylic acid, can, advantageously in accordance with the invention, be conducted into at least one zone from the group consisting of absorption zone I, condensation zone I, absorption zone II, an optional cooling zone and an optional condensation zone II. Appropriately in application terms, it is supplied predominantly or exclusively into absorption zone I. Advantageously, the recycling into absorption zone I is effected into absorbent I, or as a further absorbent stream. The recycling operating modes indicated can minimize acrylic acid losses. In all cases described, the stripping section of the rectification column can be operated with external trace heating in order to avoid unwanted acrylic acid condensation on the inner column wall.

In the second limiting case preferred in accordance with the invention, the organic extractant (e.g. toluene) used for the aldehyde extraction of the aqueous intermediate has a boiling point at standard pressure (1.01 bar) lower than that of acrylic acid at the same pressure.

In this case, the organic extract conducted continuously out of the aldehyde extraction is supplied to the rectification column continuously in the middle section thereof or higher (but at least 2 (generally up to 5) theoretical plates below the top of the column). The feed is advantageously likewise at a temperature elevated essentially to the temperature present at the feed point in the rectification column. At the top of the column, a working pressure below standard pressure will preferably likewise be adjusted (this may typically (appropriately likewise set with a liquid ring pump) be in the range of 70 to 250 mbar). The bottom pressure results from the top pressure, the number and type of separating column internals, and the fluid-dynamic requirements of the rectification, and is frequently 200 to 350 mbar. In general, 5 to 10 theoretical plates in the rectification unit (in the rectification column) are sufficient. At the top of the rectification column, in the same way as in the case of the other limiting case already described, the constituents which are present in the incoming low boiler stream and have a boiling point at temperatures of $\geq 0°$ C. at standard pressure (1.01 bar) are substantially condensed out of it.

The uncondensed constituents are supplied to offgas disposal (for example by incineration) as an offgas stream (which constitutes a further acrolein outlet) via the liquid ring pump. A portion of the condensate formed (which is essentially free of aldehydes) is used as reflux liquid for the rectification column. The other portion of condensate formed, which consists essentially of the organic extractant, can be recycled directly as "fresh" extractant into the aldehyde extraction of the aqueous intermediate. The acrylic acid contents present therein are not troublesome.

The bottoms liquid conducted continuously out of the column bottom comprises the unwanted aldehydes in enriched form and can be disposed of directly (for example by incineration). In principle, the bottoms liquid comprising the higher-boiling aldehydes than acrylic acid, but also acrylic acid, can alternatively be sent at least partly to the acrylic acid recovery, described below, from absorbate I which is conducted out of absorption zone I and is not used for cooling of product gas mixture from the partial oxidation zone. It should also be emphasized at this point that air or lean air can be conducted through the rectification column from the bottom upward for reasons of inhibition of polymerization in all rectification variants described. It should also be pointed out that, in the case of the second limiting case described, the rectificative separation between aldehydes and organic extractant can be facilitated by adding at least one aldehyde scavenger to the organic extract comprising the aldehydes in dissolved form prior to the rectificative treatment thereof in analogy to the procedure indicated in DE-A 10138101. This aldehyde scavenger converts the aldehydes, by chemical reaction therewith, to compounds with a boiling point at even higher temperatures. Useful aldehyde scavengers of this kind include nitrogen compounds having at least one primary amino group (one example is aminoguanidine hydrogencarbonate, which is a particularly preferred aldehyde scavenger).

Based on the redissociation processes disclosed in documents DE-A 102007055086, DE-A 10336386, WO 2009/133042, WO 2004/035514 and WO 00/53560, it is appropriate in the inventive procedure not to send the stream of absorbate I which is conducted out of absorption zone I and comprises not only the high boilers benzoic acid, maleic acid, phthalic acid and anhydrides thereof, but also acrylic acid, and which is not used as cooling liquid for direct cooling of product gas mixture formed in the partial oxidation zone, directly to disposal thereof. Instead, this proportion of absorbate I conducted out of absorption zone I, advantageously in accordance with the invention, will be sent to a recovery unit for recovery of acrylic acid present therein as a monomer or as a Michael adduct onto itself.

The recovery unit used may be any separating space comprising separating internals or free of separating internals. In a simple embodiment, a recovery column which may be equipped with the separating internals known per se is used. In general, 1 to 2 theoretical plates are sufficient here. Due to the comparatively simple separation task, it is also possible to dispense with internals and reflux liquid.

Absorbate I is fed, conveyed by pumps, into the lower region of the recovery column, preferably directly into the column bottom. The bottom temperature is appropriately adjusted to a value in the range from 140 to 230° C., preferably to a value in the range from 160° C. to 210° C. The heat can be supplied via internal and/or external indirect heat exchangers of conventional design (cf. WO 2009/133042) and/or via jacket heating. Preference is given to external circulation evaporators with natural or forced circulation. Particular preference is given to external circulation evaporators with forced circulation, for example forced circulation flash evaporators (forced circulation flash heat transferors). It is also possible to use thin-film evaporators for this purpose.

The pressure at the top of the recovery column can be set either to a value below standard pressure (1.01 bar) or to a value above standard pressure (it is generally not more than 2 bar and not less than 200 mbar). The residence time in the recovery unit should be 0.5 to 3 h. The low boiler fraction which comprises the acrylic acid and is converted to the vapor phase in the recovery column can be conducted directly (i.e. without formation of reflux liquid) into absorption zone I. When the pressure at the top of the column is adjusted to a value above standard pressure, the conveying of the low boiler fraction is normally borne by the autogenous pressure. If the product gas mixture conducted out of the partial oxidation zone in the process according to the invention is cooled in a cooling zone prior to supply thereof to absorption zone I, the aforementioned low boiler fraction will, however, preferably be conducted into this cooling zone together with the product gas mixture. The high boiler fraction remaining in the column bottom is discharged and sent to incineration. The residence time in the bottom of the column is preferably regulated via the viscosity of the bottoms residue (the bottom preferably has a constriction with reduced cross section (cf. EP-A 1095685)), such that the bottoms liquid withdrawn is still pumpable. More preferably, the bottoms liquid is discharged at regular intervals and sent to disposal by incineration, for example. For better conveyability, the bottoms liquid withdrawn can be diluted with hydrophilic liquids such as organic acids (e.g. ethylhexanoic acid, propionic acid), or with alkanols such as ethanol or methanol, or with liquids such as dimethylformamide.

As described in WO 2004/035514, DE-C 2407236, WO 2010/066601, WO 2009/133042, WO 2008/077767 and WO 00/53560, it may be appropriate in accordance with the invention to perform the acrylic acid recovery with addition of active compounds (splitting catalysts) which facilitate the redissociation of monomeric acrylic acid from diacrylic acid (Michael adduct). They can be introduced directly into the bottom of the recovery column. Alternatively, they can also be added to the proportion of absorbate I supplied to the acrylic acid recovery. Redissociation catalysts suitable in accordance with the invention are, for example, KOH, $K_2CO_3$, $KHCO_3$, NaOH, $Na^2CO_3$, $NaHCO_3$, LiOH, $Li_2CO_3$ and $CaCO_3$. Further redissociation catalysts suitable in accordance with the invention are especially the alkali metal and/or alkaline earth metal salts of weak organic or inorganic Brønsted acids, for example phosphoric acid, boric acid, formic acid or acetic acid. In other words, suitable redissociation catalysts are thus in particular alkali metal and/or alkaline earth metal phosphates, borates, formates and acetates. However, such redissociation catalysts may also be quaternary ammonium salts, a tertiary amine or a salt of such a tertiary amine with a Brønsted acid. Among these, preference is given to those recommended by WO 2008/077767. Preferably, the redissociation catalysts will be selected such that they are soluble in the bottoms liquid discharged from the bottom of the recovery column under the recovery conditions selected. According to U.S. Pat. No. 4,293,347, presence of dialkyl phthalates also has an advantageous effect on the relevant redissociation.

As described in U.S. Pat. No. 5,733,075 and in DE-A 4101879, the redissociation of the acrylic acid oligomers can in principle also be performed without addition of splitting catalysts, i.e. essentially purely thermally. This procedure is preferred in accordance with the invention. However, it is also possible to use acidic splitting catalysts. Useful catalysts of this kind include dodecylbenzenesulfonic acid, p-toluenesulfonic acid, sulfuric acid or the solid acidic catalysts of JP 3-178949. Appropriately in application terms, a molecular oxygen-comprising gas, for example air or lean air, may also flow through the recovery unit. In a particularly simple embodiment, the recovery unit may also be a stirred reactor equipped with a jacket (for reasons of heatability), with a splash guard on top (for example a short column filled with Raschig rings), by means of which the low boiler stream comprising the acrylic acid can be removed in gaseous form and without reflux and recycled directly into absorption zone I and/or into the cooling zone for the product gas mixture of the partial oxidation.

In principle, it is possible to subject the low boiler fraction obtained in the acrylic acid recovery column to a countercurrent rectification, as is indispensable in the process of WO 2004/035514. However, one specific advantage of the inventive procedure is that such a countercurrent rectification can be dispensed with.

Typically, the recovery unit is also manufactured from austenitic steel, preferably from material 1.4571 (to DIN EN 10020).

It will be appreciated that, in the process according to the invention, all process steps, especially when liquid phases comprising acrylic acid and/or the conjugate base thereof are involved therein, are performed with addition of polymerization inhibitors which counteract unwanted (premature) free-radical polymerization of acrylic acid and/or the conjugate base thereof. Useful polymerization inhibitors of this kind include all inhibitor systems recommended as polymerization retardants for acrylic acid in the documents cited as prior art in this application. These include especially alkylphenols such as o-, m- and p-cresol (methylphenol), 2-tert-butyl-4-methylphenol, 6-tert-butyl-2,4-dimethylphenol, 2,6-di-tert-butyl-4-methylphenol, 2-tert-butylphenol, 4-tert-butylphenol, 2,4-di-tert-butylphenol, 2-methyl-4-tert-butylphenol, 4-tert-butyl-2,6-dimethylphenol and 2,2'-methylenebis(6-tert-butyl-4-methylphenol), hydroxyphenols such as hydroquinone, 2-methylhydroquinone, 2,5-di-tert-butylhydroquinone, catechol (1,2-dihydroxyphenol) and benzoquinone, aminophenols, for example para-aminophenol, nitrosophenols, for example para-nitrosophenol, alkoxyphenols, for example 2-methoxyphenol, 2-ethoxyphenol, 2-isopropoxyphenol, 4-methoxyphenol (MEHQ=hydroquinone monomethyl ether), mono- or di-tert-butyl-4-methoxyphenol (MEHQ=hydroquinone monomethyl ether), mono- or di-tert-butyl-4-methoxyphenol, tocopherols, for example o-tocopherol, N-oxyls such as 4-hydroxy-2,2,6,6-tetramethylpiperidine N-oxyl (4-OH TEMPO) and 4-acetoxy-2,2,6,6-tetramethylpiperidine N-oxyl, aromatic amines or phenylenediamines, for example N,N-diphenylamine and N-nitrosodiphenylamine, hydroxylamines, for example N,N-diethylhydroxylamine, phosphorus compounds, for example triphenylphosphine, triphenyl phosphite, hypophosphorous acid and triethyl phosphite, sulfur compounds, for example diphenyl sulfide, methylene blue and phenothiazine (PTZ), optionally in each case combined with one or more metal salts, for example the chlorides, dithiocarbamates, sulfates, salicylates and acetates of copper, manganese, cerium, nickel and chromium. It will be appreciated that it is also possible to use mixtures of the polymerization inhibitors mentioned. The process recommended in DE-A 102010042216 for inhibiting the polymerization of acrylic acid can also be employed. Advantageously in accordance with the invention (especially in the case of use of MEHQ; since it is consumed over prolonged periods in a continuous process, it has to be replenished continuously), molecular oxygen is generally used as a coinhibitor. Advantageously, the essential steps of the process according to the invention can be performed at comparatively low temperatures (for example absorption zones I and II, condensation zone I, the aldehyde extraction, the cooling zone, the rectificative removal of extractant from aqueous raffinate). This is advantageous in that use of MEHQ as a process inhibitor in these process steps is normally sufficient (in a condensation zone II optionally operated in addition in accordance with the invention, it is generally possible to entirely dispense with active inhibition, since both the operating temperature and the acrylic acid contents are normally sufficiently low). In addition, the amounts of polymerization inhibitor used (which may be guided by the recommendations in DE-A 10336386 and DE-A 10220494) can be kept comparatively low. This is advantageous in that polymerization inhibitor present only in very small amounts in the "ready mix" (e.g. aqueous raffinate III) prepared in accordance with the invention, in the case of subsequent use of the "ready mix" in an actively initiated free-radical polymerization, is no longer capable of being troublesome to a perceptible degree. Molecular oxygen still present in dissolved form in the "ready mix" can be displaced with molecular nitrogen prior to any such active inhibition of free-radical polymerization. In those process steps where elevated temperatures have to be employed, it is advantageous in accordance with the invention to costabilize or exclusively stabilize with PTZ (for example in the acrylic acid recovery unit or in the removal of an extractant having a lower boiling point (at standard pressure) than benzaldehyde from the organic extract). In general, due to the high boiling point of PTZ, there is no risk that phenothiazine thus used will be entrained into the aqueous target product solution. If, for example, PTZ is used for coinhibition in condensation zone I, it generally likewise does not get into the aqueous target product since it is absorbed essentially quantitatively into the organic extractant in the aldehyde extraction. Also advantageously suitable for coinhibition both in the case of aqueous solutions and in the case of organic solutions is 4-OH TEMPO. Since it is more volatile than MEHQ, it would normally also be stripped in the course of steam stripping of organic extractant which remains in aqueous raffinate II, III or I and II and is troublesome in a further use thereof, and reused in the course of extractant recycling.

The at least one $C_3$ precursor compound for the reaction gas input mixture in the partial oxidation zone in the process according to the invention is particularly propane, propene, acrolein, propionic acid, propanol, propionaldehyde and/or glycerol. A $C_3$ precursor compound particularly preferred in accordance with the invention is propene.

The proportion of the at least one $C_3$ precursor compound in the reaction gas input mixture in the process according to the invention may, for example, be in the range from 4 to 20% by volume, or from 5 to 15% by volume, or from 6 to 12% by volume.

Normally, the reaction gas input mixture for the partial oxidation zone comprises, based on the stoichiometry of the partial oxidation reaction of the at least one $C_3$ precursor compound to acrylic acid, an excess of molecular oxygen in order to reoxidize the generally oxidic catalysts. Overall, the composition of the reaction gas input mixture for the partial oxidation zone is preferably generally adjusted such that no ignitable mixture is present under the reaction conditions (cf., for example, DE-A 10232482).

Otherwise, the process for heterogeneously catalyzed partial gas phase oxidation to prepare acrylic acid in the partial oxidation zone can be performed as described in the prior art (cf., for example, DE-A 10220494, column 14). In general, the reaction gas input mixture for the partial oxidation zone will comprise, based on the volume thereof, at least 1% by volume of water. Frequently, the water content of the reaction gas input mixture, on a corresponding basis, will be 2 to 30% by volume.

When the $C_3$ precursor compound is acrolein, for example, the heterogeneously catalyzed partial gas phase oxidation to prepare acrylic acid can be performed, for example, as described in documents EP-A 609750, EP-A 700893, WO 00/53559, DE-A 4442346, WO 2004/108267, DE-A 10325488, DE-A 102004021763, DE-A 102004021763 and WO 2008/104577.

When the $C_3$ precursor compound is glycerol, for example, the heterogeneously catalyzed partial gas phase oxidation to prepare acrylic acid can be performed, for example, as described in documents WO 2007/090991, WO 2006/114506, WO 2006/073160, WO 2006/114506, WO 2006/092272 and WO 2005/073160.

When the $C_3$ precursor compound is propane, for example, the heterogeneously catalyzed partial gas phase oxidation to prepare acrylic acid can be performed, for example, as described in documents EP-A 608838, DE-A 19835247, DE-A 10245585, DE-A 10246119, DE-A 102007029053 and DE 60124481 T2, and the prior art cited in these documents.

The $C_3$ precursor compound preferred in accordance with the invention is propene. It has also already been proposed that propene be obtained as the $C_3$ precursor compound by a dehydrogenation and/or oxydehydrogenation of propane upstream of the partial gas phase oxidation, and the propene formed subsequently be supplied, accompanied by the propane unconverted in the dehydrogenation, to the heterogeneously catalyzed partial oxidation to acrylic acid. The propane in this case, within the heterogeneously catalyzed propene partial oxidation, constitutes an inert diluent gas, which as such is also part of the product gas mixture which results in the partial oxidation zone.

When the inventive procedure is applied to such a product gas mixture comprising not only acrylic acid but especially also propane, the result is residual gas mixtures II or III which still comprise this propane.

Advantageously in accordance with the invention, such a propane-comprising residual gas mixture II or III would then at least partly not be recycled into the reaction gas input mixture for the partial oxidation zone, but rather into the reaction gas input mixture for the heterogeneously catalyzed partial dehydrogenation and/or oxydehydrogenation of propane to propene, connected upstream thereof. It is found to be particularly advantageous in this case that residual gas mixture II or III may have been washed to essentially free it of $CO_2$ in the inventive absorption zone II (especially in the case of an inventive preparation of aqueous intermediate III using an increased ratio MR*).

The process according to the invention is particularly advantageous when the partial oxidation zone in the case of a $C_3$ precursor compound "propene" is preceded by an upstream heterogeneously catalyzed partial dehydrogenation of propane to propene, in which the propene required in the partial oxidation zone is obtained and from which the propene thus obtained is conducted into the partial oxidation zone without removal of residual propane accompanying it.

Preferred procedures therefore arise under circumstances including those when, in the processes of DE-A 10245585, DE-A 10246119, WO 01/96270, WO 01/96271, WO 2006/2703, DE-A 102004032129, DE-A 102005013039, DE-A 102005056377, DE-A 102005057197, DE-A 102006024901 and DE-A 102005022798, the process, integrated into these processes, for removal or acrylic acid from the product gas mixture of the propene partial oxidation is replaced by an inventive removal process (especially by one in which residual gas mixture II or III is washed to essentially free it of $CO_2$ in the inventive absorption zone II).

When the process according to the invention is a heterogeneously catalyzed partial oxidation of propene to acrylic acid, the propene source used may especially be polymer grade propene or chemical grade propene according to DE-A 102004021764.

According to documents EP-A 257565 and EP-A 253409, by-product formation of acetic acid in a heterogeneously catalyzed partial gas phase oxidation of propene to acrylic acid is particularly marked when the reaction gas input mixture comprises steam as an inert diluent gas (conversely, a steam-free reaction gas input mixture enables low acetic acid by-product formation).

The inventive procedure has therefore been found to be advantageous especially when the reaction gas input mixture for the partial oxidation zone comprises, in addition to 4 to 20% by volume of propene, or 5 to 15% by volume of propene, or 6 to 12% by volume of propene, at least ($\geq$) 1% by volume of $H_2O$, or $\geq$2% by volume of $H_2O$, or $\geq$3% by volume of $H_2O$, or $\geq$4% by volume of $H_2O$, or $\geq$5% by volume of $H_2O$, or $\geq$7% by volume of $H_2O$, or $\geq$9% by volume, or $\geq$15% by volume of $H_2O$, or $\geq$20% by volume of steam. In general, the steam content of the reaction gas input mixture for the propene partial oxidation will be not more than ($\leq$) 40% by volume, frequently not more than ($\leq$) 30% by volume.

It is also known from documents WO 2007/074045 and WO 2007/074044 that, when the propene source used for propene partial oxidation to acrylic acid, still comprises a small amount of cyclopropane, propionic acid by-product formation is particularly marked in the heterogeneously catalyzed partial oxidation of propene to acrylic acid (conversely, vanishingly small cyclopropane contents enable a reduction in propionic acid by-product formation).

The inventive procedure is therefore found to be advantageous especially when the reaction gas input mixture for the partial oxidation zone, based on the molar amount of propene present therein, comprises >0 to 3 mol % of cyclopropane.

In other words, the process according to the invention is particularly suitable, for example, when the reaction gas input mixture comprises, based on the molar amount of propene present therein, 10 molar ppb to 3 mol %, or 50 molar ppb to 2 mol %, or 100 molar ppb to 1 mol %, or 1 molar ppm to 8000 molar ppm, or 10 molar ppm to 5000 molar ppm, or 100 molar ppm to 3000 molar ppm, or 200 molar ppm to 2500 molar ppm, or 300 molar ppm to 2000 molar ppm, or 400 molar ppm to 1500 molar ppm, or 700 molar ppm to 1300 molar ppm of cyclopropane.

Further factors influencing propionic acid by-product formation in a heterogeneously catalyzed gas phase partial oxidation of propene are taught in JP-A 11-35519 and WO 01/96270.

A reduction in by-product formation in a heterogeneously catalyzed gas phase partial oxidation of propene to acrylic acid is also enabled by the postreactor operating mode disclosed in DE-A 102004021764.

Otherwise, a heterogeneously catalyzed partial gas phase oxidation of propene to acrylic acid performed in the partial oxidation zone in the process according to the invention can be performed as described in the prior art (for example in documents DE-A 10353014, WO 2004/007450, DE-A 10360396, DE-A 10336386, DE-A 10313208, DE-A 10313209, DE-A 10351269, DE-A 102004021764, EP-A 990636, EP-A 1106598, DE-A 102004025445, DE-A 102005009891, WO 2007/082827, WO 2004/085369, WO 00/53557, WO 00/53558, DE-A 19927624, DE-A 19948248, DE-A 1995516, DE-A 19955176, WO 2007/074045 and WO 2007/074044).

In other words, the partial oxidation zone of the process according to the invention, in the case of a heterogeneously catalyzed partial gas phase oxidation of propene to acrylic acid, normally comprises two reaction stages 1 and 2 (a "first" reaction stage and a "second" reaction stage). In the first reaction stage essentially propene is partially oxidized to acrolein, and in the second reaction stage essentially the acrolein formed in the first reaction stage (normally without being separated beforehand from the product gas mixture of the first reaction stage) is partially oxidized to acrylic acid. The two reaction stages can be implemented in a single reactor (for example what is called a two-zone shell and tube reactor (or else "single reactor"), as detailed by way of example in U.S. Pat. No. 4,256,783) or in two reactors connected (arranged) in spatial succession (for example shell and tube reactors, as described, for example, in documents DE-A 4431957 and DE-A 4431949), which are charged with the catalysts required for the heterogeneously catalyzed gas phase partial oxidation. The first reaction stage typically has a first catalyst bed (e.g. a fixed catalyst bed), the catalysts of which have, as an active composition, at least one multimetal oxide comprising Mo, Fe and Bi. The second reaction stage generally has a second catalyst bed (e.g. a fixed catalyst bed), the catalysts of which have, as an active composition, a multimetal oxide comprising Mo and V.

The partial oxidation is then normally performed in such a way that a reaction gas input mixture 1 comprising propene, molecular oxygen (preferably in a molar $O_2:C_3H_6$ ratio of $\geq 1$) and at least one inert diluent gas other than $CO_2$ and steam (this is the reaction gas input mixture supplied to the partial oxidation zone) is conducted, initially at elevated temperature (this is normally in the range of 250 to 490° C., preferably in the range of 270 to 450° C. or in the range of 280 to 420° C. and more preferably in the range of 300 to 380° C.), through the first catalyst bed of the first reaction stage, so as to establish a propene conversion of $\geq 80$ or $\geq 90$ mol % in single pass of reaction gas input mixture 1 through the first catalyst bed.

Thereafter, the temperature of product gas mixture 1 leaving the first reaction stage can optionally be reduced (this can be done by direct cooling, by indirect cooling, or by direct and indirect cooling), and secondary gas in the form of molecular oxygen, or of inert gas (this may comprise $CO_2$ and/or steam and/or be different therefrom), or of inert gas and molecular oxygen, can optionally be added to product gas mixture 1. Subsequently, product gas mixture 1 is conducted, as reaction gas input mixture 2 comprising acrolein, molecular oxygen (preferably in a molar $O_2:C_3H_4O$ ratio of $\geq 0.5$), steam and at least one inert diluent gas other than $CO_2$ and steam is conducted at elevated temperature (this is normally in the range of 180 to 390° C., preferably in the range of 200 to 370° C. or in the range of 200 to 320° C., and more preferably in the range of 220 to 300° C.) through the second catalyst bed of the second reaction stage so as to establish an acrolein conversion of $\geq 80$ or $\geq 90$ mol % in single pass of reaction gas input mixture 2 through the second catalyst bed. In general, the aforementioned propene conversion will be $\leq 99.9$ mol % or $\leq 99.8$ mol %, and the aforementioned acrolein conversion $\leq 99.99$ mol % or $\leq 99.98$ mol %.

The product gas mixture 2 which leaves the second reaction stage and comprises the acrylic acid formed (the target product) constitutes the product gas mixture formed in the partial oxidation zone in the process according to the invention.

In general, the molar ratio of molecular oxygen present in reaction gas input mixture 1 to propene present in this mixture will be $\geq 1$ and $\leq 3$. This ratio is usually $\geq 1.3$ and $\leq 2.5$, often in the range of $\geq 1.5$ to $\leq 2.3$.

The amount of molecular oxygen in reaction gas input mixture 2 will normally be such that the molar ratio of molecular oxygen present in reaction gas input mixture 2 to acrolein present in this mixture is $\geq 0.5$ to $\leq 2$, frequently $\geq 0.75$ to $\leq 1.5$.

It is favorable when product gas mixture 2 still comprises up to 5% or up to 3% by volume of molecular oxygen.

Apart from molecular oxygen which is still present in residual gas mixture II or residual gas mixture III and is optionally recycled into the partial oxidation zone in cycle gas mode (propene unconverted in the course of partial oxidation would also be recycled as part of residual gas mixture II or III), the source used for the molecular oxygen present in reaction gas input mixture 1 or in reaction gas input mixture 2 is normally air. However, it is also possible to use molecular nitrogen-depleted air or pure molecular oxygen as the oxygen source.

In general, reaction gas input mixture 1 in the process according to the invention comprises 3 to 25% by volume, in many cases 5 to 20% by volume and usually 6 to 13% by volume of propene.

The steam content of reaction gas input mixture 1 may be 0 to 40% by volume, frequently 1 to 25% by volume, or 3 to 15% by volume, or 5 to 10% by volume.

In addition, reaction gas input mixture 1 will normally comprise at least one inert diluent gas other than $CO_2$ and steam, from the group consisting of $N_2$, CO, methane, ethane, propane and the noble gases, in a proportion, based on the volume of reaction gas input mixture 1, of 30 to 90% by volume, frequently 40 to 90% by volume, preferably 50 to 85% by volume or 60 to 85% by volume, and more preferably 70 to 85% by volume or 75 to 85% by volume.

It will be appreciated that reaction gas input mixture 1 may also already comprise $CO_2$ as an inert diluent gas. The proportion thereof will, however, based on the total volume of reaction gas input mixture 1, advantageously in accordance with the invention not be more than 20% by volume, or not more than 15% by volume, or not more than 10% by volume, preferably not more than 7% by volume and more preferably not more than 5% by volume or not more than 4% by volume. It will be appreciated that the $CO_2$ content in reaction gas input mixture 1 may also be above the aforementioned values.

When reaction gas input mixture 1 comprises elevated proportions by volume of $CO_2$, the proportion by volume of the at least one inert diluent gas other than $CO_2$ and $H_2O$ in reaction gas input mixture 1 may be comparatively small. In extreme cases it may be less than 1% by volume or even less than 0.1% by volume. According to the invention, however, it must not be vanishingly small. In other words, $CO_2$ may also be by far the predominant inert gas other than $H_2O$ in reaction gas input mixture 1. However, such a process is less preferred in accordance with the invention.

For example, all compositions for reaction gas input mixtures 1 detailed in documents WO 2007/074045 and WO 2007/074044 are also useful for the process according to the invention.

Catalysts which are suitable for the first reaction stage and whose active composition is at least one multimetal oxide comprising Mo, Fe and Bi can be found in the cited prior art (for example WO 02/24620 and DE-A 19855913).

A multitude of the multimetal oxide active compositions comprising Mo, Fe and Bi therein can be summarized by the general formula I

$$Mo_{12}Bi_aFe_bX^1_cX^2_dX^3_eX^4_fO_n \qquad (I),$$

in which the variables are each defined as follows:
$X^1$=nickel and/or cobalt,
$X^2$=thallium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a=0.5 to 5,
b=0.01 to 5, preferably 2 to 4,
c=0 to 10, preferably 3 to 10,
d=0 to 2, preferably 0.02 to 2,
e=0 to 8, preferably 0 to 5,
f=0 to 10, and
n=a number which is determined by the valency and frequency of the non-oxygen elements in I.

The above is true particularly when they are obtained in a manner known per se (see, for example, DE-A 4 023 239) and are shaped, for example, in substance to give spheres, rings or cylinders, or else are used in accordance with the invention in the form of eggshell catalysts, i.e. preshaped inert support bodies coated with the active composition. It will be appreciated that the statements made are also true when they are employed in powder form as catalysts for the first reaction stage (for example in fluidized bed reactors).

In principle, active compositions of the general formula I are generally prepared in a simple manner by obtaining, from suitable sources of the elemental constituents thereof, a very intimate, preferably finely divided, dry mixture whose composition corresponds to the stoichiometry thereof, and calcining it at temperatures of 350 to 650° C. The calcination can be effected either under inert gas or under an oxidative atmosphere, for example air (mixture of inert gas and oxygen), or else under a reducing atmosphere (for example mixture of inert gas, $NH_3$, CO and/or $H_2$). The calcination time may be a few minutes to a few hours and typically decreases with temperature. Useful sources for the elemental constituents of the multimetal oxide active compositions I include those compounds which are already oxides and/or those compounds which can be converted to oxides by heating, at least in the presence of oxygen.

In addition to the oxides, useful such starting compounds are in particular halides, nitrates, formates, oxalates, citrates, acetates, carbonates, amine complexes, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ and/or ammonium oxalate, which decompose and/or can be broken down to compounds which escape in gaseous form no later than in the course of the later calcining, can additionally be incorporated into the intimate dry mixture).

The intimate mixing of the starting compounds to prepare multimetal oxide active compositions I can be effected in dry or wet form. When it is effected in dry form, the starting compounds are appropriately used in the form of fine powder and, after the mixing and optional compaction, subjected to calcination. Preference is given, however, to intimate mixing in wet form. This typically involves mixing the starting compounds with one another in the form of an aqueous solution and/or suspension. Particularly intimate dry mixtures are obtained in the mixing process described when the starting materials are exclusively sources of the elemental constituents present in dissolved form. The solvent used is preferably water. Subsequently, the resulting aqueous material is dried, the drying operation preferably being effected by spray-drying the aqueous mixture in a hot gas stream (e.g. air or nitrogen) with gas exit temperatures of 100 to 160° C. Typical gas inlet temperatures are in the range from 250 to 450° C., preferably 270 to 370° C.

The multimetal oxide active compositions of the general formula I can be used in the first reaction stage of the process according to the invention either in powder form or shaped to particular catalyst geometries, in which case the shaping may precede or follow the final calcination. For example, the powder form of the active composition or the uncalcined and/or partially calcined precursor composition thereof can be used to produce unsupported catalysts by compacting to the desired catalyst geometry (for example by tableting or extruding), in which case it is optionally possible to add assistants, for example graphite or stearic acid as lubricants and/or shaping assistants, and reinforcing agents such as microfibers of glass, asbestos, silicon carbide or potassium titanate. Instead of graphite, it is also possible to use hexagonal boron nitride as an assistant in the shaping, as recommended in DE-A 10 2005 037 678. Suitable unsupported catalyst geometries are, for example, solid cylinders or hollow cylinders with an external diameter and a length of 2 to 10 mm. In the case of the hollow cylinders, a wall thickness of 1 to 3 mm is appropriate. It will be appreciated that the unsupported catalyst may also have spherical geometry, in which case the sphere diameter may be 2 to 10 mm.

A hollow cylinder geometry of particular relevance in accordance with the invention is 5 mm×3 mm×2 mm (external diameter×length×internal diameter), especially in the case of unsupported catalysts.

It will be appreciated that the pulverulent active composition of relevance in accordance with the invention or the pulverulent precursor composition thereof, which is yet to be calcined and/or has been partially calcined, can also be shaped by application to preshaped inert catalyst supports. The coating of the support bodies to produce eggshell catalysts is generally performed in a suitable rotatable vessel, as known, for example, from DE-A 29 09 671, EP-A 293 859 or from EP-A 714 700. Appropriately, the support bodies are coated by moistening the powder material to be applied and drying it again after the application, for example by means of hot air. The layer thickness of the powder material applied to the support body is frequently selected within the range of 10 to 1000 μm, preferably in the range of 50 to 500 μm and more preferably in the range of 150 to 250 μm.

The support materials used may be customary porous or nonporous aluminum oxides, silicon dioxide, thorium dioxide, zirconium dioxide, silicon carbide, or silicates such as magnesium or aluminum silicate. They generally behave essentially inertly with regard to the target reaction underlying the process according to the invention. The support bodies may have a regular or irregular shape, preference being given to regular-shaped support bodies with distinct surface roughness, for example spheres or hollow cylinders. It is relevant in accordance with the invention to use essentially nonporous, spherical steatite supports with a rough surface, the diameter of which is 1 to 10 mm or to 8 mm, preferably 4 to 5 mm. However, it is also relevant in accordance with the invention to use cylinders as support bodies, the length of which is 2 to 10 mm and the external diameter of which is 4 to 10 mm. In the case of rings as support bodies, the wall thickness is additionally typically 1 to 4 mm. Annular support bodies for use in accordance with the invention have a length of 2 to 6 mm, an external diameter of 4 to 8 mm and a wall thickness of 1 to 2 mm. Support bodies of relevance in accordance with the invention are also rings of geometry 7 mm×3 mm×4 mm (external diameter×length×internal diameter). The fineness of the catalytically active oxide compositions to be applied to the surface of the support body is of course adjusted to the desired shell thickness (cf. EP-A 714 700).

Catalysts which are suitable for the second reaction stage and whose active composition is at least one multimetal oxide comprising Mo and V can be found in the prior art cited.

A multitude of the multimetal oxide active compositions comprising Mo and V therein can be summarized by the general formula II $$Mo_{12}V_aX^1_bX^2_cX^3_dX^4_eX^5_fX^6_gO_n, \quad (II)$$

in which the variables are each defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one or more alkaline earth metals,
$X^6$=Si, Al, Ti and/or Zr,
a=1 to 6,
b=0.2 to 4,
c=0.5 to 18,
d=0 to 40,
e=0 to 2,
f=0 to 4,
g=0 to 40, and
n=a number which is determined by the valency and frequency of the non-oxygen elements in II.

Embodiments of particular relevance in accordance with the invention among the active multimetal oxides II are those which are covered by the following definitions of the variables of the general formula II:
$X^1$=W, Nb, and/or Cr,
$X^2$=Cu, Ni, Co, and/or Fe,
$X^3$=Sb,
$X^4$=Na and/or K,
$X^5$=Ca, Sr and/or Ba,
$X^6$=Si, Al, and/or Ti,
a=1.5 to 5,
b=0.5 to 2,
c=0.5 to 3,
d=0 to 2,
e=0 to 0.2,
f=0 to 1, and n=a number which is determined by the valency and frequency of the non-oxygen elements in II.

The multimetal oxide active compositions II relevant in accordance with the invention are obtainable in a manner known per se, for example that disclosed in DE-A 43 35 973 or in EP-A 714 700.

In general terms, multimetal oxide active compositions of the general formula II can be prepared in a simple manner by obtaining, from suitable sources of the elemental constituents thereof, a very intimate, preferably finely divided, dry mixture whose composition corresponds to the stoichiometry thereof, and calcining it at temperatures of 350 to 600° C. The calcination can be performed either under inert gas or under an oxidative atmosphere, for example air (or mixtures of inert gas and oxygen), or else under a reducing atmosphere (for example mixtures of inert gas and reducing gases such as $H_2$, $NH_3$, CO, methane and/or acrolein, or the reducing gases mentioned alone). The calcination time may be a few minutes to a few hours and typically decreases with temperature. Useful sources for the elemental constituents of the multimetal oxide active compositions II include those compounds which are already oxides and/or those compounds which can be converted to oxides by heating, at least in the presence of oxygen.

The intimate mixing of the starting compounds to prepare multimetal oxide compositions II can be effected in dry or wet form. When it is effected in dry form, the starting compounds are appropriately used in the form of fine powder and, after the mixing and optional compaction, subjected to calcination. Preference is given, however, to intimate mixing in wet form.

This typically involves mixing the starting compounds with one another in the form of an aqueous solution and/or suspension. Particularly intimate dry mixtures are obtained in the mixing process described when the starting materials are exclusively sources of the elemental constituents present in dissolved form. The solvent used is preferably water. Subsequently, the resulting aqueous composition is dried, the drying operation preferably being effected by spray-drying the aqueous mixture (as in the case of preparation of multimetal oxide active compositions I) with gas exit temperatures of 100 to 160° C.

The resulting multimetal oxide compositions of the general formula II can be used in the second reaction stage either in powder form (for example in fluidized bed reactors) or shaped to particular catalyst geometries, in which case the shaping may precede or follow the final calcination. For example, the powder form of the active composition or the uncalcined precursor composition thereof can be used to produce unsupported catalysts by compacting to the desired catalyst geometry (for example by tableting or extruding), in which case it is optionally possible to add assistants, for example graphite or stearic acid as lubricants and/or shaping assistants, and reinforcing agents such as microfibers of glass, asbestos, silicon carbide or potassium titanate. Relevant unsupported catalyst geometries are, for example, solid cylinders or hollow cylinders with an external diameter and a length of 2 to 10 mm. In the case of the hollow cylinders, a wall thickness of 1 to 3 mm is appropriate. It will be appreciated that the unsupported catalyst may also have spherical geometry, in which case the sphere diameter may be 2 to 10 mm (e.g. 8.2 mm or 5.1 mm).

It will be appreciated that the pulverulent active composition or the pulverulent, as yet uncalcined precursor composition thereof can also be shaped by application to preshaped inert catalyst supports. The coating of the support bodies to produce eggshell catalysts is generally performed in a suitable rotatable vessel, as known, for example, from DE-A 29 09 671, EP-A 293 859 or from EP-A 714 700.

Appropriately, the support bodies are coated by moistening the powder composition to be applied and drying it again after the application, for example by means of hot air. The layer thickness of the powder composition applied to the support body is, in a manner relevant in accordance with the invention, frequently selected within the range of 10 to 1000 µm, preferably in the range of 50 to 500 µm and more preferably in the range of 150 to 250 µm.

The support materials used may be customary porous or nonporous aluminum oxides, silicon dioxide, thorium dioxide, zirconium dioxide, silicon carbide, or silicates such as magnesium or aluminum silicate. The support bodies may have a regular or irregular shape, preference being given to regular-shaped support bodies with distinct surface roughness, for example spheres or hollow cylinders with a grit layer. It is suitable to use essentially nonporous, spherical steatite supports with a rough surface, the diameter of which is 1 to 10 mm or to 8 mm, preferably 4 to 5 mm. In other words, suitable sphere geometries may have diameters of 8.2 mm or of 5.1 mm. However, it is also suitable to use cylinders as support bodies, the length of which is 2 to 10 mm and the external diameter of which is 4 to 10 mm. In the case of rings as support bodies, the wall thickness is additionally typically 1 to 4 mm. Annular support bodies for use with preference have a length of 2 to 6 mm, an external diameter of 4 to 8 mm and a wall thickness of 1 to 2 mm. Of particular relevance as support bodies are also rings of geometry 7 mm×3 mm×4 mm (external diameter×length×internal diameter). The fineness of the catalytically active oxide compositions to be applied to the surface of the support body is of course adjusted to the desired shell thickness (cf. EP-A 714 700).

As already mentioned, both the first and the second catalyst bed is preferably a fixed catalyst bed (in principle, however, both or only one may be, for example, a fluidized or moving bed). The latter may consist only of the catalysts suitable for the first or second reaction stage, but also mixtures thereof with inert shaped bodies. The volume-specific activity both of the first and of the second catalyst bed advantageously increases in flow direction of the reaction gas mixture.

Both the first and the second catalyst bed is preferably present as a fixed bed in the tubes of shell and tube reactors. For the purpose of controlling the temperature thereof, at least one fluid heat carrier (preferably a salt melt) flows around the outside of these reaction tubes (cf., for example, DE-A 4431957, DE-A 4431949, DE-A 19910508, DE-A 19948523, DE-A 19910506, DE-A 19948241, DE-C 2830765, DE-C 2513405, U.S. Pat. No. 3,147,084, DE-A 2201528, EP-A 383224, DE-A 2903218).

Alternatively, the first and/or second catalyst bed may also be within the intermediate spaces of what are called thermoplate reactors, as recommended, for example, in DE-A 10361456, DE-A 10361515, DE-A 102004017150 and DE-A 102004017151.

The working pressure in the partial oxidation zone (i.e. both in the first reaction stage and in the second reaction stage) may quite generally be either below standard pressure (for example down to 0.5 bar; the reaction gas mixture is sucked through) or above standard pressure. Frequently, the working pressure in the partial oxidation zone (both in the first reaction stage and in the second reaction stage) will be at values of 1 to 5 bar, frequently 1.5 to 3.5 bar.

The molecular oxygen required in the second reaction stage may already be present in the reaction gas input mixture for the first reaction stage.

However, it can also be supplied to product gas mixture 1 between the two reaction stages (for example in the form of air or molecular nitrogen-depleted air (e.g. ≥90% by volume of $O_2$, ≥10% by volume of $N_2$)).

Beds consisting only of inert shaped bodies upstream and/or downstream of the first catalyst bed or the second catalyst bed can supplement the reactor charge. Useful materials for inert shaped bodies include, for example, porous or nonporous aluminum oxides, silicon dioxide, thorium dioxide, zirconium dioxide, silicon carbide, silicates such as magnesium silicate or aluminum silicate, or steatite.

The propene loading of the first catalyst bed (in this context, sections consisting only of inert shaped bodies are not counted as part of the first catalyst bed) may be, for example, ≥80 l (STP)/l·h to ≤250 l (STP)/l·h or to ≤300 l (STP)/l·h. Acrolein loadings of analogous definition in the range of ≥60 l (STP)/l·h to ≤250 l (STP)/l·h or to ≤300 l (STP)/l·h can be employed in a corresponding manner for the second catalyst bed (cf. WO 2007/074045 and WO 2007/074044).

Typically, the product gas mixture of a heterogeneously catalyzed gas phase partial oxidation of at least one $C_3$ precursor of acrylic acid (especially when the $C_3$ precursor is propene and the propene source used was chemical grade and/or polymer grade propene) in the partial oxidation zone of the process according to the invention has the following contents:

0.4 to 40% by weight, preferably 1 to 25% by weight and more preferably 3 to 15% by weight, based in each case on the weight of the product gas mixture, of water, 0.05 to 15% by weight, preferably 0.1 to 10% by weight or 0.3 to 5% by weight, based in each case on the weight of the product gas mixture, of $CO_2$, 1 to 30% by weight, preferably 5 to 20% by weight, based in each case on the weight of the product gas mixture, of acrylic acid, and, based on the total weight of acrylic acid present in the product gas mixture, ≥50 ppm by weight to ≤0.25% by weight of propionic acid,
≥200 ppm by weight to ≤2.5% by weight of formic acid,
≥3000 ppm by weight to ≤12% by weight of acetic acid,
≥15 ppm by weight to ≤1% by weight of benzoic acid,
≥15 ppm by weight to ≤5% by weight of total amount of maleic anhydride and maleic acid, calculated as maleic anhydride,
≥15 ppm by weight to ≤1% by weight of total amount of phthalic anhydride and phthalic acid, calculated as phthalic anhydride,
≥55 ppm by weight to ≤5% by weight of acrolein,
≥55 ppm by weight to ≤1% by weight of benzaldehyde,
≥55 ppm by weight to ≤0.5% by weight of 2-furaldehyde, and, based on the residual amount remaining up to 100% by weight of product gas mixture, at least 80% by weight, preferably at least 85% by weight, more preferably at least 90% by weight and most preferably at least 95% by weight of at least one constituent from the group consisting of $N_2$, CO, methane, ethane, propane and the noble gases, with the proviso that the total amount of $N_2$, CO, $CO_2$, methane, ethane, propane and the noble gases present in the product gas mixture, based on the total volume of the product gas mixture, is at least 30% by volume.

It should be emphasized here that "propane" in this document means "n-propane". In the case that the product gas mixture formed in the partial oxidation zone of the process according to the invention also comprises glyoxal and/or formaldehyde, the inventive procedure is found to be advantageous in that both are converted in aqueous medium to less troublesome compounds (e.g. methylene glycol, glycolic acid (hydroxyacetic acid) and hydrates of polyglyoxal and glyoxal (cf., for example, WO 2010/12586)). This is especially true of aqueous media whose pH is >7. Remaining formaldehyde would also generally escape in gaseous form from the polymeric structure in the course of gel drying and postcrosslinking at the elevated temperatures to be employed in the preparation of aqueous solutions of superabsorbent polymer.

It is quite generally the case that the product gas mixture formed in the partial oxidation zone in the process according to the invention comprises a lower proportion of by-products and/or intermediates other than acrylic acid when the heterogeneously catalyzed partial gas phase oxidation of the at least one $C_3$ precursor compound of acrylic acid is performed at comparatively low reaction temperatures and/or comparatively low conversions, based on a single pass of the reaction gas input mixture through the partial oxidation zone, of the at least one $C_3$ precursor compound. Comparatively low working pressures are likewise advantageous for increased selectivities of target product formation.

It is likewise found to be advantageous with regard to low by-product formation when the source used for the at least one $C_3$ precursor compound is a raw material which comprises the $C_3$ precursor compound in maximum purity (e.g. polymer grade propene rather than chemical grade propene).

Use of comparatively selective catalysts in the partial oxidation zone likewise has a limiting effect on by-product formation in the process according to the invention (especially on $CO_2$ by-product formation).

In this context, multimetal oxide active compositions which comprise Mo, Fe and Bi and are favorable for the first reaction stage of a propene partial oxidation are the multimetal oxide active compositions of the general formula I of DE-A 199 55 176, the multimetal oxide active compositions of the general formula I of DE-A 199 48 523, the multimetal oxide active compositions of the general formulae I, II and III of DE-A 101 01 695, the multimetal oxide active compositions of the general formulae I, II and III of DE-A 199 48 248 and the multimetal oxide active compositions of the general formulae I, II and III of DE-A 199 55 168, and also the multimetal oxide active compositions specified in EP-A 700 714.

Also suitable from this aspect for the first reaction stage of a propene partial oxidation are the multimetal oxide catalysts which comprise Mo, Fe and Bi and are described in the publications Research Disclosure No. 497012 dated Aug. 29, 2005, DE-A 100 46 957, DE-A 100 63 162, DE-C 3 338 380, DE-A 199 02 562, EP-A 15 565, DE-C 2 380 765, EP-A 8 074 65, EP-A 27 93 74, DE-A 330 00 44, EP-A 575897, U.S. Pat. No. 4,438,217, DE-A 19855913, WO 98/24746, DE-A 197 46 210 (those of the general formula II), JP-A 91/294239, EP-A 293 224 and EP-A 700 714. This is especially true of the illustrative embodiments in these documents, among which particular preference is given to those of EP-A 15565, EP-A 575897, DE-A 197 46 210 and DE-A 198 55 913. Particular emphasis should be given in this context to a catalyst according to Example 1c from EP-A 15 565 and a catalyst which is to be prepared in a corresponding manner but whose active composition has the composition $Mo_{12}Ni_{6.5}Zn_2Fe_2Bi_1P_{0.0065}K_{0.06}O_x \cdot 10SiO_2$. Emphasis should additionally be given to the example with serial No. 3 from DE-A 198 55 913 (stoichiometry: $Mo_{12}Co_7Fe_3Bi_{0.6}K_{0.08}Si_{1.6}O_x$) as an unsupported hollow cylindrical catalyst of geometry 5 mm×3 mm×2 mm (external diameter×height×internal diameter) and the unsupported multimetal oxide II catalyst according to Example 1 of DE-A 197 46 210. Mention should additionally be made of the multimetal oxide catalysts of U.S. Pat. No. 4,438,217. The latter is especially true when these hollow cylinders have a geometry of 5.5 mm×3 mm×3.5 mm, or 5 mm×2 mm×2 mm, or 5 mm×3 mm×2 mm, or 6 mm×3 mm×3 mm, or 7 mm×3 mm×4 mm (in each case external diameter×height×internal diameter). Further possible catalyst geometries in this context are extrudates (e.g. length 7.7 mm and diameter 7 mm; or length 6.4 mm and diameter 5.7 mm). Likewise recommended in this context is the unsupported catalyst according to Example 1 of DE-A 10046957.

Multimetal oxide active compositions which comprise Mo and V and are favorable for the second reaction stage of a propene partial oxidation are, for example, those of DE-A 10046928, of DE-A 19815281, of DE-A 4335973, of EP-A 714700, of EP-A 668104, of DE-A 19736105, of DE-A 10046928, of DE-A 19740493 and of DE-A 19528646. Particularly favorable are the eggshell catalysts of DE-A 10046928 (e.g. preparation example 5) and those of DE-A 10360057, of DE-A 10325488, of DE-A 102010028328 and of DE-A 102010023312.

By the inventive procedure, it is possible to obtain, as aqueous raffinate II, as aqueous raffinate III or as a mixture of aqueous raffinate I and aqueous raffinate II, aqueous (target product) solutions which comprise acrylic acid and the conjugate base thereof in a total amount, calculated as acrylic acid, of at least 10% by weight, based on the weight of the aqueous solution, and, based on the total amount of acrylic acid and the conjugate base thereof present in the aqueous solution, calculated as acrylic acid, ≥50 ppm by weight total amount of propionic acid and the conjugate base thereof, calculated as propionic acid,
≥200 ppm by weight total amount of formic acid and the conjugate base thereof, calculated as formic acid,
≥3000 ppm by weight total amount of acetic acid and the conjugate base thereof, calculated as acetic acid,
≤10 ppm by weight total amount of benzoic acid and the conjugate base thereof, calculated as benzoic acid,
≤10 ppm by weight total amount of maleic anhydride, maleic acid and the conjugate bases thereof, calculated as maleic acid,
≤10 ppm by weight total amount of phthalic anhydride, phthalic acid and the conjugate bases thereof, calculated as phthalic acid,
≤50 ppm by weight acrolein,
≤50 ppm by weight benzaldehyde,
≤50 ppm by weight 2-furaldehyde, and
at least 20 mol % of at least one alkali metal cation.

These aqueous solutions shall be referred to in this document as aqueous solutions $L_A$.

The wording "total amount of carboxylic acid and the conjugate base thereof, calculated as carboxylic acid" means that, for the calculation of the total amount, the molar amount of conjugate base present in the aqueous solution is treated as if the conjugate base of the carboxylic acid were likewise present as the carboxylic acid in the aqueous solution.

The wording "total amount of acid anhydride, acid and the conjugate bases thereof, calculated as acid" means that, for the calculation of the total amount, the molar amount of acid anhydride present in the aqueous solution and the molar amount of conjugate bases present in the aqueous solution is treated as if the acid anhydride and the conjugate bases were likewise present as the acid in the aqueous solution.

In a corresponding manner, the wording "total amount of acid and acid anhydride, calculated as acid anhydride" with regard to the composition of the product gas mixture or of a liquid phase means that, for the calculation of the total amount, the molar amount of acid present in the product gas mixture or in the liquid phase is treated as if the acid were likewise present as the acid anhydride in the product gas mixture or in the liquid phase.

Conversely, the wording "total amount of acid and acid anhydride, calculated as acid" means that, for the calculation of the total amount, the molar amount of acid anhydride present is treated as if it were likewise present as the acid.

Among the aqueous solutions $L_A$, particular preference is given in accordance with the invention to those which, based on the total amount of acrylic acid and the conjugate base thereof present in the aqueous solution, calculated as acrylic acid, comprise ≤5 ppm by wt. of total amount of benzoic acid and the conjugate base thereof, calculated as benzoic acid,
≤5 ppm by wt. of total amount of maleic anhydride, maleic acid and the conjugate bases thereof, calculated as maleic acid, and
≤5 ppm by wt. of total amount of phthalic anhydride, phthalic acid and the conjugate bases thereof, calculated as phthalic acid.

These aqueous solutions shall be referred to in this document as aqueous solutions $L_B$.

Among the aqueous solutions $L_A$, preference is given in accordance with the invention to those which, based on the total amount of acrylic acid and the conjugate base thereof present in the aqueous solution, calculated as acrylic acid, comprise ≤1 ppm by wt. of total amount of benzoic acid and the conjugate base thereof, calculated as benzoic acid,
≤1 ppm by wt. of total amount of maleic anhydride, maleic acid and the conjugate bases thereof, calculated as maleic acid, and
≤1 ppm by wt. of total amount of phthalic anhydride, phthalic acid and the conjugate bases thereof, calculated as phthalic acid.

These aqueous solutions shall be referred to in this document as aqueous solutions $L_C$.

Among the aqueous solutions $L_A$, $L_B$ and $L_C$, preference is in each case given to those which, based on the total amount of acrylic acid and the conjugate base thereof present in the particular aqueous solution, calculated as acrylic acid, comprise ≤40 ppm by wt. of acrolein,
≤40 ppm by wt. of benzaldehyde, and
≤40 ppm by wt. of 2-furaldehyde.

These aqueous solutions shall be referred to in this document as aqueous solutions $L_D$.

Among the aqueous solutions $L_A$, $L_B$ and $L_C$, preference is in each case given to those which, based on the total amount of acrylic acid and the conjugate base thereof present in the particular aqueous solution, calculated as acrylic acid, comprise ≤30 ppm by wt. of acrolein,
≤30 ppm by wt. of benzaldehyde, and
≤30 ppm by wt. of 2-furaldehyde.

These aqueous solutions shall be referred to in this document as aqueous solutions $L_E$. Among the aqueous solutions $L_A$, $L_B$ and $L_C$, particular preference is in each case given to those which, based on the total amount of acrylic acid and the conjugate base thereof present in the particular aqueous solution, calculated as acrylic acid, comprise ≤20 ppm by wt. of acrolein,
≤20 ppm by wt. of benzaldehyde, and
≤20 ppm by wt. of 2-furaldehyde.

These aqueous solutions shall be referred to in this document as aqueous solutions $L_F$.

Among the aqueous solutions $L_A$, $L_B$ and $L_C$, very particular preference is in each case given to those which, based on the total amount of acrylic acid and the conjugate base thereof present in the particular aqueous solution, calculated as acrylic acid, comprise ≤10 ppm by wt. of acrolein,
≤10 ppm by wt. of benzaldehyde, and
≤10 ppm by wt. of 2-furaldehyde.

These aqueous solutions shall be referred to in this document as aqueous solutions $L_G$.

Among the aqueous solutions $L_G$, preference is given to those which, based on the total amount of acrylic acid and the conjugate base thereof present in the aqueous solution, calculated as acrylic acid, comprise ≤5 ppm by wt. of acrolein,
≤5 ppm by wt. of benzaldehyde, and
≤5 ppm by wt. of 2-furaldehyde.

These aqueous solutions shall be referred to in this document as aqueous solutions $L_H$.

Among the aqueous solutions $L_G$, very particular preference is given to those which, based on the total amount of acrylic acid and the conjugate base thereof present in the aqueous solution, calculated as acrylic acid, comprise ≤1 ppm by wt. of acrolein,
≤1 ppm by wt. of benzaldehyde, and
≤1 ppm by wt. of 2-furaldehyde.

These aqueous solutions shall be referred to in this document as aqueous solutions $L_I$. If such solutions (or aqueous solutions $L_A$, $L_B$, $L_C$, $L_D$, $L_E$, $L_F$, $L_G$, $L_H$) still comprise formaldehyde or methylene glycol in equilibrium therewith in dissolved form, it can be removed from these aqueous solutions if required by chemisorption onto amine-functionalized adsorbents, for example benzylamine-functionalized polystyrene resin, or onto propyldiethylenetriamine-functionalized silica. For this purpose, in the simplest embodiment, the particular aqueous solution is stirred with the particular adsorbent and then filtered off from the adsorbate. Such adsorbents may be, for example, substances commercially available on the market, such as Envisorb B+, Perlcat 97-0 and 46-10, KC-Trockenperlen, Benzylamin@PS, ScavengerPore® SC11102 and DETA-PKS from BASF SE, Rapp Polymere and Sigma-Aldrich. The remaining filtrates shall likewise be covered by "aqueous solutions $L_I$" (or $L_A$, $L_B$, $L_C$, $L_D$, $L_E$, $L_F$, $L_G$, $L_H$).

In general, the aqueous solutions $L_A$, $L_B$, $L_C$, $L_D$, $L_E$, $L_F$, $L_G$, $L_H$ and $L_I$, based on the total amount of acrylic acid and the conjugate base thereof present in the particular aqueous solution, calculated as acrylic acid, will each comprise ≤0.25% by wt. of total amount of propionic acid and the conjugate base thereof, calculated as propionic acid,
≤2.5% by wt. of total amount of formic acid and the conjugate base thereof, calculated as formic acid, and
≤12% by wt. of total amount of acetic acid and the conjugate base thereof, calculated as acetic acid.

These aqueous solutions shall be referred to in this document as aqueous solutions $L_J$.

In other words, inventive aqueous solutions are also those aqueous solutions $L_A$, $L_B$, $L_C$, $L_D$, $L_E$, $L_F$, $L_G$, $L_H$, $L_I$ and $L_J$ which, based on the total amount of acrylic acid and the conjugate base thereof present in the particular aqueous solution, calculated as acrylic acid, each comprise ≥100 ppm by wt. of total amount of propionic acid and the conjugate base thereof, calculated as propionic acid,
≥500 ppm by wt. of total amount of formic acid and the conjugate base thereof, calculated as formic acid, and
≥5000 ppm by wt. of total amount of acetic acid and the conjugate base thereof, calculated as acetic acid.

These aqueous solutions shall be referred to in this document as aqueous solutions $L_K$.

Inventive aqueous solutions are, however, also those aqueous solutions $L_A$, $L_B$, $L_C$, $L_D$, $L_E$, $L_F$, $L_G$, $L_H$, $L_I$, $L_J$ and $L_K$ which, based on the total amount of acrylic acid and the conjugate base thereof present in the particular aqueous solution, calculated as acrylic acid, each comprise ≤0.20% by wt. of total amount of propionic acid and the conjugate base thereof, calculated as propionic acid, ≤2.0% by wt. of total amount of formic acid and the conjugate base thereof, calculated as formic acid, and ≤10% by wt. of total amount of acetic acid and the conjugate base thereof, calculated as acetic acid.

These aqueous solutions shall be referred to in this document as aqueous solutions $L_L$.

Inventive aqueous solutions are thus also those aqueous solutions $L_A$, $L_B$, $L_C$, $L_D$, $L_E$, $L_F$, $L_G$, $L_H$, $L_I$, $L_J$, $L_K$ and $L_L$ which, based on the total amount of acrylic acid and the conjugate base thereof present in the particular aqueous solution, calculated as acrylic acid, each comprise ≥150 ppm by wt. of total amount of propionic acid and the conjugate base thereof, calculated as propionic acid, ≥750 ppm by wt. of total amount of formic acid and the conjugate base thereof, calculated as formic acid, and ≥7500 ppm by wt. of total amount of acetic acid and the conjugate base thereof, calculated as acetic acid.

These aqueous solutions shall be referred to in this document as aqueous solutions $L_M$.

The inventive aqueous solutions (those obtainable in accordance with the invention) also include those aqueous solutions $L_A$, $L_B$, $L_C$, $L_D$, $L_E$, $L_F$, $L_G$, $L_H$, $L_I$, $L_J$, $L_K$, $L_L$ and $L_M$ which, based on the total amount of acrylic acid and the conjugate base thereof present in the particular aqueous solution, calculated as acrylic acid, each comprise ≤0.15% by wt. of total amount of propionic acid and the conjugate base thereof, calculated as propionic acid, ≤1.5% by wt. of total amount of formic acid and the conjugate base thereof, calculated as formic acid, and ≤8% by wt. of total amount of acetic acid and the conjugate base thereof, calculated as acetic acid.

These aqueous solutions shall be referred to in this document as aqueous solutions $L_N$.

The inventive aqueous solutions also include those aqueous solutions $L_A$, $L_B$, $L_C$, $L_D$, $L_E$, $L_F$, $L_G$, $L_H$, $L_I$, $L_J$, $L_K$, $L_L$, $L_M$ and $L_N$ which, based on the total amount of acrylic acid and the conjugate base thereof present in the particular aqueous solution, calculated as acrylic acid, each comprise ≥180 ppm by wt. of total amount of propionic acid and the conjugate base thereof, calculated as propionic acid, ≥1000 ppm by wt. of total amount of formic acid and the conjugate base thereof, calculated as formic acid, and ≥1% by wt. of total amount of acetic acid and the conjugate base thereof, calculated as acetic acid.

These aqueous solutions shall be referred to in this document as aqueous solutions $L_O$.

The inventive aqueous solutions thus also include those aqueous solutions $L_A$, $L_B$, $L_C$, $L_D$, $L_E$, $L_F$, $L_G$, $L_H$, $L_I$, $L_J$, $L_K$, $L_L$, $L_M$, $L_N$ and $L_O$ which, based on the total amount of acrylic acid and the conjugate base thereof present in the particular aqueous solution, calculated as acrylic acid, each comprise ≤0.1% by wt. of total amount of propionic acid and the conjugate base thereof, calculated as propionic acid, ≤1% by wt. of total amount of formic acid and the conjugate base thereof, calculated as formic acid, and ≤5% by wt. of total amount of acetic acid and the conjugate base thereof, calculated as acetic acid.

These aqueous solutions shall be referred to in this document as aqueous solutions $L_P$.

Inventive aqueous solutions are thus also those aqueous solutions $L_A$, $L_B$, $L_C$, $L_D$, $L_E$, $L_F$, $L_G$, $L_H$, $L_I$, $L_J$, $L_K$, $L_L$, $L_M$, $L_N$, $L_O$, and $L_P$ which, based on the total amount of acrylic acid and the conjugate base thereof present in the particular aqueous solution, calculated as acrylic acid, each comprise ≥200 ppm by wt. of total amount of propionic acid and the conjugate base thereof, calculated as propionic acid, ≥1500 ppm by wt. of total amount of formic acid and the conjugate base thereof, calculated as formic acid, and ≥1.3% by wt. of total amount of acetic acid and the conjugate base thereof, calculated as acetic acid.

These aqueous solutions shall be referred to in this document as aqueous solutions $L_Q$.

Based on the (molar) total amount of acrylic acid and the conjugate base thereof present therein, the inventive aqueous solutions $L_A$, $L_B$, $L_C$, $L_D$, $L_E$, $L_F$, $L_G$, $L_H$, $L_I$, $L_J$, $L_K$, $L_L$, $L_M$, $L_N$, $L_O$, $L_P$ and $L_Q$ may each comprise at least one alkali metal cation to an extent of 20 to 200 mol %, or of 20 to 150 mol %, or 30 to 140 mol %, or 40 to 120 mol %, or 50 to 110 mol %, or 50 to 100 mol %, or 50 to 95 mol %, preferably 60 to 90 mol %, more preferably 60 to 80 mol % and more preferably 60 to 75 mol %, or 65 to 75 mol %. The at least one alkali metal cation is preferably $Li^+$, $K_+$ and/or $Na^+$.

Advantageously in accordance with the invention, all inventive aqueous solutions (those obtainable in accordance with the invention), especially the inventive aqueous solutions $L_A$, $L_B$, $L_C$, $L_D$, $L_E$, $L_F$, $L_G$, $L_H$, $L_I$, $L_J$, $L_K$, $L_L$, $L_M$, $L_N$, $L_O$, $L_P$ and $L_Q$, irrespective of the rest of their composition, based on the molar total amount of alkali metal cations present therein, comprise $Na^+$ to an extent of at least 50 mol %, preferably $Na^+$ to an extent of at least 75 mol %, more preferably $Na^+$ to an extent of at least 90 mol %, even more preferably $Na^+$ to an extent of at least 95 mol % and particularly advantageously $Na^+$ to an extent of at least 98 mol %, or to an extent of at least 99 mol %, or to an extent of 100 mol %.

In principle, all inventive aqueous solutions, especially the inventive aqueous solutions $L_A$, $L_B$, $L_C$, $L_D$, $L_E$, $L_F$, $L_G$, $L_H$, $L_I$, $L_J$, $L_K$, $L_L$, $L_M$, $L_N$, $L_O$, $L_P$ and $L_Q$), irrespective of the rest of their composition, based on the molar total amount of alkali metal cations present therein, may comprise $K_+$ and/or $Na^+$ to an extent of at least 50 mol %, advantageously $K_+$ and/or $Na^+$ to an extent of at least 75 mol %, better $K^+$ and/or $Na^+$ to an extent of at least 90 mol %, even better to an extent of at least 95 mol %, or to an extent of at least 98 mol %, preferably $K_+$ and/or $Na^+$ to an extent of at least 99 mol % or to an extent of 100 mol %.

Aqueous intermediate II comprises, advantageously in accordance with the invention, based on the molar total amount of acrylic acid and the conjugate base thereof, present therein, at least 80 mol %, or at least 90 mol %, or at least 100 mol %, preferably at least 100.1 or at least 102 mol %, more preferably at least 104 mol % or at least 106 mol % of at least one alkali metal cation. Advantageously, the at least one alkali metal cation is generally $Li^+$, $K^+$ and/or $Na^+$, particularly advantageously $K^+$ and/or $Na^+$ and very particularly advantageously $Na^+$.

In principle, aqueous intermediate II, based on the molar total amount of acrylic acid and the conjugate base thereof present therein, may comprise 20 to 400 or to 300 mol %, or 20 to 250 mol %, or 20 to 200 mol %, or 20 to 150 mol %, or 30 to 140 mol %, or 40 to 120 mol %, or 50 to 110 mol %, or 50 to 100 mol %, or 50 to 95 mol %, or 60 to 90 mol %, or 60 to 80 mol %, or 60 to 75 mol %, or 65 to 75 mol % of at least one alkali metal cation. The at least one alkali metal cation is preferably $Li^+$, $K^+$ and/or $Na^+$.

Advantageously in accordance with the invention, all aqueous intermediates II comprise, irrespective of the rest of their composition, based on the molar total amount of alkali metal cations present therein, $K^+$ and/or $Na^+$ to an extent of at least 50 mol %, preferably $K^+$ and/or $Na^+$ to an extent of at least 75 mol %, particularly preferably $K^+$ and/or $Na^+$ to an extent of at least 90 mol %, very particularly preferably $K^+$ and/or $Na^+$ to an extent of at least 95 mol %, and particularly advantageously $K^+$ and/or $Na^+$ to an extent of at least 98 mol %, or to an extent of at least 99 mol %, or to an extent of 100 mol %, preference being given to $Na^+$ as the sole alkali metal cation in all cases.

Irrespective of their content of alkali metal cations and the type thereof, the water content of all inventive aqueous solutions $L_A$, $L_B$, $L_C$, $L_D$, $L_E$, $L_F$, $L_G$, $L_H$, $L_I$, $L_J$, $L_K$, $L_L$, $L_M$, $L_N$, $L_O$, $L_P$ and $L_Q$, based on the weight of the aqueous solution, may be 15 to 85% by weight, or 30 to 80% by weight, or 40 to 70% by weight, or preferably 50 to 65% by weight or 55 to 60% by weight. Preferably in accordance with the invention, the aforementioned water content is ≤65% by weight, more preferably 60% by weight.

The above water contents, but now based on the weight of the particular aqueous intermediate, apply correspondingly to the aqueous intermediates I, II and III.

In addition, it is advantageous in accordance with the invention when the inventive aqueous solutions $L_A$, $L_B$, $L_C$, $L_D$, $L_E$, $L_F$, $L_G$, $L_H$, $L_I$, $L_J$, $L_K$, $L_L$, $L_M$, $L_N$, $L_O$, $L_P$ and $L_Q$, irrespective of their content of alkali metal cations and the type thereof, comprise acrylic acid and the conjugate base thereof in a total amount, calculated as acrylic acid and based on the weight of the aqueous solution, of at least 15% by weight, preferably of at least 20% by weight and more preferably of at least 25% by weight.

In general, the inventive aqueous solutions $L_A$, $L_B$, $L_C$, $L_D$, $L_E$, $L_F$, $L_G$, $L_H$, $L_I$, $L_J$, $L_K$, $L_L$, $L_M$, $L_N$, $L_O$, $L_P$ and $L_Q$ will each comprise acrylic acid and the conjugate base thereof in a total amount, calculated as acrylic acid and based on the weight of the aqueous solution, of not more than 70% by weight, frequently of not more than 60% by weight, and usually of not more than 50% by weight. More preferably in accordance with the invention, the aqueous solutions $L_A$, $L_B$, $L_C$, $L_D$, $L_E$, $L_F$, $L_G$, $L_H$, $L_I$, $L_J$, $L_K$, $L_L$, $L_M$, $L_N$, $L_O$, $L_P$ and $L_Q$ each comprise acrylic acid and the conjugate base thereof in a total amount, calculated as acrylic acid and based on the weight of the aqueous solution, of 25 to 40% by weight, and most preferably of 25 to 35% by weight.

Aqueous solutions $L_A$, $L_B$, $L_C$, $L_D$, $L_E$, $L_F$, $L_G$, $L_H$, $L_I$, $L_J$, $L_K$, $L_L$, $L_M$, $L_N$, $L_O$, $L_P$ and $L_Q$ very particularly preferred in accordance with the invention each comprise acrylic acid and the conjugate base thereof in a total amount, calculated as acrylic acid and based on the weight of the aqueous solution, of 20 to 40% by weight, and, based on the molar total amount of acrylic acid and the conjugate base thereof present in the aqueous solution, 60 to 80 mol % of at least one alkali metal cation, and, based on the weight of the aqueous solution, 50 to 65% by weight of water, the at least one alkali metal cation being $Li^+$, $Na^+$ and/or $K_+$ (the at least one alkali metal cation is advantageously $Na^+$ to an extent of at least 90 mol %, better $Na^+$ to an extent of at least 95 mol % and at best $Na^+$ to an extent of at least 99 mol % or to an extent of 100 mol % (in each case of the total molar amount thereof)).

The above aqueous solutions are referred to in this document as aqueous solutions $L_R$.

While the aqueous intermediates II, preferably in accordance with the invention, have a pH >7, the pH of preferred inventive aqueous solutions (for example of preferred aqueous solutions $L_A$, $L_B$, $L_C$, $L_D$, $L_E$, $L_F$, $L_G$, $L_H$, $L_I$, $L_J$, $L_K$, $L_L$, $L_M$, $L_N$, $L_O$, $L_P$, $L_Q$ and $L_R$), advantageously in accordance with the invention, is in the range of 5 to 6.5, particularly advantageously in the range of 5.2 to 6.

Aqueous solutions which are obtainable in accordance with the invention (especially aqueous solutions $L_A$, $L_B$, $L_C$, $L_D$, $L_E$, $L_F$, $L_G$, $L_H$, $L_I$, $L_J$, $L_K$, $L_L$, $L_M$, $L_N$, $L_O$, $L_P$, $L_Q$ and $L_R$) and which have a pH of 4 to 5.7, or of 4.4 to 5.1, are likewise particularly advantageous, following the teaching of WO 03/002623.

It will be appreciated, however, that aqueous solutions $L_A$, $L_B$, $L_C$, $L_D$, $L_E$, $L_F$, $L_G$, $L_H$, $L_I$, $L_J$, $L_K$, $L_L$, $L_M$, $L_N$, $L_O$, $L_P$, $L_Q$ and $L_R$ which are obtainable in accordance with the invention and whose pH is >6.5, or >7, are also of significance for numerous further uses.

In general, all aqueous solutions obtainable in accordance with the invention (for example solutions $L_A$, $L_B$, $L_C$, $L_D$, $L_E$, $L_F$, $L_G$, $L_H$, $L_I$, $L_J$, $L_K$, $L_L$, $L_M$, $L_N$, $L_O$, $L_P$, $L_Q$ and $L_R$), based on the molar total amount of alkali metal cations present therein, comprise ≤5 mol %, preferably ≤4 mol %, more preferably ≤3 mol %, even more preferably ≤2 mol % or ≤1 mol %, of cations other than alkali metal cations and other than $H^+$ (and reaction products thereof with water). Such aqueous solutions are referred to in this document as aqueous solutions $L_S$.

In general, all aqueous solutions obtainable in accordance with the invention (for example solutions $L_A$, $L_B$, $L_C$, $L_D$, $L_E$, $L_F$, $L_G$, $L_H$, $L_I$, $L_J$, $L_K$, $L_L$, $L_M$, $L_N$, $L_O$, $L_P$, $L_Q$, $L_R$ and $L_S$), based on the molar total amount of alkali metal cations present therein, comprise ≤5 mol %, preferably ≤4 mol %, more preferably ≤3 mol %, even more preferably ≤2 mol % or ≤1 mol % of anions other than $CO_3^{2-}$, $HCO_3^-$, $^-OH$ (and the reaction products thereof with water), conjugate bases of carboxylic acids and carboxylic anhydrides present in the product gas mixture of the partial oxidation, other than conjugate bases of the Michael adducts of acrylic acid, and other than conjugate bases of oligomers containing free-radically polymerized acrylic acid. Such aqueous solutions are referred to in this document as aqueous solution $L_T$. In other words, the amount of at least one alkali metal cation in mol % present in the aqueous solutions $L_A$, $L_B$, $L_C$, $L_D$, $L_E$, $L_F$, $L_G$, $L_H$, $L_I$, $L_J$, $L_K$, $L_L$, $L_M$, $L_N$, $L_O$, $L_P$, $L_Q$, $L_R$, $L_S$ and $L_T$ obtainable in accordance with the invention, based on the molar total amount of acrylic acid and the conjugate base thereof present therein, normally corresponds essentially to the degree of neutralization of the molar total amount of acrylic acid and the conjugate base thereof present in these aqueous solutions overall, calculated as acrylic acid.

The inventive embodiments of this document also include aqueous solutions (obtainable in accordance with the invention) $L_A$, $L_B$, $L_C$, $L_D$, $L_E$, $L_F$, $L_G$, $L_H$, $L_I$, $L_J$, $L_K$, $L_L$, $L_M$, $L_N$, $L_O$, $L_P$, $L_Q$, $L_R$, $L_S$ and $L_T$ which, based on the molar amount of acrylic acid and the conjugate base thereof present therein, comprise 0.001 to 5 mol % of at least one compound having at least two ethylenically unsaturated double bonds which may also be conjugated to one another. When the product gas mixture formed in the partial oxidation zone of the process according to the invention also comprises 3-furaldehyde as a by-product, the characteristics thereof in the process according to the invention are as indicated for 2-furaldehyde in the present document. The same applies to protoanemonin if the product gas mixture comprises it as a by-product. Based on the molar amount of 2-furaldehyde present in the product gas mixture, the product gas mixture comprises both 3-furaldehyde and protoanemonin normally each in amounts of only <10 mol % (this is especially true when the $C_3$ precursor compound of acrylic acid is propene).

When the product gas mixture formed in the partial oxidation zone of the process according to the invention also comprises allyl acrylate and/or allyl formate as a by-product, the characteristics of these two compounds in the process according to the invention are as indicated for acrolein in the present document. The same applies to propionaldehyde if the product gas mixture comprises it as a by-product. If propene is the at least one $C_3$ precursor compound, the product gas mixture comprises both allyl acrylate and allyl formate, and propionaldehyde, based on the molar amount of acrolein present in the product gas mixture, normally in each case in an amount of <2 mol %.

In principle, it is possible to use aqueous solutions of superabsorbent polymers obtained using aqueous solutions $L_A, L_B, L_C, L_D, L_E, L_F, L_G, L_H, L_I, L_J, L_K, L_L, L_M, L_N, L_O, L_P, L_Q, L_R, L_S$ and/or $L_T$ prepared in accordance with the invention in the hygiene sector too.

It is advantageous in accordance with the invention that the aqueous solutions $L_A, L_B, L_C, L_D, L_E, L_F, L_G, L_H, L_I, L_J, L_K, L_L, L_M, L_N, L_O, L_P, L_Q, L_R, L_S$ and $L_T$ are obtainable by the inventive procedure with an MEHQ content which is generally, based on the weight of the aqueous solution, not more than 200 ppm by weight, advantageously not more than 100 ppm by weight, particularly advantageously not more than 50 ppm by weight and particularly advantageously not more than 20 ppm by weight. Normally, the MEHQ content in these aqueous solutions on this basis will, however, be 5 ppm by weight. As a coinhibitor, the aqueous solutions, appropriately in application terms, comprise molecular oxygen in dissolved form. Further polymerization inhibitors are typically not present in aforementioned aqueous solutions. More particularly, the content therein of methylene blue, phenothiazine and $Cu^{2+}/Cu^+$, each constituent taken alone and based on the weight of the aqueous solution, normally does not exceed 10 ppm by weight, preferably 5 ppm by weight, more preferably 1 ppm by weight and more preferably 0.1 ppm by weight. Particularly advantageously, the aforementioned polymerization inhibitors (retarders) are analytically undetectable in aqueous solutions obtainable in accordance with the invention.

It is also possible for the aqueous solutions $L_A, L_B, L_C, L_D, L_E, L_F, L_G, L_H, L_I, L_J, L_K, L_L, L_M, L_N, L_O, L_P, L_Q, L_R, L_S$ and $L_T$ obtainable in accordance with the invention, based on the weight thereof, to comprise 1 to 1000 ppm by weight of an organic solvent (of an organic extractant) (as recommended, for example, by US 2008/0119626 A1) which was neither part of the product gas mixture formed in the partial oxidation zone nor has formed through chemical reaction of constituents of this mixture in the course of the inventive preparation thereof.

The composition of mixtures which occur in the course of a preparation process according to the invention is obtainable by the methods of gas chromatography—GC, High-Pressure Liquid Chromatography—HPLC—(determination of the aldehydes preferably as hydrazines after reaction with 2,4-dinitrophenylhydrazine; determination of the carboxylic acids by ion exclusion chromatography) and of optical emission spectroscopy (determination of the alkali metal cations; especially ICP (inductively coupled plasma)—OES. pH values (especially in the value range of 4 to 10) relate to measurement at 25° C. and 1 atm (1.01 bar) with a glass electrode configured as a combination electrode. The latter was calibrated by means of buffer solutions which had a known pH close to the measurement sought. Water in condensed phases was determined by the Karl Fischer method. The compositions and flow rates cited in the examples which follow are based not only on analytical determinations but also on calculation elements from component balances, mass balances and energy (heat) balances.

Since formaldehyde and 2-methylene glycol cannot normally be differentiated analytically (for example by gas chromatography), the amounts detected analytically in the working examples were reported as entirely methylene glycol in the case of water-comprising liquid phases, and entirely as formaldehyde in the case of gas phases. To determine the "total formaldehyde content" in liquid phases, 10 ml of a 10% by weight aqueous sulfuric acid with hydrolyzing action were first added to a sample volume of 100 to 200 mg for analysis. By subsequent distillation at standard pressure (Eppendorf Micro Distiller, 112 to 120° C., approx. 2 h) and absorption in an initial charge of water, the formaldehyde was removed. Then the formaldehyde was reacted with acetyl acetone in an aqueous medium buffered with ammonium acetate/acetic acid (Hantzsch reaction). This formed a yellow dihydrolutidine derivative which was quantified on the basis of its UV/VIS absorbance at 412 nm using a calibration curve drawn up beforehand (cf. also B. Kakac, Z. J. Vejdelek, Handbuch der photometrischen Analyse organischer Verbindungen [Handbook of Photometric Analysis of Organic Compounds], volume 1, Verlag Chemie, 1974).

The present patent application thus comprises especially the following inventive embodiments:

1. An aqueous solution comprising acrylic acid and the conjugate base thereof in a total amount, calculated as acrylic acid, of at least 10% by weight, based on the weight of the aqueous solution, and, based on the total amount of acrylic acid and the conjugate base thereof present in the aqueous solution, calculated as acrylic acid,
   - ≥50 ppm by weight in total of propionic acid and the conjugate base thereof, calculated as propionic acid,
   - ≥200 ppm by weight in total of formic acid and the conjugate base thereof, calculated as formic acid,
   - ≥3000 ppm by weight in total of acetic acid and the conjugate base thereof, calculated as acetic acid,
   - ≤10 ppm by weight in total of benzoic acid and the conjugate base thereof, calculated as benzoic acid,
   - ≤10 ppm by weight in total of maleic anhydride, maleic acid and the conjugate bases thereof, calculated as maleic acid,
   - ≤10 ppm by weight in total of phthalic anhydride, phthalic acid and the conjugate bases thereof, calculated as phthalic acid,
   - ≤50 ppm by weight of acrolein,
   - ≤50 ppm by weight of benzaldehyde,
   - ≤50 ppm by weight of 2-furaldehyde, and
   at least 20 mol % of at least one alkali metal cation.

2. The aqueous solution according to embodiment 1, which comprises, based on the total amount of acrylic acid and the conjugate base thereof present in the aqueous solution, calculated as acrylic acid,
   - ≤5 ppm by weight in total of benzoic acid and the conjugate base thereof, calculated as benzoic acid,
   - ≤5 ppm by weight in total of maleic anhydride, maleic acid and the conjugate bases thereof, calculated as maleic acid, and
   - ≤5 ppm by weight in total of phthalic anhydride, phthalic acid and the conjugate bases thereof, calculated as phthalic acid.

3. The aqueous solution according to embodiment 1, which comprises, based on the total amount of acrylic acid and the conjugate base thereof present in the aqueous solution, calculated as acrylic acid, ≤1 ppm by weight in total of benzoic acid and the conjugate base thereof, calculated as benzoic acid,
≤1 ppm by weight in total of maleic anhydride, maleic acid and the conjugate bases thereof, calculated as maleic acid, and
≤1 ppm by weight in total of phthalic anhydride, phthalic acid and the conjugate bases thereof, calculated as phthalic acid.

4. The aqueous solution according to any of embodiments 1 to 3, which comprises, based on the total amount of acrylic acid and the conjugate base thereof present in the aqueous solution, calculated as acrylic acid,
≤40 ppm by weight of acrolein,
≤40 ppm by weight of benzaldehyde, and
≤40 ppm by weight of 2-furaldehyde.

5. The aqueous solution according to any of embodiments 1 to 3, which comprises, based on the total amount of acrylic acid and the conjugate base thereof present in the aqueous solution, calculated as acrylic acid,
≤30 ppm by weight of acrolein,
≤30 ppm by weight of benzaldehyde, and
≤30 ppm by weight of 2-furaldehyde.

6. The aqueous solution according to any of embodiments 1 to 3, which comprises, based on the total amount of acrylic acid and the conjugate base thereof present in the aqueous solution, calculated as acrylic acid,
≤20 ppm by weight of acrolein,
≤20 ppm by weight of benzaldehyde, and
≤20 ppm by weight of 2-furaldehyde.

7. The aqueous solution according to any of embodiments 1 to 3, which comprises, based on the total amount of acrylic acid and the conjugate base thereof present in the aqueous solution, calculated as acrylic acid,
≤10 ppm by weight of acrolein,
≤10 ppm by weight of benzaldehyde, and
≤10 ppm by weight of 2-furaldehyde.

8. The aqueous solution according to any of embodiments 1 to 3, which comprises, based on the total amount of acrylic acid and the conjugate base thereof present in the aqueous solution, calculated as acrylic acid,
≤5 ppm by weight of acrolein,
≤5 ppm by weight of benzaldehyde, and
≤5 ppm by weight of 2-furaldehyde.

9. The aqueous solution according to any of embodiments 1 to 3, which comprises, based on the total amount of acrylic acid and the conjugate base thereof present in the aqueous solution, calculated as acrylic acid,
≤1 ppm by weight of acrolein,
≤1 ppm by weight of benzaldehyde, and
≤1 ppm by weight of 2-furaldehyde.

10. The aqueous solution according to any of embodiments 1 to 9, which comprises, based on the total amount of acrylic acid and the conjugate base thereof present in the aqueous solution, calculated as acrylic acid,
≤0.25% by weight in total of propionic acid and the conjugate base thereof, calculated as propionic acid,
≤2.5% by weight in total of formic acid and the conjugate base thereof, calculated as formic acid, and
≤12% by weight in total of acetic acid and the conjugate base thereof, calculated as acetic acid.

11. The aqueous solution according to any of embodiments 1 to 9, which comprises, based on the total amount of acrylic acid and the conjugate base thereof present in the aqueous solution, calculated as acrylic acid,
≤0.20% by weight in total of propionic acid and the conjugate base thereof, calculated as propionic acid,
≤2.0% by weight in total of formic acid and the conjugate base thereof, calculated as formic acid, and
≤10% by weight in total of acetic acid and the conjugate base thereof, calculated as acetic acid.

12. The aqueous solution according to any of embodiments 1 to 9, which comprises, based on the total amount of acrylic acid and the conjugate base thereof present in the aqueous solution, calculated as acrylic acid,
≤0.15% by weight in total of propionic acid and the conjugate base thereof, calculated as propionic acid,
≤1.5% by weight in total of formic acid and the conjugate base thereof, calculated as formic acid, and
≤8% by weight in total of acetic acid and the conjugate base thereof, calculated as acetic acid.

13. The aqueous solution according to any of embodiments 1 to 9, which comprises, based on the total amount of acrylic acid and the conjugate base thereof present in the aqueous solution, calculated as acrylic acid,
≤0.1% by weight in total of propionic acid and the conjugate base thereof, calculated as propionic acid,
≤1% by weight in total of formic acid and the conjugate base thereof, calculated as formic acid, and
≤5% by weight in total of acetic acid and the conjugate base thereof, calculated as acetic acid.

14. The aqueous solution according to any of embodiments 1 to 13, which comprises, based on the total amount of acrylic acid and the conjugate base thereof present in the aqueous solution, calculated as acrylic acid,
≥100 ppm by weight in total of propionic acid and the conjugate base thereof, calculated as propionic acid,
≥500 ppm by weight in total of formic acid and the conjugate base thereof, calculated as formic acid, and
≥5000 ppm by weight in total of acetic acid and the conjugate base thereof, calculated as acetic acid.

15. The aqueous solution according to any of embodiments 1 to 13, which comprises, based on the total amount of acrylic acid and the conjugate base thereof present in the aqueous solution, calculated as acrylic acid,
≥150 ppm by weight in total of propionic acid and the conjugate base thereof, calculated as propionic acid,
≥750 ppm by weight in total of formic acid and the conjugate base thereof, calculated as formic acid, and
≥7500 ppm by weight in total of acetic acid and the conjugate base thereof, calculated as acetic acid.

16. The aqueous solution according to any of embodiments 1 to 13, which comprises, based on the total amount of acrylic acid and the conjugate base thereof present in the aqueous solution, calculated as acrylic acid,
≥180 ppm by weight in total of propionic acid and the conjugate base thereof, calculated as propionic acid,
≥1000 ppm by weight in total of formic acid and the conjugate base thereof, calculated as formic acid, and
≥1% by weight in total of acetic acid and the conjugate base thereof, calculated as acetic acid.

17. The aqueous solution according to any of embodiments 1 to 13, which comprises, based on the total amount of acrylic acid and the conjugate base thereof present in the aqueous solution, calculated as acrylic acid,
≥200 ppm by weight in total of propionic acid and the conjugate base thereof, calculated as propionic acid,
≥1500 ppm by weight in total of formic acid and the conjugate base thereof, calculated as formic acid, and
≥1.3% by weight in total of acetic acid and the conjugate base thereof, calculated as acetic acid.

18. The aqueous solution according to any of embodiments 1 to 17, which comprises, based on the molar total amount of acrylic acid and the conjugate base thereof present in the aqueous solution, 20 to 150 mol % of at least one alkali metal cation.

19. The aqueous solution according to any of embodiments 1 to 18, which comprises, based on the molar total amount of acrylic acid and the conjugate base thereof present in the aqueous solution, 30 to 140 mol % of at least one alkali metal cation.

20. The aqueous solution according to any of embodiments 1 to 19, which comprises, based on the molar total amount of acrylic acid and the conjugate base thereof present in the aqueous solution, 40 to 120 mol % of at least one alkali metal cation.

21. The aqueous solution according to any of embodiments 1 to 20, which comprises, based on the molar total amount of acrylic acid and the conjugate base thereof present in the aqueous solution, 50 to 110 mol % of at least one alkali metal cation.

22. The aqueous solution according to any of embodiments 1 to 21, which comprises, based on the molar total amount of acrylic acid and the conjugate base thereof present in the aqueous solution, 50 to 100 mol % of at least one alkali metal cation.

23. The aqueous solution according to any of embodiments 1 to 22, which comprises, based on the molar total amount of acrylic acid and the conjugate base thereof present in the aqueous solution, 50 to 95 mol % of at least one alkali metal cation.

24. The aqueous solution according to any of embodiments 1 to 23, which comprises, based on the molar total amount of acrylic acid and the conjugate base thereof present in the aqueous solution, 60 to 90 mol % of at least one alkali metal cation.

25. The aqueous solution according to any of embodiments 1 to 24, which comprises, based on the molar total amount of acrylic acid and the conjugate base thereof present in the aqueous solution, 60 to 80 mol % of at least one alkali metal cation.

26. The aqueous solution according to any of embodiments 1 to 25, which comprises, based on the molar total amount of acrylic acid and the conjugate base thereof present in the aqueous solution, 60 to 75 mol % of at least one alkali metal cation.

27. The aqueous solution according to any of embodiments 1 to 26, which comprises, based on the molar total amount of acrylic acid and the conjugate base thereof present in the aqueous solution, 65 to 75 mol % of at least one alkali metal cation.

28. The aqueous solution according to any of embodiments 1 to 27, wherein the at least one alkali metal cation is $Li^+$, $K^+$ and/or $Na^+$.

29. The aqueous solution according to any of embodiments 1 to 28, wherein the at least one alkali metal cation is $K^+$ and/or $Na^+$ to an extent of at least 50 mol % of the molar total amount thereof.

30. The aqueous solution according to any of embodiments 1 to 28, wherein the at least one alkali metal cation is $K^+$ and/or $Na^+$ to an extent of at least 75 mol % of the molar total amount thereof.

31. The aqueous solution according to any of embodiments 1 to 28, wherein the at least one alkali metal cation is $K^+$ and/or $Na^+$ to an extent of at least 90 mol % of the molar total amount thereof.

32. The aqueous solution according to any of embodiments 1 to 28, wherein the at least one alkali metal cation is $K^+$ and/or $Na^+$ to an extent of at least 95 mol % of the molar total amount thereof.

33. The aqueous solution according to any of embodiments 1 to 28, wherein the at least one alkali metal cation is $K^+$ and/or $Na^+$ to an extent of at least 98 mol % of the molar total amount thereof.

34. The aqueous solution according to any of embodiments 1 to 28, wherein the at least one alkali metal cation is $K^+$ and/or $Na^+$ to an extent of at least 99 mol % of the molar total amount thereof.

35. The aqueous solution according to any of embodiments 1 to 28, wherein the at least one alkali metal cation is $K^+$ and/or $Na^+$ to an extent of 100 mol % of the molar total amount thereof.

36. The aqueous solution according to any of embodiments 1 to 35, wherein the at least one alkali metal cation is Na to an extent of at least 50 mol % of the molar total amount thereof.

37. The aqueous solution according to any of embodiments 1 to 35, wherein the at least one alkali metal cation is $Na^+$ to an extent of at least 75 mol % of the molar total amount thereof.

38. The aqueous solution according to any of embodiments 1 to 35, wherein the at least one alkali metal cation is $Na^+$ to an extent of at least 90 mol % of the molar total amount thereof.

39. The aqueous solution according to any of embodiments 1 to 35, wherein the at least one alkali metal cation is $Na^+$ to an extent of at least 95 mol % of the molar total amount thereof.

40. The aqueous solution according to any of embodiments 1 to 35, wherein the at least one alkali metal cation is $Na^+$ to an extent of at least 98 mol % of the molar total amount thereof.

41. The aqueous solution according to any of embodiments 1 to 35, wherein the at least one alkali metal cation is $Na^+$ to an extent of at least 99 mol % of the molar total amount thereof.

42. The aqueous solution according to any of embodiments 1 to 35, wherein the at least one alkali metal cation is $Na^+$ to an extent of 100 mol % of the molar total amount thereof.

43. The aqueous solution according to any of embodiments 1 to 42, which comprises, based on the weight of the aqueous solution, 15 to 85% by weight of water.

44. The aqueous solution according to any of embodiments 1 to 43, which comprises, based on the weight of the aqueous solution, 30 to 80% by weight of water.

45. The aqueous solution according to any of embodiments 1 to 44, which comprises, based on the weight of the aqueous solution, 40 to 70% by weight of water.

46. The aqueous solution according to any of embodiments 1 to 45, which comprises, based on the weight of the aqueous solution, 50 to 65% by weight of water.

47. The aqueous solution according to any of embodiments 1 to 46, which comprises, based on the weight of the aqueous solution, 55 to 60% by weight of water.

48. The aqueous solution according to any of embodiments 1 to 45, which comprises, based on the weight of the aqueous solution, ≤65% by weight of water.

49. The aqueous solution according to any of embodiments 1 to 46, which comprises, based on the weight of the aqueous solution, 60% by weight of water.

50. The aqueous solution according to any of embodiments 1 to 49, comprising acrylic acid and the conjugate base thereof in a total amount, calculated as acrylic acid and based on the weight of the aqueous solution, of at least 15% by weight.

51. The aqueous solution according to any of embodiments 1 to 49, comprising acrylic acid and the conjugate base thereof in a total amount, calculated as acrylic acid and based on the weight of the aqueous solution, of at least 20% by weight.
52. The aqueous solution according to any of embodiments 1 to 49, comprising acrylic acid and the conjugate base thereof in a total amount, calculated as acrylic acid and based on the weight of the aqueous solution, of at least 25% by weight.
53. The aqueous solution according to any of embodiments 1 to 52, comprising acrylic acid and the conjugate base thereof in a total amount, calculated as acrylic acid and based on the weight of the aqueous solution, of not more than 70% by weight.
54. The aqueous solution according to any of embodiments 1 to 52, comprising acrylic acid and the conjugate base thereof in a total amount, calculated as acrylic acid and based on the weight of the aqueous solution, of not more than 60% by weight.
55. The aqueous solution according to any of embodiments 1 to 52, comprising acrylic acid and the conjugate base thereof in a total amount, calculated as acrylic acid and based on the weight of the aqueous solution, of not more than 50% by weight.
56. The aqueous solution according to any of embodiments 1 to 52, comprising acrylic acid and the conjugate base thereof in a total amount, calculated as acrylic acid and based on the weight of the aqueous solution, of 25 to 40% by weight.
57. The aqueous solution according to any of embodiments 1 to 52, comprising acrylic acid and the conjugate base thereof in a total amount, calculated as acrylic acid and based on the weight of the aqueous solution, of 25 to 35% by weight.
58. The aqueous solution according to any of embodiments 1 to 17, comprising acrylic acid and the conjugate base thereof in a total amount, calculated as acrylic acid and based on the weight of the aqueous solution, of 20 to 40% by weight, and, based on the molar total amount of acrylic acid and the conjugate base thereof present in the aqueous solution, 60 to 80 mol % of at least one alkali metal cation, and, based on the weight of the aqueous solution, 50 to 65% by weight of water, where the at least one alkali metal cation is $Li^+$, $Na^+$ and/or $K^+$.
59. The aqueous solution according to embodiment 58, wherein the at least one alkali metal cation is $Na^+$ to an extent of at least 90 mol % of the total molar amount thereof.
60. The aqueous solution according to embodiment 58, wherein the at least one alkali metal cation is $Na^+$ to an extent of at least 95 mol % of the total molar amount thereof.
61. The aqueous solution according to embodiment 58, wherein the at least one alkali metal cation is $Na^+$ to an extent of at least 99 mol % of the total molar amount thereof.
62. The aqueous solution according to embodiment 58, wherein the at least one alkali metal cation is $Na^+$ to an extent of 100 mol % of the total molar amount thereof.
63. The aqueous solution according to any of embodiments 1 to 62, the pH of which is 5 to 6.5.
64. The aqueous solution according to any of embodiments 1 to 62, the pH of which is 5.2 to 6.
65. The aqueous solution according to any of embodiments 1 to 62, the pH of which is 4 to 5.7.
66. The aqueous solution according to any of embodiments 1 to 62, the pH of which is 4.4 to 5.1.
67. The aqueous solution according to any of embodiments 1 to 62, the pH of which is >6.5.
68. The aqueous solution according to any of embodiments 1 to 62, the pH of which is >7.
69. The aqueous solution according to any of embodiments 1 to 68, comprising, based on the molar total amount of alkali metal cations present in the aqueous solution, ≤5 mol % of cations other than alkali metal cations and other than $H^+$ and the reaction products thereof with water.
70. The aqueous solution according to any of embodiments 1 to 68, comprising, based on the molar total amount of alkali metal cations present in the aqueous solution, ≤4 mol % of cations other than alkali metal cations and other than $H^+$ and the reaction products thereof with water.
71. The aqueous solution according to any of embodiments 1 to 68, comprising, based on the molar total amount of alkali metal cations present in the aqueous solution, ≤3 mol % of cations other than alkali metal cations and other than $H^+$ and the reaction products thereof with water.
72. The aqueous solution according to any of embodiments 1 to 68, comprising, based on the molar total amount of alkali metal cations present in the aqueous solution, 2 mol % of cations other than alkali metal cations and other than $H^+$ and the reaction products thereof with water.
73. The aqueous solution according to any of embodiments 1 to 68, comprising, based on the molar total amount of alkali metal cations present in the aqueous solution, ≤1 mol % of cations other than alkali metal cations and other than $H^+$ and the reaction products thereof with water.
74. The aqueous solution according to any of embodiments 1 to 73, comprising, based on the molar total amount of alkali metal cations present in the aqueous solution, ≤5 mol % of anions other than $CO_3^{2-}$, other than $HCO_3^-$, other than $^-OH$ and the reaction products thereof with water, other than conjugate bases of carboxylic acids and carboxylic anhydrides present in the product gas mixture of the partial oxidation, other than conjugate bases of the Michael adducts of acrylic acid, and other than conjugate bases of oligomers comprising free-radically polymerized acrylic acid.
75. The aqueous solution according to any of embodiments 1 to 73, comprising, based on the molar total amount of alkali metal cations present in the aqueous solution, ≤4 mol % of anions other than $CO_3^{2-}$, other than $HCO_3^-$, other than $^-OH$ and the reaction products thereof with water, other than conjugate bases of carboxylic acids and carboxylic anhydrides present in the product gas mixture of the partial oxidation, other than conjugate bases of the Michael adducts of acrylic acid, and other than conjugate bases of oligomers comprising free-radically polymerized acrylic acid.
76. The aqueous solution according to any of embodiments 1 to 73, comprising, based on the molar total amount of alkali metal cations present in the aqueous solution, ≤2 mol % of anions other than $CO_3^{2-}$, other than $HCO_3^-$, other than $^-OH$ and the reaction products thereof with water, other than conjugate bases of carboxylic acids and carboxylic anhydrides present in the product gas mixture of the partial oxidation, other than conjugate bases of the Michael adducts of acrylic acid, and other than conjugate bases of oligomers comprising free-radically polymerized acrylic acid.
77. The aqueous solution according to any of embodiments 1 to 73, comprising, based on the molar total amount of alkali metal cations present in the aqueous solution, ≤1 mol % of anions other than $CO_3^{2-}$, other than $HCO_3—$, other than $^-OH$ and the reaction products thereof with water, other than conjugate bases of carboxylic acids and carboxylic anhydrides present in the product gas mixture of the partial oxidation, other than conjugate bases of the Michael adducts of acrylic acid, and other than conjugate bases of oligomers comprising free-radically polymerized acrylic acid.

78. The aqueous solution according to any of embodiments 1 to 77, which comprises, based on the molar amount of acrylic acid and the conjugate base thereof present in the aqueous solution, 0.001 to 5 mol % of at least one compound having at least two ethylenically unsaturated double bonds which may be conjugated to one another.

79. The aqueous solution according to any of embodiments 1 to 78, comprising, based on the weight of the aqueous solution, ≤200 ppm by weight of 4-methoxyphenol.

80. The aqueous solution according to any of embodiments 1 to 78, comprising, based on the weight of the aqueous solution, ≤100 ppm by weight of 4-methoxyphenol.

81. The aqueous solution according to any of embodiments 1 to 78, comprising, based on the weight of the aqueous solution, ≤50 ppm by weight and 5 ppm by weight of 4-methoxyphenol.

82. The aqueous solution according to any of embodiments 1 to 78, comprising, based on the weight of the aqueous solution, ≤20 ppm by weight of 4-methoxyphenol.

83. The aqueous solution according to any of embodiments 1 to 82, comprising methylene blue, phenothiazine, $Cu^{2+}$ and $Cu^+$, each constituent taken alone and based on the weight of the aqueous solution, in amounts of ≤10 ppm by weight.

84. The aqueous solution according to any of embodiments 1 to 82, comprising methylene blue, phenothiazine, $Cu^{2+}$ and $Cu^+$, each constituent taken alone and based on the weight of the aqueous solution, in amounts of ≤5 ppm by weight.

85. The aqueous solution according to any of embodiments 1 to 82, comprising methylene blue, phenothiazine, $Cu^{2+}$ and $Cu^+$, each constituent taken alone and based on the weight of the aqueous solution, in amounts of ≤1 ppm by weight.

86. The aqueous solution according to any of embodiments 1 to 82, comprising methylene blue, phenothiazine, $Cu^{2+}$ and $Cu^+$, each constituent taken alone and based on the weight of the aqueous solution, in amounts of ≤0.1 ppm by weight.

87. The aqueous solution according to any of embodiments 1 to 82, comprising methylene blue, phenothiazine, $Cu^{2+}$ and $Cu^+$, each constituent taken alone and based on the weight of the aqueous solution, in analytically undetectable amounts.

88. An aqueous mixture obtainable by adding up to 40 mol % of at least one monoethylenically unsaturated compound other than acrylic acid and the conjugate base thereof to an aqueous solution according to any of embodiments 1 to 87, based on the molar total amount of acrylic acid and the conjugate base thereof present in the aqueous solution.

89. An aqueous mixture obtainable by adding up to 30 mol % of at least one monoethylenically unsaturated compound other than acrylic acid and the conjugate base thereof to an aqueous solution according to any of embodiments 1 to 87, based on the molar total amount of acrylic acid and the conjugate base thereof present in the aqueous solution.

90. An aqueous mixture obtainable by adding up to 20 mol % of at least one monoethylenically unsaturated compound other than acrylic acid and the conjugate base thereof to an aqueous solution according to any of embodiments 1 to 87, based on the molar total amount of acrylic acid and the conjugate base thereof present in the aqueous solution.

91. An aqueous mixture obtainable by adding up to 10 mol % of at least one monoethylenically unsaturated compound other than acrylic acid and the conjugate base thereof to an aqueous solution according to any of embodiments 1 to 87, based on the molar total amount of acrylic acid and the conjugate base thereof present in the aqueous solution.

92. An aqueous mixture obtainable by adding up to 5 mol % of at least one monoethylenically unsaturated compound other than acrylic acid and the conjugate base thereof to an aqueous solution according to any of embodiments 1 to 87, based on the molar total amount of acrylic acid and the conjugate base thereof present in the aqueous solution.

93. The aqueous mixture according to any of embodiments 88 to 92, wherein the at least one monoethylenically unsaturated compound other than acrylic acid and the conjugate base thereof is selected from the group consisting of methacrylic acid, maleic acid, itaconic acid, 2-acrylamido-2-methylpropanesulfonic acid, amides of the acids mentioned, alkali metal salts of the acids mentioned, ammonium salts of the acids mentioned, monohydroxyalkyl esters of acrylic acid, monohydroxyalkyl esters of methacrylic acid, N-vinylformamide, styrene, (meth)acrylic esters of monohydric alcohols, acrylonitrile, methacrylonitrile, and vinyl esters such as vinyl acetate and vinyl propionate.

94. A process for preparing an aqueous target product solution comprising acrylic acid and the conjugate base thereof, which comprises the following process measures:
at least one $C_3$ precursor compound of acrylic acid is passed as a constituent of a reaction gas input mixture comprising the at least one $C_3$ precursor compound of acrylic acid, molecular oxygen and at least one inert diluent gas other than $CO_2$ and water through a partial oxidation zone (charged with catalysts in the solid state) and partially oxidized therein to acrylic acid by a heterogeneously catalyzed gas phase partial oxidation over (the) catalysts present in the solid state with the molecular oxygen to obtain a product gas mixture comprising $CO_2$, water, the target product acrylic acid, the secondary constituents formic acid, acetic acid, propionic acid, benzoic acid, acrolein, benzaldehyde, 2-furaldehyde, phthalic anhydride and/or phthalic acid, maleic anhydride and/or maleic acid, and at least one inert diluent gas other than $CO_2$ and water, the product gas mixture conducted out of the partial oxidation zone, optionally after its temperature has been reduced in a cooling zone by direct and/or indirect cooling, is conducted through an absorption zone I in which an absorbent I conducted in cocurrent or in countercurrent to the product gas mixture, on the route of the product gas mixture through absorption zone I, scrubs the secondary constituents benzoic acid, phthalic acid and/or the anhydride thereof and maleic acid and/or the anhydride thereof out of the product gas mixture by absorption to form an absorbate I, the absorbate I is discharged from absorption zone I and the scrubbed product gas mixture conducted out of absorption zone I is conducted through a condensation zone I and, on the route of the scrubbed product gas mixture through condensation zone I, an aqueous acrylic acid solution also comprising the secondary constituents formic acid, acetic acid, propionic acid, acrolein, benzaldehyde and 2-furaldehyde in dissolved form is condensed as condensate I out of the scrubbed product gas mixture by direct and/or indirect cooling thereof, with the proviso that there remains a $CO_2$— and water-comprising residual gas mixture I which, aside from the at least one inert diluent gas other than $CO_2$ and water, and acetic acid, propionic acid, acrolein, benzaldehyde and 2-furaldehyde as secondary constituents, still comprises at least 10% of the amount of acrylic acid present in the product gas mixture, at least a portion of condensate I is conducted as absorbent I into the absorption zone I, and any remaining residual amount of condensate I is conducted out of condensation zone I as aqueous intermediate I, the residual gas mixture I conducted out of condensation zone I is passed through an absorption zone II in which an aqueous alkali metal base is conducted in cocurrent or in countercurrent to the residual gas mixture I as absorbent II and, on the route of the residual gas mixture I through the absorption zone II, scrubs out not only acrylic acid but also $CO_2$, and also the secondary constituents formic acid, acetic acid, propionic acid, acrolein, benzaldehyde and 2-furaldehyde, out of residual gas mixture I by absorption to form an aqueous alkali metal acrylate solution as absorbate II, leaving a residual gas mixture II which comprises, aside from the at least one inert diluent gas other than $CO_2$ and water and a residual amount of acrylic acid, also water, residual gas mixture II is conducted out of absorption zone II, and absorbate II is withdrawn from absorption zone II as aqueous intermediate II, if no aqueous intermediate I is conducted out of condensation zone I, the acrolein, benzaldehyde and 2-furaldehyde secondary constituents present in the aqueous intermediate II are absorbed therefrom by extraction with an organic extractant, and the remaining aqueous raffinate II is removed from the organic extract II formed as the aqueous target product solution comprising acrylic acid and the conjugate base thereof, if aqueous intermediate I is conducted out of condensation zone I, the acrolein, benzaldehyde and 2-furaldehyde secondary constituents present in the aqueous intermediate II are absorbed therefrom by extraction with an organic extractant, and the remaining aqueous raffinate II is removed from the organic extract II formed, and the acrolein, benzaldehyde and 2-furaldehyde secondary constituents present in the aqueous intermediate I are absorbed therefrom by extraction with an organic extractant, and the remaining aqueous raffinate I is removed from the organic extract I formed, and the aqueous raffinate II and the aqueous raffinate I are combined (merged) to give the aqueous target product solution comprising the acrylic acid and the conjugate base thereof, from which $CO_2$ is optionally outgassed, or the aqueous intermediate II and the aqueous intermediate I are combined (merged) to give an aqueous intermediate III, and the acrolein, benzaldehyde and 2-furaldehyde secondary constituents present in the aqueous intermediate III, from which $CO_2$ is optionally outgassed beforehand, are absorbed therefrom by extraction with an organic extractant, and the remaining aqueous raffinate III is removed from the organic extract III formed as the aqueous target product solution comprising acrylic acid and the conjugate base thereof.

95. The process according to embodiment 94, wherein the product gas mixture is conducted through absorption zone I after its temperature has been reduced in a cooling zone by direct cooling with a cooling liquid.

96. The process according to embodiment 95, wherein the cooling liquid and the product gas mixture are conducted in cocurrent in the cooling zone.

97. The process according to embodiment 95 or 96, wherein the cooling liquid used in absorption zone I is absorbate I which has been formed and discharged therefrom, and the cooled product gas mixture is conducted into absorption zone I in a mixture with the absorbate I used for cooling thereof from the cooling zone.

98. The process according to embodiment 97, wherein the temperature of the absorbate I used as cooling liquid is 90 to 120° C.

99. The process according to any of embodiments 94 to 98, wherein the temperature of the product gas mixture comprising acrylic acid as the target product on entry thereof into absorption zone I is 90 to 180° C.

100. The process according to any of embodiments 94 to 99, wherein the temperature of the product gas mixture comprising acrylic acid as the target product on entry thereof into absorption zone I is 95 to 170° C.

101. The process according to any of embodiments 94 to 100, wherein the temperature of the product gas mixture comprising acrylic acid as the target product on entry thereof into absorption zone I is 100 to 150° C.

102. The process according to any of embodiments 94 to 101, wherein the temperature of the product gas mixture comprising acrylic acid as the target product on exit thereof from the partial oxidation zone is 150 to 350° C.

103. The process according to any of embodiments 94 to 102, wherein the temperature of the product gas mixture comprising acrylic acid as the target product on exit thereof from the partial oxidation zone is 200 to 300° C.

104. The process according to any of embodiments 94 to 103, wherein absorbent I in absorption zone I is conducted in countercurrent to the product gas mixture conducted through absorption zone I, and absorption zone I has separating internals.

105. The process according to embodiment 104, wherein absorption zone I has 1 to 5 theoretical plates.

106. The process according to embodiment 104 or 105, wherein absorption zone I has 1 to 3 theoretical plates.

107. The process according to any of embodiments 94 to 106, wherein absorption zone I is operated with thermal insulation from the environment.

108. The process according to any of embodiments 94 to 107, wherein the absorbent I used is condensate I formed in condensation zone I and conducted out of it.

109. The process according to embodiment 108, wherein condensate I, based on the weight thereof, comprises at least 20% by weight of acrylic acid.

110. The process according to embodiment 108, wherein condensate I, based on the weight thereof, comprises at least 30% by weight of acrylic acid.

111. The process according to embodiment 108, wherein condensate I, based on the weight thereof, comprises at least 40% by weight of acrylic acid.

112. The process according to embodiment 108, wherein condensate I, based on the weight thereof, comprises at least 50% by weight of acrylic acid.

113. The process according to any of embodiments 108 to 112, wherein condensate I, based on the weight thereof, comprises ≤95% by weight of acrylic acid.

114. The process according to any of embodiments 108 to 113, wherein condensate I, based on the weight thereof, comprises ≤90% by weight of acrylic acid.

115. The process according to any of embodiments 108 to 114, wherein condensate I, based on the weight thereof, comprises 50 to 80% by weight of acrylic acid.

116. The process according to any of embodiments 108 to 115, wherein condensate I, based on the weight thereof, comprises 50 to 70% by weight of acrylic acid.

117. The process according to any of embodiments 94 to 116, wherein absorbent I is supplied to absorption zone I with a temperature of 40 to 70° C.
118. The process according to any of embodiments 94 to 117, wherein absorbent I is supplied to absorption zone I with a temperature of 45 to 65° C.
119. The process according to any of embodiments 94 to 118, wherein no condensate I is conducted as aqueous intermediate I out of condensation zone I.
120. The process according to any of embodiments 94 to 119, wherein the product gas mixture scrubbed in absorption zone I is cooled in condensation zone I by direct cooling with a cooling liquid.
121. The process according to embodiment 120, wherein condensate I withdrawn from condensation zone I as cooling liquid is cooled in an indirect heat exchanger and then recycled into condensation zone I.
122. The process according to embodiment 121, wherein the difference between that temperature with which condensate I is withdrawn from condensation zone I and that temperature with which it is recycled into condensation zone I is 10 to 30° C.
123. The process according to embodiment 121, wherein the difference between that temperature with which condensate I is withdrawn from condensation zone I and that temperature with which it is recycled into condensation zone I is 15 to 25° C.
124. The process according to any of embodiments 120 to 123, wherein condensation zone I has separating internals and the cooling liquid is conducted in condensation zone I in countercurrent to the product gas mixture which has been conducted through condensation zone I and scrubbed in absorption zone I.
125. The process according to any of embodiments 94 to 124, wherein the residual gas mixture I conducted out of condensation zone I comprises at least 10% of the acrylic acid present in the product gas mixture conducted out of the partial oxidation zone.
126. The process according to any of embodiments 94 to 124, wherein the residual gas mixture I conducted out of condensation zone I comprises at least 15% of the acrylic acid present in the product gas mixture conducted out of the partial oxidation zone.
127. The process according to any of embodiments 94 to 124, wherein the residual gas mixture I conducted out of condensation zone I comprises at least 20% of the acrylic acid present in the product gas mixture conducted out of the partial oxidation zone.
128. The process according to any of embodiments 94 to 124, wherein the residual gas mixture I conducted out of condensation zone I comprises at least 25% of the acrylic acid present in the product gas mixture conducted out of the partial oxidation zone.
129. The process according to any of embodiments 94 to 124, wherein the residual gas mixture I conducted out of condensation zone I comprises at least 30% of the acrylic acid present in the product gas mixture conducted out of the partial oxidation zone.
130. The process according to any of embodiments 94 to 129, wherein the residual gas mixture I conducted out of condensation zone I comprises ≤99.8% of the acrylic acid present in the product gas mixture conducted out of the partial oxidation zone.
131. The process according to any of embodiments 94 to 129, wherein the residual gas mixture I conducted out of condensation zone I comprises ≤99.5% of the acrylic acid present in the product gas mixture conducted out of the partial oxidation zone.
132. The process according to any of embodiments 121 to 131, wherein an absorption of acrylic acid present in the product gas mixture stream scrubbed in absorption zone I into water is additionally superimposed on the condensation of an aqueous acrylic acid solution brought about in condensation zone I by direct cooling of the product gas mixture scrubbed in absorption zone I with cooled condensate I withdrawn beforehand from condensation zone I.
133. The process according to embodiment 132, wherein the flow rate in kg/h of the water stream supplied as absorbent to condensation zone I is less than the flow rate in kg/h of the stream of cooled condensate I supplied simultaneously as cooling liquid to condensation zone I.
134. The process according to embodiment 133, wherein the flow rate of the water stream is less than 50% of the flow rate of the stream of cooled condensate I supplied.
135. The process according to embodiment 133, wherein the flow rate of the water stream is less than 40% of the flow rate of the stream of cooled condensate I supplied.
136. The process according to embodiment 133, wherein the flow rate of the water stream is less than 30% of the flow rate of the stream of cooled condensate I supplied.
137. The process according to embodiment 133, wherein the flow rate of the water stream is less than 20% of the flow rate of the stream of cooled condensate I supplied.
138. The process according to any of embodiments 133 to 137, wherein the flow rate of the water stream is not less than 1% of the flow rate of the stream of cooled condensate I supplied.
139. The process according to any of embodiments 133 to 137, wherein the flow rate of the water stream is not less than 5% of the flow rate of the stream of cooled condensate I supplied.
140. The process according to any of embodiments 94 to 118 or according to any of embodiments 120 to 139, wherein aqueous intermediate I is conducted out of condensation zone I.
141. The process according to embodiment 140, wherein the molar ratio M=TI/TII of the molar total amount TI of acrylic acid and the conjugate base thereof present in the aqueous intermediate I to the molar total amount TII of acrylic acid and the conjugate base thereof present in the aqueous intermediate II is >0 to 6:1.
142. The process according to embodiment 141, wherein M is 1:6 to 6:1.
143. The process according to embodiment 141, wherein M is >0 to 5:1.
144. The process according to embodiment 141, wherein M is 1:5 to 5:1.
145. The process according to embodiment 141, wherein M is >0 to 4:1.
146. The process according to embodiment 141, wherein M is 1:4 to 4:1.
147. The process according to embodiment 141, wherein M is 2:1 to 5:1.
148. The process according to embodiment 141, wherein M is 2:1 to 4:1.
149. The process according to any of embodiments 94 to 148, wherein the aqueous target product solution comprising acrylic acid and the conjugate base thereof, based on the weight of the aqueous solution, comprises 15 to 85% by weight of water.
150. The process according to any of embodiments 94 to 149, wherein the aqueous target product solution comprising acrylic acid and the conjugate base thereof, based on the weight of the aqueous solution, comprises 30 to 80% by weight of water.

151. The process according to any of embodiments 94 to 150, wherein the aqueous target product solution comprising acrylic acid and the conjugate base thereof, based on the weight of the aqueous solution, comprises 40 to 70% by weight of water.

152. The process according to any of embodiments 94 to 151, wherein the aqueous target product solution comprising acrylic acid and the conjugate base thereof, based on the weight of the aqueous solution, comprises 50 to 65% by weight of water.

153. The process according to any of embodiments 149 to 152, wherein the aqueous target product solution comprising acrylic acid and the conjugate base thereof, based on the weight of the aqueous solution, comprises not more than 65% by weight of water.

154. The process according to any of embodiments 149 to 152, wherein the aqueous target product solution comprising acrylic acid and the conjugate base thereof, based on the weight of the aqueous solution, comprises not more than 60% by weight of water.

155. The process according to any of embodiments 94 to 154, wherein the aqueous alkali metal base is an aqueous solution comprising at least one alkali metal salt from the group consisting of the alkali metal oxides, the alkali metal hydroxides, the alkali metal carbonates, the alkali metal hydrogencarbonates and the hydrates of the aforementioned salts, in dissolved or dissolved and suspended form.

156. The process according to embodiment 155, wherein the at least one alkali metal salt is at least one salt from the group consisting of $Li_2O$, $LiOH$, $LiHCO_3$, $Li_2CO_3$, $Na_2O$, $NaOH$, $NaHCO_3$, $Na_2CO_3$, $K_2O$, $KOH$, $KHCO_3$, $K_2CO_3$ and the hydrates of the aforementioned salts.

157. The process according to embodiment 155 or 156, wherein the at least one alkali metal salt is a salt of potassium and/or sodium.

158. The process according to embodiment 155 or 156, wherein the at least one alkali metal salt is a salt of sodium.

159. The process according to embodiment 155 or 156, wherein the at least one alkali metal salt is KOH and/or NaOH.

160. The process according to embodiment 155 or 156, wherein the at least one alkali metal salt is NaOH.

161. The process according to any of embodiments 155 to 160, wherein the aqueous alkali metal base, based on the weight thereof, comprises at least 10% by weight of the at least one alkali metal salt.

162. The process according to any of embodiments 155 to 160, wherein the aqueous alkali metal base, based on the weight thereof, comprises at least 20% by weight of the at least one alkali metal salt.

163. The process according to any of embodiments 155 to 160, wherein the aqueous alkali metal base, based on the weight thereof, comprises at least 30% by weight of the at least one alkali metal salt.

164. The process according to any of embodiments 155 to 160, wherein the aqueous alkali metal base, based on the weight thereof, comprises at least 40% by weight of the at least one alkali metal salt.

165. The process according to any of embodiments 155 to 164, wherein the aqueous alkali metal base, based on the weight thereof, comprises not more than 60% by weight of the at least one alkali metal salt.

166. The process according to any of embodiments 155 to 164, wherein the aqueous alkali metal base, based on the weight thereof, comprises not more than 50% by weight of the at least one alkali metal salt.

167. The process according to embodiment 155, wherein the aqueous alkali metal base, based on the weight thereof, comprises 20 to 40% by weight of NaOH and/or KOH.

168. The process according to embodiment 155, wherein the aqueous alkali metal base, based on the weight thereof, comprises 20 to 30% by weight of NaOH and/or KOH.

169. The process according to any of embodiments 94 to 168, wherein absorbent II is supplied to absorption zone II with a temperature of 0 to 60° C.

170. The process according to any of embodiments 94 to 169, wherein absorbent II is supplied to absorption zone II with a temperature of 5 to 60° C.

171. The process according to any of embodiments 94 to 170, wherein absorbent II is supplied to absorption zone II with a temperature of 10 to 50° C.

172. The process according to any of embodiments 94 to 171, wherein absorbent II is supplied to absorption zone II with a temperature of 15 to 40° C.

173. The process according to any of embodiments 94 to 172, wherein absorbent II is supplied to absorption zone II with a temperature of 15 to 30° C.

174. The process according to any of embodiments 94 to 173, wherein the pH of absorbent II is at least 8.

175. The process according to any of embodiments 94 to 173, wherein the pH of absorbent II is at least 10.

176. The process according to any of embodiments 94 to 173, wherein the pH of absorbent II is at least 12.

177. The process according to any of embodiments 94 to 173, wherein the pH of absorbent II is at least 14.

178. The process according to any of embodiments 94 to 177, wherein absorbent II and the residual gas mixture I conducted out of the condensation zone I and through absorption zone II are conducted in countercurrent to one another within absorption zone II.

179. The process according to embodiment 178, wherein absorption zone II has separating internals.

180. The process according to any of embodiments 94 to 179, wherein the molar ratio MR=TAI/TAII of the molar total amount TAI of alkali metal cations present in absorbent II to the molar total amount TAII of acrylic acid present in the product gas mixture scrubbed in absorption zone I is at least 20:100.

181. The process according to any of embodiments 94 to 180, wherein the molar ratio MR=TAI/TAII of the molar total amount TAI of alkali metal cations present in absorbent II to the molar total amount TAII of acrylic acid present in the product gas mixture scrubbed in absorption zone I is at least 40:100.

182. The process according to any of embodiments 94 to 181, wherein the molar ratio MR=TAI/TAII of the molar total amount TAI of alkali metal cations present in absorbent II to the molar total amount TAII of acrylic acid present in the product gas mixture scrubbed in absorption zone I is at least 60:100.

183. The process according to any of embodiments 94 to 182, wherein the molar ratio MR=TAI/TAII of the molar total amount TAI of alkali metal cations present in absorbent II to the molar total amount TAII of acrylic acid present in the product gas mixture scrubbed in absorption zone I is ≤200:100.

184. The process according to any of embodiments 94 to 183, wherein the molar ratio MR=TAI/TAII of the molar total amount TAI of alkali metal cations present in absorbent II 184. (continued) to the molar total amount TAII of acrylic acid present in the product gas mixture scrubbed in absorption zone I is ≤150:100.
185. The process according to any of embodiments 94 to 184, wherein the molar ratio MR=TAI/TAII of the molar total amount TAI of alkali metal cations present in absorbent II to the molar total amount TAII of acrylic acid present in the product gas mixture scrubbed in absorption zone I is ≤110:100.
186. The process according to any of embodiments 94 to 181, wherein the molar ratio MR=TI/TAII of the molar total amount TAI of alkali metal cations present in absorbent II to the molar total amount TAII of acrylic acid present in the product gas mixture scrubbed in absorption zone I is 50 to 95:100.
187. The process according to any of embodiments 94 to 181, wherein the molar ratio MR=TAI/TAII of the molar total amount TAI of alkali metal cations present in absorbent II to the molar total amount TAII of acrylic acid present in the product gas mixture scrubbed in absorption zone I is 60 to 85:100.
188. The process according to any of embodiments 94 to 181, wherein the molar ratio MR=TAI/TAII of the molar total amount TAI of alkali metal cations present in absorbent II to the molar total amount TAII of acrylic acid present in the product gas mixture scrubbed in absorption zone I is 65 to 75:100.
189. The process according to any of embodiments 94 to 188, wherein the molar ratio MR*=TAI/TAII* of the molar total amount TAI of alkali metal cations present in absorbent II to the molar total amount TAII* of acrylic acid present in residual gas mixture I is ≥50:100.
190. The process according to any of embodiments 94 to 188, wherein the molar ratio MR*=TAI/TAII* of the molar total amount TAI of alkali metal cations present in absorbent II to the molar total amount TAII* of acrylic acid present in residual gas mixture I is ≥70:100.
191. The process according to any of embodiments 94 to 188, wherein the molar ratio MR*=TAI/TAII* of the molar total amount TAI of alkali metal cations present in absorbent II to the molar total amount TAII* of acrylic acid present in residual gas mixture I is ≥90:100.
192. The process according to any of embodiments 94 to 188, wherein the molar ratio MR*=TAI/TAII* of the molar total amount TAI of alkali metal cations present in absorbent II to the molar total amount TAII* of acrylic acid present in residual gas mixture I is ≥100:100.
193. The process according to any of embodiments 94 to 188, wherein the molar ratio MR*=TAI/TAII* of the molar total amount TAI of alkali metal cations present in absorbent II to the molar total amount TAII* of acrylic acid present in residual gas mixture I is ≥150:100.
194. The process according to any of embodiments 94 to 188, wherein the molar ratio MR*=TAI/TAII* of the molar total amount TAI of alkali metal cations present in absorbent II to the molar total amount TAII* of acrylic acid present in residual gas mixture I is ≥200:100.
195. The process according to any of embodiments 94 to 188, wherein the molar ratio MR*=TAI/TAII* of the molar total amount TAI of alkali metal cations present in absorbent II to the molar total amount TAII* of acrylic acid present in residual gas mixture I is ≥250:100.
196. The process according to any of embodiments 94 to 188, wherein the molar ratio MR*=TAI/TAII* of the molar total amount TAI of alkali metal cations present in absorbent II to the molar total amount TAII* of acrylic acid present in residual gas mixture I is ≥300:100.
197. The process according to any of embodiments 94 to 188, wherein the molar ratio MR*=TAI/TAII* of the molar total amount TAI of alkali metal cations present in absorbent II to the molar total amount TAII* of acrylic acid present in residual gas mixture I is ≤1000:100.
198. The process according to any of embodiments 94 to 188, wherein the molar ratio MR*=TAI/TAII* of the molar total amount TAI of alkali metal cations present in absorbent II to the molar total amount TAII* of acrylic acid present in residual gas mixture I is ≤800:100.
199. The process according to any of embodiments 94 to 188, wherein the molar ratio MR*=TAI/TAII* of the molar total amount TAI of alkali metal cations present in absorbent II to the molar total amount TAII* of acrylic acid present in residual gas mixture I is ≤600:100.
200. The process according to any of embodiments 94 to 199, wherein the number of theoretical plates in absorption zone II is not more than five.
201. The process according to embodiment 200, wherein the number of theoretical plates in absorption zone II is at least 1.
202. The process according to any of embodiments 94 to 201, wherein cooling of the residual gas mixture I conducted through absorption zone II by direct and/or indirect cooling is superimposed on the absorption in absorption zone II.
203. The process according to embodiment 202, wherein the cooling is brought about by direct cooling with a cooling liquid.
204. The process according to embodiment 203, wherein the cooling liquid is absorbate II withdrawn from absorption zone II, cooled in an indirect heat exchanger and then recycled into absorption zone II.
205. The process according to embodiment 204, wherein the difference between that temperature with which absorbate II is withdrawn from absorption zone II and that temperature with which it is recycled in cooled form into absorption zone II after flowing through the indirect heat exchanger is 5 to 30° C.
206. The process according to embodiment 204, wherein the difference between that temperature with which absorbate II is withdrawn from absorption zone II and that temperature with which it is recycled in cooled form into absorption zone II after flowing through the indirect heat exchanger is 5 to 15° C.
207. The process according to any of embodiments 94 to 206, wherein the aqueous intermediate II conducted out of absorption zone II has a temperature of 40 to 60° C.
208. The process according to any of embodiments 94 to 207, wherein the residual gas mixture II conducted out of absorption zone II comprises at least 60% of the acrolein present in the product gas mixture conducted out of the partial oxidation zone.
209. The process according to any of embodiments 94 to 207, wherein the residual gas mixture II conducted out of absorption zone II comprises at least 70% of the acrolein present in the product gas mixture conducted out of the partial oxidation zone.
210. The process according to any of embodiments 94 to 207, wherein the residual gas mixture II conducted out of absorption zone II comprises at least 80% of the acrolein present in the product gas mixture conducted out of the partial oxidation zone.
211. The process according to any of embodiments 94 to 207, wherein the residual gas mixture II conducted out of absorption zone II comprises at least 90% of the acrolein present in the product gas mixture conducted out of the partial oxidation zone.

212. The process according to any of embodiments 94 to 211, wherein a portion of residual gas mixture II is recycled as cycle gas into the reaction gas input mixture of the partial oxidation zone.
213. The process according to any of embodiments 94 to 211, wherein the residual gas mixture II conducted out of absorption zone II is conducted through a condensation zone II and, on the route of residual gas mixture II through condensation zone II, an aqueous condensate II is conducted out of residual gas mixture II by direct and/or indirect cooling thereof, and condensate II formed and the residual gas mixture remaining in gaseous form in the condensation is conducted out of condensation zone II as residual gas mixture III.
214. The process according to embodiment 213, wherein the condensate II conducted out of condensation zone II has a temperature of 30 to 50° C.
215. The process according to embodiment 213 or 214, wherein residual gas mixture II is cooled by direct cooling with a cooling liquid.
216. The process according to embodiment 215, wherein the cooling liquid withdrawn from condensation zone II is condensate II which is cooled in an indirect heat exchanger and then recycled into condensation zone II.
217. The process according to embodiment 216, wherein the difference between that temperature with which the condensate II is withdrawn from condensation zone II and that temperature with which it is recycled into condensation zone II in cooled form after passing through the indirect heat exchanger is 5 to 30° C.
218. The process according to embodiment 216, wherein the difference between that temperature with which the condensate II is withdrawn from condensation zone II and that temperature with which it is recycled into condensation zone II in cooled form after passing through the indirect heat exchanger is 5 to 15° C.
219. The process according to any of embodiments 216 to 218, wherein condensate II after passing through the indirect heat exchanger has a temperature of 20 to 40° C.
220. The process according to any of embodiments 215 to 219, wherein the cooling liquid is conducted in condensation zone II in countercurrent to the residual gas mixture II conducted through condensation zone II.
221. The process according to any of embodiments 213 to 220, wherein condensate II is conducted out of condensation zone II and supplied to the preparation of the aqueous alkali metal base used as absorbent II and/or supplied additionally to the absorbent II of absorption zone II.
222. The process according to any of embodiments 213 to 221, wherein condensation zone II has separating internals.
223. The process according to any of embodiments 213 to 222, wherein residual gas mixture III comprises at least 60% of the acrolein present in the product gas mixture conducted out of the partial oxidation zone.
224. The process according to any of embodiments 213 to 222, wherein residual gas mixture III comprises at least 70% of the acrolein present in the product gas mixture conducted out of the partial oxidation zone.
225. The process according to any of embodiments 213 to 222, wherein residual gas mixture III comprises at least 80% of the acrolein present in the product gas mixture conducted out of the partial oxidation zone.
226. The process according to any of embodiments 213 to 222, wherein residual gas mixture III comprises at least 90% of the acrolein present in the product gas mixture conducted out of the partial oxidation zone.
227. The process according to any of embodiments 213 to 226, wherein a portion of residual gas mixture III is recycled as cycle gas into the reaction gas input mixture of the partial oxidation zone.
228. The process according to any of embodiments 94 to 227, wherein the at least one inert diluent gas which is different than $CO_2$ and water and is present in the reaction gas input mixture has a boiling point at standard pressure of $\leq -10°$ C.
229. The process according to any of embodiments 94 to 228, wherein the reaction gas input mixture, based on the volume thereof, comprises 30 to 90% by volume of the at least one inert diluent gas other than $CO_2$ and water.
230. The process according to embodiment 229, wherein the reaction gas input mixture, based on the volume thereof, comprises 40 to 90% by volume of the at least one inert diluent gas other than $CO_2$ and water.
231. The process according to any of embodiments 94 to 230, wherein the reaction gas input mixture, based on the volume thereof, comprises 60 to 85% by volume of the at least one inert diluent gas other than $CO_2$ and water.
232. The process according to any of embodiments 94 to 231, wherein the reaction gas input mixture, based on the volume thereof, comprises 70 to 85% by volume of the at least one inert diluent gas other than $CO_2$ and water.
233. The process according to any of embodiments 94 to 229, wherein the product gas mixture of the partial oxidation zone, based on the volume thereof, comprises 30 to 90% by volume of the at least one inert diluent gas other than $CO_2$ and water.
234. The process according to any of embodiments 94 to 230, wherein the product gas mixture of the partial oxidation zone, based on the volume thereof, comprises 40 to 90% by volume of the at least one inert diluent gas other than $CO_2$ and water.
235. The process according to any of embodiments 94 to 231, wherein the product gas mixture of the partial oxidation zone, based on the volume thereof, comprises 60 to 85% by volume of the at least one inert diluent gas other than $CO_2$ and water.
236. The process according to any of embodiments 94 to 232, wherein the product gas mixture of the partial oxidation zone, based on the volume thereof, comprises 70 to 85% by volume of the at least one inert diluent gas other than $CO_2$ and water.
237. The process according to any of embodiments 94 to 236, wherein the product gas mixture of the partial oxidation zone, based on its volume, comprises at least 0.05% by volume of $CO_2$.
238. The process according to any of embodiments 94 to 237, wherein the product gas mixture of the partial oxidation zone, based on its volume, comprises 0.1 to 20% by volume of $CO_2$.
239. The process according to any of embodiments 94 to 238, wherein the product gas mixture of the partial oxidation zone, based on its volume, comprises 0.2 to 10% by volume of $CO_2$.
240. The process according to any of embodiments 94 to 239, wherein the at least one inert diluent gas other than $CO_2$ and water consists of molecular nitrogen to an extent of at least 60% by volume of the total amount thereof.
241. The process according to any of embodiments 94 to 239, wherein the at least one inert diluent gas other than $CO_2$ and water consists of molecular nitrogen to an extent of at least 80% by volume of the total amount thereof.
242. The process according to any of embodiments 94 to 239, wherein the at least one inert diluent gas other than $CO_2$ and 243. The process according to any of embodiments 94 to 239, wherein the at least one inert diluent gas other than $CO_2$ and water consists of molecular nitrogen to an extent of at least 90% by volume of the total amount thereof.

244. The process according to any of embodiments 94 to 239, wherein the at least one inert diluent gas other than $CO_2$ and water consists of molecular nitrogen to an extent of at least 95% by volume of the total amount thereof.

245. The process according to any of embodiments 94 to 239, wherein the at least one inert diluent gas other than $CO_2$ and water consists of propane to an extent of up to 50% by volume of the total amount thereof.

246. The process according to any of embodiments 94 to 244, wherein the product gas mixture of the partial oxidation zone, based on the volume thereof, comprises 1 to 50% by volume of $H_2O$.

247. The process according to any of embodiments 94 to 245, wherein the product gas mixture of the partial oxidation zone, based on the volume thereof, comprises 3 to 25% by volume of $H_2O$.

248. The process according to any of embodiments 94 to 246, wherein the product gas mixture of the partial oxidation zone, based on the volume thereof, comprises 0.5 to 20% by volume of acrylic acid.

249. The process according to any of embodiments 94 to 247, wherein the product gas mixture of the partial oxidation zone, based on the volume thereof, comprises 2 to 15% by volume of acrylic acid.

250. The process according to any of embodiments 94 to 248, wherein the working pressure in the different zones of the process is in the range of 0.5 to 5 bar.

251. The process according to any of embodiments 94 to 249, wherein the working pressure in the different zones of the process is in the range of 1.05 to 4 bar.

252. The process according to any of embodiments 94 to 250, wherein the working pressure in the different zones of the process is in the range of 1.1 to 3 bar.

253. The process according to any of embodiments 94 to 251, wherein the working pressure in the different zones of the process is in the range of 1.5 to 3 bar.

254. The process according to any of embodiments 94 to 252, wherein absorption zone I, condensation zone I, absorption zone II and an optional additional condensation zone II are configured as column sections which are present in one and the same separating column and are arranged one on top of another in the aforementioned sequence, and the product gas mixture flows through the separating column from the bottom upward.

255. The process according to embodiment 253, wherein a column section which forms an absorption or condensation zone is delimited by at least one chimney tray from the column section which adjoins it in the upward direction.

256. The process according to embodiment 254, wherein the chimney tray which delimits the column section which forms condensation zone I from the column section which forms absorption zone II is impervious to absorbate II formed in the column section which forms absorption zone II.

257. The process according to embodiment 254 or 255, wherein the chimney tray which delimits the column section which forms absorption zone I from the column section which forms condensation zone I is pervious to condensate I formed in the column section which forms condensation zone I.

258. The process according to any of embodiments 254 to 256, wherein the chimney tray which delimits the column section which forms absorption zone II from the column section which forms condensation zone II is pervious to condensate II formed in the column section which forms condensation zone II.

259. The process according to any of embodiments 94 to 118 or 120 to 257, wherein aqueous intermediate I conducted out of condensation zone I and aqueous intermediate II conducted out of absorption zone II are combined to give aqueous intermediate III, and $CO_2$ outgassing of aqueous intermediate III is performed.

260. The process according to embodiment 258, wherein the $CO_2$ outgassing of the aqueous intermediate III is performed at a temperature of 95 to 115° C.

261. The process according to embodiment 259, wherein the $CO_2$ outgassing of the aqueous intermediate III is performed at a temperature of 100 to 110° C.

262. The process according to any of embodiments 258 to 260, wherein the end of $CO_2$ outgassing of the aqueous intermediate III is followed by dissolution of molecular oxygen in the aqueous intermediate III.

263. The process according to any of embodiments 94 to 261, wherein the extraction of aqueous intermediate III which has optionally been outgassed beforehand to remove $CO_2$, or of aqueous intermediate II, or of aqueous intermediate I and aqueous intermediate II, is performed in an extraction column.

264. The process according to embodiment 262, wherein the extraction column is a pulsed sieve tray column.

265. The process according to embodiment 262 or 263, wherein the ratio $V_C:V_D$ of total volume $V_C$ of continuous phase present in the extraction column to total volume $V_D$ present in the extraction column of disperse phase present in the extraction column is 10:1 to 1.1:1.

266. The process according to embodiment 264, wherein the ratio $V_C:V_D$ is 5:1 to 1.5:1.

267. The process according to any of embodiments 262 to 265, wherein the particular aqueous intermediate and the organic extractant are supplied to the extraction column at a temperature within the range of 1 to 80° C.

268. The process according to embodiment 266, wherein the temperature difference between that temperature with which the particular aqueous intermediate is supplied to the extraction column and that temperature with which the organic extractant is supplied to the extraction column is not more than 20° C.

269. The process according to embodiment 267, wherein the temperature difference is 0 to 15° C.

270. The process according to embodiment 267, wherein the temperature difference is 0 to 10° C.

271. The process according to any of embodiments 262 to 269, wherein the extraction column has 1 to 15 theoretical plates.

272. The process according to embodiment 270, wherein the extraction column has 3 to 10 theoretical plates.

273. The process according to embodiment 270 or 271, wherein the extraction column has 4 to 8 theoretical plates.

274. The process according to any of embodiments 262 to 272, wherein the organic extractant is supplied to the extraction column with a mass flow rate $M_O$ [kg/h] and the respective aqueous intermediate to the extraction column with a mass flow rate Mz [kg/h], and the ratio $M_O:M_Z$ is 0.1 to 10.

275. The process according to embodiment 273, wherein the ratio $M_O:M_Z$ is 0.1 to 5.

276. The process according to embodiment 273 or 274, wherein the ratio $M_O:M_Z$ is 0.1 to 2.

277. The process according to any of embodiments 273 to 275, wherein the ratio $M_O:M_Z$ is 0.1 to 1.

277. The process according to any of embodiments 262 to 276, wherein the particular aqueous intermediate is supplied to the extraction column as a disperse phase and the organic extractant to the extraction column as a continuous phase.
278. The process according to any of embodiments 94 to 277, wherein the organic extractant at 20° C. and standard pressure has a solubility in water of less than 7% by weight, based on the weight of the solution.
279. The process according to any of embodiments 94 to 277, wherein the organic extractant at 20° C. and standard pressure has a solubility in water of less than 5% by weight, based on the weight of the solution.
280. The process according to any of embodiments 94 to 277, wherein the organic extractant at 20° C. and standard pressure has a solubility in water of less than 1% by weight, based on the weight of the solution.
281. The process according to any of embodiments 94 to 280, wherein the organic extractant does not have any amine group —$NH_2$, any sulfo group —$SO_3$, any carboxyl group —COOH or any anhydride group —COOCO—.
282. The process according to any of embodiments 94 to 281, wherein the organic extractant is at least one organic solvent from the group consisting of:
 aromatic hydrocarbons, alkyl-substituted aromatic hydrocarbons, halogenated aromatic hydrocarbons, linear, branched and cyclic paraffinic hydrocarbons, halogenated paraffinic hydrocarbons, alkyl ethers of aromatic hydrocarbons, aryl ethers of aromatic hydrocarbons, aliphatic and cycloaliphatic ethers having at least 4 carbon atoms, aromatic carbonyl compounds, aliphatic and cycloaliphatic ketones having at least 5 carbon atoms, esters of aliphatic $C_1$-$C_4$-monocarboxylic acids and $C_1$-$C_6$-alkanols or cycloalkanols, halogenated alkanols, halogenated aryl-substituted alkanols and the dialkyl esters of aliphatic, olefinic and aromatic dicarboxylic acids.
283. The process according to any of embodiments 94 to 282, wherein the organic extractant is at least one organic solvent from the group consisting of:
 benzene, diphenyl, toluene, ethylbenzene, o-xylene, m-xylene, p-xylene, cumene, monochlorobenzene, monobromobenzene, monofluorobenzene, hexane, heptane, octane, cyclohexane, tetradecane, petroleum ether, gasoline fractions, chloroform, dichloromethane, chloroethane, 1,1-dichloroethane, 1,2-dichloroethane, dichloropropane, 1,3-dichloropropane, 1,2-dichloropropane, trichloroethane, 2,4-di-tert-butylphenol, 2,6-di-tert-butylphenol, anisole, diphenyl ether, diethyl ether, methyl tert-butyl ether, diisopropyl ether, di-n-butyl ether, ethyl tert-butyl ether, benzophenone, methyl propyl ketone, methyl isopropyl ketone, methyl butyl ketone, methyl isobutyl ketone, methyl amyl ketone, methyl isoamyl ketone, diethyl ketone, ethyl propyl ketone, ethyl butyl ketone, diisopropyl ketone, diisobutyl ketone, cyclohexanone, trimethylcyclohexanone, isobutyl formate, ethyl acetate, isobutyl acetate, amyl acetate, isoamyl acetate, cyclohexyl acetate, n-hexyl acetate, isobutyl propionate, isobutyl butyrate, isobutyl isobutyrate, hexafluoro-2-phenyl-2-propanol, diethyl maleate, dimethyl phthalate and diethyl phthalate.
284. The process according to any of embodiments 94 to 282, wherein the organic extractant is at least one organic solvent from the group consisting of 1,3-dichloropropane, 1,2-dichloropropane, 1,1-dichloroethane, the eutectic mixture of 2,4-di-tert-butylphenol and 2,6-di-tert-butylphenol, Diphyl, toluene, chlorobenzene, fluorobenzene and benzene.
285. The process according to any of embodiments 94 to 284, wherein the dynamic viscosity of the organic extractant under the extraction conditions is in the range of 0.3 mPa·s to 50 mPa·s.
286. The process according to any of embodiments 94 to 285, wherein the dynamic viscosity of the organic extractant under the extraction conditions is in the range of 0.3 mPa·s to 1 mPa·s.
287. The process according to any of embodiments 94 to 286, wherein the difference between the mass density of the organic extractant and the mass density of the particular aqueous intermediate under the extraction conditions is ≥10 kg/m³ and ≤300 kg/m³.
288. The process according to any of embodiments 94 to 287, wherein the difference between the mass density of the organic extractant and the mass density of the particular aqueous intermediate under the extraction conditions is ≥15 kg/m³ and ≤250 kg/m³.
289. The process according to any of embodiments 94 to 288, wherein the difference between the mass density of the organic extractant and the mass density of the particular aqueous intermediate under the extraction conditions is ≥25 kg/m³ and ≤200 kg/m³.
290. The process according to any of embodiments 94 to 289, wherein the difference between the mass density of the organic extractant and the mass density of the particular aqueous intermediate under the extraction conditions is ≥30 kg/m³ and ≤150 kg/m³.
291. The process according to any of embodiments 94 to 290, wherein the difference between the mass density of the organic extractant and the mass density of the particular aqueous intermediate under the extraction conditions is ≥40 kg/m³ and ≤150 kg/m³.
292. The process according to any of embodiments 94 to 291, wherein the difference between the mass density of the organic extractant and the mass density of the particular aqueous intermediate under the extraction conditions is ≥50 kg/m³ and ≤150 kg/m³.
293. The process according to any of embodiments 94 to 292, wherein the aqueous raffinate removed from the particular organic extract comprises organic extractant in dissolved form, and the organic extractant present in dissolved form is removed from the aqueous raffinate by extraction, adsorption and/or rectification.
294. The process according to embodiment 293, wherein the organic extractant removed is recycled into the extraction of the particular aqueous intermediate.
295. The process according to embodiment 293, wherein the organic extractant is removed by rectification from the aqueous raffinate and recycled into the extraction column of the processes according to any of embodiments 262 to 277.
296. The process according to any of embodiments 293 to 295, wherein the organic extractant is removed by rectification from the aqueous raffinate and the rectificative removal is performed in a rectification column which has separating internals and has only a stripping section.
297. The process according to embodiment 296, wherein the aqueous raffinate of the rectification column is supplied to the uppermost theoretical plate thereof.
298. The process according to any of embodiments 94 to 297, wherein the extractant present in the particular organic extract is removed from the organic extract and recycled into the extraction of the particular aqueous intermediate.

299. The process according to embodiment 298, wherein the removal of the extractant from the organic extract is performed by rectification in a rectification column which has a stripping section and a rectifying section.
300. The process according to embodiment 299, wherein the organic extractant at standard pressure has a boiling point above that of benzaldehyde at the appropriate pressure, and the organic extract is supplied to the rectification column in the middle part thereof or below, but at least two theoretical plates above the column bottom, and the organic extractant removed is withdrawn from the bottom of the rectification column.
301. The process according to embodiment 300, wherein the stripping section of the rectification column is configured as a side draw column in which a collecting tray is present between the top of the column and the point at which the organic extract is supplied to the rectification column, and a portion of the liquid which accumulates on this collecting tray is conducted out of the rectification column as aldehyde outlet.
302. The process according to embodiment 299, wherein the organic extractant at standard pressure has a boiling point lower than that of acrylic acid at the appropriate pressure, and the organic extract is supplied to the rectification column in the middle part thereof or higher, but at least two theoretical plates below the top of the column, and the organic extractant removed is withdrawn from the extraction column at the top of the column.
303. The process according to any of embodiments 94 to 302, wherein the absorbate I discharged from absorption zone I comprises acrylic acid as a monomer and as a Michael adduct onto itself, and a portion of absorbate I discharged from the absorption zone I is supplied to a recovery unit for acrylic acid present in absorbate I as a monomer and as a Michael adduct onto itself.
304. The process according to embodiment 303, wherein the recovery unit is a recovery column, and the absorbate I is fed into the bottom of the recovery column.
305. The process according to embodiment 304, wherein the temperature in the bottom of the recovery column is 140 to 230° C.
306. The process according to embodiment 304 or 305, wherein the temperature in the bottom of the recovery column is 160 to 210° C.
307. The process according to any of embodiments 304 to 306, wherein the recovery column has separating internals or is free of separating internals.
308. The process according to any of embodiments 304 to 307, wherein, in the recovery column, a low boiler fraction comprising the acrylic acid is converted to the vapor phase and this vapor phase is conducted into absorption zone I.
309. The process according to any of embodiments 304 to 307, wherein the product gas mixture conducted out of the partial oxidation zone, before it is conducted through absorption zone I, is cooled in a cooling zone and, in the recovery column, a low boiler fraction comprising the acrylic acid is converted to the vapor phase, and this vapor phase is conducted into the cooling zone together with the product gas mixture.
310. The process according to any of embodiments 94 to 309, wherein the at least one $C_3$ precursor compound is propane, propene, acrolein, propionic acid, propanol, propionaldehyde and/or glycerol.
311. The process according to any of embodiments 94 to 310, wherein the proportion of the at least one $C_3$ precursor compound in the reaction gas input mixture is 4 to 20% by volume.
312. The process according to any of embodiments 94 to 311, wherein the proportion of the at least one $C_3$ precursor compound in the reaction gas input mixture is 5 to 15% by volume.
313. The process according to any of embodiments 94 to 312, wherein the proportion of the at least one $C_3$ precursor compound in the reaction gas input mixture is 6 to 12% by volume.
314. The process according to any of embodiments 94 to 313, wherein the reaction gas input mixture, based on the stoichiometry of the partial oxidation reaction, has an excess of molecular oxygen.
315. The process according to any of embodiments 94 to 314, wherein the reaction gas input mixture, based on the volume thereof, has at least 1% by volume of water.
316. The process according to any of embodiments 94 to 315, wherein the at least one $C_3$ precursor compound is propene and/or acrolein.
317. The process according to any of embodiments 94 to 316, wherein the at least one $C_3$ precursor compound is propene.
318. The process according to embodiment 316 or 317, wherein the propene has been obtained by a process for heterogeneously catalyzed partial dehydrogenation and/or oxydehydrogenation of propane to propene and is present in the reaction gas input mixture for the partial oxidation zone together with unconverted propane.
319. The process according to embodiment 318, wherein at least a portion of residual gas mixture II or of residual gas mixture III is recycled into the process for heterogeneously catalyzed partial dehydrogenation and/or oxydehydrogenation.
320. The process according to embodiment 317, wherein the source used for the propene present in the reaction gas input mixture is polymer grade propene or chemical grade propene.
321. The process according to any of embodiments 317 to 320, wherein the reaction gas input mixture comprises 4 to 20% by volume of propene.
322. The process according to any of embodiments 317 to 321, wherein the reaction gas input mixture comprises 5 to 15% by volume of propene.
323. The process according to any of embodiments 317 to 322, wherein the reaction gas input mixture comprises 6 to 12% by volume of propene.
324. The process according to any of embodiments 317 to 323, wherein the reaction gas input mixture, based on the molar amount of propene present therein, comprises >0 to 3 mol % of cyclopropane.
325. The process according to any of embodiments 317 to 324, wherein the reaction gas input mixture, based on the molar amount of propene present therein, comprises ≥10 molar ppb to 3 mol % of cyclopropane.
326. The process according to any of embodiments 317 to 325, wherein the reaction gas input mixture, based on the molar amount of propene present therein, comprises ≥50 molar ppb to 2 mol % of cyclopropane.
327. The process according to any of embodiments 317 to 326, wherein the reaction gas input mixture, based on the molar amount of propene present therein, comprises ≥100 molar ppb to 1 mol % of cyclopropane.
328. The process according to any of embodiments 317 to 327, wherein the reaction gas input mixture, based on the molar amount of propene present therein, comprises ≥1 molar ppb to 0.8 mol % of cyclopropane.
329. The process according to any of embodiments 317 to 328, wherein the reaction gas input mixture, based on the molar amount of propene present therein, comprises ≥10 molar ppm to 0.5 mol % of cyclopropane.

330. The process according to any of embodiments 317 to 329, wherein the reaction gas input mixture, based on the volume thereof, comprises at least 1% by volume of water.

331. The process according to any of embodiments 317 to 330, wherein the reaction gas input mixture, based on the volume thereof, comprises at least 2% by volume of water.

332. The process according to any of embodiments 317 to 331, wherein the reaction gas input mixture, based on the volume thereof, comprises at least 3% by volume of water.

333. The process according to any of embodiments 317 to 332, wherein the reaction gas input mixture, based on the volume thereof, comprises at least 4% by volume of water.

334. The process according to any of embodiments 317 to 333, wherein the reaction gas input mixture, based on the volume thereof, comprises at least 5% by volume of water.

335. The process according to any of embodiments 317 to 334, wherein the reaction gas input mixture, based on the volume thereof, comprises at least 7% by volume of water.

336. The process according to any of embodiments 317 to 335, wherein the reaction gas input mixture, based on the volume thereof, comprises at least 9% by volume of water.

337. The process according to any of embodiments 317 to 336, wherein the reaction gas input mixture, based on the volume thereof, comprises at least 15% by volume of water.

338. The process according to any of embodiments 317 to 337, wherein the reaction gas input mixture, based on the volume thereof, comprises not more than 30% by volume of water.

339. The process according to any of embodiments 317 to 338, wherein the partial oxidation zone comprises a first reaction stage 1 and a second reaction stage 2, reaction stage I comprising partial oxidation essentially of the propene present in the reaction gas input mixture to acrolein, and reaction stage 2 comprising the partial oxidation essentially of the acrolein formed in reaction stage I to acrylic acid.

340. The process according to embodiment 339, wherein the acrolein formed in reaction stage 1 is partially oxidized to acrylic acid in reaction stage 2 without being removed from the product gas mixture of reaction stage 1 beforehand.

341. The process according to any of embodiments 317 to 340, wherein reaction stage 1 has a fixed catalyst bed 1 whose catalysts have, as an active composition, at least one multimetal oxide comprising Mo, Fe and Bi.

342. The process according to any of embodiments 317 to 341, wherein reaction stage 2 has a fixed catalyst bed 2 whose catalysts have, as an active composition, at least one multimetal oxide comprising Mo and V.

343. The process according to embodiment 341 or 342, wherein the propene is supplied to the reaction stage 1 as part of a reaction gas input mixture which comprises molecular oxygen and propene in a molar $O_2:C_3H_6$ ratio of ≥1, and the reaction gas input mixture is conducted through fixed catalyst bed 1 at a temperature in the range of 250 to 490° C.

344. The process according to any of embodiments 341 to 343, wherein the propene is supplied to the reaction stage 1 as part of a reaction gas input mixture which comprises molecular oxygen and propene in a molar $O_2:C_3H_6$ ratio of ≥1, and the reaction gas input mixture is conducted through fixed catalyst bed 1 at a temperature in the range of 270 to 450° C.

345. The process according to any of embodiments 341 to 344, wherein the propene is supplied to the reaction stage 1 as part of a reaction gas input mixture which comprises molecular oxygen and propene in a molar $O_2:C_3H_6$ ratio of ≥1, and the reaction gas input mixture is conducted through fixed catalyst bed 1 at a temperature in the range of 280 to 420° C.

346. The process according to any of embodiments 341 to 345, wherein the propene is supplied to the reaction stage 1 as part of a reaction gas input mixture which comprises molecular oxygen and propene in a molar $O_2:C_3H_6$ ratio of ≥1, and the reaction gas input mixture is conducted through fixed catalyst bed 1 at a temperature in the range of 300 to 380° C.

347. The process according to any of embodiments 341 to 346, wherein the acrolein is supplied to reaction stage 2 as part of a reaction gas input mixture 2 which comprises molecular oxygen and the acrolein in a molar $O_2:C_3H_4O$ ratio of ≥0.5, and reaction gas input mixture 2 is conducted through fixed catalyst bed 2 at a temperature in the range of 180 to 390° C.

348. The process according to any of embodiments 341 to 347, wherein the acrolein is supplied to reaction stage 2 as part of a reaction gas input mixture 2 which comprises molecular oxygen and the acrolein in a molar $O_2:C_3H_2O$ ratio of ≥0.5, and reaction gas input mixture 2 is conducted through fixed catalyst bed 2 at a temperature in the range of 200 to 370° C.

349. The process according to any of embodiments 341 to 348, wherein the acrolein is supplied to reaction stage 2 as part of a reaction gas input mixture 2 which comprises molecular oxygen and the acrolein in a molar $O_2:C_3H_4O$ ratio of ≥0.5, and reaction gas input mixture 2 is conducted through fixed catalyst bed 2 at a temperature in the range of 200 to 320° C.

350. The process according to any of embodiments 341 to 349, wherein the acrolein is supplied to reaction stage 2 as part of a reaction gas input mixture 2 which comprises molecular oxygen and the acrolein in a molar $O_2:C_3H_4O$ ratio of ≥0.5, and reaction gas input mixture 2 is conducted through fixed catalyst bed 2 at a temperature in the range of 220 to 300° C.

351. The process according to any of embodiments 341 to 350, wherein the propene conversion in the first reaction stage, based on a single pass of the propene-comprising reaction gas input mixture through the first reaction stage, is ≥80 mol %.

352. The process according to any of embodiments 341 to 351, wherein the propene conversion in the first reaction stage, based on a single pass of the propene-comprising reaction gas input mixture through the first reaction stage, is ≥90 mol %.

353. The process according to any of embodiments 341 to 352, wherein the propene conversion in the first reaction stage, based on a single pass of the propene-comprising reaction gas input mixture through the first reaction stage, is ≤99.9 mol %.

354. The process according to any of embodiments 341 to 353, wherein the acrolein conversion in the second reaction stage, based on a single pass of the acrolein through the second reaction stage, is ≥80 mol %.

355. The process according to any of embodiments 341 to 353, wherein the acrolein conversion in the second reaction stage, based on a single pass of the acrolein through the second reaction stage, is ≥90 mol %.

356. The process according to any of embodiments 341 to 355, wherein the acrolein conversion in the second reaction stage, based on a single pass of the acrolein through the second reaction stage, is ≤99.99 mol %.

357. The process according to any of embodiments 343 to 357, wherein the propene is supplied to reaction stage 1 as part of a reaction gas input mixture which comprises molecular oxygen and propene in a molar $O_2:C_3H_6$ ratio of $\geq 1$ and $\leq 3$.

358. The process according to any of embodiments 343 to 357, wherein the acrolein is supplied to reaction stage 2 as part of a reaction gas input mixture 2 which comprises molecular oxygen and the acrolein in a molar $O_2:C_3H_4O$ ratio of $\geq 0.5$ and $\leq 2$.

359. The process according to any of embodiments 341 to 358, wherein the reaction stage 1 has a fixed catalyst bed 1 whose catalysts have, as an active composition, at least one multimetal oxide which comprises Mo, Fe and Bi and is of the general formula I

$$Mo_{12}Bi_aFe_bX^1_cX^2_dX^3_eX^4_fO_n \quad (I)$$

in which the variables are each defined as follows:
$X^1$=nickel and/or cobalt,
$X^2$=thallium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a=0.5 to 5,
b=0.01 to 5, preferably 2 to 4,
c=0 to 10, preferably 3 to 10,
d=0 to 2, preferably 0.02 to 2,
e=0 to 8, preferably 0 to 5,
f=0 to 10, and
n=a number which is determined by the valency and frequency of the non-oxygen elements in I.

360. The process according to any of embodiments 341 to 349, wherein reaction stage 2 has a fixed catalyst bed 2 whose catalysts have, as an active composition, at least one multimetal oxide which comprises Mo and V and is of the general formula II,

$$Mo_{12}V_aX^1_bX^2_cX^3_dX^4_eX^5_fX^6_gO_n \quad (II)$$

in which the variables are each defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one or more alkaline earth metals,
$X^6$=Si, Al, Ti and/or Zr,
a=1 to 6,
b=0.2 to 4,
c=0.5 to 18,
d=0 to 40,
e=0 to 2,
f=0 to 4,
g=0 to 40, and
n=a number which is determined by the valency and frequency of the non-oxygen elements in II.

361. The process according to any of embodiments 341 to 360, wherein the space velocity of propene on fixed catalyst bed 1 is $\geq 80$ l (STP)/l·h to $\leq 250$ l (STP)/l·h.

362. The process according to any of embodiments 341 to 360, wherein the space velocity of acrolein on fixed catalyst bed 2 is $\geq 60$ l (STP)/l·h to $\leq 250$ l (STP)/l·h.

363. The process according to any of embodiments 339 to 362, wherein the working pressure in reaction stage 1 and in reaction stage 2 is 0.5 to 5 bar.

364. The process according to any of embodiments 94 to 363, wherein the product gas mixture obtained in the partial oxidation zone has the following contents:

0.4 to 40% by weight, based on the weight of the product gas mixture, of water,
0.05 to 15% by weight, based on the weight of the product gas mixture, of $CO_2$,
1 to 30% by weight, based on the weight of the product gas mixture, of acrylic acid,
and, based on the total weight of acrylic acid present in the product gas mixture,
$\geq 50$ ppm by weight to $\leq 0.25\%$ by weight of propionic acid,
$\geq 200$ ppm by weight to $\leq 2.5\%$ by weight of formic acid,
$\geq 3000$ ppm by weight to $\leq 12\%$ by weight of acetic acid,
$\geq 15$ ppm by weight to $\leq 1\%$ by weight of benzoic acid,
$\geq 15$ ppm by weight to $\leq 5\%$ by weight of total amount of maleic anhydride and maleic acid, calculated as maleic anhydride,
$\geq 15$ ppm by weight to $\leq 1\%$ by weight of total amount of phthalic anhydride and phthalic acid, calculated as phthalic anhydride,
$\geq 55$ ppm by weight to $\leq 5\%$ by weight of acrolein,
$\geq 55$ ppm by weight to $\leq 1\%$ by weight of benzaldehyde,
$\geq 55$ ppm by weight to $\leq 0.5\%$ by weight of 2-furaldehyde,
and,
based on the remaining amount up to 100% by weight of product gas mixture, at least 80% by weight of at least one constituent from the group consisting of $N_2$, CO, methane, ethane, propane and the noble gases,
with the proviso that the total amount of $N_2$, CO, $CO_2$, methane, ethane, propane and the noble gases present in the product gas mixture, based on the total volume of the product gas mixture, is at least 30% by volume.

365. The process according to embodiment 364, wherein, based on the remaining amount up to 100% by weight of product gas mixture, at least 85% by weight of at least one constituent from the group consisting of $N_2$, CO, methane, ethane, propane and the noble gases is present in the product gas mixture.

366. The process according to embodiment 364, wherein, based on the remaining amount up to 100% by weight of product gas mixture, at least 90% by weight of at least one constituent from the group consisting of $N_2$, CO, methane, ethane, propane and the noble gases is present in the product gas mixture.

367. The process according to embodiment 364, wherein, based on the remaining amount up to 100% by weight of product gas mixture, at least 95% by weight of at least one constituent from the group consisting of $N_2$, CO, methane, ethane, propane and the noble gases is present in the product gas mixture.

368. The process according to any of embodiments 364 to 367, wherein the product gas mixture, based on the weight thereof, comprises 5 to 20% by weight of acrylic acid.

369. The process according to any of embodiments 364 to 368, wherein the product gas mixture, based on the weight thereof, comprises 0.1 to 10% by weight of $CO_2$.

370. The process according to any of embodiments 364 to 369, wherein the product gas mixture, based on the weight thereof, comprises 0.3 to 5% by weight of $CO_2$.

371. The process according to any of embodiments 364 to 370, wherein the product gas mixture, based on the weight thereof, comprises 1 to 25% by weight of $H_2O$.

372. The process according to any of embodiments 364 to 371, wherein the product gas mixture, based on the weight thereof, comprises 3 to 15% by weight of $H_2O$.

373. The aqueous solution according to any of embodiments 1 to 77 or 79 to 93, which is obtainable by a process according to embodiments 94 to 372.

374. The aqueous solution according to embodiment 373, which comprises, based on the weight thereof, 1 to 1000 ppm by weight of the organic extractant.
375. An aqueous mixture obtainable by adding up to 40 mol % of at least one monoethylenically unsaturated compound other than acrylic acid and the conjugate base thereof to an aqueous solution according to embodiment 373 or 374, based on the molar total amount of acrylic acid and the conjugate base thereof present in the aqueous solution.
376. An aqueous mixture obtainable by adding up to 30 mol % of at least one monoethylenically unsaturated compound other than acrylic acid and the conjugate base thereof to an aqueous solution according to embodiment 373 or 374, based on the molar total amount of acrylic acid and the conjugate base thereof present in the aqueous solution.
377. An aqueous mixture obtainable by adding up to 20 mol % of at least one monoethylenically unsaturated compound other than acrylic acid and the conjugate base thereof to an aqueous solution according to embodiment 373 or 374, based on the molar total amount of acrylic acid and the conjugate base thereof present in the aqueous solution.
378. An aqueous mixture obtainable by adding up to 10 mol % of at least one monoethylenically unsaturated compound other than acrylic acid and the conjugate base thereof to an aqueous solution according to embodiment 373 or 374, based on the molar total amount of acrylic acid and the conjugate base thereof present in the aqueous solution.
379. An aqueous mixture obtainable by adding up to 5 mol % of at least one monoethylenically unsaturated compound other than acrylic acid and the conjugate base thereof to an aqueous solution according to embodiment 373 or 374, based on the molar total amount of acrylic acid and the conjugate base thereof present in the aqueous solution.
380. The aqueous mixture according to any of embodiments 375 to 379, wherein the at least one monoethylenically unsaturated compound other than acrylic acid and the conjugate base thereof is selected from the group consisting of methacrylic acid, maleic acid, itaconic acid, 2-acrylamido-2-methylpropanesulfonic acid, amides of the acids mentioned, alkali metal salts of the acids mentioned, ammonium salts of the acids mentioned, monohydroxyalkyl esters of acrylic acid, monohydroxyalkyl esters of methacrylic acid, N-vinylformamide, styrene, (meth)acrylic esters of monohydric alcohols, acrylonitrile, methacrylonitrile, and vinyl esters such as vinyl acetate and vinyl propionate.
381. The aqueous mixture according to any of embodiments 375 to 380, which comprises, based on the total molar amount of acrylic acid, of the conjugate base thereof and of monoethylenically unsaturated compounds other than acrylic acid and the conjugate base thereof present in the aqueous mixture, 0.001 to 5 mol % of at least one added compound having at least two ethylenically unsaturated double bonds which may be conjugated to one another.
382. The aqueous mixture according to embodiment 381, which is an aqueous solution.
383. The aqueous solution according to embodiment 373 or 374, which comprises, based on the molar amount of acrylic acid and the conjugate base thereof present in the aqueous solution, 0.001 to 5 mol % of at least one added compound having at least two ethylenically unsaturated double bonds which may be conjugated to one another.
384. A process for free-radical polymerization, which is effected from an aqueous solution according to any of embodiments 1 to 87, or 373, or 374, or 383.
385. A process for free-radical polymerization, which is effected from an aqueous mixture according to any of embodiments 88 to 93 or 375 to 382.
386. The process according to any of embodiments 94 to 372, which is followed by a process for free-radical polymerization which is effected from the aqueous target product solution prepared, optionally after organic extractant still present therein has been removed beforehand.
387. The process according to any of embodiments 94 to 372, which is followed by a process for free-radical polymerization in which acrylic acid and the conjugate base thereof present in the aqueous target product solution, optionally after organic extractant still present therein has been removed, and optionally at least monoethylenically unsaturated compounds other than acrylic acid and the conjugate base thereof, are polymerized into the polymer.
388. The use of aqueous solutions according to any of embodiments 1 to 87, or 373, or 374, or 383 for preparation of polymers obtained by free-radical initiation.
389. The use of aqueous mixtures according to any of embodiments 88 to 93 or 375 to 382 for preparation of polymers obtained by free-radical initiation.

EXAMPLES

The Steady Operating State is Described

Example 1

0.23 kg/h of propene which was of chemical grade purity and which comprised, based on the total volume thereof, ≥3.85% by volume of propane and ≥96% by volume of propene, 1.15 kg/h of air and 1.17 kg/h of cycle gas were used to obtain 2.55 kg/h of reaction gas input mixture (reaction gas input mixture 1) which had the following contents:
78.83% by vol. of $N_2$,
10.52% by vol. of $O_2$,
3.74% by vol. of $H_2O$,
0.03% by vol. of $CO_2$,
0.015% by vol. of acrolein,
0.48% by vol. of propane,
0.40% by vol. of CO, and
5.88% by vol. of propene.

The partial oxidation zone had two tubular reactors which were connected in series as in the example of WO 2007/074045. The interior of each of the reaction tubes was charged with a fixed catalyst bed which corresponded to the reaction tube charge in the example of WO 2007/074045. In other words, the unsupported catalyst according to example 1 of DE-A 10046957 with an active composition comprising Mo, Bi and Fe was used for the fixed catalyst bed of the first reaction stage, and the eggshell catalyst according to preparation example 5 of DE-A 10046928 with an active composition comprising Mo and V was used for the fixed catalyst bed of the second reaction stage. To structure the activity of the fixed catalyst bed, rings of steatite were also used, the geometry of which corresponded in each case to the particular catalyst geometry.

In contrast to the example of WO 2007/074045, however, the oxygen fed in at the intermediate stage was not in the form of essentially pure molecular oxygen, but rather air (0.17 kg/h). The inlet pressure into the first reaction stage was 2.135 bar. The inlet pressure into the second reaction stage was 1.83 bar. The temperature of the reaction tubes was controlled with the aid of the salt melt detailed in the example of WO 2007/074045. The temperature thereof in the first reaction stage was adjusted such that a propene conversion of 96.8±0.1 mol % was established in single pass of the reaction gas input mixture through the first reaction stage. The salt melt temperature of the second reaction stage was adjusted such that an acrolein conversion of 99.2±0.1 mol % was established in single pass of reaction gas input mixture 2 through the second reaction stage. The propene loading of the fixed catalyst bed of the first reaction stage was set to 145 l (STP)/l·h (the term "propene loading" is used as defined in WO 2007/074045). The acrolein loading of the fixed catalyst bed of the second reaction stage was 127 l (STP)/l·h (the term "acrolein loading" is used as defined in WO 2007/074045). Otherwise, the procedure was as described in the example of WO 2007/074045.

The flow rate of product gas mixture flowing out of the second reaction stage was 2.72 kg/h. The temperature thereof was 260° C. and the outlet pressure was 1.5 bar. The product gas mixture had the following contents, based on the total weight thereof:
76.13% by wt. of $N_2$,
2.41% by wt. of $O_2$,
6.01% by wt. of $H_2O$,
1.03% by wt. of $CO_2$,
589 ppm by wt. of acrolein,
12.08% by wt. of acrylic acid,
2246 ppm by wt. of acetic acid,
30 ppm by wt. of 2-furaldehyde,
0.132% by wt. of maleic anhydride,
30 ppm by wt. of benzaldehyde,
0.69% by wt. of propane,
0.69% by wt. of CO,
0.143% by wt. of formaldehyde,
309 ppm by wt. of formic acid,
30 ppm by wt. of propionic acid,
110 ppm by wt. of benzoic acid,
150 ppm by wt. of phthalic anhydride, and
0.171% by wt. of propene.

This corresponded to the following contents, based on the total weight of acrylic acid present in the product gas mixture:
248 ppm by wt. of propionic acid,
2557 ppm by wt. of formic acid,
1.86% by wt. of acetic acid,
911 ppm by wt. of benzoic acid,
1.09% by wt. of maleic anhydride,
1241 ppm by wt. of phthalic anhydride,
4875 ppm by wt. of acrolein,
413 ppm by wt. of benzaldehyde, and
248 ppm by wt. of 2-furaldehyde.

Based on the total volume of the product gas mixture, it comprised:
80.42% by vol. of $N_2$,
2.23% by vol. of $O_2$,
0.69% by vol. of $CO_2$,
0.46% by vol. of propane, and
0.73% by vol. of CO.

The product gas mixture stream was supplied together with 0.02 kg/h of the low boiler stream conducted out of the recovery unit R which is still to be described hereinafter (this had a temperature of 181.5° C. and a pressure of 1.5 bar) to a spray cooler operated in cocurrent (=cooling zone). 7.60 kg/h of bottoms liquid having a temperature of 100.3° C. were sprayed as cooling liquid therein and withdrawn at a temperature of 100.2° C. from the bottom of the separating column K which has an absorption zone I, a condensation zone I, an absorption zone II and a condensation zone II and is still to be described hereinafter, and conveyed with a pump to the spray cooler.

The bottoms liquid had the following contents:
2.09% by wt. of water,
70.11% by wt. of acrylic acid (monomer and as Michael adduct),
0.44% by wt. of acetic acid,
320 ppm by wt. of 2-furaldehyde,
21.0% by wt. of MAn and MAc, calculated as MAc,
888 ppm by wt. of benzaldehyde,
1.53% by wt. of PAn and PAc, calculated as PAc,
0.19% by wt. of formic acid,
210 ppm by wt. of propionic acid,
1.28% by wt. of benzoic acid,
2.43% by wt. of methylene glycol, and
0.45% by wt. of MEHQ.

The biphasic mixture of product gas mixture stream, low boiler stream and cooling liquid (10.34 kg/h in total) was conducted into the bottom space of the separating column K at a temperature of 102.6° C. below the lowermost separating internal and above the bottoms level. The pressure in the bottom space of the separating column K was 1.34 bar (immediately above the bottoms level).

A schematic diagram of separating column K is shown in FIG. 1. The length (height) of separating column K was 4400 mm. The height of the circular cylindrical bottom space of the separating column K was 500 mm and it had an internal diameter of 100 mm. For the rest of its length, the internal diameter of the circular cylindrical cross section of separating column K was a uniform 50 mm. It was manufactured from pressure-tested glass.

The bottom space of separating column K was of jacketed design. A heat carrier oil was conducted through the intermediate space in order to ensure a temperature of the bottoms liquid (of absorbate I) of 100.2° C.

Atop the column bottom, four column sections were placed one on top of another in succession in the upward direction. The lengths of the first and second sections in the upward direction were each 650 mm. The length of the third section from the bottom was 1000 mm, and the fourth section from the bottom had a length of 500 mm. Each of the four sections was equipped for part of its length with structured packings of the Rombopak 9M type as separating internals.

The packed length in the first section (from the bottom) extended to 500 mm. The packed length of the second section (from the bottom) extended to 620 mm. The packed length of the third section (from the bottom) extended to 900 mm. The packed length of the fourth section (from the bottom) extended to 450 mm. The external diameter of the packings was such that the outer face thereof rested with pressure against the inner wall of the particular column section without requiring support. The distance from the upper end of the packed length of any section to the upper end of the section and the distance from the lower end of the packed length of any section to the lower end of the section corresponded to one another within the same section.

Between two successive column sections was in each case an intermediate column section likewise manufactured from glass, which had a length of 300 mm.

Figure 2:
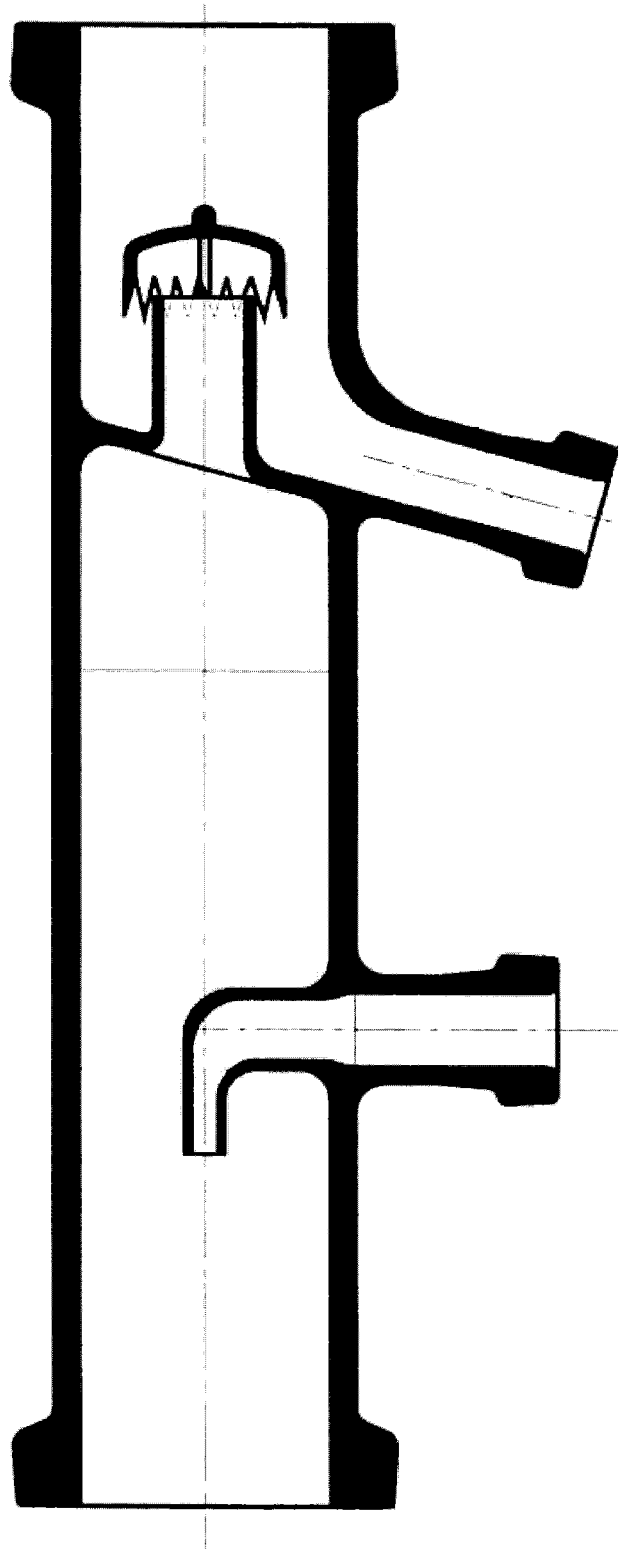
FIG. 2 shows a schematic diagram of an intermediate column section.

FIG. 2 shows a diagram of such an intermediate column section. It was equipped in each case with a chimney tray likewise manufactured from glass, which had a central circular cylindrical chimney. The internal chimney diameter was 17 mm. The chimney height was 30 mm (determined at its centered longitudinal axis). At the upper end of the chimney was mounted a slotted covering hood as a concluding element. The chimney tray itself was not horizontal, but instead oblique (the angle formed with the inner wall of the column was 75°). The chimney tray was pervious to the gas stream flowing upward in the upward direction. The chimney tray was impervious for the liquid which accumulated thereon from the section above it. Via an outlet likewise shown in FIG. 2, liquid accumulating on the particular chimney tray was removed therefrom.

In addition, the intermediate column section was in each case equipped with an inlet directed downward, as shown in FIG. 2. Via this inlet, it was possible to conduct liquid from outside into the separating column K to the top of the packing of the section present below the intermediate column section. The center of the chimney tray in the intermediate section having a length (height) of 300 mm was at a height of 215 mm in each case, viewed in the upward direction from the lower end thereof. 120 mm below the center of the chimney tray was the outlet of the inlet directed downward. The internal diameter of the outlet was 8 mm.

Each of the four sections and each intermediate column section was of jacketed configuration. A fluid heat carrier was conducted through each intermediate space in order to substantially avoid heat losses from the column interior to the environment (adiabatic operation of separating column K). For the three upper sections of separating column K and for the intermediate column sections, heated water was used as the heat carrier in each case. In the lowermost section, heat carrier oil was likewise used for the trace heating. The particular fluid heat carrier was fed into the intermediate space flowing from the bottom upward. The temperature with which the fluid heat carrier was supplied in each case was adjusted in each case with respect to that temperature with which the liquid left the lower end of the packing of the particular section, or with the temperature that the liquid leaving the chimney tray had.

In total, 7.63 kg/h of bottoms liquid (absorbate I) were conducted out of the bottom of separating column K. 0.03 kg/h thereof was fed to recovery unit R, while the remaining 7.60 kg/h were sprayed as described as cooling liquid in the cooling zone.

The lowermost section of separating column K formed absorption zone I together with the bottom space.

The second section of separating column K from the bottom formed condensation zone I. The gas stream scrubbed in absorption zone I flowed into this through the chimney of the first chimney tray in the upward direction. The flow rate thereof was 3.31 kg/h. The temperature thereof was 85.1° C. and the pressure thereof was 1.34 bar.

The contents of this gas stream were, based on the total weight thereof,
62.7% by wt. of $N_2$,
1.99% by wt. of $O_2$,
10.5% by wt. of $H_2O$,
0.85% by wt. of $CO_2$,
517 ppm by wt. of acrolein,
21.56% by wt. of acrylic acid,
3804 ppm by wt. of acetic acid,
41 ppm by wt. of 2-furaldehyde,
<1 ppm by wt. of MAn and MAc, calculated as MAn
76 ppm by wt. of benzaldehyde,
0.57% by wt. of propane,
0.57% by wt. of CO,
2824 ppm by wt. of formaldehyde,
541 ppm by wt. of formic acid,
60 ppm by wt. of propionic acid,
<1 ppm by wt. of MEHQ,
<1 ppm by wt. of benzoic acid,
<1 ppm by wt. of PAn and PAc, calculated as PAn, and
0.144% by wt. of propene.

Via the outlet of the first chimney tray from the bottom, 16.78 kg/h of condensate I were conducted out of condensation zone I at a temperature of 55° C.

Based on the total weight thereof, the condensate I had the following contents:
31.17% by wt. of water,
179 ppm by wt. of acrolein,
65.72% by wt. of acrylic acid,
1.10% by wt. of acetic acid,
120 ppm by wt. of 2-furaldehyde,
220 ppm by wt. of benzaldehyde,
    MAn and MAc,
220 ppm by wt. of benzaldehyde,
1.51% by wt. of methylene glycol,
0.17% by wt. of formic acid,
179 ppm by wt. of propionic acid,
    benzoic acid,
    PAn and PAc, and
160 ppm by wt. of MEHQ.

A stream of 0.12 kg/h of a solution of MEHQ in water at a temperature of 25° C. was added to this stream of condensate I conducted out of separating column K. The MEHQ content of the aqueous solution was such that the resulting overall stream of polymerization-inhibited condensate I contained 169 ppm by weight of MEHQ (based on the total weight thereof).

The overall stream of polymerization-inhibited condensate I was supplied to a stirred jacketed vessel. Water was conducted within the intermediate space as a cooling liquid. The stirred vessel functioned as an indirect heat exchanger (as an indirect heat transferor). The residence time in this vessel was 3 min.

The cooled overall stream of polymerization-inhibited condensate I conducted out of it had a temperature of 35° C. 0.59 kg/h of this overall stream was supplied via the inlet directed downward in the first intermediate column section from the bottom as absorbent I to the top of the uppermost structured packing in absorption zone I. 15.93 kg/h of this overall stream were recycled via the inlet directed downward in the second intermediate column section from the bottom as cooling liquid to the top of the uppermost structured packing in condensation zone I. 0.38 kg/h of this overall stream was conducted away from separating column K as aqueous intermediate I.

The residual gas mixture I remaining in gaseous form in condensation zone I had, based on the total weight thereof, the following contents:
84.54% by wt. of $N_2$,
2.68% by wt. of $O_2$,
6.36% by wt. of $H_2O$,
1.14% by wt. of $CO_2$,
628 ppm by wt. of acrolein,
3.18% by wt. of acrylic acid,
788 ppm by wt. of acetic acid,
10 ppm by wt. of 2-furaldehyde,
    MAn and MAc,
10 ppm by wt. of benzaldehyde,
0.76% by wt. of propane,
0.76% by wt. of CO,
118 ppm by wt. of formaldehyde,
80 ppm by wt. of formic acid,
10 ppm by wt. of propionic acid,
    benzoic acid,
    PAn and PAc, and
0.19% by wt. of propene.

The stream of residual gas mixture I flowing out of condensation zone I into the third section from the bottom (into absorption zone II) had a temperature of 55° C. and a flow rate of 2.45 kg/h. The pressure thereof was 1.325 bar.

Via the outlet of the second chimney tray from the bottom, 3.37 kg/h of absorbate II were conducted out of absorption zone II at a temperature of 50° C.

Based on the total weight thereof, the absorbate II had the following contents:
68.42% by wt. of water,
119 ppm by wt. of acrolein,
30 ppm by wt. of 2-furaldehyde,
40 ppm by wt. of benzaldehyde,
800 ppm by wt. of methylene glycol,
60 ppm by wt. of MEHQ, and
13.28% by wt. of total amount of acrylic acid and the conjugate base thereof, calculated as acrylic acid,
and, based on the total amount of acrylic acid and the conjugate base thereof present in the aqueous absorbate II, calculated as acrylic acid,
305 ppm by wt. of total amount of propionic acid and the conjugate base thereof, calculated as propionic acid,
0.23% by wt. of total amount of formic acid and the conjugate base thereof, calculated as formic acid,
2.49% by wt. of total amount of acetic acid and the conjugate base thereof, calculated as acetic acid,
benzoic acid,
MAn and MAc,
PAn and PAc, and
245 mol % of Na+.

A stream (0.26 kg/h; temperature=20° C.) of a 50% by weight aqueous solution of NaOH (purity of the NaOH >99.9% by weight) and a stream (0.23 kg/h; temperature=20° C.) of an aqueous inhibiting solution of MEHQ in water were supplied to this stream of absorbate II conducted out of absorption zone II. The MEHQ content of the aqueous inhibiting solution was such that the absorbate II conducted out of absorption zone II had an MEHQ content, based on the total weight thereof, of 60 ppm by weight.

This polymerization-inhibited overall stream was supplied to a stirred jacketed vessel (as always in this example 1, such stirred vessels were manufactured from pressure-tested glass, unless stated otherwise). Water was conducted as a cooling liquid within the intermediate space. The stirred vessel functioned as an indirect heat exchanger (as an indirect heat transferor). The residence time in this vessel was 15 min. The cooled overall stream conducted out of it had a temperature of 40° C. 0.67 kg/h of this cooled polymerization-inhibited overall stream was conducted away from separating column K as aqueous intermediate II.

The other 3.19 kg/h of the cooled polymerization-inhibited overall stream were combined with 0.03 kg/h of aqueous condensate II which had been conducted out of condensation zone II via the outlet of the third chimney tray from the bottom and cooled to 30° C. in an indirect heat exchanger.

The resultant overall stream was supplied via the inlet directed downward in the third intermediate column section from the bottom as a mixture of absorbent II and condensate II circulated as cooling liquid to the top of the uppermost structured packing in absorption zone II.

The aqueous condensate II had, based on the total weight thereof, the following contents:
99.87% by wt. of water,
110 ppm by wt. of acrolein,
10 ppm by wt. of 2-furaldehyde, and
0.027% by wt. of methylene glycol.

The stream of residual gas mixture II flowing out of absorption zone II into the fourth section from the bottom (into condensation zone II) had a temperature of 50° C., a flow rate of 2.30 kg/h and a pressure of 1.315 bar. Based on the total weight thereof, the residual gas mixture II had the following contents ($CO_2$ was no longer present therein):
90.13% by wt. of $N_2$,
2.85% by wt. of $O_2$,
5.07% by wt. of $H_2O$,
640 ppm by wt. of acrolein,
10 ppm by wt. of benzaldehyde,
0.815% by wt. of propane,
0.817% by wt. of CO, and
0.197% by wt. of propene.

The aqueous intermediate II had the following contents (based on the total weight thereof):
69.16% by wt. of water,
110 ppm by wt. of acrolein,
20 ppm by wt. of 2-furaldehyde,
30 ppm by wt. of benzaldehyde,
710 ppm by wt. of methylene glycol,
60 ppm by wt. of MEHQ,
11.6% by wt. of total amount of acrylic acid and the conjugate base thereof, calculated as acrylic acid,
and, based on the total amount of acrylic acid and the conjugate base thereof present in aqueous intermediate II, calculated as acrylic acid,
305 ppm by wt. of total amount of propionic acid and the conjugate base thereof, calculated as propionic acid,
0.23% by wt. of total amount of formic acid and the conjugate base thereof, calculated as formic acid,
2.49% by wt. of total amount of acetic acid and the conjugate base thereof, calculated as acetic acid,
benzoic acid and the conjugate base thereof,
MAn and MAc and the conjugate bases thereof,
PAn and PAc and the conjugate bases thereof, and
299 mol % of $Na^+$.

Via the outlet of the third chimney tray from the bottom, 2.56 kg/h of condensate II were conducted out of condensation zone II at a temperature of 40° C. This stream of condensate II was supplied to a stirred jacketed vessel. Water was conducted within the intermediate space as a cooling liquid. The stirred vessel functioned as an indirect heat exchanger (as an indirect heat transferor). The residence time in this vessel was 25 min. The stream of 2.56 kg/h of cooled condensate II conducted out of it had a temperature of 30° C. 0.03 kg/h of this stream was sent to the preparation of the aqueous absorbent II. The remaining 2.53 kg/h were recycled via the inlet directed downward in the third intermediate column section from the bottom as cooling liquid to the top of the uppermost structured packing in condensation zone II.

The residual gas mixture III remaining in gaseous form in condensation zone II had, based on the total weight thereof, the following contents (the $CO_2$ content thereof was vanishingly small):
91.45% by wt. of $N_2$,
2.90% by wt. of $O_2$,
3.67% by wt. of $H_2O$,
640 ppm by wt. of acrolein,
acrylic acid,
10 ppm by wt. of benzaldehyde,
0.827% by wt. of propane,
0.829% by wt. of CO, and
0.2% by wt. of propene.

The temperature thereof was 40° C. and the pressure thereof was 1.305 bar. The flow rate thereof was 2.26 kg/h.

Atop the fourth section of separating column K was attached an end section of length 500 mm, the internal diameter of which was likewise 50 mm. A wire braid (demister; droplet separator) was present therein, in order to counteract unwanted droplet entrainment. The end section was likewise of jacketed configuration and was trace-heated with warm water to the leaving temperature of residual gas mixture III.

The stream of residual gas mixture III was conducted through an indirect heat transferor and heated to a temperature of 55° C. in the course of flow through it. 1.09 kg/h of the heated residual gas mixture III were sent to incineration (in a flare). 1.17 kg/h of residual gas mixture III were compressed to a pressure of 2.135 bar as cycle gas, and recycled into the preparation of the reaction gas input mixture.

The stream of aqueous intermediate I (0.38 kg/h) and the stream (0.67 kg/h) of aqueous intermediate II were combined in a heated and stirred vessel. In the course of combination of the two aqueous intermediate streams, $CO_2$ outgassing set in. This was promoted by keeping the temperature in the heated stirred vessel at 103.1° C. The gas stream removed continuously from the stirred vessel (0.25 kg/h) had the following contents (based on the total weight thereof):
79.77% by wt. of water,
13.89% by wt. of $CO_2$,
0.137% by wt. of acrolein,
5.54% by wt. of acrylic acid,
0.347% by wt. of acetic acid,
70 ppm by wt. of 2-furaldehyde,
240 ppm by wt. of benzaldehyde,
50 ppm by wt. of propane,
50 ppm by wt. of CO,
0.08% by wt. of formaldehyde,
100 ppm by wt. of formic acid,
40 ppm by wt. of propionic acid, and
0.12% by wt. of propene.

The pressure thereof was 1.013 bar and the temperature thereof was 103.1° C.

This gas stream was conducted through an indirect heat exchanger configured as a jacketed water-cooled cooling coil, the extended length of which was 4 m. In the course of flow through the cooling coil, comparatively easily condensable constituents of the gas stream were condensed out, and the condensate stream which formed (0.22 kg/h) ran back into the stirred vessel at a temperature of 30° C. In this way, it was possible to very substantially avoid acrylic acid losses associated with the $CO_2$ outgassing.

The gas stream which leaves the cooling coil at a temperature of 30° C. and a pressure of 1.013 bar (0.03 kg/h) had the following contents (based on the total weight thereof):
1.70% by wt. of water,
97.35% by wt. of $CO_2$,
0.338% by wt. of acrolein,
0.065% by wt. of acrylic acid,
40 ppm by wt. of acetic acid,
10 ppm by wt. of 2-furaldehyde,
70 ppm by wt. of benzaldehyde,
0.043% by wt. of propane,
0.045% by wt. of CO, and
0.43% by wt. of propene.

For the purpose of disposal thereof, it was conducted to a flare system and incinerated.

The flow rate of the stream of aqueous intermediate III conducted continuously out of the stirred outgassing vessel at a temperature of 103.1° C. was 1.02 kg/h. It had the following contents (based on the total weight thereof):
59.65% by wt. of water,
50 ppm by wt. of acrolein,
60 ppm by wt. of 2-furaldehyde,
100 ppm by wt. of benzaldehyde,
0.61% by wt. of methylene glycol,
70 ppm by wt. of MEHQ,
31.92% by wt. of total amount of acrylic acid and the conjugate base thereof, calculated as acrylic acid,
and, based on the total amount of acrylic acid and the conjugate base thereof present in aqueous intermediate III, calculated as acrylic acid,
281 ppm by wt. of total amount of propionic acid and the conjugate base thereof, calculated as propionic acid,
0.25% by wt. of total amount of formic acid and the conjugate base thereof, calculated as formic acid,
1.87% by wt. of total amount of acetic acid and the conjugate base thereof, calculated as acetic acid,
benzoic acid and the conjugate base thereof,
MAn and MAc and the conjugate bases thereof,
PAn and PAc and the conjugate bases thereof, and
71.29 mol % of $Na^+$.

The mean residence time of the constituents of aqueous intermediate III in the outgassing vessel was 15 min.

Aqueous intermediate III was supplied to a stirred jacketed vessel. Water was conducted as a cooling liquid within the intermediate jacket space. The cylindrical stirred vessel functioned firstly as an indirect heat exchanger in order to cool the aqueous intermediate III to 50° C. as preparation for the subsequent aldehyde extraction. At the same time, a sparging ring installed within the stirred cylindrical vessel close to the base could be used to inject lean air ($N_2$-diluted air; $O_2$ content=5% by weight) into aqueous intermediate III via the nozzles thereof (0.01 kg/h, which had a temperature of 30° C.). This measure was for reasons of inhibiting polymerization (preferably until saturation of intermediate III with lean air). The mean residence time of aqueous intermediate III in the cooling and $O_2$ injection vessels was 15 min.

The lean air fractions not absorbed by aqueous intermediate III had a negligible stripping effect and were sent to disposal.

The cooled and polymerization-inhibited intermediate III was then sent to an extraction column. The extraction column was a pulsed sieve tray column manufactured from glass. The internal diameter of the circular cylindrical sieve tray column was 25 mm. The extraction column had essentially three sections in succession from the bottom upward. The lowermost section was a substantially empty bottom space with a height (length) of 315 mm. The uppermost of the three sections was a substantially empty top space with a height (length) likewise of 315 mm. Between these two sections was the actual active section. This had 40 sieve trays which were arranged one on top of another equidistantly (the clear distance between two successive sieve trays was 10 mm). The sieve trays were of uniform design and each had 16 circular orifices (holes), the internal diameter of which was 3 mm in each case and which were distributed equidistantly (from hole center to hole center) over the individual tray. A pole manufactured from stainless steel (DIN material 1.4571), which had an external diameter of 3 mm, was conducted in the longitudinal axis of the extraction column along the length of the second section thereof. The column trays, the diameter of which was likewise 25 mm, were threaded onto it (each column tray had a corresponding bore in the middle thereof, through which the pole ran). The extraction column was jacketed, and warm water was conducted through the jacket in order to thermostat the extraction column to 50° C. over the entire length thereof. The column trays were manufactured from stainless steel (DIN material 1.4571) and were 2 mm thick. 20 cm above the uppermost column tray (in a manner corresponding to that shown schematically in FIG. 2), a first inlet pipe with an outlet projecting downward was run. The diameter of inlet pipe and outlet was 3 mm in each case. 20 cm below the lowermost column tray, a corresponding second inlet pipe with outlet projecting upward was run. Both inlet pipes projected into the middle of the column cross section. Via the first inlet pipe, the aqueous intermediate III was conducted into the extraction column. The organic extractant was supplied via the second inlet pipe. After the top space (in the upward direction) was a phase separation section having a length of 50 cm. The internal diameter of the phase separation section was extended to 50 mm. The mass density of the aqueous intermediate III at 50° C. was 1142 kg/m$^3$. The mass density of the organic extractant at 50° C. was 1053 kg/m$^3$. The pressure in the gas phase at the top of the extraction column, which was open to the atmosphere, was 1.01 bar. Aqueous intermediate III was supplied to the extraction column at a flow rate of 1.02 kg/h. The organic extractant was supplied to the extraction column at a flow rate of 0.66 kg/h and a feed temperature of likewise 50° C. When the extraction was started up, the extraction column was filled completely with aqueous intermediate III. Subsequently, extraction material and extractant were supplied continuously as described. The organic extractant formed the disperse phase and the aqueous intermediate III formed the continuous phase.

The pulsator used was a piston pump. This was at the lower end of the pulsed sieve tray column and was in fluid connection to the column interior. Periodic movement of the displacer (piston) of the piston pump back and forth moved the entire liquid column present in the extraction column back and forth in an oscillating (pulsed) manner in the pulsed sieve tray column, with a stroke of 5 mm. The product of stroke (amplitude A) and frequency F was 600 mm/min. The pulsation caused disperse distribution. The organic extractant used was Diphyl which comprised 70 ppm by weight of MEHQ in dissolved form, based on the total weight thereof.

In the phase separation section, the organic extract III of lower specific gravity floated on top and was conducted continuously out of the extraction column at a flow rate of 0.655 kg/h. 1.025 kg/h of aqueous raffinate III were withdrawn continuously as aqueous target product solution from the bottom space of the extraction column. The temperature of aqueous raffinate III and of organic extract III was 50° C.

Aqueous raffinate III had, based on the total weight thereof, the following contents:
59.93% by wt. of water,
  acrolein,
10 ppm by wt. of 2-furaldehyde,
  benzaldehyde,
0.080% by wt. of Diphyl,
0.61% by wt. of methylene glycol,
70 ppm by wt. of MEHQ,
31.57% by wt. of total amount of acrylic acid and the conjugate base thereof, calculated as acrylic acid,
and, based on the total amount of acrylic acid and the conjugate base thereof present in aqueous raffinate III, calculated as acrylic acid,
286 ppm by wt. of total amount of propionic acid and the conjugate base thereof, calculated as propionic acid,
0.24% by wt. of total amount of formic acid and the conjugate base thereof, calculated as formic acid,
1.88% by wt. of total amount of acetic acid and the conjugate base thereof, calculated as acetic acid,
  benzoic acid and the conjugate base thereof,
  MAn and MAc and the conjugate bases thereof,
  PAn and PAc and the conjugate bases thereof, and
72.42 mol % of Na$^+$.

The content of carbonate and hydrogencarbonate anions in aqueous raffinate III was vanishingly small.

Organic extract III had, based on the total weight thereof, the following contents:
0.105% by wt. of water,
70 ppm by wt. of acrolein,
0.840% by wt. of acrylic acid,
0.011% by wt. of acetic acid,
80 ppm by wt. of 2-furaldehyde,
0.016% by wt. of benzaldehyde,
98.90% by wt. of Diphyl,
20 ppm by wt. of methylene glycol,
50 ppm by wt. of formic acid,
  propionic acid,
  benzoic acid,
  MAn and MAc,
  PAn and PAc, and
70 ppm by wt. of MEHQ.

From the aqueous raffinate III, generally after molecular oxygen dissolved therein has been displaced by molecular nitrogen, after optional addition of substances such as comonomers (optionally also glacial acrylic acid (GAA)), internal crosslinkers and polymerization initiators, the desired free-radical subsequent polymerization was performed directly. The specific procedure was as described in the cited prior art documents.

To recover the organic extractant present in organic extract III, it was sent to a rectification column having a rectifying section and a stripping section. The rectification column was manufactured from glass and jacketed. The intermediate jacket space was evacuated (the internal pressure of the intermediate space was <10$^{-6}$ bar) and was mirrored on the inside. Prior to the supply of extract III to the rectification column, it was conducted through an indirect heat exchanger in order to increase the temperature thereof to the supply value of 179.2° C.

The bottom space of the rectification column, which was essentially free of internals, had a height of 30 cm and an internal diameter of 100 mm. Between the upper end of the bottom space and the feed point for the heated organic extract III, the internal diameter of the rectification column was 50 mm. In this stripping section of the rectification column, it was equipped with 24 bubble-cap trays. The bubble-cap trays were mounted equidistantly one on top of another. The clear distance between two successive bubble-cap trays was a uniform 52 mm. Each bubble-cap tray had one bubble cap. The bubble cap height was 35 mm. The external diameter of the bubble cap was 30.2 mm. Each bubble cap had 12 slots distributed homogeneously over the circumference thereof, the width of which was 2.5 mm and the height of which 5 mm. Reflux liquid was supplied to the particular bubble-cap tray, and liquid was removed from the particular bubble-cap tray via inlet and outlet pipes which had an internal diameter of 8 mm. The inlet and outlet were mounted alongside one another in each case and separated from one another by a barrier with a height which corresponded to the bubble-cap height. In the center thereof, the bubble-cap trays had an open stub directed upward into the particular bubble cap. This was sheathed by the bubble cap such that an intermediate space was present between the upper part of the stub and the bubble cap. The stub length was 20 mm and the internal stub diameter was 14.5 mm. The edge of the bubble cap reached down to the bubble-cap tray.

In the rectifying section of the rectification column (this is the section above the feed of organic extract III into the rectification column), the internal diameter of the rectification column was only 32 mm. Only 12 bubble-cap trays were accommodated therein in equidistant (38 mm) arrangement. The design of these bubble-cap trays corresponded to that for the stripping section. However, the bubble caps were smaller. The height thereof was 24 mm and the external diameter thereof was 22.2 mm. The individual bubble caps had only 9 slots distributed homogeneously over the circumference thereof, the width of which was 2.5 mm and the height of which 3.0 mm. The length of the internal stubs thereof was 16 mm and the internal stub diameter was 12 mm. All bubble caps/bubble-cap trays were likewise manufactured from glass.

The rectification column was provided with external electrical safeguard heating. In the particular section, the outer wall temperature was regulated to the internal temperature. The top pressure of the rectification column was set to 100 mbar. The vapor pressure in the column bottom was 155 mbar.

A conveying pump was used to continuously conduct 17.11 kg/h of Diphyl having a purity of ≥99.99% by weight and comprising 70 ppm by weight of MEHQ in dissolved form out of the bottom space. The temperature of the bottoms liquid was 185.5° C.

0.66 kg/h of this withdrawal stream was supplied to a jacketed stirred vessel. Temperature-controlled water was conducted within the intermediate jacket space. In addition, losses of Diphyl could be compensated for by supplying fresh Diphyl to this stirred vessel. The temperature in the stirred vessel was kept at 50° C. The internal volume of the stirred vessel was 5 l. The organic extractant was removed from this stirred vessel and supplied to the pulsed sieve tray column.

The remaining 16.45 kg/h of the withdrawal stream were circulated by means of the same conveying pump via a Sambay evaporator (thin-film evaporator) made of stainless steel, which ensured the energy input required for the rectification. The heat carrier was heat carrier oil.

The mixture of vapor and liquid phase (T=185.5° C.) leaving the Sambay evaporator was recycled into the bottom space of the rectification column above the liquid level.

The temperature at the top of the column was 69.9° C. The vapor stream leaving the rectification column with this temperature was conducted through a condenser configured as an indirect heat transferor. As a cooling element, it comprised a cooling coil through which cold water flowed. The constituents which do not condense in the condenser were drawn off as a gas stream having a temperature of 30° C. via the vacuum pump (membrane vacuum pump). The condensate stream formed was divided into two substreams. 0.70 kg/h was recycled at a temperature of 30° C. as reflux liquid to the uppermost bubble-cap tray of the rectification column. 0.01 kg/h of condensate was disposed of as aldehyde discharge (for this purpose, the entire condensate stream was conducted through a buffer vessel which had a capacity of 1 l and was jacketed, in the intermediate space of which water at a controlled temperature of 30° C. was conducted; every 12 h, 120 g of condensate were discharged from the buffer vessel for disposal).

Based on the total weight thereof, the condensate had the following contents:
10.08% by wt. of $H_2O$,
0.399% by wt. of acrolein,
85.07% by wt. of acrylic acid,
1.11% by wt. of acetic acid,
0.83% by wt. of 2-furaldehyde,
1.60% by wt. of benzaldehyde,
0.25% by wt. of methylene glycol,
0.51% by wt. of formic acid, and
0.01% by wt. of propionic acid.

In the case of further uses of the aqueous target product solution for which the Diphyl content of the aqueous target product solution was found to be too high, the procedure was as follows.

The aqueous raffinate III having a temperature of 50° C., for the purpose of rectificative removal of the Diphyl still present therein, was supplied to a rectification column having only a stripping section. The rectification column was manufactured from glass. The bottom space thereof, which was essentially free of internals, had a height of 30 cm and an internal diameter of 100 mm. It had a single wall and an electrical heating band was wound around it for the purpose of trace heating. In addition, a layer of mineral insulating material was applied over the electrical heating band. The temperature of the outer wall of the bottom space was kept at 63.5° C.

Atop the bottom space was connected the actual stripping section of the rectification column. The internal diameter thereof was 50 mm over the entire length thereof. It consisted of four sections, all four of which were jacketed. The intermediate jacket space was evacuated in each case (the internal diameter of the intermediate space was <$10^{-6}$ bar) and was mirrored on the inside. Each of the four sections were provided with external electrical safeguard heating. This involved regulating the outer wall temperature to the internal temperature over the particular section. This was 61.55° C. over the lowermost section; this was 57.2° C. over the second section from the bottom; this was 52.85° C. over the third section from the bottom, and this was 48.5° C. over the uppermost section.

As separating internals, each of the four sections comprised 12 bubble-cap trays arranged equidistantly one on top of another. The clear distance between two successive bubble-cap trays was 10 cm. The bubble-cap trays were likewise manufactured from glass.

Each bubble-cap tray had one bubble cap. The external diameter of the bubble cap was 30.2 mm. The bubble-cap height was 35 mm. Each bubble cap had 12 slots distributed homogeneously over its circumference, the width of which was 2.5 mm and the height of which 5 mm. The supply of reflux liquid to the particular bubble-cap tray and the removal of liquid from the particular bubble-cap tray were via inlet and outlet pipes which had an internal diameter of 8 mm. The inlet and outlet were in each case mounted alongside one another and separated from one another by an overflow barrier (by an overflow weir), the height of which corresponded to the bubble-cap height. In the center thereof, the bubble-cap trays had an open stub directed upward into the particular bubble-cap. This was sheathed by the bubble cap such that an intermediate space was present between the upper part of the stub and the bubble cap. The stub length was 20 mm and the internal stub diameter was 14.5 mm. The edge of the bubble cap reached down to the bubble-cap tray. All bubble caps/bubble-cap trays were likewise manufactured from glass. The top pressure of the stripping column was adjusted to 100 mbar by means of a vacuum pump (membrane vacuum pump). The vapor pressure in the column bottom was 195 mbar. The aqueous raffinate III (1.025 kg/h) was supplied at its temperature of 50° C. to the uppermost bubble-cap tray. The vapor stream leaving the stripping column at a temperature of 47.4° C. was conducted through a condenser configured as an indirect heat transferor. As a cooling element, it comprised a cooling coil through which cold water flowed. The constituents which cannot be condensed in the condenser were drawn off as a gas stream having a temperature of 25° C. by means of the vacuum pump.

The condensate stream formed was supplied to a phase separator at a temperature of 25° C. The phase separator was a jacketed cylindrical glass vessel with an internal diameter of 80 mm. The length thereof was 250 mm. It was horizontal. Water at a temperature 25° C. flowed through the intermediate jacket space. The condensate stream flowed from left to right in the phase separator and, as it did so, separated into an organic phase and an aqueous phase. The aqueous phase (0.77 kg/h; T=25° C.; mass density=998.8 kg/m$^3$) was recycled to the uppermost tray of the stripping column. The organic phase was collected and disposed of (incinerated).

By means of a conveying pump, 9.44 kg/h of bottoms liquid at a temperature of 63.5° C. were conducted continuously out of the bottom space. 8.42 kg/h of this stream were circulated by means of a stainless steel Sambay evaporator, which ensured the energy input required for the rectification. The heat carrier used was heat carrier oil. The mixture of vapor and liquid phase (T=64.1° C.) which leaves the Sambay evaporator was recycled into the bottom space of the rectification column above the liquid level. For reasons of inhibiting polymerization, 0.01 kg/h of lean air ($O_2$ content=5% by weight) (the temperature of which was 30° C.) was conducted continuously into the bottom of the stripping column.

The remaining 1.02 kg/h of the stream of bottoms liquid conducted continuously out of the bottom space constituted essentially Diphyl-free "ready mix" which, generally after molecular oxygen still dissolved therein has been displaced by molecular nitrogen, after optional addition of substances such as comonomers (optionally also glacial acrylic acid (GAA)), internal crosslinker and polymerization initiator, was subjected to the desired free-radical subsequent polymerization.

Alternatively, the "ready mix" was cooled to 25° C., in the course of flow through an indirect heat exchanger and supplied to a reservoir vessel adjusted to this temperature, in which it was stored blanketed with lean air (due to the constant consumption of molecular oxygen, the blanketing, appropriately in application terms, was effected as a constantly flowing lean air stream (0.01 kg/h; $O_2$ content=5% by weight)).

Based on the total weight thereof, the "ready mix" had the following contents:
59.94% by wt. of water,
  acrolein,
  2-furaldehyde,
  benzaldehyde,
10 ppm by wt. of Diphyl,
0.61% by wt. of methylene glycol,
70 ppm by wt. of MEHQ,
31.6% by wt. of total amount of acrylic acid and the conjugate base thereof, calculated as acrylic acid,
and, based on the total amount of acrylic acid and the conjugate base thereof present in the "ready mix", calculated as acrylic acid,
286 ppm by wt. of total amount of propionic acid and the conjugate base thereof, calculated as propionic acid,
0.24% by wt. of total amount of formic acid and the conjugate base thereof, calculated as formic acid,
1.88% by wt. of total amount of acetic acid and the conjugate base thereof, calculated as acetic acid,
  benzoic acid and the conjugate base thereof,
  MAn and MAc and the conjugate bases thereof,
  PAn and PAc and the conjugate bases thereof, and
72.60 mol % of $Na^+$.

The steam raised in the bottom of the stripping column stripped aqueous raffinate III to free it not only of the extractant used but also of the 2-furaldehyde still present.

By means of a conveying pump, 7.63 kg/h of bottoms liquid which had a temperature of 100.2° C. were conducted continuously out of the bottom of separating column K. 7.60 kg/h thereof, conveyed by the pump, were sprayed as cooling liquid in the spray cooler operated in cocurrent for the purpose of direct cooling of the product gas mixture from the partial oxidation zone.

The remaining 0.03 kg/h were supplied to the recovery unit R for recovery of acrylic acid present therein as monomer and as Michael adduct.

The recovery unit R was a cylindrical pressure-resistant glass vessel which was free of internals and whose internal diameter was 60.3 mm and whose height was 350 mm. The vessel was heated externally by means of a coiled electrical heating band. The temperature of the liquid contents thereof was kept at 181.5° C. The internal pressure of the vapor phase was 1.5 bar. A Blackmere C8 ring piston pump was used to continuously withdraw 0.25 kg/h of the liquid contents from the recovery vessel R through a thermally insulated pipe, and to recycle it back into the recovery vessel R into the liquid phase present in the recovery vessel R above the withdrawal point (in this way, the contents of the recovery vessel R were kept in motion, which ensured sufficient mixing and satisfactory mass transfer). At the upper end of the cylindrical vessel was, as a splash guard, a short column filled with Raschig rings. Every 12 hours, 120 g of high-boiling residue remaining in the recovery were discharged via a valve of the Contiflow-TRF-HM type from AZ-Armaturen. It constituted the outlet for the unwanted MAn and MAc, PAn and PAc, and benzoic acid constituents. The gas phase which formed in the recovery vessel R, without formation of reflux liquid, was conducted as a low boiler stream at a flow rate of 0.02 kg/h and with a temperature of 181.5° C., together with the product gas mixture from the partial oxidation zone, into the cooling zone described (into the spray cooler described for the product gas mixture).

The low boiler stream conducted out of the recovery vessel R had the following contents (based on the total weight thereof):
5.46% by wt. of water,
30 ppm by wt. of $CO_2$,
60 ppm by wt. of acrolein,
82.20% by wt. of acrylic acid,
0.54% by wt. of acetic acid,
0.036% by wt. of 2-furaldehyde,
8.40% by wt. of MAn and MAc, calculated as MAn,
0.094% by wt. of benzaldehyde,
80 ppm by wt. of propane,
1.90% by wt. of formaldehyde,
0.092% by wt. of formic acid,
0.024% by wt. of propionic acid,
0.447% by wt. of benzoic acid,
0.325% by wt. of PAn and PAc, calculated as PAn,
20 ppm by wt. of propene, and
0.18% by wt. of MEHQ.

Example 2

Example 2 was performed with the same oxidation reactors and other apparatuses as described in example 1. The partial oxidation conditions corresponded to those from example 1 (including the charging of the oxidation reactors with fixed catalyst bed and the intermediate air feeding between the two reaction stages). Aqueous intermediate I was not withdrawn. No $CO_2$ outgassing of aqueous intermediate II was required, which is why this element was not integrated into the apparatus.

Reaction gas input mixture 1 was obtained from 0.23 kg/h of propene which was of chemical grade purity and which, based on the total volume thereof, comprised ≥3.85% by volume of propane and ≥96% by volume of propene, and 1.15 kg/h of air and 1.19 kg/h of cycle gas. The total flow rate thereof was 2.57 kg/h and it had the following contents:
78.11% by vol. of $N_2$,
10.50% by vol. of $O_2$,
3.73% by vol. of $H_2O$,
0.79% by vol. of $CO_2$,
0.015% by vol. of acrolein,
0.48% by vol. of propane,
0.39% by vol. of CO, and
5.89% by vol. of propene.

The flow rate of product gas mixture flowing out of the second reaction stage was 2.74 kg/h. The temperature thereof was 260° C. and the outlet pressure thereof was 1.50 bar. Based on the total weight thereof, it had the following contents:
75.17% by wt. of $N_2$,
2.39% by wt. of $O_2$,
5.97% by wt. of $H_2O$,
2.11% by wt. of $CO_2$,
589 ppm by wt. of acrolein,
12.05% by wt. of acrylic acid,
2256 ppm by wt. of acetic acid,
30 ppm by wt. of 2-furaldehyde,
0.133% by wt. of maleic anhydride,
50 ppm by wt. of benzaldehyde,
0.68% by wt. of propane,
0.68% by wt. of CO,
0.14% by wt. of formaldehyde,
309 ppm by wt. of formic acid,
30 ppm by wt. of propionic acid,
109 ppm by wt. of benzoic acid,
150 ppm by wt. of phthalic anhydride, and
0.169% by wt. of propene.

This corresponded, based on the total weight of acrylic acid present in the product gas mixture, to the following contents:
249 ppm by wt. of propionic acid,
2564 ppm by wt. of formic acid,
1.87% by wt. of acetic acid,
905 ppm by wt. of benzoic acid,
1.10% by wt. of maleic anhydride,
1244 ppm by wt. of phthalic anhydride,
4887 ppm by wt. of acrolein,
414 ppm by wt. of benzaldehyde, and
249 ppm by wt. of 2-furaldehyde.

Based on the total volume of the product gas mixture, it comprised:
79.86% by vol. of $N_2$,
2.22% by vol. of $O_2$,
1.42% by vol. of $CO_2$,
0.46% by vol. of propane, and
0.72% by vol. of CO.

The product gas mixture stream was supplied together with 0.02 kg/h of the low boiler stream conducted out of the recovery unit R (which had a temperature of 181.8° C. and a pressure of 1.5 bar) to a spray cooler operated in cocurrent (to the cooling zone). As cooling liquid, 7.85 kg/h of bottoms liquid having a temperature of 103.8° C. were sprayed therein, which were withdrawn from the bottom of separating column K at a temperature of 103.7° C. and were conveyed to the spray cooler by means of a pump.

The bottoms liquid had the following contents:
1.70% by wt. of water,
70.13% by wt. of acrylic acid (monomer and as Michael adduct),
0.34% by wt. of acetic acid,
539 ppm by wt. of 2-furaldehyde,
21.64% by wt. of MAn and MAc, calculated as MAc,
0.18% by wt. of benzaldehyde,
1.52% by wt. of PAn and PAc, calculated as PAn,
0.12% by wt. of formic acid,
220 ppm by wt. of propionic acid,
1.27% by wt. of benzoic acid,
2.02% by wt. of methylene glycol, and
0.77% by wt. of MEHQ.

The biphasic mixture of product gas mixture stream, low boiler stream and cooling liquid (10.62 kg/h in total) was conducted into the bottom space of separating column K at a temperature of 105.2° C., below the lowermost separating internal and above the bottoms level. The pressure in the bottom space of separating column K was 1.34 bar (immediately above the bottoms level).

A heat carrier oil was conducted through the intermediate space of the jacketed bottom space of separating column K, in order to ensure a temperature of the bottoms liquid (of absorbate I) of 103.7° C.

A total of 7.88 kg/h of bottoms liquid (absorbate I) were conducted out of the bottom of separating column K. 0.03 kg/h thereof was supplied to the recovery unit R, while the remaining 7.85 kg/h were sprayed as described in the cooling zone as cooling liquid.

The flow rate of the gas stream which was scrubbed in absorption zone I and flows into condensation zone I (into the second section of separating column K from the bottom) was 3.74 kg/h. The temperature thereof was 93.9° C. and the pressure thereof was 1.34 bar.

The contents of this gas stream were, based on the total weight thereof,
55.0% by wt. of $N_2$,
1.75% by wt. of $O_2$,
6.23% by wt. of $H_2O$,
1.55% by wt. of $CO_2$,
457 ppm by wt. of acrolein,
32.85% by wt. of acrylic acid,
3944 ppm by wt. of acetic acid,
94 ppm by wt. of 2-furaldehyde,
<1 ppm by wt. of MAn and MAc, calculated as MAn
202 ppm by wt. of benzaldehyde,
0.50% by wt. of propane,
0.50% by wt. of CO,
0.62% by wt. of formaldehyde,
541 ppm by wt. of formic acid,
96 ppm by wt. of propionic acid,
<1 ppm by wt. of MEHQ,
<1 ppm by wt. of benzoic acid,
<1 ppm by wt. of PAn and PAc, calculated as PAn, and
0.125% by wt. of propene.

Via the outlet of the first chimney tray from the bottom, 16.21 kg/h of condensate I were conducted out of condensation zone I at a temperature of 70.3° C.

Based on the total weight thereof, the condensate I had the following contents:
6.68% by wt. of water,
110 ppm by wt. of acrolein,
89.0% by wt. of acrylic acid,
0.85% by wt. of acetic acid,
279 ppm by wt. of 2-furaldehyde,
MAn and MAc, 630 ppm by wt. of benzaldehyde,
3.10% by wt. of methylene glycol,
0.12% by wt. of formic acid,
259 ppm by wt. of propionic acid,
  benzoic acid,
  PAn and PAc, and
160 ppm by wt. of MEHQ.

The overall stream of condensate I conducted out of separating column K was sent to a stirred jacketed vessel. Water was conducted in the intermediate space as a cooling liquid. The stirred vessel functioned as an indirect heat exchanger (as an indirect heat transferor). The residence time in this vessel was 3 min. MEHQ was added to this vessel. The amount added was such that the stream conducted out of the stirred vessel contained 170 ppm by weight of MEHQ (based on the total weight thereof).

The cooled overall stream of polymerization-inhibited condensate I conducted out of the stirred vessel had a temperature of 35° C. 1.01 kg/h of this overall stream was supplied via the inlet directed downward in the first intermediate column section from the bottom as absorbent I to the top of the uppermost structured packing in absorption zone I. 15.92 kg/h of this overall stream were recycled via the inlet directed downward in the second intermediate column section from the bottom as cooling liquid to the top of the uppermost structured packing in condensation zone I. No portion of the overall stream of polymerization-inhibited condensate I was conducted away from separating column K as aqueous intermediate I.

The residual gas mixture I remaining in gaseous form in condensation zone I had the following contents, based on the total weight thereof:
75.39% by wt. of $N_2$,
2.39% by wt. of $O_2$,
5.91% by wt. of $H_2O$,
2.11% by wt. of $CO_2$,
589 ppm by wt. of acrolein,
12.0% by wt. of acrylic acid,
2265 ppm by wt. of acetic acid,
30 ppm by wt. of 2-furaldehyde,
  MAn and MAc,
40 ppm by wt. of benzaldehyde,
0.68% by wt. of propane,
0.68% by wt. of CO,
0.14% by wt. of formaldehyde,
300 ppm by wt. of formic acid,
30 ppm by wt. of propionic acid,
  benzoic acid,
  PAn and PAc, and
0.17% by wt. of propene.

The stream of residual gas mixture I flowing out of condensation zone I into the third section from the bottom (into absorption zone II) had a temperature of 70.3° C. and a flow rate of 2.45 kg/h. The pressure thereof was 1.325 bar.

Via the outlet of the second chimney tray from the bottom, 7.52 kg/h of absorbate II were conducted out of absorption zone II at a temperature of 50° C.

Based on the total weight thereof, absorbate II had the following contents:
57.84% by wt. of water,
120 ppm by wt. of acrolein,
50 ppm by wt. of 2-furaldehyde,
90 ppm by wt. of benzaldehyde,
0.60% by wt. of methylene glycol,
60 ppm by wt. of MEHQ, and
31.76% by wt. of total amount of acrylic acid and the conjugate base thereof, calculated as acrylic acid,
and, based on the total amount of acrylic acid and the conjugate base thereof present in aqueous absorbate II, calculated as acrylic acid,
252 ppm by wt. of total amount of propionic acid and the conjugate base thereof, calculated as propionic acid,
0.25% by wt. of total amount of formic acid and the conjugate base thereof, calculated as formic acid,
1.86% by wt. of total amount of acetic acid and the conjugate base thereof, calculated as acetic acid,
  benzoic acid,
  MAn and MAc,
  PAn and PAc, and
91.11 mol % of $Na^+$.

A stream (0.38 kg/h; temperature=20° C.) of a 50% by weight aqueous solution of NaOH (purity of the NaOH >99.9% by weight) and a stream (0.32 kg/h; temperature=20° C.) of an aqueous inhibiting solution of MEHQ in water were supplied to this stream of absorbate II conducted out of absorption zone II. The MEHQ content of the aqueous inhibiting solution was such that the absorbate II conducted out of absorption zone II had an MEHQ content, based on the total weight thereof, of 60 ppm by weight.

This polymerization-inhibited overall stream was supplied as in example I to a stirred jacketed vessel. Water was conducted in the intermediate space as a cooling liquid. The stirred vessel functioned as an indirect heat exchanger (as an indirect heat transferor). The residence time in this vessel was 10 min. The cooled overall stream conducted out of it had a temperature of 40° C. 1.12 kg/h of this cooled polymerization-inhibited overall stream were conducted away from separating column K as aqueous intermediate II.

The other 7.10 kg/h of the cooled polymerization-inhibited overall stream were combined with 0.03 kg/h of aqueous condensate II which had been conducted out of condensation zone II via the outlet of the third chimney tray from the bottom and cooled to 30° C. in an indirect heat exchanger.

The resulting overall stream was supplied via the inlet directed downward in the third intermediate column section from the bottom as a mixture of absorbent II and condensate II circulated as cooling liquid to the top of the uppermost structured packing in absorption zone II.

The aqueous condensate II had the following contents, based on the total weight thereof:
97.02% by wt. of water,
110 ppm by wt. of acrolein,
2.25% by wt. of acrylic acid,
0.27% by wt. of acetic acid,
30 ppm by wt. of 2-furaldehyde,
10 ppm by wt. of benzaldehyde,
0.25% by wt. of methylene glycol,
90 ppm by wt. of formic acid, and
20 ppm by wt. of propionic acid.

The stream of residual gas mixture II flowing out of absorption zone II into the fourth section from the bottom (into condensation zone II) had a temperature of 50° C., a flow rate of 2.34 kg/h and a pressure of 1.315 bar. Based on the total weight thereof, residual gas mixture II had the following contents:
87.90% by wt. of $N_2$,
2.79% by wt. of $O_2$,
4.82% by wt. of $H_2O$,
2.44% by wt. of $CO_2$,
629 ppm by wt. of acrolein,
749 ppm by wt. of acrylic acid,
90 ppm by wt. of acetic acid,
10 ppm by wt. of furfural,
10 ppm by wt. of benzaldehyde, 0.79% by wt. of propane,
0.79% by wt. of CO,
25 ppm by wt. of formaldehyde, and
0.192% by wt. of propene.

The aqueous intermediate II had the following contents (based on the total weight thereof):
59.18% by wt. of water,
120 ppm by wt. of acrolein,
50 ppm by wt. of 2-furaldehyde,
90 ppm by wt. of benzaldehyde,
0.55% by wt. of methylene glycol,
60 ppm by wt. of MEHQ,
29.06% by wt. of total amount of acrylic acid and the conjugate base thereof, calculated as acrylic acid,
and, based on the total amount of acrylic acid and the conjugate base thereof present in aqueous intermediate II, calculated as acrylic acid,
252 ppm by wt. of total amount of propionic acid and the conjugate base thereof, calculated as propionic acid,
0.25% by wt. of total amount of formic acid and the conjugate base thereof, calculated as formic acid,
1.86% by wt. of total amount of acetic acid and the conjugate base thereof, calculated as acetic acid,
benzoic acid and the conjugate base thereof,
MAn and MAc and the conjugate bases thereof,
PAn and PAc and the conjugate bases thereof, and
105.5 mol % of $Na^+$.

Via the outlet of the third chimney tray from the bottom, 2.38 kg/h of condensate II were conducted out of condensation zone II at a temperature of 40° C. This stream of condensate II was sent to a stirred jacketed vessel. Water was conducted in the intermediate space as a cooling liquid. The stirred vessel functioned as an indirect heat exchanger (as an indirect heat transferor). The residence time in this vessel was 25 min. The stream of 2.38 kg/h of cooled condensate II conducted out of it had a temperature of 30° C. 0.03 kg/h of this stream was sent to the preparation of aqueous absorbent II. The other 2.35 kg/h were recycled via the inlet directed downward in the third intermediate column section from the bottom as cooling liquid to the top of the uppermost structured packing in condensation zone II.

The residual gas mixture III remaining in gaseous form in condensation zone II had the following contents, based on the total weight thereof:
89.11% by wt. of $N_2$,
2.82% by wt. of $O_2$,
3.61% by wt. of $H_2O$,
2.48% by wt. of $CO_2$,
639 ppm by wt. of acrolein,
459 ppm by wt. of acrylic acid,
50 ppm by wt. of acetic acid,
10 ppm by wt. of 2-furaldehyde,
10 ppm by wt. of benzaldehyde,
0.80% by wt. of propane,
0.81% by wt. of CO,
10 ppm by wt. of formaldehyde, and
0.19% by wt. of propene.

The temperature thereof was 40° C. and the pressure thereof was 1.305 bar. The flow rate thereof was 2.31 kg/h.

The stream of residual gas mixture III was conducted through an indirect heat transferor and heated to a temperature of 55° C. as it flowed through. 1.12 kg/h of the heated residual gas mixture III were sent to incineration. 1.19 kg/h of residual gas mixture III were compressed as cycle gas to a pressure of 2.135 bar and recycled into the preparation of the reaction gas input mixture.

The stream of aqueous intermediate II (1.12 kg/h) was, without having been subjected to $CO_2$ outgassing beforehand, sent to the stirred jacketed vessel to be used for heat exchange and for $O_2$ injection (in the form of lean air). Water was conducted in the intermediate jacket space as a heat carrier. The cylindrical stirred vessel functioned firstly as an indirect heat exchanger in order to heat the aqueous intermediate II to 50° C. as preparation for the subsequent aldehyde extraction. At the same time, a sparging ring installed close to the base within the stirred cylindrical vessel was used to inject, via the nozzle thereof, lean air ($N_2$-diluted air; $O_2$ content=5% by weight) into aqueous intermediate II (0.01 kg/h which had a temperature of 30° C.). This measure was effected for reasons of inhibiting polymerization (preferably up to saturation of intermediate II with lean air). The mean residence time of aqueous intermediate II in the heating and $O_2$ injection vessel was 15 min.

The lean air fractions not absorbed by aqueous intermediate II had a negligible stripping effect and were sent to disposal.

The polymerization-inhibited intermediate II heated to 50° C. was then supplied via the first inlet pipe to the pulsed extraction column. The organic extractant was supplied via the second inlet pipe. The mass density of aqueous intermediate II at 50° C. was 1140 kg/m$^3$. The mass density of the organic extractant at 50° C. was 1053 kg/m$^3$. The pressure in the gas phase at the top of the extraction column, which was open to the atmosphere, was 1.01 bar. Aqueous intermediate II was supplied to the extraction column at the flow rate of 1.12 kg/h. The organic extractant was supplied to the extraction column at a flow rate of 0.73 kg/h and at a feed temperature of likewise 50° C. On startup of the extraction, the extraction column was completely filled with aqueous intermediate II. Subsequently, extraction material and extractant were supplied continuously as described. The organic extractant formed the disperse phase and the aqueous intermediate II formed the continuous phase. The organic extractant used was Diphyl which, based on the total weight thereof, comprised 70 ppm by weight of MEHQ in dissolved form.

In the phase separation section, the organic extract II of lower specific gravity floated on top and was conducted continuously out of the extraction column at a flow rate of 0.73 kg/h. 1.12 kg/h of aqueous raffinate II were withdrawn continuously from the bottom space of the extraction column as aqueous target product solution. The temperature of aqueous raffinate II and of organic extract II was 50° C.

Aqueous raffinate II had the following contents, based on the total weight thereof:
59.93% by wt. of water,
acrolein,
2-furaldehyde,
benzaldehyde,
0.080% by wt. of Diphyl,
0.55% by wt. of methylene glycol,
70 ppm by wt. of MEHQ,
29.07% by wt. of total amount of acrylic acid and the conjugate base thereof, calculated as acrylic acid,
and, based on the total amount of acrylic acid and the conjugate base thereof present in aqueous raffinate II, calculated as acrylic acid,
279 ppm by wt. of total amount of propionic acid and the conjugate base thereof, calculated as propionic acid,
0.25% by wt. of total amount of formic acid and the conjugate base thereof, calculated as formic acid,
1.86% by wt. of total amount of acetic acid and the conjugate base thereof, calculated as acetic acid,
benzoic acid and the conjugate base thereof, MAn and MAc and the conjugate bases thereof,
PAn and PAc and the conjugate bases thereof,
105.6 mol % of Na$^+$, and
<0.2 mol % of total amount of carbonate and hydrogencarbonate anions.

Organic extract II had the following contents, based on the total weight thereof:
0.105% by wt. of water,
0.018% by wt. of acrolein,
70 ppm by wt. of 2-furaldehyde,
0.013% by wt. of benzaldehyde,
99.83% by wt. of Diphyl,
20 ppm by wt. of methylene glycol,
  acrylic acid,
  formic acid,
  acetic acid,
  propionic acid,
  benzoic acid,
  MAn and MAc,
  PAn and PAc, and
70 ppm by wt. of MEHQ.

From aqueous raffinate II, generally after molecular oxygen still dissolved therein had been displaced by molecular nitrogen, after optional addition of substances such as comonomers (optionally also glacial acrylic acid (GAA)), internal crosslinkers and polymerization initiators, the desired free-radical subsequent polymerization was performed directly. The specific procedure was as described in the prior art documents cited.

To recover the organic extractant present in organic extract II, it was sent to the rectification column having a rectifying section and a stripping section. Prior to the supply of extract II to the rectification column, it was conducted through an indirect heat exchanger in order to increase its temperature to the supply value of 171.7° C.

The top pressure of the rectification column was adjusted to 100 mbar. The vapor pressure in the column bottom was 155 mbar.

A conveying pump was used to continuously conduct 51.08 kg/h of Diphyl which had a purity of ≥99.99% by weight and comprised 70 ppm by weight of MEHQ in dissolved form out of the bottom space. The temperature of the bottoms liquid was 185.5° C.

0.73 kg/h of this withdrawal stream was sent to a jacketed stirred vessel. Temperature-controlled water was conducted within the intermediate jacket space. In addition, losses of Diphyl were compensated for in this stirred vessel by supplying fresh Diphyl. The temperature in the stirred vessel was kept at 50° C. The capacity of the stirred vessel was 5 l. The organic extractant was withdrawn from this stirred vessel and sent to the pulsed extraction column.

The remaining 50.35 kg/h of the withdrawal stream were circulated by means of the same conveying pump through a stainless steel Sambay evaporator, which ensured the energy input required for the rectification. The heat carrier was heat carrier oil.

The mixture of vapor and liquid phase leaving the Sambay evaporator (T=185.5° C.) was recycled into the bottom space of the rectification column above the liquid level.

The temperature at the top of the column was 47.1° C. The vapor stream leaving the rectification column at this temperature was conducted through a condenser designed as an indirect heat transferor. As a cooling element, it comprised a cooling coil through which cold water flowed. The constituents which do not condense in the condenser were drawn off as a gas stream at a temperature of 30° C. by means of the vacuum pump (water-jet pump). The condensate stream formed was divided into two substreams. 0.70 kg/h was recycled at a temperature of 30° C. as reflux liquid to the uppermost bubble-cap tray of the rectification column. The residual stream of the condensate was, as in example 1, discharged at intervals via a buffer vessel as the aldehyde outlet.

Based on the total weight thereof, the condensate had the following contents:
81.24% by wt. of H$_2$O,
1.22% by wt. of acrolein,
  acrylic acid,
  acetic acid,
5.08% by wt. of 2-furaldehyde,
9.95% by wt. of benzaldehyde,
1.87% by wt. of methylene glycol,
  formic acid, and
  propionic acid.

In the case of further uses of the aqueous target product solution for which the Diphyl content of the aqueous target product solution was found to be too high, the procedure was as follows.

The aqueous raffinate II having a temperature of 50° C., for the purpose of rectificative removal of the Diphyl still present therein, was supplied to the rectification column which had only a stripping section. The temperature of the outer wall of the bottom space was kept at 64.6° C.

The four sections connected atop the bottom space were again provided with external safeguard heating to the particular internal temperature.

The top temperature of the stripping column was adjusted to 100 mbar by means of a vacuum pump (membrane vacuum pump). The vapor pressure in the column bottom was 195 mbar. Aqueous raffinate II (1.12 kg/h) was supplied at its temperature of 50° C. to the uppermost bubble-cap tray. The vapor stream leaving the stripping column at a temperature of 47.8° C. was conducted through a condenser designed as an indirect heat transferor. As a cooling element, it comprised a cooling coil through which cold water flowed. The constituents which do not condense in the condenser were drawn off as a gas stream at a temperature of 25° C. by means of the vacuum pump.

The condensate stream formed was supplied at a temperature of 25° C. to the phase separator at a controlled temperature of 25° C. The condensate stream flowed from left to right in the phase separator and, as it did so, separated into an organic phase and an aqueous phase. The aqueous phase (0.88 kg/h; T=25° C.; mass density=998 kg/m$^3$) was recycled to the uppermost tray of the stripping column. The organic phase was incinerated.

By means of a conveying pump, 10.58 kg/h of bottoms liquid at a temperature of 64.7° C. were conducted continuously out of the bottom space. 9.46 kg/h of this stream were circulated by means of the stainless steel Sambay evaporator, which ensured the energy input required for the rectification. The heat carrier used was heat carrier oil. The mixture of vapor and liquid phase leaving the Sambay evaporator (T=65.5° C.) was recycled into the bottom space of the rectification column above the liquid level. For reasons of inhibiting polymerization, 0.01 kg/h of lean air (O$_2$ content=5% by weight) (at a temperature of 30° C.) was conducted continuously into the bottom of the stripping column.

The remaining 1.12 kg/h of the stream of bottoms liquid conducted continuously out of the bottom space formed essentially Diphyl-free aqueous target product solution which, generally after molecular oxygen still dissolved therein had been displaced by molecular nitrogen, after optional addition of substances such as comonomers (optionally also glacial acrylic acid (GAA)), internal crosslinkers and polymerization initiator, was subjected to the desired free-radical subsequent polymerization.

Alternatively, the aqueous target product solution was cooled to 25° C. as it flowed through an indirect heat exchanger and was supplied to a reservoir vessel temperature-controlled at this temperature, in which it was stored blanketed with lean air (due to the constant consumption of molecular oxygen, the blanketing, appropriately in application terms, was effected as a constantly flowing lean air stream (0.01 kg/h; $O_2$ content=5% by weight)).

Based on the total weight thereof, the aqueous target product solution had the following contents:
59.94% by wt. of water,
  acrolein,
  2-furaldehyde,
  benzaldehyde,
10 ppm by wt. of Diphyl,
0.55% by wt. of methylene glycol,
70 ppm by wt. of MEHQ,
29.23% by wt. of total amount of acrylic acid and the conjugate base thereof, calculated as acrylic acid,
and, based on the total amount of acrylic acid and the conjugate base thereof present in the aqueous target product solution, calculated as acrylic acid,
278 ppm by wt. of total amount of propionic acid and the conjugate base thereof, calculated as propionic acid,
0.25% by wt. of total amount of formic acid and the conjugate base thereof, calculated as formic acid,
1.86% by wt. of total amount of acetic acid and the conjugate base thereof, calculated as acetic acid,
  benzoic acid and the conjugate base thereof,
  MAn and MAc and the conjugate bases thereof,
  PAn and PAc and the conjugate bases thereof, and
105.6 mol % of $Na^+$.

The steam raised in the bottom of the stripping column stripped the aqueous raffinate II to essentially free it of the extractant used.

By means of a conveying pump, 7.88 kg/h of bottoms liquid which had a temperature of 100.7° C. were conducted continuously out of the bottom of separating column K. 7.85 kg/h thereof, conveyed by the pump, were sprayed as cooling liquid in the spray cooler operated in cocurrent for the purpose of direct cooling of the product gas mixture from the partial oxidation zone.

The remaining 0.03 kg/h was supplied to the recovery unit R for recovery of acrylic acid present therein as monomer and as Michael adduct.

The recovery unit R was the cylindrical pressure-resistant glass vessel which was free of internals and whose internal diameter was 60.3 mm and whose height was 350 mm. The vessel was heated externally by means of a coiled electrical heating band. The temperature of the liquid contents thereof was kept at 181.8° C. The internal pressure of the vapor phase was 1.5 bar. The Blackmere C8 ring piston pump was used to continuously withdraw 0.25 kg/h of the liquid contents from the recovery vessel R through a thermally insulated pipe, and to recycle it back into the recovery vessel R into the liquid phase present in the recovery vessel R above the withdrawal point (in this way, the contents of the recovery vessel R were kept in motion, which ensured sufficient mixing and satisfactory mass transfer). At the upper end of the cylindrical vessel was, as a splash guard, the short column filled with Raschig rings. Every 12 hours, 120 g of high-boiling residue remaining in the recovery were discharged via a valve of the Conti-flow-TRF-HM type from AZ-Armaturen. It constituted the outlet for the unwanted MAn and MAc, PAn and PAc, and benzoic acid constituents. The gas phase which formed in the recovery vessel R, without formation of reflux liquid, was conducted as a low boiler stream at a flow rate of 0.02 kg/h and with a temperature of 181.8° C., together with the product gas mixture from the partial oxidation zone, into the cooling zone described (into the spray cooler described for the product gas mixture).

The low boiler stream conducted out of the recovery vessel R had the following contents (based on the total weight thereof):
4.68% by wt. of water,
50 ppm by wt. of $CO_2$,
50 ppm by wt. of acrolein,
82.11% by wt. of acrylic acid,
0.41% by wt. of acetic acid,
0.059% by wt. of 2-furaldehyde,
9.06% by wt. of MAn and MAc, calculated as MAn,
0.19% by wt. of benzaldehyde,
70 ppm by wt. of propane,
2.00% by wt. of formaldehyde,
0.055% by wt. of formic acid,
0.025% by wt. of propionic acid,
0.437% by wt. of benzoic acid,
0.317% by wt. of PAn and PAc, calculated as PAn,
20 ppm by wt. of propene, and
0.31% by wt. of MEHQ.

Example 3

Example 3 was performed with the same oxidation reactors and other apparatuses as described in example 1. The partial oxidation conditions corresponded to those from example 1 (including the charging of the oxidation reactors with fixed catalyst bed and the intermediate air feeding between the two reaction stages). No $CO_2$ outgassing of aqueous intermediate III was required, which is why this element was not integrated into the apparatus.

Reaction gas input mixture 1 was obtained from 0.23 kg/h of propene which was of chemical grade purity and which, based on the total volume thereof, comprised >3.85% by volume of propane and >96% by volume of propene, and 1.15 kg/h of air and 1.19 kg/h of cycle gas. The total flow rate thereof was 2.57 kg/h and it had the following contents:
78.10% by vol. of $N_2$,
10.50% by vol. of $O_2$,
3.74% by vol. of $H_2O$,
0.79% by vol. of $CO_2$,
0.016% by vol. of acrolein,
0.47% by vol. of propane,
0.39% by vol. of CO, and
5.89% by vol. of propene.

The flow rate of product gas mixture flowing out of the second reaction stage was 2.73 kg/h. The temperature thereof was 260° C. and the outlet pressure thereof was 1.50 bar. Based on the total weight thereof, it had the following contents:
75.18% by wt. of $N_2$,
2.39% by wt. of $O_2$,
5.99% by wt. of $H_2O$,
2.10% by wt. of $CO_2$,
589 ppm by wt. of acrolein,
12.03% by wt. of acrylic acid,
2236 ppm by wt. of acetic acid,
29 ppm by wt. of 2-furaldehyde,
0.132% by wt. of maleic anhydride,
52 ppm by wt. of benzaldehyde,
0.67% by wt. of propane,
0.69% by wt. of CO, 0.14% by wt. of formaldehyde,
310 ppm by wt. of formic acid,
31 ppm by wt. of propionic acid,
110 ppm by wt. of benzoic acid,
151 ppm by wt. of phthalic anhydride, and
0.17% by wt. of propene.

This corresponded, based on the total weight of acrylic acid present in the product gas mixture, to the following contents:
258 ppm by wt. of propionic acid,
2577 ppm by wt. of formic acid,
1.86% by wt. of acetic acid,
914 ppm by wt. of benzoic acid,
1.10% by wt. of maleic anhydride,
1255 ppm by wt. of phthalic anhydride,
4896 ppm by wt. of acrolein,
432 ppm by wt. of benzaldehyde, and
241 ppm by wt. of 2-furaldehyde.

Based on the total volume of the product gas mixture, it comprised:
79.73% by vol. of $N_2$,
2.22% by vol. of $O_2$,
1.42% by vol. of $CO_2$,
0.46% by vol. of propane, and
0.72% by vol. of CO.

The product gas mixture stream was supplied together with 0.02 kg/h of the low boiler stream conducted out of the recovery unit R (which had a temperature of 181.5° C. and a pressure of 1.5 bar) to a spray cooler operated in cocurrent (to the cooling zone). As cooling liquid, 7.63 kg/h of bottoms liquid having a temperature of 100.4° C. were sprayed therein, which were withdrawn from the bottom of separating column K at a temperature of 100.2° C. and were conveyed to the spray cooler by means of a pump.

The bottoms liquid had the following contents:
2.15% by wt. of water,
70% by wt. of acrylic acid (monomer and as Michael adduct),
0.44% by wt. of acetic acid,
329 ppm by wt. of 2-furaldehyde,
21% by wt. of MAn and MAc, calculated as MAc,
918 ppm by wt. of benzaldehyde,
1.53% by wt. of PAn and PAc, calculated as PAn,
0.19% by wt. of formic acid,
210 ppm by wt. of propionic acid,
1.28% by wt. of benzoic acid,
2.40% by wt. of methylene glycol, and
0.45% by wt. of MEHQ.

The biphasic mixture of product gas mixture stream, low boiler stream and cooling liquid (10.38 kg/h in total) was conducted into the bottom space of separating column K at a temperature of 102.7° C., below the lowermost separating internal and above the bottoms level. The pressure in the bottom space of separating column K was 1.34 bar (immediately above the bottoms level).

A heat carrier oil was conducted through the intermediate space of the jacketed bottom space of separating column K, in order to ensure a temperature of the bottoms liquid (of absorbate I) of 100.2° C.

A total of 7.66 kg/h of bottoms liquid (absorbate I) were conducted out of the bottom of separating column K. 0.03 kg/h thereof was supplied to the recovery unit R, while the remaining 7.63 kg/h were sprayed as described in the cooling zone as cooling liquid.

The flow rate of the gas stream which was scrubbed in absorption zone I and flows into condensation zone I (into the second section of separating column K from the bottom) was 3.32 kg/h. The temperature thereof was 85.1° C. and the pressure thereof was 1.34 bar.

The contents of this gas stream were, based on the total weight thereof,
62.01% by wt. of $N_2$,
1.97% by wt. of $O_2$,
10.48% by wt. of $H_2O$,
1.74% by wt. of $CO_2$,
515 ppm by wt. of acrolein,
21.47% by wt. of acrylic acid,
0.38% by wt. of acetic acid,
42 ppm by wt. of 2-furaldehyde,
<1 ppm by wt. of MAn and MAc, calculated as MAn,
79 ppm by wt. of benzaldehyde,
0.56% by wt. of propane,
0.56% by wt. of CO,
0.28% by wt. of formaldehyde,
540 ppm by wt. of formic acid,
60 ppm by wt. of propionic acid,
<1 ppm by wt. of MEHQ,
<1 ppm by wt. of benzoic acid,
<1 ppm by wt. of PAn and PAc, calculated as PAn, and
0.143% by wt. of propene.

Via the outlet of the first chimney tray from the bottom, 16.81 kg/h of condensate I were conducted out of condensation zone I at a temperature of 55° C.

Based on the total weight thereof, the condensate I had the following contents:
31.16% by wt. of water,
180 ppm by wt. of acrolein,
65.75% by wt. of acrylic acid,
1.10% by wt. of acetic acid,
120 ppm by wt. of 2-furaldehyde,
230 ppm by wt. of benzaldehyde,
MAn and MAc,
1.51% by wt. of methylene glycol,
0.17% by wt. of formic acid,
179 ppm by wt. of propionic acid,
benzoic acid,
PAn and PAc, and
160 ppm by wt. of MEHQ.

A stream of 0.12 kg/h of a solution of MEHQ in water at a temperature of 25° C. was added to this stream of condensate I conducted out of separating column K. The MEHQ content of the aqueous solution was such that the resulting overall stream of polymerization-inhibited condensate I contained 169 ppm by weight of MEHQ (based on the total weight thereof).

As in example 1, the overall stream of polymerization-inhibited condensate I was supplied to a stirred jacketed vessel. Water was conducted in the intermediate space as a cooling liquid. The stirred vessel functioned as an indirect heat exchanger (as an indirect heat transferor). The residence time in this vessel was 3 min.

The cooled overall stream of polymerization-inhibited condensate I conducted out of it had a temperature of 35° C. 0.59 kg/h of this overall stream was supplied via the inlet directed downward in the first intermediate column section from the bottom as absorbent I to the top of the uppermost structured packing in absorption zone I. 15.96 kg/h of this overall stream were recycled via the inlet directed downward in the second intermediate column section from the bottom as cooling liquid to the top of the uppermost structured packing in condensation zone I. 0.38 kg/h of this overall stream was conducted away from separating column K as aqueous intermediate I.

The residual gas mixture I remaining in gaseous form in condensation zone I had the following contents, based on the total weight thereof:

83.45% by wt. of $N_2$,
2.65% by wt. of $O_2$,
6.34% by wt. of $H_2O$,
2.33% by wt. of $CO_2$,
619 ppm by wt. of acrolein,
3.17% by wt. of acrylic acid,
788 ppm by wt. of acetic acid,
10 ppm by wt. of 2-furaldehyde,
MAn and MAc,
10 ppm by wt. of benzaldehyde,
0.75% by wt. of propane,
0.76% by wt. of CO,
129 ppm by wt. of formaldehyde,
70 ppm by wt. of formic acid,
10 ppm by wt. of propionic acid,
benzoic acid,
PAn and PAc, and
0.19% by wt. of propene.

The stream of residual gas mixture I flowing out of condensation zone I into the third section from the bottom (into absorption zone II) had a temperature of 55° C. and a flow rate of 2.46 kg/h. The pressure thereof was 1.325 bar.

Via the outlet of the second chimney tray from the bottom, 2.69 kg/h of absorbate II were conducted out of absorption zone II at a temperature of 50° C.

Based on the total weight thereof, absorbate II had the following contents:
75.57% by wt. of water,
100 ppm by wt. of acrolein,
20 ppm by wt. of 2-furaldehyde,
30 ppm by wt. of benzaldehyde,
0.11% by wt. of methylene glycol,
60 ppm by wt. of MEHQ, and
17.85% by wt. of total amount of acrylic acid and the conjugate base thereof, calculated as acrylic acid,
and, based on the total amount of acrylic acid and the conjugate base thereof present in aqueous absorbate II, calculated as acrylic acid,
283 ppm by wt. of total amount of propionic acid and the conjugate base thereof, calculated as propionic acid,
0.23% by wt. of total amount of formic acid and the conjugate base thereof, calculated as formic acid,
2.45% by wt. of total amount of acetic acid and the conjugate base thereof, calculated as acetic acid,
benzoic acid,
MAn and MAc,
PAn and PAc, and
103.7 mol % of Na+.

A stream (0.11 kg/h; temperature=20° C.) of a 50% by weight aqueous solution of NaOH (purity of the NaOH >99.9% by weight) and a stream (0.23 kg/h; temperature=20° C.) of an aqueous inhibiting solution of MEHQ in water were supplied to this stream of absorbate II conducted out of absorption zone II. The MEHQ content of the aqueous inhibiting solution was such that the absorbate II conducted out of absorption zone II had an MEHQ content, based on the total weight thereof, of 60 ppm by weight.

This polymerization-inhibited overall stream was supplied as in example 1 to a stirred jacketed vessel. Water was conducted in the intermediate space as a cooling liquid. The stirred vessel functioned as an indirect heat exchanger (as an indirect heat transferor). The residence time in this vessel was 10 min. The cooled overall stream conducted out of it had a temperature of 40° C. 0.49 kg/h of this cooled polymerization-inhibited overall stream was conducted away from separating column K as aqueous intermediate II.

The other 2.54 kg/h of the cooled polymerization-inhibited overall stream were combined with 0.04 kg/h of aqueous condensate II which had been conducted out of condensation zone II via the outlet of the third chimney tray from the bottom and cooled to 30° C. in an indirect heat exchanger.

The resulting overall stream was supplied via the inlet directed downward in the third intermediate column section from the bottom as a mixture of absorbent II and condensate II circulated as cooling liquid to the top of the uppermost structured packing in absorption zone II.

The aqueous condensate II had the following contents, based on the total weight thereof:
99.75% by wt. of water,
110 ppm by wt. of acrolein,
0.015% by wt. of acrylic acid,
50 ppm by wt. of acetic acid,
20 ppm by wt. of 2-furaldehyde,
10 ppm by wt. of benzaldehyde, and
0.032% by wt. of methylene glycol.

The stream of residual gas mixture II flowing out of absorption zone II into the fourth section from the bottom (into condensation zone II) had a temperature of 50° C., a flow rate of 2.35 kg/h and a pressure of 1.315 bar. Based on the total weight thereof, residual gas mixture II had the following contents:
87.42% by wt. of $N_2$,
2.77% by wt. of $O_2$,
5.44% by wt. of $H_2O$,
2.42% by wt. of $CO_2$,
639 ppm by wt. of acrolein,
10 ppm by wt. of acrylic acid,
10 ppm by wt. of benzaldehyde,
0.79% by wt. of propane,
0.79% by wt. of CO,
6 ppm by wt. of formaldehyde, and
0.194% by wt. of propene.

The aqueous intermediate II had the following contents (based on the total weight thereof):
76.58% by wt. of water,
90 ppm by wt. of acrolein,
20 ppm by wt. of 2-furaldehyde,
30 ppm by wt. of benzaldehyde,
995 ppm by wt. of methylene glycol,
60 ppm by wt. of MEHQ,
15.87% by wt. of total amount of acrylic acid and the conjugate base thereof, calculated as acrylic acid,
and, based on the total amount of acrylic acid and the conjugate base thereof present in aqueous intermediate II, calculated as acrylic acid,
283 ppm by wt. of total amount of propionic acid and the conjugate base thereof, calculated as propionic acid,
0.23% by wt. of total amount of formic acid and the conjugate base thereof, calculated as formic acid,
2.45% by wt. of total amount of acetic acid and the conjugate base thereof, calculated as acetic acid,
benzoic acid and the conjugate base thereof,
MAn and MAc and the conjugate bases thereof,
PAn and PAc and the conjugate bases thereof, and
123.9 mol % of $Na^+$.

Via the outlet of the third chimney tray from the bottom, 3.18 kg/h of condensate II were conducted out of condensation zone II at a temperature of 40° C. This stream of condensate II, as in example 1, was sent to a stirred jacketed vessel. Water was conducted in the intermediate space as a cooling liquid. The stirred vessel functioned as an indirect heat exchanger (as an indirect heat transferor). The residence time in this vessel was 20 min. The stream of 3.18 kg/h of cooled condensate II conducted out of it had a temperature of 30° C. 0.04 kg/h of this stream was sent to the preparation of aqueous absorbent II. The other 3.14 kg/h were recycled via the inlet directed downward in the third intermediate column section from the bottom as cooling liquid to the top of the uppermost structured packing in condensation zone II.

The residual gas mixture III remaining in gaseous form in condensation zone II had the following contents, based on the total weight thereof:
89.09% by wt. of $N_2$,
2.83% by wt. of $O_2$,
3.64% by wt. of $H_2O$,
2.47% by wt. of $CO_2$,
649 ppm by wt. of acrolein,
acrylic acid,
10 ppm by wt. of benzaldehyde,
0.806% by wt. of propane,
0.806% by wt. of CO, and
0.2% by wt. of propene.

The temperature thereof was 40° C. and the pressure thereof was 1.305 bar. The flow rate
thereof was 2.31 kg/h.

The stream of residual gas mixture III was conducted through an indirect heat transferor and heated to a temperature of 55° C. as it flowed through. 1.12 kg/h of the heated residual gas mixture III were sent to incineration. 1.19 kg/h of residual gas mixture III were compressed as cycle gas to a pressure of 2.135 bar and recycled into the preparation of the reaction gas input mixture.

The stream of aqueous intermediate I (0.38 kg/h), the stream (0.49 kg/h) of aqueous intermediate II and a stream of 0.15 kg/h of the 50% by weight aqueous NaOH solution also used for preparation of aqueous absorbent II (T=20° C.) were conducted through a static mixer and mixed therein to give aqueous intermediate III.

The flow rate of the stream of aqueous intermediate III conducted continuously out of the static mixer at a temperature of 31.5° C. was 1.02 kg/h. It had the following contents (based on the total weight thereof):
59.67% by wt. of water,
110 ppm by wt. of acrolein,
60 ppm by wt. of 2-furaldehyde,
100 ppm by wt. of benzaldehyde,
0.61% by wt. of methylene glycol,
70 ppm by wt. of MEHQ,
31.89% by wt. of total amount of acrylic acid and the conjugate base thereof, calculated as acrylic acid,
and, based on the total amount of acrylic acid and the conjugate base thereof present in aqueous intermediate III, calculated as acrylic acid,
284 ppm by wt. of total amount of propionic acid and the conjugate base thereof, calculated as propionic acid,
0.25% by wt. of total amount of formic acid and the conjugate base thereof, calculated as formic acid,
1.87% by wt. of total amount of acetic acid and the conjugate base thereof, calculated as acetic acid,
benzoic acid and the conjugate base thereof,
MAn and MAc and the conjugate bases thereof,
PAn and PAc and the conjugate bases thereof, and
71.57 mol % of $Na^+$.

The stream of aqueous intermediate III (1.02 kg/h) was, without having been subjected to $CO_2$ outgassing beforehand, sent to the stirred jacketed vessel to be used for heat exchange and for $O_2$ injection (in the form of lean air). Water was conducted in the intermediate jacket space as a heat carrier. The cylindrical stirred vessel functioned firstly as an indirect heat exchanger in order to heat the aqueous intermediate II to 50° C. as preparation for the subsequent aldehyde extraction. At the same time, a sparging ring installed close to the base within the stirred cylindrical vessel was used to inject, via the nozzle thereof, lean air ($N_2$-diluted air; $O_2$ content=5% by weight) into aqueous intermediate III (0.01 kg/h which had a temperature of 30° C.). This measure was effected for reasons of inhibiting polymerization (preferably up to saturation of intermediate III with lean air). The mean residence time of aqueous intermediate III in the heating and $O_2$ injection vessel was 15 min.

The lean air fractions not absorbed by aqueous intermediate III had a negligible stripping effect and were sent to disposal.

The polymerization-inhibited intermediate III heated to 50° C. was then supplied via the first inlet pipe to the pulsed extraction column. The organic extractant was supplied via the second inlet pipe. The mass density of aqueous intermediate III at 50° C. was 1141 kg/m³. The mass density of the organic extractant at 50° C. was 1053 kg/m³. The pressure in the gas phase at the top of the extraction column, which was open to the atmosphere, was 1.01 bar. Aqueous intermediate III was supplied to the extraction column at the flow rate of 1.02 kg/h. The organic extractant was supplied to the extraction column at a flow rate of 0.66 kg/h and at a feed temperature of likewise 50° C. On startup of the extraction, the extraction column was completely filled with aqueous intermediate III. Subsequently, extraction material and extractant were supplied continuously as described. The organic extractant formed the disperse phase and the aqueous intermediate III formed the continuous phase. The organic extractant used was Diphyl which, based on the total weight thereof, comprised 70 ppm by weight of MEHQ in dissolved form.

In the phase separation section, the organic extract III of lower specific gravity floated on top and was conducted continuously out of the extraction column at a flow rate of 0.665 kg/h. 1.015 kg/h of aqueous raffinate II were withdrawn continuously from the bottom space of the extraction column as aqueous target product solution. The temperature of aqueous raffinate II and of organic extract III was 50° C.

Aqueous raffinate III had the following contents, based on the total weight thereof:
59.93% by wt. of water,
acrolein,
2-furaldehyde,
benzaldehyde,
0.080% by wt. of Diphyl,
0.61% by wt. of methylene glycol,
70 ppm by wt. of MEHQ,
31.54% by wt. of total amount of acrylic acid and the conjugate base thereof, calculated as acrylic acid,
and, based on the total amount of acrylic acid and the conjugate base thereof present in aqueous raffinate III, calculated as acrylic acid,
286 ppm by wt. of total amount of propionic acid and the conjugate base thereof, calculated as propionic acid,
0.24% by wt. of total amount of formic acid and the conjugate base thereof, calculated as formic acid,
1.88% by wt. of total amount of acetic acid and the conjugate base thereof, calculated as acetic acid,
benzoic acid and the conjugate base thereof,
MAn and MAc and the conjugate bases thereof,
PAn and PAc and the conjugate bases thereof,
72.8 mol % of $Na^+$, and
<0.02 mol % of total amount of carbonate and hydrogencarbonate anions.

Organic extract III had the following contents, based on the total weight thereof:
0.105% by wt. of water,
0.016% by wt. of acrolein,
0.84% by wt. of acrylic acid,
90 ppm by wt. of acetic acid,
80 ppm by wt. of 2-furaldehyde,
0.015% by wt. of benzaldehyde,
98.84% by wt. of Diphyl,
20 ppm by wt. of methylene glycol,
60 ppm by wt. of formic acid,
propionic acid,
benzoic acid,
MAn and MAc,
PAn and PAc, and
70 ppm by wt. of MEHQ.

From aqueous raffinate III, generally after molecular oxygen still dissolved therein had been displaced by molecular nitrogen, after optional addition of substances such as comonomers (optionally also glacial acrylic acid (GAA)), internal crosslinkers and polymerization initiators, the desired free-radical subsequent polymerization was performed directly. The specific procedure was as described in the prior art documents cited.

To recover the organic extractant present in organic extract III, it was sent to the rectification column having a rectifying section and a stripping section. Prior to the supply of extract III to the rectification column, it was conducted through an indirect heat exchanger in order to increase its temperature to the supply value of 179.2° C.

The top pressure of the rectification column was adjusted to 100 mbar. The vapor pressure in the column bottom was 155 mbar.

A conveying pump was used to continuously conduct 17.02 kg/h of Diphyl which had a purity of ≥99.99% by weight and comprised 70 ppm by weight of MEHQ in dissolved form out of the bottom space. The temperature of the bottoms liquid was 185.5° C.

0.66 kg/h of this withdrawal stream was sent to a jacketed stirred vessel. Temperature-controlled water was conducted within the intermediate jacket space. In addition, looses of Diphyl were compensated for in this stirred vessel by supplying fresh Diphyl. The temperature in the stirred vessel was kept at 50° C. The capacity of the stirred vessel was 5 l. The organic extractant was withdrawn from this stirred vessel and sent to the pulsed extraction column.

The remaining 16.36 kg/h of the withdrawal stream were circulated by means of the same conveying pump through a stainless steel Sambay evaporator, which ensured the energy input required for the rectification. The heat carrier was heat carrier oil.

The mixture of vapor and liquid phase leaving the Sambay evaporator (T=185.5° C.) was recycled into the bottom space of the rectification column above the liquid level.

The temperature at the top of the column was 69.9° C. The vapor stream leaving the rectification column at this temperature was conducted through a condenser designed as an indirect heat transferor. As a cooling element, it comprised a cooling coil through which cold water flowed.

The constituents which do not condense in the condenser were drawn off as a gas stream at a temperature of 30° C. by means of the vacuum pump (membrane vacuum pump). The condensate stream formed was divided into two substreams. 0.70 kg/h was recycled at a temperature of 30° C. as reflux liquid to the uppermost bubble-cap tray of the rectification column. The residual stream of the condensate was, as in example 1, discharged at intervals via a buffer vessel as the aldehyde outlet.

Based on the total weight thereof, the condensate had the following contents:
9.97% by wt. of $H_2O$,
0.83% by wt. of acrolein,
84.98% by wt. of acrylic acid,
0.90% by wt. of acetic acid,
0.80% by wt. of 2-furaldehyde,
1.55% by wt. of benzaldehyde,
0.25% by wt. of methylene glycol,
0.54% by wt. of formic acid, and
0.01% by wt. of propionic acid.

In the case of further uses of the aqueous target product solution for which the Diphyl content of the aqueous target product solution was found to be too high, the procedure was as follows.

The aqueous raffinate III having a temperature of 50° C., for the purpose of rectificative removal of the Diphyl still present therein, was supplied to the rectification column which had only a stripping section. The temperature of the outer wall of the bottom space was kept at 63.5° C.

The four sections connected atop the bottom space were again provided with external safeguard heating to the particular internal temperature.

The top temperature of the stripping column was adjusted to 100 mbar by means of a vacuum pump (membrane vacuum pump). The vapor pressure in the column bottom was 195 mbar. Aqueous raffinate III (1.015 kg/h) was supplied at a temperature of 50° C. to the uppermost bubble-cap tray. The vapor stream leaving the stripping column at a temperature of 47.5° C. was conducted through a condenser designed as an indirect heat transferor. As a cooling element, it comprised a cooling coil through which cold water flowed. The constituents which do not condense in the condenser were drawn off as a gas stream at a temperature of 25° C. by means of the vacuum pump.

The condensate stream formed was supplied at a temperature of 25° C. to the phase separator at a controlled temperature of 25° C. The condensate stream flowed from left to right in the phase separator and, as it did so, separated into an organic phase and an aqueous phase. The aqueous phase (0.77 kg/h; T=25° C.; mass density=998.7 kg/m$^3$) was recycled to the uppermost tray of the stripping column. The organic phase was incinerated.

By means of a conveying pump, 9.46 kg/h of bottoms liquid at a temperature of 63.5° C. were conducted continuously out of the bottom space. 8.44 kg/h of this stream were circulated by means of the stainless steel Sambay evaporator, which ensured the energy input required for the rectification. The heat carrier used was heat carrier oil. The mixture of vapor and liquid phase leaving the Sambay evaporator (T=64.2° C.) was recycled into the bottom space of the rectification column above the liquid level. For reasons of inhibiting polymerization, 0.01 kg/h of lean air ($O_2$ content=5% by weight) (at a temperature of 30° C.) were conducted continuously into the bottom of the stripping column.

The remaining 1.02 kg/h of the stream of bottoms liquid conducted continuously out of the bottom space formed essentially Diphyl-free "ready mix" which, generally after molecular oxygen still dissolved therein had been displaced by molecular nitrogen, after optional addition of substances such as comonomers (optionally also glacial acrylic acid (GAA)), internal crosslinkers and polymerization initiator, was subjected to the desired free-radical subsequent polymerization.

Alternatively, the "ready mix" was cooled to 25° C. as it flowed through an indirect heat exchanger and was supplied to a reservoir vessel temperature-controlled at this temperature, in which it was stored blanketed with lean air (due to the constant consumption of molecular oxygen, the blanketing, appropriately in application terms, was effected as a constantly flowing lean air stream (0.01 kg/h; $O_2$ content=5% by weight)).

Based on the total weight thereof, the "ready mix" had the following contents:
59.88% by wt. of water,
  acrolein,
  2-furaldehyde,
  benzaldehyde,
10 ppm by wt. of Diphyl,
0.61% by wt. of methylene glycol,
70 ppm by wt. of MEHQ,
31.68% by wt. of total amount of acrylic acid and the conjugate base thereof, calculated as acrylic acid,
and, based on the total amount of acrylic acid and the conjugate base thereof present in the aqueous target product solution, calculated as acrylic acid,
285 ppm by wt. of total amount of propionic acid and the conjugate base thereof, calculated as propionic acid,
0.24% by wt. of total amount of formic acid and the conjugate base thereof, calculated as formic acid,
1.88% by wt. of total amount of acetic acid and the conjugate base thereof, calculated as acetic acid,
  benzoic acid and the conjugate base thereof,
  MAn and MAc and the conjugate bases thereof,
  PAn and PAc and the conjugate bases thereof,
72.90 mol % of $Na^+$.

The steam raised in the bottom of the stripping column stripped the aqueous raffinate III to essentially free it of the extractant used.

By means of a conveying pump, 7.66 kg/h of bottoms liquid which had a temperature of 100.2° C. were conducted continuously out of the bottom of separating column K. 7.63 kg/h thereof, conveyed by the pump, were sprayed as cooling liquid in the spray cooler operated in cocurrent for the purpose of direct cooling of the product gas mixture from the partial oxidation zone.

The remaining 0.03 kg/h were supplied to the recovery unit R for recovery of acrylic acid present therein as monomer and as Michael adduct.

The recovery unit R was the cylindrical pressure-resistant glass vessel which was free of internals and whose internal diameter was 60.3 mm and whose height was 350 mm. The vessel was heated externally by means of a coiled electrical heating band. The temperature of the liquid contents thereof was kept at 181.5° C. The internal pressure of the vapor phase was 1.5 bar. The Blackmere C8 ring piston pump was used to continuously withdraw 0.25 kg/h of the liquid contents from the recovery vessel R through a thermally insulated pipe, and to recycle it back into the recovery vessel R into the liquid phase present in the recovery vessel R above the withdrawal point (in this way, the contents of the recovery vessel R were kept in motion, which ensured sufficient mixing and satisfactory mass transfer). At the upper end of the cylindrical vessel was, as a splash guard, the short column filled with Raschig rings. Every 12 hours, 120 g of high-boiling residue remaining in the recovery were discharged via a valve of the Contiflow-TRF-HM type from AZ-Armaturen. It constituted the outlet for the unwanted MAn and MAc, PAn and PAc, and benzoic acid constituents. The gas phase which formed in the recovery vessel R, without formation of reflux liquid, was conducted as a low boiler stream at a flow rate of 0.02 kg/h and with a temperature of 181.5° C., together with the product gas mixture from the partial oxidation zone, into the cooling zone described (into the spray cooler described for the product gas mixture).

The low boiler stream conducted out of the recovery vessel R had the following contents (based on the total weight thereof):
5.44% by wt. of water,
60 ppm by wt. of $CO_2$,
60 ppm by wt. of acrolein,
82.25% by wt. of acrylic acid,
0.54% by wt. of acetic acid,
0.037% by wt. of 2-furaldehyde,
8.43% by wt. of MAn and MAc, calculated as MAn,
979 ppm by wt. of benzaldehyde,
70 ppm by wt. of propane,
1.87% by wt. of formaldehyde,
0.091% by wt. of formic acid,
0.024% by wt. of propionic acid,
0.44% by wt. of benzoic acid,
0.32% by wt. of PAn and PAc, calculated as PAn,
20 ppm by wt. of propene, and
0.19% by wt. of MEHQ.

U.S. Provisional Patent Application No. 61/492,822, Jun. 3, 2011, is incorporated into the present patent application by literature reference.

With regard to the abovementioned teachings, numerous changes and deviations from the present invention are possible. It can therefore be assumed that the invention, within the scope of the appended claims, can be performed differently than the way described specifically herein.

The invention claimed is:

1. A process for preparing an aqueous target product solution comprising acrylic acid and the conjugate base thereof, which comprises the following:
   (1) at least one $C_3$ precursor compound of acrylic acid is passed through a partial oxidation zone and partially oxidized therein to acrylic acid,
   wherein the at least one $C_3$ precursor compound of acrylic acid is a constituent of a reaction gas input mixture comprising the at least one $C_3$ precursor compound of acrylic acid, molecular oxygen and at least one inert diluent gas other than $CO_2$ and water, and
   the at least one $C_3$ precursor compound of acrylic acid is partially oxidized by a heterogeneously catalyzed gas phase partial oxidation in the partial oxidation zone over catalysts present in the solid state with the molecular oxygen to obtain a product gas mixture comprising $CO_2$, water, the target product acrylic acid, and as secondary constituents formic acid, acetic acid, propionic acid, benzoic acid, acrolein, benzaldehyde, 2-furaldehyde, phthalic anhydride and/or phthalic acid, maleic anhydride and/or maleic acid, and at least one inert diluent gas other than $CO_2$ and water,
   (2) the product gas mixture conducted out of the partial oxidation zone, optionally after its temperature has been reduced in a cooling zone by direct and/or indirect cooling, is conducted through an absorption zone I in which an absorbent I scrubs the secondary constituents benzoic acid, phthalic acid and/or the anhydride thereof and maleic acid and/or the anhydride thereof out of the product gas mixture by absorption to form an absorbate I,
   wherein the absorbent I is conducted in concurrent or in countercurrent to the product gas mixture,
   (3) the absorbate I is discharged from absorption zone I and the scrubbed product gas mixture conducted out of absorption zone I is conducted through a condensation zone I, in which an aqueous acrylic acid solution is condensed as condensate I out of the scrubbed product gas mixture by direct and/or indirect cooling thereof, with the proviso that there remains a $CO_2$- and water-comprising residual gas mixture I which comprises the at least one inert diluent gas other than $CO_2$ and water, the secondary constituents formic acid, acetic acid, propionic acid, acrolein, benzaldehyde and 2-furaldehyde and at least 10% of the amount of acrylic acid present in the product gas mixture, wherein the aqueous acrylic acid solution comprises the secondary constituents formic acid, acetic acid, propionic acid, acrolein, benzaldehyde and 2-furaldehyde in dissolved form, at least a portion of condensate I is conducted as absorbent I into the absorption zone I, and any remaining residual amount of condensate I is conducted out of condensation zone I as aqueous intermediate I, (4) the residual gas mixture I, conducted out of condensation zone I, is passed through an absorption zone II in which an aqueous alkali metal base scrubs acrylic acid, $CO_2$, and the secondary constituents formic acid, acetic acid, propionic acid, acrolein, benzaldehyde and 2-furaldehyde, out of residual gas mixture I by absorption to form an aqueous alkali metal acrylate solution as absorbate II, leaving a residual gas mixture II which comprises the at least one inert diluent gas other than $CO_2$ and water, a residual amount of acrylic acid and water, wherein the aqueous alkali metal base is conducted in concurrent or in countercurrent to the residual gas mixture I as absorbent II, residual gas mixture II is conducted out of absorption zone II, and absorbate II is withdrawn from absorption zone II as aqueous intermediate II, (5) carrying out the following (5A) or (5B)

(5A) if no aqueous intermediate I is conducted out of condensation zone I, the acrolein, benzaldehyde and 2-furaldehyde secondary constituents present in the aqueous intermediate II are absorbed therefrom by extraction with an organic extractant, and remaining aqueous raffinate II is removed from an organic extract II formed as the aqueous target product solution comprising acrylic acid and the conjugate base thereof, formic acid and the conjugate base thereof, acetic acid and the conjugate base thereof, propionic acid and the conjugate base thereof, (5B) if aqueous intermediate I is conducted out of condensation zone I, the acrolein, (1) benzaldehyde and 2-furaldehyde secondary constituents present in the aqueous intermediate II are absorbed therefrom by extraction with an organic extractant, and remaining aqueous raffinate II is removed from an organic extract II formed, and the acrolein, benzaldehyde and 2-furaldehyde secondary constituents present in the aqueous intermediate I are absorbed therefrom by extraction with an organic extractant, and remaining aqueous raffinate I is removed from the organic extract I formed, wherein the aqueous raffinate II and the aqueous raffinate I are combined to give the aqueous target product solution comprising the acrylic acid and the conjugate base thereof, formic acid and the conjugate base thereof, acetic acid and the conjugate base thereof, propionic acid and the conjugate base thereof, optionally $CO_2$ is outgassed from the aqueous target product solution, or (2) the aqueous intermediate II and the aqueous intermediate I are combined to give an aqueous intermediate III, and the acrolein, benzaldehyde and 2-furaldehyde secondary constituents present in the aqueous intermediate III are absorbed therefrom by extraction with an organic extractant, optionally $CO_2$ is outgassed from the aqueous intermediate III beforehand, and the remaining aqueous raffinate III is removed from the organic extract III formed as the aqueous target product solution comprising acrylic acid and the conjugate base thereof, formic acid and the conjugate base thereof, acetic acid and the conjugate base thereof, propionic acid and the conjugate base thereof.

2. The process according to claim 1, wherein each of the aqueous raffinate removed from the corresponding organic extracts comprises organic extractant in dissolved form, and the organic extractant present in dissolved form is removed from the aqueous raffinate by extraction, adsorption and/or rectification.

3. The process according to claim 1, which is followed by a process for free-radical polymerization which is effected from the aqueous target product solution, optionally after organic extractant still present therein has been removed beforehand.

4. The process according to claim 1, which is followed by a process for free-radical polymerization in which acrylic acid and the conjugate base thereof present in the aqueous target product solution, optionally after organic extractant present therein has been removed therefrom, and optionally at least monoethylenically unsaturated compounds other than acrylic acid and the conjugate base thereof, are polymerized into polymer.

5. The process according to claim 2, which is followed by a process for free-radical polymerization which is effected from the aqueous target product solution, optionally after organic extractant still present therein has been removed beforehand.

6. The process according to claim 2, which is followed by a process for free-radical polymerization in which acrylic acid and the conjugate base thereof present in the aqueous target product solution, optionally after organic extractant present therein has been removed therefrom, and optionally at least monoethylenically unsaturated compounds other than acrylic acid and the conjugate base thereof, are polymerized into polymer.

7. The process according to claim 1, wherein in (5), aqueous intermediate I is not conducted out of condensation zone I.

8. The process according to claim 1, wherein in (5), aqueous intermediate I is conducted out of condensation zone I.

9. The process according to claim 2, wherein in (5), aqueous intermediate I is not conducted out of condensation zone I.

10. The process according to claim 2, wherein in (5), aqueous intermediate I is conducted out of condensation zone I.

11. The process according to claim 1, wherein in (2), the product gas mixture is conducted through absorption zone I after its temperature has been reduced in a cooling zone by direct and/or indirect cooling.

12. The process according to claim 1, wherein in (2), the product gas mixture is conducted through absorption zone I without its temperature having been reduced in a cooling zone by direct and/or indirect cooling.

13. The process according to claim 2, wherein in (2), the product gas mixture is conducted through absorption zone I after its temperature has been reduced in a cooling zone by direct and/or indirect cooling.

14. The process according to claim 2, wherein in (2), the product gas mixture is conducted through absorption zone I without its temperature having been reduced in a cooling zone by direct and/or indirect cooling.

\* \* \* \* \*